(12) United States Patent
Loy et al.

(10) Patent No.: US 12,180,163 B2
(45) Date of Patent: *Dec. 31, 2024

(54) PICOLINAMIDES AS FUNGICIDES

(71) Applicant: CORTEVA AGRISCIENCE LLC, Indianapolis, IN (US)

(72) Inventors: Brian A. Loy, Indianapolis, IN (US); Nicolaas Vermeulen, Chicago, IL (US); Brannon Sam, Indianapolis, IN (US); Kevin G. Meyer, Zionsville, IN (US); Chenglin Yao, Westfield, IN (US); Nicholas R. Babij, Carmel, IN (US); Jeff Petkus, Indianapolis, IN (US)

(73) Assignee: CORTEVA AGRISCIENCE LLC, IN (US)

( * ) Notice: Subject to any disclaimer, the term of this patent is extended or adjusted under 35 U.S.C. 154(b) by 211 days.

This patent is subject to a terminal disclaimer.

(21) Appl. No.: 17/483,232

(22) Filed: Sep. 23, 2021

(65) Prior Publication Data

US 2023/0049481 A1 Feb. 16, 2023

Related U.S. Application Data

(63) Continuation of application No. 16/296,324, filed on Mar. 8, 2019, now Pat. No. 11,155,520.

(60) Provisional application No. 62/640,424, filed on Mar. 8, 2018, provisional application No. 62/640,434, filed on Mar. 8, 2018.

(51) Int. Cl.
| | | |
|---|---|---|
| C07D 213/81 | (2006.01) | |
| A01N 37/02 | (2006.01) | |
| A01N 43/10 | (2006.01) | |
| A01N 43/40 | (2006.01) | |
| A01N 43/84 | (2006.01) | |
| A01N 47/18 | (2006.01) | |
| C07B 53/00 | (2006.01) | |
| C07C 229/28 | (2006.01) | |
| C07C 271/18 | (2006.01) | |
| C07D 213/83 | (2006.01) | |
| C07D 333/08 | (2006.01) | |
| C07D 409/12 | (2006.01) | |
| C07D 498/04 | (2006.01) | |

(52) U.S. Cl.
CPC ........... *C07D 213/81* (2013.01); *A01N 37/02* (2013.01); *A01N 43/10* (2013.01); *A01N 43/40* (2013.01); *A01N 43/84* (2013.01); *A01N 47/18* (2013.01); *C07B 53/00* (2013.01); *C07C 229/28* (2013.01); *C07C 271/18* (2013.01); *C07D 213/83* (2013.01); *C07D 333/08* (2013.01); *C07D 409/12* (2013.01); *C07D 498/04* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 4,051,173 | A | 9/1977 | Schacht |
| 4,588,735 | A | 5/1986 | Spatz |
| 5,342,835 | A | 8/1994 | Pepin et al. |
| 5,401,871 | A | 3/1995 | Talley |
| 5,475,132 | A | 12/1995 | Pepin et al. |
| 5,563,165 | A | 10/1996 | Talley |
| 5,760,068 | A | 6/1998 | Talley et al. |
| 5,852,042 | A | 12/1998 | Jakobi |
| 6,355,660 | B1 | 3/2002 | Ricks |
| 6,410,572 | B1 | 6/2002 | Schelberger |
| 6,436,421 | B1 | 8/2002 | Schindler |
| 6,521,622 | B1 | 2/2003 | Ricks |
| 6,706,740 | B2 | 3/2004 | Ricks |
| 6,812,237 | B2 | 11/2004 | Cowen et al. |
| 6,812,238 | B1 | 11/2004 | Fukuda et al. |
| 6,861,390 | B2 | 3/2005 | Meyer |
| 6,903,219 | B2 | 6/2005 | Niyaz |
| 6,916,932 | B2 | 7/2005 | Meyer |
| 6,927,225 | B2 | 8/2005 | Ricks |
| 6,953,807 | B2 | 10/2005 | Hutin et al. |
| 7,034,035 | B2 | 4/2006 | Ricks |
| 7,183,278 | B1 | 2/2007 | Imamura |
| 7,241,804 | B1 | 7/2007 | Hockenberry |
| 7,250,389 | B1 | 7/2007 | Sakanaka |
| RE39,991 | E | 1/2008 | Ricks |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Anonymous, Synergistic Fungicidal Composition of Heterocyclic Aromatic Amides and Triazoles, ip.com Journal, ip.com, Electronic Publication, West Henrietta, NY, US, Jul. 2004, 11 pages.

(Continued)

*Primary Examiner* — John Pak

(57) ABSTRACT

This disclosure relates to picolinamides of Formula I and their use as fungicides.

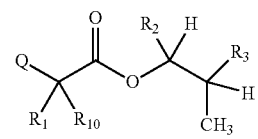

5 Claims, No Drawings

(56) References Cited

U.S. PATENT DOCUMENTS

| | | |
|---|---|---|
| 7,442,672 B2 | 10/2008 | Muller |
| 7,459,581 B2 | 12/2008 | Derrer |
| 7,560,565 B2 | 7/2009 | Bacque |
| 7,927,617 B2 | 4/2011 | Koltzenburg |
| 8,008,231 B2 | 8/2011 | Leatherman |
| 8,153,819 B2 | 4/2012 | Dietz |
| 8,236,962 B2 | 8/2012 | Hoekstra |
| 8,349,877 B2 | 1/2013 | Brix |
| 8,415,274 B2 | 4/2013 | Wachendorff-Neumann |
| 8,465,562 B2 | 6/2013 | Chen |
| 8,470,840 B2 | 6/2013 | Klittich |
| 8,476,193 B2 | 7/2013 | Keeney |
| 8,580,959 B2 | 11/2013 | Devasthale |
| 8,586,550 B2 | 11/2013 | Lee et al. |
| 8,604,215 B2 | 12/2013 | Phiasivongsa |
| 8,785,479 B2 | 7/2014 | Meyer |
| 8,835,462 B2 | 9/2014 | Meyer |
| 8,883,811 B2 | 11/2014 | Owen |
| 8,916,579 B2 | 12/2014 | Boebel |
| 9,006,259 B2 | 4/2015 | Boebel |
| 9,084,418 B2 | 7/2015 | Ehr |
| 9,131,690 B2 | 9/2015 | Meyer |
| 9,144,239 B2 | 9/2015 | Meyer |
| 9,155,305 B2 | 10/2015 | Gary |
| 9,156,816 B2 | 10/2015 | Ito |
| 9,179,674 B2 | 11/2015 | Martin |
| 9,185,911 B2 | 11/2015 | Inami |
| 9,198,419 B2 | 12/2015 | Owen |
| 9,247,741 B2 | 2/2016 | DeLorbe |
| 9,265,253 B2 | 2/2016 | Li |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin |
| 9,482,661 B2 | 11/2016 | Ross |
| 9,549,555 B2 | 1/2017 | DeLorbe |
| 9,549,556 B2 | 1/2017 | DeKorver |
| 9,629,365 B2 | 4/2017 | Li |
| 9,681,664 B2 | 6/2017 | Lalonde |
| 9,686,984 B2 | 6/2017 | DeKorver |
| 9,700,047 B2 | 7/2017 | Lu |
| 9,750,248 B2 | 9/2017 | Ouimette |
| 9,828,408 B2 | 11/2017 | Kalayanov et al. |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 10,015,964 B2 | 7/2018 | Ogawa et al. |
| 10,015,966 B2 | 7/2018 | Taggi et al. |
| 10,111,432 B2 | 10/2018 | Rigoli |
| 10,172,354 B2 | 1/2019 | Ouimette et al. |
| 10,173,971 B2 | 1/2019 | Yao |
| 10,173,981 B2 | 1/2019 | Buchan |
| 10,182,568 B2 | 1/2019 | Bravo-Altamirano |
| 10,188,109 B2 | 1/2019 | Yao |
| 10,252,989 B2 | 4/2019 | Yao |
| 10,433,555 B2 | 10/2019 | Bravo-Altamirano et al. |
| 11,395,489 B2 * | 7/2022 | Rendine ............... C07D 213/81 |
| 2002/0119979 A1 | 8/2002 | Degenhardt |
| 2002/0177578 A1 | 11/2002 | Ricks |
| 2003/0018052 A1 | 1/2003 | Ricks |
| 2003/0022902 A1 | 1/2003 | Ricks |
| 2003/0022903 A1 | 1/2003 | Ricks |
| 2005/0239873 A1 | 10/2005 | Hockenberry |
| 2006/0167281 A1 | 7/2006 | Meijer |
| 2007/0010401 A1 | 1/2007 | Noon |
| 2007/0066629 A1 | 3/2007 | Tormo i Biasco |
| 2009/0203770 A1 | 8/2009 | Hockenberry |
| 2009/0306142 A1 | 12/2009 | Carson |
| 2010/0016163 A1 | 1/2010 | Keiper |
| 2011/0070278 A1 | 3/2011 | Lopez |
| 2011/0082162 A1 | 4/2011 | Lorsbach |
| 2012/0245031 A1 | 9/2012 | Gewehr |
| 2013/0296372 A1 | 11/2013 | Owen |
| 2014/0051678 A1 | 2/2014 | Clement-Schatlo |
| 2014/0357713 A1 | 12/2014 | Damaj |
| 2015/0289508 A1 | 10/2015 | Meyer |
| 2015/0322051 A1 | 11/2015 | Lu |
| 2016/0037774 A1 | 2/2016 | Schulz |
| 2016/0183526 A1 | 6/2016 | Hopkins |
| 2016/0183527 A1 | 6/2016 | Hopkins |
| 2017/0183324 A1 | 6/2017 | Li |
| 2017/0273303 A1 | 9/2017 | DeKorver |
| 2017/0273306 A1 | 9/2017 | Lalonde |
| 2017/0290333 A1 | 10/2017 | Bravo-Altamirano |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2020/0255400 A1 | 8/2020 | Lamberth et al. |

FOREIGN PATENT DOCUMENTS

| | | |
|---|---|---|
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 199741103 | 6/1997 |
| WO | 1997019908 | 6/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | 2012020777 | 8/2011 |
| WO | 2012016989 | 2/2012 |
| WO | 2016109301 | 12/2012 |
| WO | 2013136275 | 9/2013 |
| WO | 2016007525 | 7/2015 |
| WO | 2016109288 | 12/2015 |
| WO | 2016109289 | 12/2015 |
| WO | 2016109290 | 12/2015 |
| WO | 2016109291 | 12/2015 |
| WO | 2016109300 | 12/2015 |
| WO | 2016109302 | 12/2015 |
| WO | 2016109303 | 12/2015 |
| WO | 2016109304 | 12/2015 |
| WO | 2016109305 | 12/2015 |
| WO | 2015005355 | 3/2017 |

OTHER PUBLICATIONS

Backman, P., Fungicide Formulation: Relationship to Biological Activity, Ann. Rev. Phytopathol, 1978, 16, pp. 211-237.

BASF New Fungicide Xemium Got Full Approval in EU, Agronews, Jul. 18, 2012 [retrieved on Feb. 4, 2014]. Retrieved from the Internet: ,URL:http://news.agropages.com/News/NewsDetail---7386.htm, 1 page.

Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.

Cantacuzene, D., "Optimization of the papain catalyzed esterification of amino acids by alcohols and diols," Tetrahedron 45, 3 (1989): 741-748.

FRAC Code List: Fungicides Sorted by Mode of Action (including FRAC Code numbering), Fungicide Resistance Action Committee, Dec. 2008, 10 pages.

(56) References Cited

OTHER PUBLICATIONS

Fungicidal Mixtures, IP.com Prior Art Database Technical Disclosure, (Jul. 5, 2005), XP055073888, DOI: http:/ip.com/pdf/ipcompad/IPCOM000126160D.pdf, 12 pages.
Gisi, U., "Synergistic Interaction of Fungicides in Mixtures," The American Phytopathology Society, vol. 86, No. 11, 1996, pp. 1273-1279.
Guseynov et al: "Study of the reaction of aminoacetic acid with dihydric alcohols and production of epoxy esters" Chemical Problems, 2009 (1), pp. 188-190.
Hu, Z. et al., "Synthesis of Novel Analogues of Antimycin A3," Tetrahedron Letters 49 (2008), pp. 5192-5195.
Huang, C. et al., "Synergistic Interactions between Chitinase ChiCW and Fungicides Against Plant Fungal Pathogens," J. Microbiol. Biotechnol., 2008, 18(4), pp. 784-787.
Kissling, E., "Crop Protection Pipeline Value Jumps to Euro 2.4 Billion," BASF SE, Mar. 10, 2011 [retrieved on Feb. 4, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control," GCM, Juky 2008, pp. 84-87.
Ueki, M., et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-34.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#/section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 6 pages.
Tani, K. et al., "UK2A, B, C, and D, Novel Antifungal Antibiotics—from *Streptomyces* sp. 517-02.," The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., "UK-2A, B, C, and D, Novel Antifungal Antibiotics from *Streptomyces* sp. 517-02 VI (2). Structure-activity Relationships of UK-2A," Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Goellner et al. "Phakopsora pachyrhizi, the causal agent of Asian soybean rust." Molecular Plant Pathology, vol. 11, No. 2, pp. 169-177 (2010).
Fujita T, Ed. "Quantitative structure-activity analysis and database-aided bioisosteric structural transformation procedure as methodologies of agrochemical design"; Classical and Three Dimensional QSAR in Agrochemistry, ACS Symposium Series Washington, D.C. vol. 606, pp. 13-34 (1995).
Patani et al. Biosterism: A rational approach in drug design. Chemical Reviews, vol. 96, No. 8, pp. 3147-3176 (1996).
Kendall, S. et al. "Changes in sensitivity to DMI fungicides in Rhynchosporium secalis". Crop Protection, vol. 12, No. 5, pp. 357-362 (1993).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Shimano et al. "Total synthesis of the antifungal dilactones UK-2A and UK-3a: The determination of their relative and absolute configurations, analog synthesis and antifungal activities". Tetrahedron, vol. 54, pp. 12745-12774 (1998).
Lippard, S. "Chemical Synthesis: The Art of Chemistry". Nature, vol. 416, p. 587 (2002).
Washburn, W.N., "Identification of a nonbasic melanin hormone receptor 1 antagonist as an antiobesity clinical candidate." Journal of medicinal chemistry 57, 18 (Aug. 28, 2014): 7509-7522.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012).
Chitwood, D. "Nematicides". Encyclopedia of Agrochemicals (3), pp. 1104-1115, John Wiley & Sons, New York, NY, http://naldc.nal.usda.gov/download/43874/PDF (2003).
Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).
Shibata et al. "UK1, A Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp. 2075-2154, International Union of Pure and Applied Chemistry (2006).
Jeki, M., et al., "UK-1, A Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Jeki et al. "UK-3A, A Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US2019/021263 dated May 10, 2019, 15 pages.

* cited by examiner

PICOLINAMIDES AS FUNGICIDES

CROSS REFERENCE TO RELATED APPLICATION

This is a national phase entry under 35 U.S.C. § 371 of international patent application PCT/US2019/021263, filed on Mar. 8, 2019 and published in English as international patent publication WO2019173665 on Sep. 12, 2019, which claims priority to the benefit of of U.S. Provisional Patent Application Ser. No. 62/640,424 filed Mar. 8, 2018 and U.S. Provisional Patent Application Ser. No. 62/640,434 filed Mar. 8, 2018 the disclosure of which is hereby incorporated by reference in its entirety.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

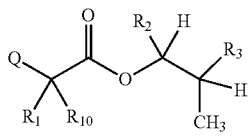

wherein:
Q is

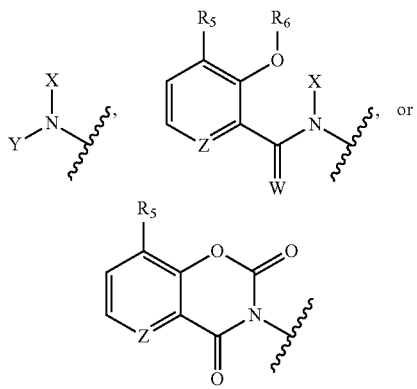

X is hydrogen or $C(O)R_4$;
Y is hydrogen or $C(O)R_4$;
Z is N or $N^+ \rightarrow O^-$ and W is O or S;
$R_1$ is hydrogen or alkyl, substituted with 0, 1 or multiple $R_7$;
$R_2$ is methyl;
$R_3$ is chosen from alkyl, aryl or heteroaryl, each optionally substituted with 0, 1 or multiple $R_7$;
$R_4$ is chosen from alkoxy or benzyloxy, each optionally substituted with 0, 1, or multiple $R_7$;
$R_5$ is chosen from hydrogen, alkoxy, or halo, each optionally substituted with 0, 1, or multiple $R_7$;
$R_6$ is chosen from hydrogen, $-C(O)R_8$, or $-CH_2OC(O)R_8$;
$R_7$ is chosen from hydrogen, alkyl, aryl, acyl, halo, alkenyl, alkynyl, alkoxy, cyano, or heterocyclyl, each optionally substituted with 0, 1, or multiple $R_9$;
$R_8$ is chosen from alkyl, alkoxy, or aryl, each optionally substituted with 0, 1, or multiple $R_7$;
$R_9$ is chosen from hydrogen, alkyl, aryl, acyl, halo, alkenyl, alkoxy, or heterocyclyl; and
$R_{10}$ is chosen from hydrogen or alkyl, each substituted with 0, 1 or multiple $R_7$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms The term "alkoxy" refers to an —OR substituent.
The term "acyloxy" refers to an —OC(O)R substituent.
The term "cyano" refers to a —C≡N substituent.
The term "hydroxyl" refers to a —OH substituent.
The term "amino" refers to an $-N(R)_2$ substituent.
The term "arylalkoxy" refers to $-O(CH_2)_n Ar$ where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a $-NO_2$ substituent.
The term thioalkyl refers to a —SR substituent.

Throughout the disclosure, reference to the compounds of Formula I is read as also including all stereoisomers, for example diastereomers, enantiomers, and mixtures thereof. In another embodiment, Formula (I) is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and used as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oilsoluble salts (e.g., calcium) of alkylaryl sulphonic acids, oil-soluble salts or sulfated polyglycol ethers and appropriate salts of phosphated-polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+ urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, aminopyrifen, amisulbrom, antimycin, *Ampelomyces quisqualis*, azaconazole, *Bacillus subtilis, Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, fluindapyr, flumorph, fluopicolide, fluopyram, fluoroimide, fluoxapiprolin, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), inpyrfluxam, iodocarb, ipconazole, ipfenpyrazolone, iprobenfos, iprodione, iprovalicarb, isofetamide, isoflucypram, isoprothiolane, isopyrazam, isotianil, kasugamycin, kasugamycin hydrochloride hydrate, kresoxium-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pydiflumetofen, pyrametostrobin, pyraoxystrobin, pyraclostrobin, pyraziflumid, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, coumoxystrobin, cufraneb, cupric hydrazinium sulfate, cuprobam, cyclafuramid, cypendazole, cyprofuram, decafentin, dichlobentiazox, dichlone, dichlozoline, diclobutrazol, dimethirimol, dinocton, dinosulfon, dinoterbon, dipymetitrone, dipyrithione, ditalimfos, dodicin, drazoxolon, EBP, enoxastrobin, ESBP, etaconazole, etem, ethirim, fenaminstrobin, fenaminosulf, fenapanil, fenitropan, fenpicoxamid, florylpicoxamid, flufenoxystrobin, fluopimomide, fluotrimazole, furcarbanil, furconazole, furconazole-cis, furmecyclox, furophanate, glyodine, griseofulvin, halacrinate, Hercules 3944, hexylthiofos, ICIA0858, ipfentrifluconazole, ipflufenoquin, isopamphos, isovaledione, mandestrobin, mebenil, mecarbinzid, mefentrifluconazole, metazoxolon, methfuroxam, methylmercury dicyandiamide, metsulfovax, metyltetraprole, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyrapropoyne, pyridachlometyl, pyridinitril, pyrisoxazole, pyroxychlor, pyroxyfur, quinacetol; quinacetol sulfate, quinazamid, quinconazole, quinofumelin, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, triclopyricarb, triflumezopyrim, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, acynonapyr, afidopyropen, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, benzpyrimoxan, beta-cyfluthrin, beta-cypermethrin, bifenthrin, bioallethrin, bioethanomethrin, biopermethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chloroprallethrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cyfluthrin, cyhalodiamide, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, epsilon-metofluthrin, epsilon-momfluorothrin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, fluazaindolizine, flubendiamide, flucofuron, flucycloxuron, flucythrinate, fluensulfone, flufenerim, flufenoxuron, flufenprox, flufiprole, fluhexafon, flupyradifurone, flupyrimin, fluvalinate, fluxametamide, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptafluthrin, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isocycloseram, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, momfluorothrin, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxazosulfyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocssene II, precocene III, primidophos, profenofos, profluralin, promacyl, promecarb, propaphos, propetamphos, propoxur, prothidathion, prothiofos, prothoate, protrifenbute, pyflubumide, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyriminostrobin, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spiropidion, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachlorantraniliprole, tetrachloroethane, tetrachlorvinphos, tetramethrin, tetramethylfluthrin, tetraniliprole, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tioxazafen, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, tyclopyrazoflor, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, aciflurofen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, beflubutamid-M, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, bixlozone, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clacyfos, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclopyranil, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenquinotrione, fenteracol, fenthiaprop, fentrazamide, fenuron, ferrous sulfate, flamprop, flamprop-M, flazasulfuron, florasulam, florpyrauxifen, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lancotrione, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, tolpyralate, topramezone, tralkoxydim, triafamone, tri-allate, triasulfuron, triaziflam, tribenuron, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Parastagonospora nodorum*), powdery mildew of wheat (*Blumeria graminis* f. sp.*tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Racemic mixtures of Formulas 1.2-Rac, 1.3-Rac and 1.5-Rac, 1.6-Rac, wherein $R_3$ is as previously defined, can be prepared by the method shown in Scheme 1, step a. Submission of racemic epoxide mixtures of Formulas 1.0-Rac and 1.4-Rac, to reaction with an organometallic nucleophile, such

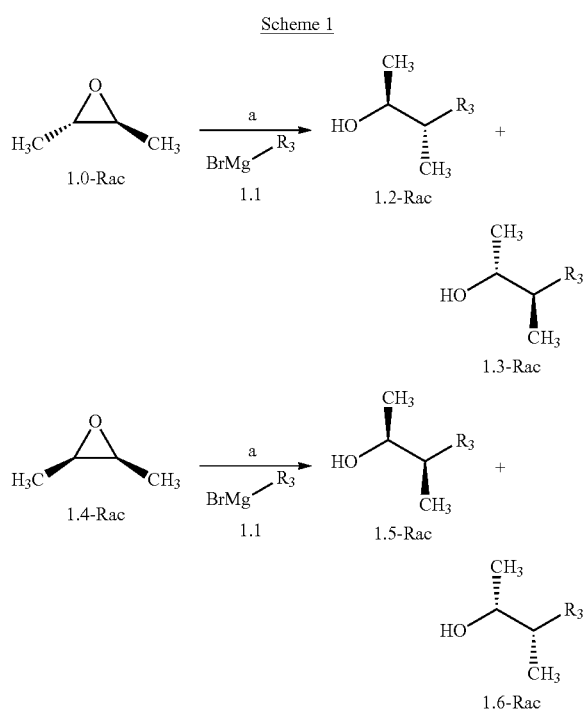

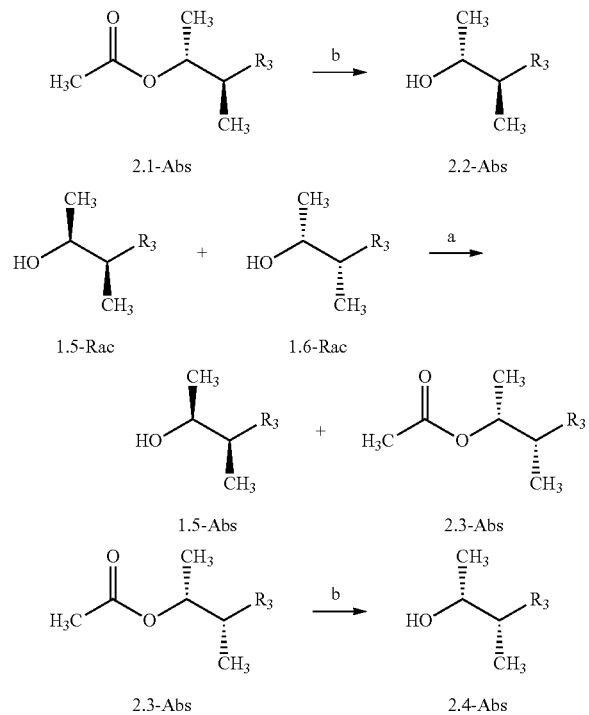

as an aryl magnesium halide, in the presence of a metal halide, such as copper iodide, in a polar, aprotic solvent, such as tetrahydrofuran (THF) or diethyl ether (Et$_2$O), at a temperature of about −78° C. to 55° C., affords racemic mixtures of Formulas 1.2-Rac, 1.3-Rac and 1.5-Rac, 1.6-Rac, wherein R$_3$ is as previously defined, and shown in step a.

Racemic mixtures of Formulas 1.2-Rac, 1.3-Rac and 1.5-Rac, 1.6-Rac, wherein R$_3$ is as previously defined, can be separated into their individual enantiomers utilizing a lipase-catalyzed kinetic resolution described by Akita (*Tetrahedron: Asymmetry* 2009, 20, 1286-1294) and outlined in Scheme 2, steps a and b. Subjection of racemic mixtures of Formulas 1.2-Rac, 1.3-Rac and 1.5-Rac, 1.6-Rac, wherein R$_3$ is as previously defined, to *Candida antarctica* lipase B (CAL-B) in an acetylating solvent, such as vinyl acetate, at a temperature of about 25° C. to about 60° C., affords the unreacted secondary alcohols of Formulas 1.2-Abs and 1.5-Abs, wherein R$_3$ is as originally defined, and the acetylated compounds of Formulas 2.1-Abs and 2.3-Abs, wherein R$_3$ is as originally defined. The mixtures can be purified via silica gel chromatography using a hexane-ethyl acetate mixture as the mobile phase giving the resolved secondary alcohols and acetates of Formulas 1.2-Abs, 1.5-Abs, 2.1-Abs and 2.3-Abs, wherein R$_3$ is as originally defined, and in high enantiomeric excess. The lipase recognition of the secondary alcohol of 1.2-Rac, 1.3-Rac, 1.5-Rac and 1.6-Rac, wherein R$_3$ is as originally defined, was similar to the empirical rule for the kinetic resolution of secondary alcohols (Bornscheuer and Kazlauskus, *Hydrolases in Organic Synthesis*; Wiley-VCH, 2006). Treatment of acetates of Formulas 2.1-Abs and 2.3-Abs, wherein R$_3$ is as originally defined, with a carbonate base, such as potassium carbonate, in an alcoholic solvent, such as methanol, at a temperature of about 25° C. to about 60° C., affords the resolved secondary alcohols of Formulas 2.2-Abs and 2.4-Abs, wherein R$_3$ is as originally defined.

Compounds of Formula 3.2, wherein R$_1$, R$_2$, R$_3$, and R$_{10}$, are as originally defined, may be prepared according to the method outlined in Scheme 3, step a. Alcohols of Formula 3.0, wherein R$_2$ and R$_3$, are as originally defined, can be treated with compounds of Formula 3.1, wherein R$_1$ and R$_{10}$ are as originally defined, a coupling reagent, such as 3-(ethyliminomethyleneamino)-N,N-dimethylpropan-1-amine hydrochloride (EDC) or a polymer-supported carbodiimide (PS-CDI), and a catalyst, such as N,N-dimethylpyridin-4-amine (DMAP), in a halogenated or polar, aprotic solvent, such as (CH$_2$Cl$_2$) or THF to afford compounds of Formula 3.2, wherein R$_1$, R$_2$, R$_3$, and R$_{10}$, are as originally defined, as shown in step a.

Scheme 3

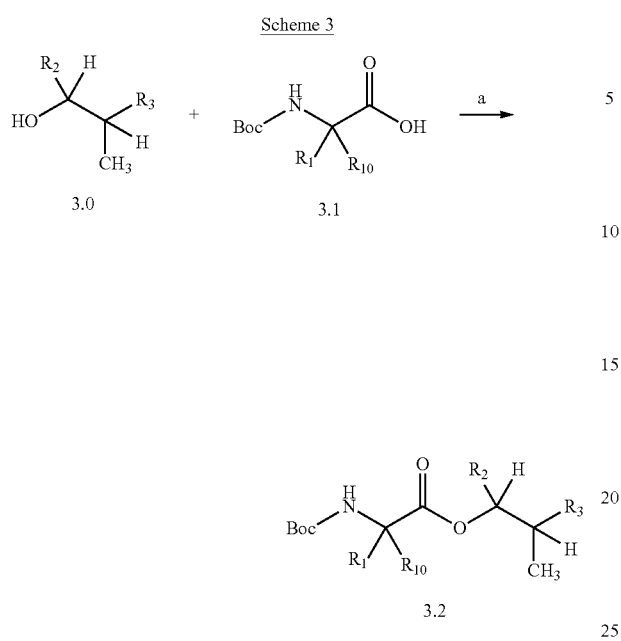

Compounds of Formula 4.5, wherein $R_1$, $R_2$, $R_3$, $R_5$, and $R_{10}$, are as originally defined, can be prepared according to the methods outlined in Scheme 4, steps a-d. Compounds of Formula 3.2, wherein $R_1$, $R_2$, $R_3$, and $R_{10}$, are as originally defined, can be treated with an acid, such as a 4 Normal (N) solution of hydrogen chloride (HCl) in dioxane, in a halogenated solvent such as $CH_2Cl_2$ to afford compounds of Formula 4.1, wherein $R_1$, $R_2$, $R_3$, and $R_{10}$, as shown in step a. Compounds of Formula 4.2, wherein $R_1$, $R_2$, $R_3$, and $R_{10}$, are as originally defined, can be prepared by treating compounds of Formula 3.2, wherein $R_1$, $R_2$, $R_3$, and $R_{10}$, are as originally defined, with an acid, such as 2,2,2-trifluoroacetic acid, in a halogenated solvent such as $CH_2Cl_2$, as shown in step c. Compounds of Formulas 4.1 and 4.2, wherein $R_1$, $R_2$, $R_3$, and $R_{10}$, are as originally defined, can be treated with compounds of Formula 4.3, wherein $R_5$ is as originally defined, in the presence of a base, such as diisopropylethylamine, and a peptide coupling reagent, such as benzotriazol-1-yl-oxytripyrrolidinophosphonium hexafluorophosphate (PyBOP) or O-(7-azabenzo-triazol-1-yl)-N,N,N',N'-tetramethyluronium hexafluorophosphate (HATU), in a halogenated solvent such as $CH_2Cl_2$, to afford compounds of Formula 4.5, wherein $R_1$, $R_2$, $R_3$, $R_5$ and $R_{10}$, are as originally defined, as shown in steps b and d.

Scheme 4

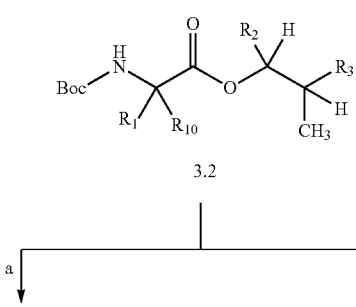

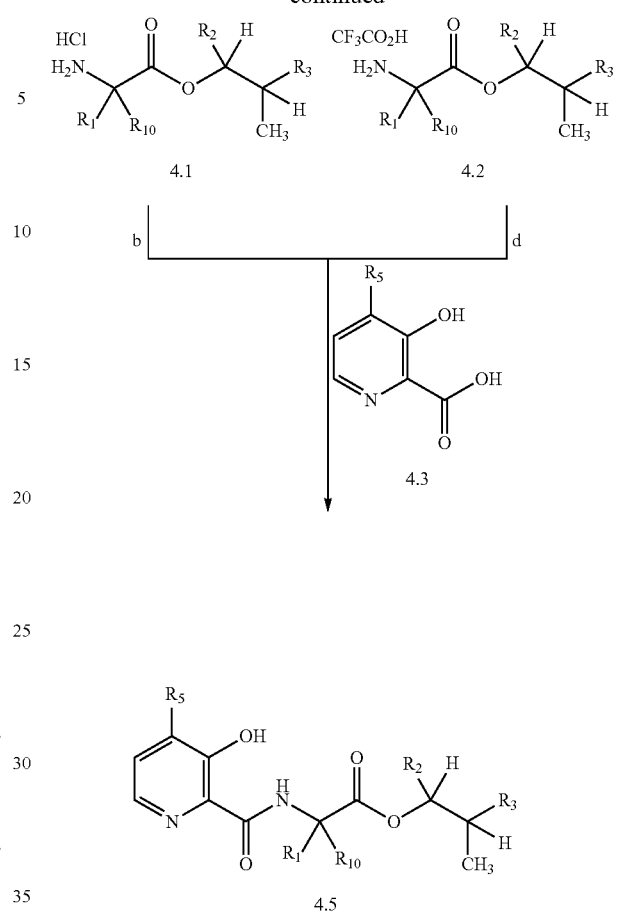

Compounds of Formula 5.1, wherein $R_1$, $R_2$, $R_3$, $R_5$ and $R_{10}$, are as originally defined, can be prepared according to the method outlined in Scheme 5, steps a or b. Compounds of Formula 4.5, wherein $R_1$, $R_2$, $R_3$, $R_5$ and $R_{10}$, are as originally defined, can be treated with an appropriate alkyl halide, with or without a reagent such as sodium iodide (NaI) and an alkali carbonate base, such as sodium ($Na_2CO_3$) or potassium carbonate ($K_2CO_3$), in a solvent such as acetone, at a temperature of about 25° C. to about 50° C., as shown in step a. Or, alternatively, by treatment with an acyl halide or anhydride in the presence of an amine base, such as pyridine, triethylamine ($NEt_3$), DMAP, or mixtures thereof, in an aprotic solvent, such as $CH_2Cl_2$, to afford compounds of Formula 5.1, wherein $R_1$, $R_2$, $R_3$, $R_5$, $R_6$, and $R_{10}$, are as originally defined, as shown in step b.

Scheme 5

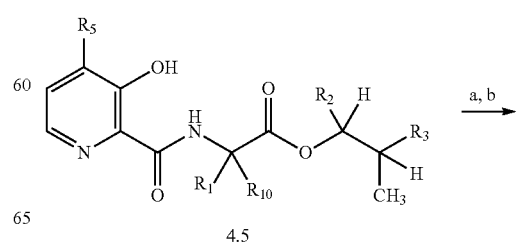

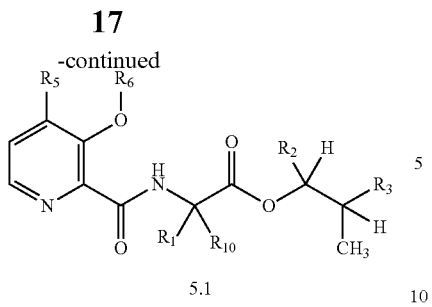

5.1

Compounds of Formula 6.1 and 6.2, wherein $R_1$, $R_2$, $R_3$, $R_5$, $R_6$, and $R_{10}$, are as originally defined, can be prepared according to the method outlined in Scheme 6, steps a and b. Compounds of Formula 4.5, wherein $R_1$, $R_2$, $R_3$, $R_5$, and $R_{10}$, are as originally defined, can be treated with a thionating reagent such as phosphorus pentasulfide, an additive, such as hexamethyldisiloxane, optionally in a polar aprotic solvent such as acetonitrile (CH$_3$CN), at a temperature of about 0° C. to 80° C. to afford compounds of Formula 6.1, wherein $R_1$, $R_2$, $R_3$, $R_5$ and $R_{10}$, are as originally defined, and shown in step a. It will be understood by those skilled in the art that compounds such as Formula 6.1 may also be prepared using other thionating agents including, but not limited to: sulfur, sulfhydric acid, sodium sulfide, sodium hydrosulfide, boron trisulfide, bis(diethylaluminum)sulfide, ammonium sulfide, Lawesson's reagent, ammonium O,O'-diethyl dithiophosphate, rhodanine, or a polymer supported thionating reagent. Additives can include, but not limited to, aluminum oxide (Al$_2$O$_3$); inorganic bases, such as potassium carbonate and sodium bicarbonate; organic bases, such as triethylamine, diethylaniline, pyridine and morpholine. Optional solvents can include, but not limited to, aliphatic, alicyclic or aromatic hydrocarbons, such as hexane, cyclohexane or toluene; halogenated hydrocarbons, such as dichloromethane, 1,2-dichloroethane and chlorobenzene; ethers, such as diethyl ether, 1,4-dioxane, THF and 1,2-dimethoxyethane; and other polar aprotic solvents such as pyridine and hexamethylphosphoramide (HMPA). In step b, treatment of compounds of Formula 6.1, wherein $R_1$, $R_2$, $R_3$, $R_5$ and $R_{10}$, are as originally defined, with an appropriate alkyl halide with or without a reagent such as sodium iodide (NaI) and an alkali carbonate base, such as sodium carbonate (Na$_2$CO$_3$) or potassium carbonate (K$_2$CO$_3$), in a polar aprotic solvent, such as acetone, at a temperature of about 55° C., or by treatment with an acyl halide or anhydride in the presence of an amine base, such as pyridine, Et$_3$N, DMAP, or mixtures thereof, in an optional aprotic solvent such as CH$_2$Cl$_2$, at a temperature of about 23° C., can afford compounds of Formula 6.2 wherein $R_1$, $R_2$, $R_3$, $R_5$, $R_6$, and $R_{10}$, are as originally defined.

Scheme 6

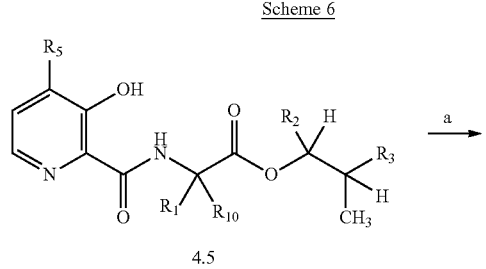

4.5

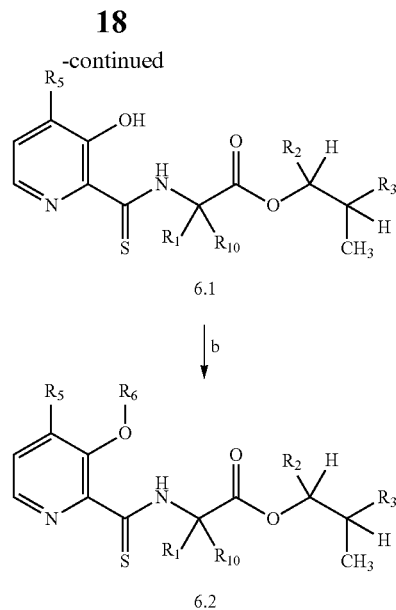

Compounds of Formula 7.1, wherein $R_1$, $R_2$, $R_3$, $R_5$ and $R_{10}$, are as originally defined, can be prepared according to the method outlined in Scheme 7, step a. Compounds of Formula 4.5, wherein $R_1$, $R_2$, $R_3$, $R_5$ and $R_{10}$, are as originally defined, can be treated with a oxidizing reagent such as m-chloroperbenzoic acid (mCPBA) in a polar solvent such as CH$_2$Cl$_2$, at a temperature of about 0° C. to 50° C., to give compounds of Formula 7.1, wherein $R_1$, $R_2$, $R_3$, $R_5$ and $R_{10}$, are as previously defined, and shown in a. It will be understood by those skilled in the art that compounds of Formula 7.1, wherein $R_1$, $R_2$, $R_3$, $R_5$ and $R_{10}$, are as originally defined, may also be prepared using other oxidizing agents, including, but not limited to: hydrogen peroxide, hydrogen Scheme 7

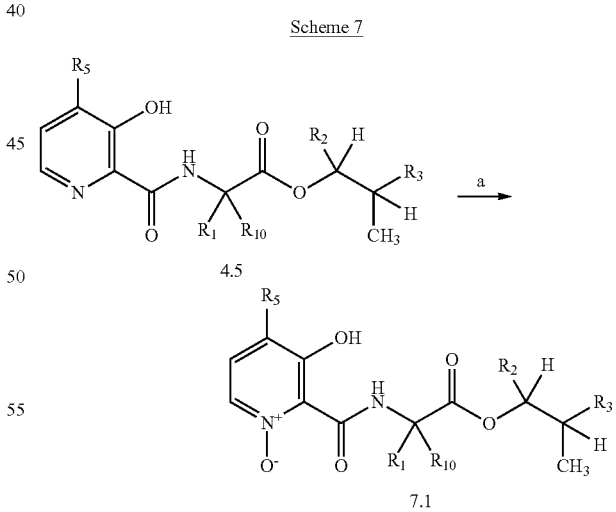

peroxide-urea complex, magnesium monoperoxyphthalate hexahydrate (MMPP), peroxyacetic acid, oxone, sodium perchlorate or dimethyl dioxirane.

Compounds of Formula 8.1 wherein $R_1$, $R_2$, $R_3$, $R_5$ and $R_{10}$, are as originally defined, can be prepared according to the method outlined in Scheme 8, step a. Compounds of Formula 4.5, wherein $R_1$, $R_2$, $R_3$, $R_5$ and $R_{10}$, are as originally defined, can be treated with a diactivated carbonyl reagent such as triphosgene, with a base, such as pyridine, and in a polar solvent, such as $CH_2Cl_2$, at a temperature of about 0° C. to 50° C. to afford compounds of Formula 8.1, wherein $R_1$, $R_2$, $R_3$, $R_5$ and $R_{10}$, are as originally defined, as depicted in a.

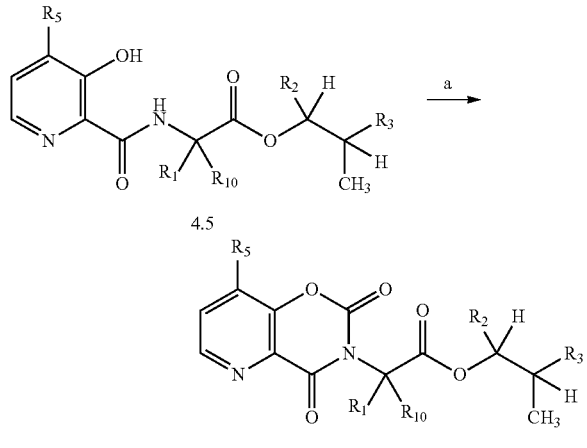

Scheme 8

4.5

8.1

EXAMPLES

Example 1A: Preparation of racemic threo-3-(2,4-dimethylphenyl)butan-2-ol

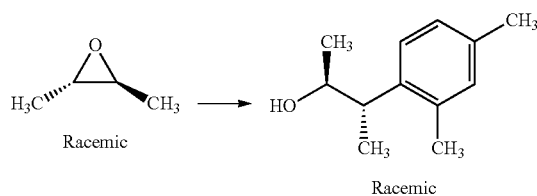

Racemic

Racemic

To a suspension of freshly activated magnesium metal shavings (1.14 g, 46.80 mmol) in anhydrous $Et_2O$ (20 mL) was added dropwise 1-bromo-2,4-dimethylbenzene (8 g, 43.20 mmol). The mixture was gently heated at slight reflux (36° C.) for 5 hours (hr). The resulting dark brown solution was added via syringe to a flask containing copper (I) iodide (4.12 g, 21.61 mmol) suspended in $Et_2O$ (50 mL) at −20° C. The dark yellow suspension was stirred for 15 minutes (min) at −20° C. and then cooled to −50° C. Racemic trans-butene epoxide (1.3 g, 18.01 mmol) was slowly added dropwise followed by warming the reaction to room temperature and stirring overnight. The mixture was then cooled to 0° C. and slowly quenched by the addition of a saturated aqueous ammonium chloride ($NH_4Cl$) solution. The mixture was filtered through a pad of Celite and the pad was rinsed thoroughly with ethyl acetate. The organic solution was washed with saturated $NH_4C_1$ solution and brine. The solution was dried (magnesium sulfate ($MgSO_4$)), filtered and concentrated under reduced pressure. The residue was purified via automated flash column chromatography ($SiO_2$, 0-40% ethyl acetate/hexanes gradient) to give racemic threo-3-(2,4-dimethylphenyl)butan-2-ol as a yellow oil (813 mg, 25%): $^1$H NMR (500 MHz, $CDCl_3$) δ 7.06 (d, J=8.5 Hz, 1H), 7.01-6.97 (m, 2H), 3.94-3.82 (m, 1H), 2.97 (p, J=6.9 Hz, 1H), 2.29 (d, J=7.7 Hz, 6H), 1.50 (d, J=3.9 Hz, 1H), 1.28 (d, J=7.0 Hz, 3H), 1.11 (d, J=6.3 Hz, 3H); $^{13}$C NMR (126 MHz, $CDCl_3$) δ 139.99, 135.49, 135.38, 131.31, 126.81, 126.18, 71.92, 41.42, 21.25, 20.87, 19.85, 16.06; EIMS m/z 178.

Example 1B: Preparation of racemic erythro-3-(o-tolyl)butan-2-ol

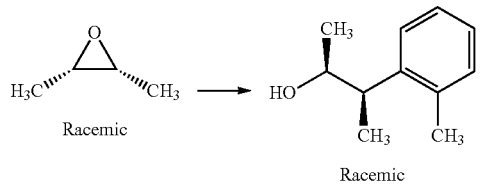

Racemic

Racemic

To a −20° C. suspension of copper(I) iodide (4.15 g, 21.60 mmol) in anhydrous $Et_2O$ (40 mL) was added 2-methylphenylmagnesium bromide (2.0 M in $Et_2O$, 22.5 mL, 43.20 mmol) slowly dropwise. After stirring for 30 min, the orange suspension was cooled to −78° C., and racemic cis-butene epoxide (1.3 g, 18.01 mmol) was slowly added. The dry ice bath was removed and the mixture was allowed to slowly warm to ambient temperature and stirred overnight. The mixture was cooled with an ice bath to 0° C. and quenched slowly by the dropwise addition of a saturated aqueous $NH_4Cl$ solution. The mixture was warmed to room temperature and filtered through Celite, followed by rinsing the pad with ethyl acetate (EtOAc). The resulting filtrate was washed with saturated aqueous $NH_4Cl$ solution and brine. The solution was then dried ($MgSO_4$) and concentrated under reduced pressure. The residue was purified automated flash column chromatography ($SiO_2$, 0-30% ethyl acetate/ hexanes gradient) to give racemic erythro-3-(o-tolyl)butan-2-ol (2.05 g, 69%) as a yellow oil: $^1$H NMR (500 MHz, $CDCl_3$) δ 7.34-7.01 (m, 4H), 3.92 (p, J=6.3 Hz, 1H), 3.01 (p, J=7.1 Hz, 1H), 2.36 (s, 3H), 1.47 (s, 1H), 1.28 (d, J=6.1 Hz, 3H), 1.19 (d, J=7.0 Hz, 3H); $^{13}$C NMR (126 MHz, $CDCl_3$) δ 142.14, 136.84, 130.61, 126.49, 125.81, 72.33, 42.62, 20.47, 19.93, 17.88; EIMS m/z 164.

Example 1C: Preparation of racemic threo-3-phenylbutan-2-ol

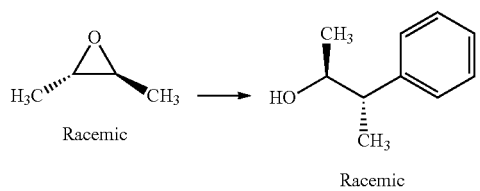

Racemic

Racemic

To a suspension of copper (I) iodide (1.86 g, 9.76 mmol) in ethyl ether (18.0 mL) was added dropwise phenyllithium (1.9 M in butyl ether, 10.3 mL, 19.53 mmol) at 0° C. under a nitrogen atmosphere. After stirring at 0° C. for 1 hr, racemic trans-2,3-dimethyloxirane (0.64 g, 8.88 mmol) was added dropwise followed by removal of the ice bath and warming to room temperature with stirring over 2 hr. The reaction mixture was quenched with water (20 mL), filtered through a pad of Celite, and extracted with ethyl ether (3×20 mL). The organics were passed through a phase separator and concentrated in vacuo. The crude residue was purified via automated flash column chromatography (SiO$_2$, 0-25% acetone/hexanes gradient) to furnish racemic threo-3-phenylbutan-2-ol (1.33 g, 8.85 mmol, 99%) as orange oil: $^1$H NMR (400 MHz, CDCl$_3$) δ 7.38-7.12 (m, 5H), 3.91-3.84 (m, 1H), 2.80-2.68 (m, 1H), 1.43 (s, 1H), 1.33 (d, J=7.1 Hz, 3H), 1.09 (d, J=6.3 Hz, 3H). The spectral data was consistent with those reported in the literature: Tetrahedron 1981, 37, 709-713.

Example 2: Preparation of (2S,3S)-3-(2,4-dimethylphenyl)butan-2-ol and (2R,3R)-3-(2,4-dimethylphenyl)butan-2-ol Step 1: Preparation of (2S,3S)-3-(2,4-dimethylphenyl)butan-2-ol and (2R,3R)-3-(2,4-dimethylphenyl)butan-2-yl acetate

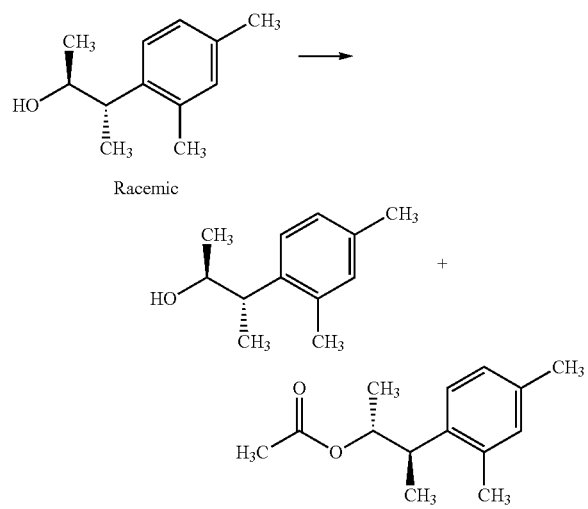

A vial containing a solution of the racemic trans-3-(2,4-dimethylphenyl)butan-2-ol (800 mg, 4.49 mmol) dissolved in vinyl acetate (15 mL) was charged with beads of Novozym 435 Lipase (CAL-B, 1.6 g, 4.49 mmol). The vial was placed in an orbital shaker and was shaken at 200 rpm and heated at 55° C. for 7.5 hrs. The reaction was cooled and filtered through a frit disk with an EtOAc rinse. The eluent was concentrated under reduced pressure to give 906 mg of a crude yellow oil. The residue was purified via flash column chromatography (SiO$_2$, 0-20% ethyl acetate/hexanes gradient) to afford (2R,3R)-3-(2,4-dimethylphenyl)butan-2-yl acetate (clear oil, 466 mg, 47%) followed by (2S,3S)-3-(2,4-dimethylphenyl)butan-2-ol (clear yellow oil, 357 mg, 43%). Acetate: $^1$H NMR (500 MHz, CDCl$_3$) δ 7.07 (d, J=7.7 Hz, 1H), 7.01-6.97 (m, 2H), 5.08 (dq, J=8.5, 6.3 Hz, 1H), 3.16-3.05 (m, 1H), 2.30 (s, 3H), 2.28 (s, 3H), 2.06 (s, 3H), 1.21 (d, J=6.9 Hz, 3H), 1.06 (d, J=6.3 Hz, 3H); $^{13}$C NMR (126 MHz, CDCl$_3$) δ 170.80, 138.92, 135.56, 135.42, 131.22, 126.93, 126.33, 75.09, 39.48, 21.34, 20.89, 19.88, 18.34, 17.96; EIMS m/z 220. Alcohol: $^1$H NMR (500 MHz, CDCl$_3$) δ 7.06 (d, J=8.5 Hz, 1H), 7.01-6.97 (m, 2H), 3.88 (tt, J=9.2, 4.7 Hz, 1H), 2.97 (p, J=6.9 Hz, 1H), 2.30 (s, 3H), 2.28 (s, 3H), 1.49 (d, J=3.5 Hz, 1H), 1.28 (d, J=7.0 Hz, 3H), 1.11 (d, J=6.3 Hz, 3H); $^{13}$C NMR (126 MHz, CDCl$_3$) δ 140.00, 135.49, 135.38, 131.31, 126.82, 126.18, 71.92, 41.43, 21.25, 20.87, 19.85, 16.07; EIMS m/z 178. The enatiomeric ratio of (2S,3S)-3-(2,4-dimethylphenyl)butan-2-ol was determined to be 96:4 by analysis via enatiomeric HPLC separation (210 nm wavelength).

Step 2: Preparation of (2R,3R)-3-(2,4-dimethylphenyl)butan-2-ol

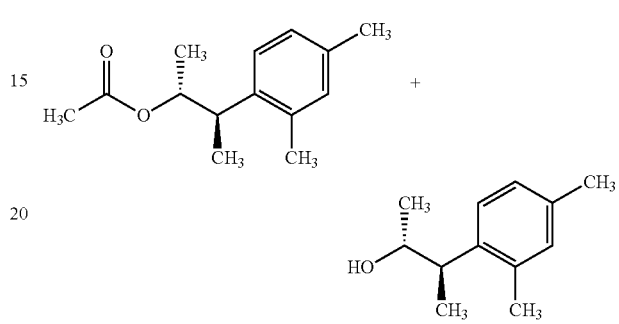

To a solution containing (2R,3R)-3-(2,4-dimethylphenyl)butan-2-yl acetate prepared above (458 mg, 2.08 mmol) dissolved in methanol (4.2 mL) was added potassium carbonate (431 mg, 3.12 mmol). The mixture was stirred at ambient temperature for 1.5 hr, then heated to 50° C. for 2 hr. The reaction was cooled and concentrated under reduced pressure. The residue was diluted with acetone and passed through a small plug of silica gel, washing the pad well with acetone. The solvent was concentrated in vacuo to give (2R,3R)-3-(2,4-dimethylphenyl)butan-2-ol (332 mg, 90%) as a yellow oil: $^1$H NMR (500 MHz, CDCl$_3$) δ 7.06 (d, J=8.5 Hz, 1H), 7.01-6.97 (m, 2H), 3.88 (p, J=6.3 Hz, 1H), 2.97 (p, J=6.9 Hz, 1H), 2.30 (s, 3H), 2.28 (s, 3H), 1.49 (s, 1H), 1.28 (d, J=7.0 Hz, 3H), 1.11 (d, J=6.3 Hz, 3H); $^{13}$C NMR (126 MHz, CDCl$_3$) δ 140.00, 135.49, 135.38, 131.31, 126.82, 126.18, 71.92, 41.43, 21.26, 20.87, 19.85, 16.07; EIMS m/z 178. The enatiomeric ratio of the alcohol was determined to be 7:93 via analysis by enatiomeric HPLC.

Example 3: Preparation of (2S,3S)-3-phenylbutan-2-ol (tert-butoxycarbonyl)-L-alaninate

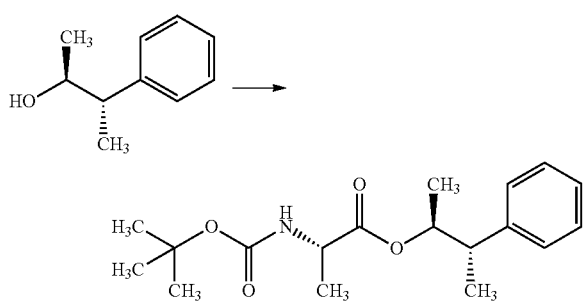

To a solution of (2S,3S)-3-phenylbutan-2-ol (0.23 g, 1.53 mmol) dissolved in methylene chloride (7.7 mL) was added N-ethyl-N-(3-dimethylaminopropyl)carbodiimide hydrochloride (0.59 g, 3.06 mmol) and N,N-dimethylpyridin-4-amine (19 mg, 0.15 mmol). The reaction mixture was purged with nitrogen, stirred over 16 hr, followed by concentration in vacuo. The crude residue was purified via automated flash column chromatography (SiO$_2$, 0-20% ethyl acetate/hexanes gradient) to afford (2S,3S)-3-phenylbutan-2-yl (tert-butoxycarbonyl)-L-alaninate (0.43 g, 1.34 mmol, 83% yield) as colorless oil: $^1$H NMR (400 MHz, CDCl$_3$) δ 7.35-7.25 (m, 2H), 7.27-7.15 (m, 3H), 5.12-5.01 (m, 2H), 4.35-4.26 (m, 1H), 2.95-2.83 (m, 1H), 1.45 (s, 9H), 1.37 (d, J=7.2 Hz, 3H), 1.29 (d, J=7.1 Hz, 3H), 1.09 (d, J=6.3 Hz, 3H); $^{13}$C NMR (126 MHz, CDCl$_3$) δ 172.9, 155.0, 143.0, 128.5, 127.8, 126.7, 79.7, 76.1, 49.5, 45.1, 28.3, 18.9, 18.3, 17.5; IR (thin film) 3355, 2978, 2934, 1711, 1495, 1452, 1366, 1161, 1087, 1065, 701 cm$^{-1}$.

Example 4: Preparation of (2S,3S)-3-phenylbutan-2-yl (3-hydroxy-4-methoxypicolinoyl)-L-alaninate Step 1: Preparation of (2S,3S)-3-phenylbutan-2-yl-L-alaninate·hydrochloride

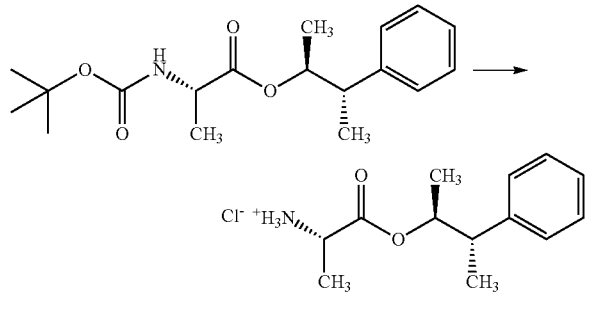

To neat (2S,3S)-3-phenylbutan-2-ol (tert-butoxycarbonyl)-L-alaninate (0.42 g, 1.31 mmol) was added dropwise a solution of HCl dissolved in dioxane (4 M, 3.3 mL, 13.07 mmol) under nitrogen. Upon stirring for 16 hr, the reaction mixture was concentrated in vacuo to afford crude (2S,3S)-3-phenylbutan-2-yl-L-alaninate·hydrogen chloride as white solid, which was directly carried to the next step: HRMS-ESI (m/z) [M+H]+ calc'd for C$_{13}$H$_{20}$NO$_2$, 222.1489; found, 222.1485.

Step 2: Preparation of (2S,3S)-3-phenylbutan-2-yl (3-hydroxy-4-methoxypicolinoyl)-L-alaninate

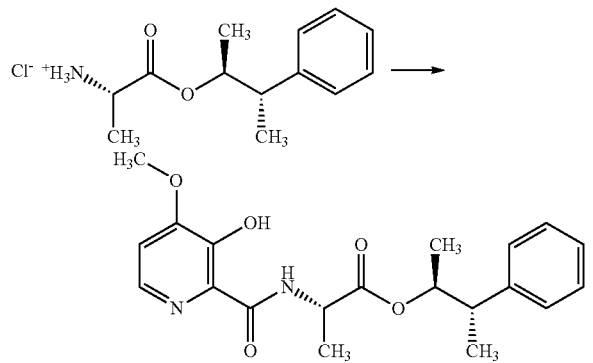

To a solution of (2S,3S)-3-phenylbutan-2-yl-L-alaninate·hydrogen chloride, 3-hydroxy-4-methoxypicolinic acid (0.24 g, 1.44 mmol), and (benzotriazol-1-yloxy)tripyrrolidinophosphonium hexafluorophosphate (0.75 g, 1.44 mmol) dissolved in methylene chloride (6.5 mL) was added dropwise N,N-diisopropylethylamine (0.75 mL, 4.31 mmol) under nitrogen. Upon stirring for 16 hr, the reaction mixture was concentrated in vacuo. The crude residue was purified via automated flash column chromatography (SiO$_2$, 0-45% acetone/hexanes gradient) to afford (2S,3S)-3-phenylbutan-2-yl (3-hydroxy-4-methoxypicolinoyl)-L-alaninate (0.46 g, 1.173 mmol, 90% yield) as colorless oil: $^1$H NMR (500 MHz, CDCl$_3$) δ 12.16 (s, 1H), 8.50 (d, J=8.0 Hz, 1H), 8.01 (d, J=5.2 Hz, 1H), 7.32-7.27 (m, 2H), 7.24-7.16 (m, 3H), 6.88 (d, J=5.2 Hz, 1H), 5.11 (dq, J=7.7, 6.3 Hz, 1H), 4.77-4.67 (m, 1H), 3.95 (s, 3H), 2.97-2.87 (m, 1H), 1.54 (d, J=7.2 Hz, 3H), 1.31 (d, J=7.0 Hz, 3H), 1.13 (d, J=6.3 Hz, 3H); IR (thin film) 2978, 2937, 1733, 1647, 1527, 1451, 1262, 1147, 701 cm$^{-1}$; HRMS-ESI (m/z) [M+H]+ calc'd for C$_{20}$H$_{25}$N$_2$O$_5$, 373.1758; found, 373.1752.

Example 5A: Preparation of (2S,3S)-3-phenylbutan-2-yl (3-acetoxy-4-methoxypicolinoyl)-L-alaninate

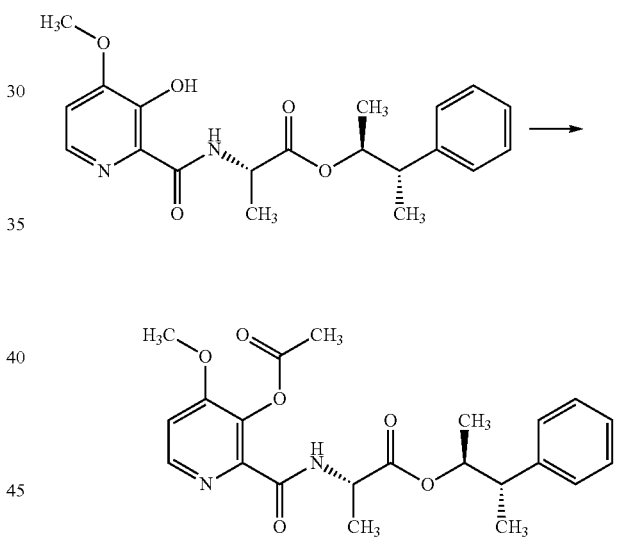

To a solution containing (2S,3S)-3-phenylbutan-2-yl (3-hydroxy-4-methoxypicolinoyl)-L-alaninate (84 mg, 0.23 mmol) dissolved in pyridine (1.0 mL) was added dropwise acetic anhydride (0.25 mL, 2.65 mmol) under nitrogen. Upon stirring for 30 min, the reaction mixture was concentrated in vacuo, followed by azeotroping with toluene (10 mL). The crude residue was purified via automated flash column chromatography (SiO$_2$, 0-40% acetone/hexanes gradient) to afford (2S,3S)-3-phenylbutan-2-yl (3-acetoxy-4-methoxypicolinoyl)-L-alaninate (90 mg, 0.21 mmol, 91% yield) as colorless oil: $^1$H NMR (500 MHz, CDCl$_3$) δ 8.56 (s, 1H), 8.34 (d, J=5.5 Hz, 1H), 7.32-7.27 (m, 2H), 7.24-7.16 (m, 3H), 7.01 (d, J=5.5 Hz, 1H), 5.09 (dq, J=7.7, 6.3 Hz, 1H), 4.77-4.67 (m, 1H), 3.91 (s, 3H), 2.96-2.86 (m, 1H), 2.41 (s, 3H), 1.49 (d, J=7.2 Hz, 3H), 1.30 (d, J=7.0 Hz, 3H), 1.10 (d, J=6.3 Hz, 3H); IR (thin film) 3377, 2980, 2938, 1770, 1732, 1674, 1507, 1310, 1198, 1174, 702 cm$^{-1}$; HRMS-ESI (m/z) [M+H]+ calc'd for C$_{22}$H$_{27}$N$_2$O$_6$, 415.1864; found, 415.1859.

Example 5B: Preparation of (2S,3R)-3-(o-tolyl)butan-2-yl (3-(acetoxymethoxy)-4-methoxypicolinoyl)-L-alaninate

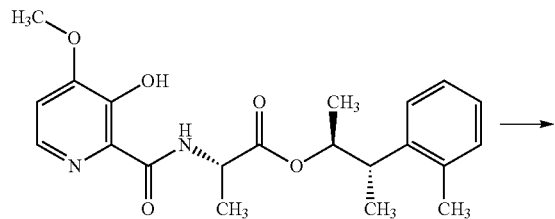

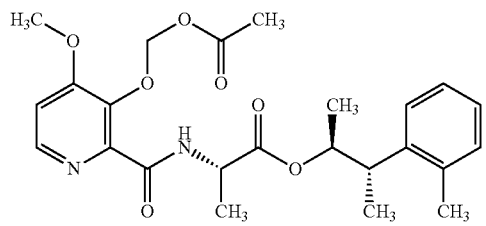

To a solution containing (2S,3R)-3-(o-tolyl)butan-2-yl (3-hydroxy-4-methoxypicolinoyl)-L-alaninate dissolved in 0.7 mL of acetone was added potassium carbonate (39 mg, 0.279 mmol) followed by bromomethyl acetate (27 μL, 0.279 mmol). The solution was heated at 50° C. for 1.5 hr. The reaction mixture was cooled and concentrated in vacuo. The crude residue was purified via automated flash column chromatography (SiO$_2$, 0-80% acetone/hexanes gradient) to afford (2S,3R)-3-(o-tolyl)butan-2-yl (3-(acetoxymethoxy)-4-methoxypicolinoyl)-L-alaninate (63 mg, 93% yield) as a thick oil: $^1$H NMR (500 MHz, CDCl$_3$) δ 8.26 (d, J=5.4 Hz, 1H), 8.22 (t, J=7.4 Hz, 1H), 7.22-7.03 (m, 4H), 6.93 (d, J=5.4 Hz, 1H), 5.73 (dd, J=5.6, 1.8 Hz, 2H), 5.16 (dq, J=8.1, 6.3 Hz, 1H), 4.58-4.51 (m, 1H), 3.90 (s, 3H), 3.31-3.22 (m, 1H), 2.37 (s, 3H), 2.06 (s, 3H), 1.31 (d, J=6.2 Hz, 3H), 1.24 (d, J=7.0 Hz, 3H), 1.03 (d, J=7.2 Hz, 3H); $^{13}$C NMR (126 MHz, CDCl$_3$) δ 172.26, 170.26, 162.87, 160.25, 145.68, 143.94, 142.57, 141.57, 136.03, 130.21, 126.16, 125.94, 109.49, 89.57, 75.57, 56.16, 48.08, 39.48, 20.87, 19.84, 17.92, 17.77, 17.05; HRMS-ESI (m/z) [M+H]$^+$ calc'd for C$_{24}$H$_{30}$N$_2$O$_7$, 459.2126; found, 459.2121.

Example 5C: Preparation of 4-methoxy-2-(((S)-1-oxo-1-(((2S,3S)-3-(2-(trifluoromethyl)phenyl)butan-2-yl)oxy)propan-2-yl)carbamoyl)pyridin-3-yl isobutyrate

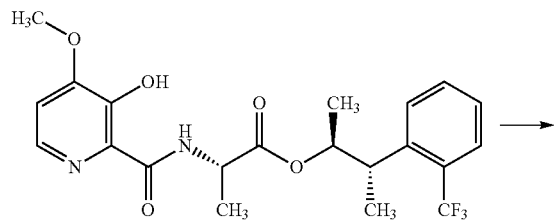

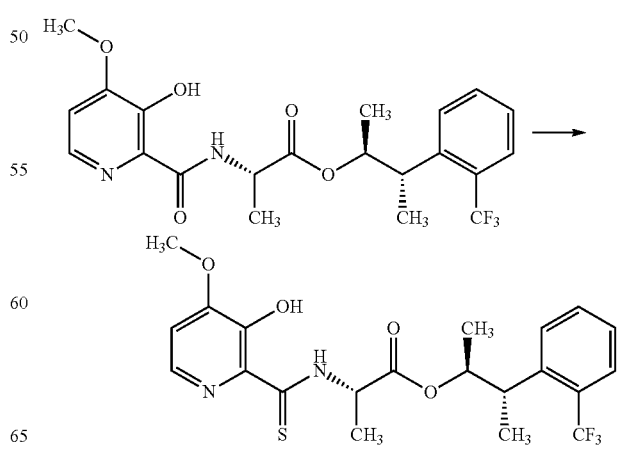

To a solution containing (2S,3S)-3-(2-(trifluoromethyl)phenyl)butan-2-yl (3-hydroxy-4-methoxypicolinoyl)-L-alaninate (283.9 mg, 0.645 mmol) and N,N-dimethylpyridin-4-amine (15.75 mg, 0.129 mmol) was prepared in CH$_2$Cl$_2$ (2 mL). To this solution was added triethylamine (0.180 mL, 1.289 mmol) followed by isobutyryl chloride (0.102 mL, 0.967 mmol). The resultant clear reaction was stirred at ambient temperature overnight. The reaction was concentrated under reduced pressure to afford an orange oil under a stream of N$_2$. The crude residue was purified via automated flash column chromatography (SiO$_2$, 0-100% ethyl acetate/hexanes gradient) to afford 4-methoxy-2-(((S)-1-oxo-1-(((2S,3S)-3-(2-(trifluoromethyl)phenyl)butan-2-yl)oxy)propan-2-yl)carbamoyl)pyridin-3-yl isobutyrate (252.3 mg, 0.494 mmol, 77% yield) as a yellow oil: $^1$H NMR (400 MHz, CDCl$_3$) δ 8.50 (d, J=7.4 Hz, 1H), 8.34 (d, J=5.4 Hz, 1H), 7.64 (dd, J=8.0, 1.3 Hz, 1H), 7.54-7.47 (m, 1H), 7.44 (d, J=7.8 Hz, 1H), 7.31 (t, J=7.5 Hz, 1H), 6.99 (d, J=5.4 Hz, 1H), 5.26-5.11 (m, 1H), 4.76 (p, J=7.3 Hz, 1H), 3.89 (s, 3H), 3.34 (p, J=6.6 Hz, 1H), 2.96 (hept, J=7.0 Hz, 1H), 1.54 (d, J=7.2 Hz, 3H), 1.36 (dd, J=7.0, 1.3 Hz, 6H), 1.28 (d, J=6.8 Hz, 3H), 1.10 (d, J=6.3 Hz, 3H); $^{19}$F NMR (376 MHz, CDCl$_3$) δ -58.25; IR (thin film) 3383, 2981, 1737, 1679, 1505, 1310, 1114, 1045, 732 cm$^{-1}$; HRMS-ESI (m/z) [M+H]$^+$ calc'd for C$_{25}$H$_{30}$F$_3$N$_2$O$_6$, 511.2050; found, 511.2048.

Example 6: Preparation of (2S,3S)-3-(2,4-dimethylphenyl)butan-2-yl (3-acetoxy-4-methoxypyridine-2-carbonothioyl)-L-alaninate Step 1: Preparation of (2S,3S)-3-(2-(trifluoromethyl)phenyl)butan-2-yl (3-hydroxy-4-methoxypyridine-2-carbonothioyl)-L-alaninate To a solution containing (2S,3S)-3-(2-(trifluoromethyl)phenyl)butan-2-yl (3-hydroxy-4-methoxypicolinoyl)-L-alaninate (120.1 mg, 0.273 mmol) dissolved in acetonitrile (2.73 mL) was added phosphorus pentasulfide (121 mg, 0.545 mmol) followed by 1,1,1,3,3,3-hexamethyldisiloxane (291 μL, 1.363 mmol) added in one portion. The reaction was heated to 45° C. for 30 min. The reaction was cooled, diluted with CH$_2$Cl$_2$ (10 mL) and quenched by the addition of saturated aqueous NaHCO$_3$ (10 mL). The layers were separated and the aqueous layer was extracted with CH$_2$Cl$_2$ (3×10 mL). The combined organic layers were passed through a phase separator and concentrated to a yellow oil. The crude material was purified via automated flash column chromatography (SiO$_2$, 0-50% acetone/hexanes gradient) to afford (2S,3S)-3-(2-(trifluoromethyl)phenyl)butan-2-yl (3-hydroxy-4-methoxypyridine-2-carbonothioyl)-L-alaninate (104.7 mg, 0.229 mmol, 84% yield) as a yellow semisolid; $^1$H NMR (400 MHz, CDCl$_3$) δ 12.93 (s, 1H), 10.74 (d, J=7.6 Hz, 1H), 8.00 (d, J=5.1 Hz, 1H), 7.73-7.59 (m, 1H), 7.51 (t, J=7.7 Hz, 1H), 7.43 (d, J=7.8 Hz, 1H), 7.33 (t, J=7.5 Hz, 1H), 6.89 (d, J=5.1 Hz, 1H), 5.30-5.18 (m, 1H), 5.14 (p, J=7.2 Hz, 1H), 3.96 (s, 3H), 3.37 (p, J=6.8 Hz, 1H), 1.69 (dd, J=7.2, 3.2 Hz, 3H), 1.30 (d, J=6.8 Hz, 3H), 1.14 (d, J=6.3 Hz, 3H); $^{19}$F NMR (376 MHz, CDCl$_3$) δ −58.23; IR (thin film) 3087, 2984, 1737, 1513, 1484, 1311, 1151, 1118, 800, 771 cm$^{-1}$; HRMS-ESI (m/z) [M+H]$^+$ calc'd for C$_{21}$H$_{24}$F$_3$N$_2$O$_4$S, 457.1403; found, 457.1399.

Step 2: Preparation of (2S,3S)-3-(2-(trifluoromethyl)phenyl)butan-2-yl (3-acetoxy-4-methoxypyridine-2-carbonothioyl)-L-alaninate

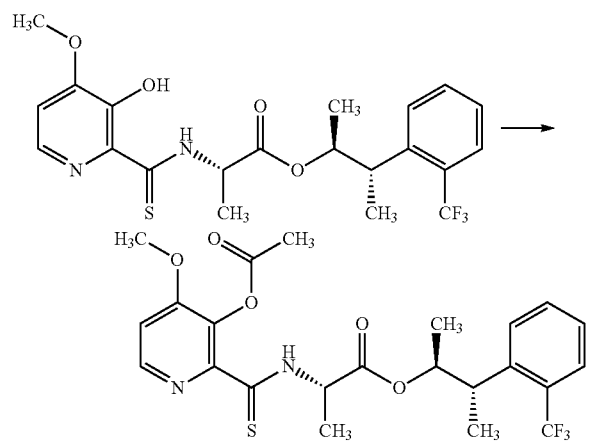

To a solution containing (2S,3S)-3-(2-(trifluoromethyl)phenyl)butan-2-yl (3-hydroxy-4-methoxypyridine-2-carbonothioyl)-L-alaninate (53.9 mg, 0.118 mmol) and N,N-dimethylpyridin-4-amine (2.89 mg, 0.024 mmol) dissolved in CH$_2$Cl$_2$ (2 mL) was added triethylamine (0.041 mL, 0.295 mmol) followed by acetyl chloride (9.23 μL, 0.130 mmol). The resultant light orange reaction was stirred at ambient temperature for 18 hr. The reaction was concentrated under reduced pressure to afford an orange oil under a stream of N$_2$. The crude residue was purified via automated flash column chromatography (SiO$_2$, 0-50% acetone/hexanes gradient) to afford (2S,3S)-3-(2-(trifluoromethyl)phenyl)butan-2-yl (3-acetoxy-4-methoxypyridine-2-carbonothioyl)-L-alaninate (51.7 mg, 0.104 mmol, 88% yield) as a yellow oil: $^1$H NMR (400 MHz, CDCl$_3$) δ 9.96 (d, J=7.3 Hz, 1H), 8.34 (d, J=5.5 Hz, 1H), 7.71-7.59 (m, 1H), 7.59-7.47 (m, 1H), 7.44 (d, J=7.8 Hz, 1H), 7.39-7.28 (m, 1H), 7.00 (d, J=5.5 Hz, 1H), 5.28-5.15 (m, 2H), 3.91 (s, 3H), 3.42-3.29 (m, 1H), 2.37 (s, 3H), 1.64 (d, J=7.2 Hz, 3H), 1.30 (d, J=6.8 Hz, 3H), 1.12 (d, J=6.3 Hz, 3H); $^{19}$F NMR (376 MHz, CDCl$_3$) δ −58.23; HRMS-ESI (m/z) [M+H]$^+$ calc'd for C$_{23}$H$_{26}$F$_3$N$_2$O$_5$S, 499.1509; found, 499.1508.

Example 7: Preparation of 3-hydroxy-4-methoxy-2-(((S)-1-oxo-1-(((2S,3S)-3-phenylbutan-2-yl)oxy)propan-2-yl)carbamoyl)pyridine 1-oxide

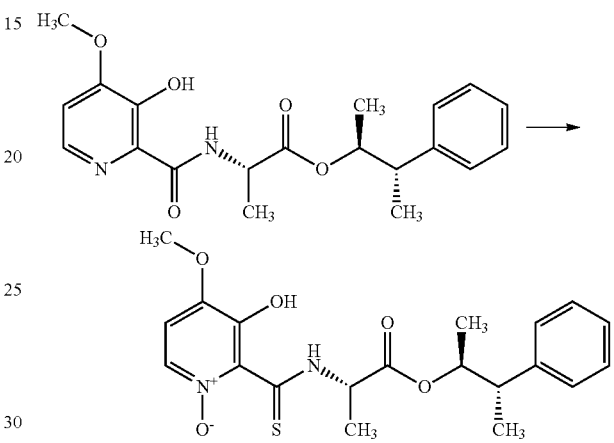

To a solution containing (2S,3S)-3-phenylbutan-2-yl (3-hydroxy-4-methoxypicolinoyl)-L-alaninate (54 mg, 0.15 mmol) dissolved in methylene chloride (1.0 mL) was added m-CPBA (50 mg, 0.29 mmol). Upon stirring for 30 min at room temperature, the reaction mixture was concentrated in vacuo. The crude residue was purified via automated flash column chromatography (SiO$_2$, 0-50% acetone/hexanes gradient) to afford 3-hydroxy-4-methoxy-2-(((S)-1-oxo-1-(((2S,3S)-3-phenylbutan-2-yl)oxy)propan-2-yl)carbamoyl)pyridine 1-oxide (51 mg, 0.13 mmol, 86% yield) as viscous, pale yellow oil: $^1$H NMR (500 MHz, CDCl$_3$) δ 14.39 (s, 1H), 12.82 (d, J=6.9 Hz, 1H), 7.89 (d, J=7.2 Hz, 1H), 7.32-7.25 (m, 2H), 7.25-7.15 (m, 3H), 6.78 (d, J=7.2 Hz, 1H), 5.10 (dq, J=8.1, 6.3 Hz, 1H), 4.75-4.64 (m, 1H), 3.97 (s, 3H), 2.96-2.86 (m, 1H), 1.56 (d, J=7.2 Hz, 3H), 1.30 (d, J=6.9 Hz, 3H), 1.12 (d, J=6.2 Hz, 3H); IR (thin film) 2978, 2937, 1735, 1643, 1569, 1479, 1452, 1211, 1154, 729, 702 cm$^{-1}$; HRMS-ESI (m/z) [M+H]+ calc'd for C$_{20}$H$_{25}$N$_2$O$_6$, 389.1707; found, 389.1703.

Example 8: Preparation of (2S,3S)-3-phenylbutan-2-yl (S)-2-(8-methoxy-2,4-dioxo-2H-pyrido[2,3-e][1,3]oxazin-3(4H)-yl)propanoate

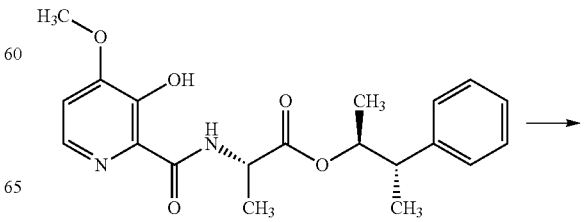

-continued

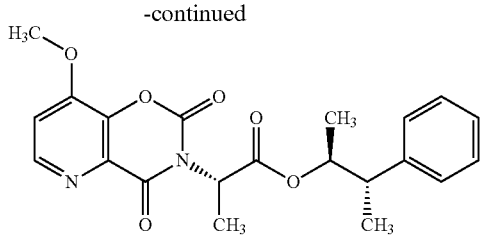

To a solution containing (2S,3S)-3-phenylbutan-2-yl (3-hydroxy-4-methoxypicolinoyl)-L-alaninate (54 mg, 0.15 mmol) and triphosgene (86 mg, 0.29 mmol) dissolved in methylene chloride (1.0 mL) was added pyridine (0.1 mL, 1.24 mmol). Upon stirring for 45 min, the reaction mixture was quenched with saturated sodium bicarbonate solution (5 mL) and extracted with methylene chloride (3×5 mL). The organics were passed through a phase separator and concentrated in vacuo. The crude residue was purified via automated flash column chromatography ($SiO_2$, 0-40% acetone/hexanes gradient) to afford (2S,3S)-3-phenylbutan-2-yl (S)-2-(8-methoxy-2,4-dioxo-2H-pyrido[2,3-e][1,3]oxazin-3(4H)-yl)propanoate (41 mg, 0.10 mmol, 67% yield) as an off-white foam: $^1$H NMR (500 MHz, $CDCl_3$) δ 8.61 (d, J=5.3 Hz, 1H), 7.24-7.17 (m, 2H), 7.17-7.06 (m, 4H), 5.61 (q, J=7.1 Hz, 1H), 5.16-5.06 (m, 1H), 4.06 (s, 3H), 2.93-2.83 (m, 1H), 1.70 (d, J=7.1 Hz, 3H), 1.27 (d, J=7.1 Hz, 3H), 1.04 (d, J=6.3 Hz, 3H); IR (thin film) 2978, 2942, 1769, 1712, 1602, 1501, 1371, 1242, 1081, 702 $cm^1$; HRMS-ESI (m/z) [M+H]+ calc'd for $C_{21}H_{23}N_2O_6$, 399.1551; found, 399.1549.

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the $1^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Synonym: *Puccinia recondita* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two week old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example D: Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example E: Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example F: Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

Example G: Evaluation of Fungicidal Activity: Wheat Glume Blotch (*Parastagonospora nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Parastagonospora nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example H: Evaluation of Fungicidal Activity: Cucumber Downy Mildew (*Pseudoperonospora cubensis*; Bayer Code PSPECU)

Cucumber seedlings (variety Bush Pickle) were grown in soil-less Metro mix, with one plant per pot, and used in the test when 12 to 14 days old. Plants were inoculated with a spore suspension 24 hr following fungicide treatments. Test plants were inoculated with an aqueous spore suspension of *Pseudoperonospora cubensis* 24 hr after fungicide treatments. After inoculation the plants were kept in a dew room at 22° C. with 100% relative humidity for 24 hr to permit spores to germinate and infect the leaf. The plants were then transferred to a greenhouse set at 20° C. until disease was fully expressed. Fungicide formulation, application and disease assessment on the sprayed leaves followed the procedures as described in the Example A.

Example I: Evaluation of Fungicidal Activity: Rice Blast (*Magnaporthe grisea; Anamorph: Pyricularia oryzae*; Bayer Code PYRIOR)

Rice seedlings (variety *Japonica*) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation, the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example J: Evaluation of Fungicidal Activity: Barley Scald (*Rhyncosporium secalis*, Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example K: Evaluation of Fungicidal Activity: Grape Powdery Mildew (*Uncinula necator*; Bayer Code UNCINE)

Grape seedlings (variety Carignane) were grown in soil-less Metro mix, with one plant per pot, and used in the test when approximately 1 month old. Plants were inoculated 24 hr after fungicide treatment by shaking spores from infected leaves over test plants. Plants were maintained in a greenhouse set at 20° C. until disease was fully developed. Fungicide formulation, application and disease assessment on sprayed leaves followed the procedures as described in the Example A.

TABLE 1

Compound Structure, Appearance, and Preparation Method

| Cmpd. No. | Structure | As Prepared According To | Appearance |
|---|---|---|---|
| 1 | 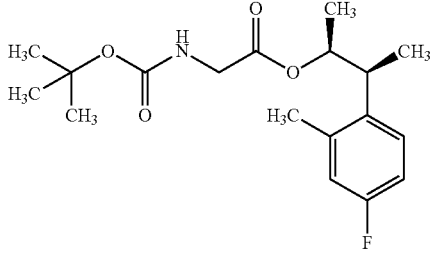 [SMILES: Cc1cc(F)ccc1[C@H](C)[C@H](C)OC(=O)CNC(=O)OC(C)(C)C] | Example 1A<br>Example 2<br>Example 3 | Oil |

TABLE 1-continued

Compound Structure, Appearance, and Preparation Method

| Cmpd. No. | Structure | As Prepared According To | Appearance |
|---|---|---|---|
| 2 | 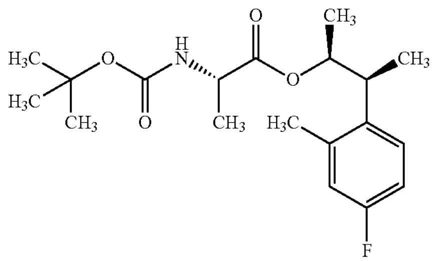 [SMILES: Cc1cc(F)ccc1[C@H](C)[C@H](C)OC(=O)[C@H](C)NC(=O)OC(C)(C)C] | Example 1A Example 2 Example 3 | Oil |
| 3 | 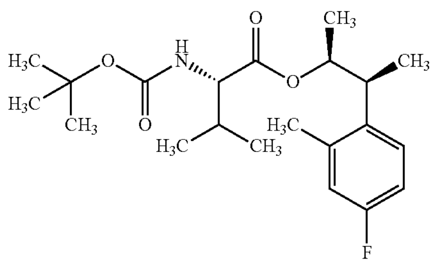 [SMILES: Cc1cc(F)ccc1[C@H](C)[C@H](C)OC(=O)[C@@H](NC(=O)OC(C)(C)C)C(C)C] | Example 1A Example 2 Example 3 | Oil |
| 4 | 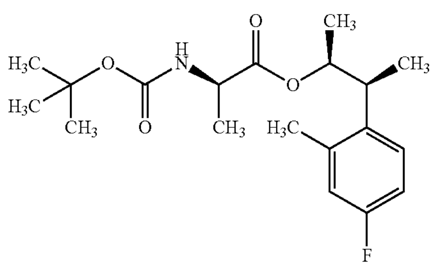 [SMILES: Cc1cc(F)ccc1[C@H](C)[C@H](C)OC(=O)[C@@H](C)NC(=O)OC(C)(C)C] | Example 1A Example 2 Example 3 | Oil |
| 5 | 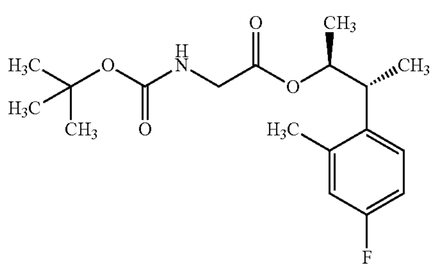 [SMILES: Cc1cc(F)ccc1[C@@H](C)[C@H](C)OC(=O)CNC(=O)OC(C)(C)C] | Example 1A Example 2 Example 3 | Oil |
| 6 | 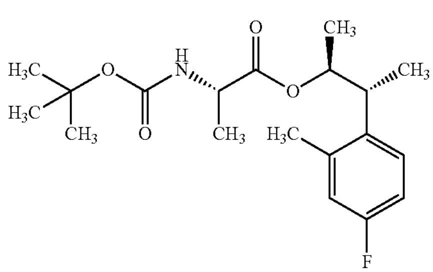 [SMILES: Cc1cc(F)ccc1[C@@H](C)[C@H](C)OC(=O)[C@H](C)NC(=O)OC(C)(C)C] | Example 1A Example 2 Example 3 | Oil |

TABLE 1-continued

Compound Structure, Appearance, and Preparation Method

| Cmpd. No. | Structure | As Prepared According To | Appearance |
|---|---|---|---|
| 7 | 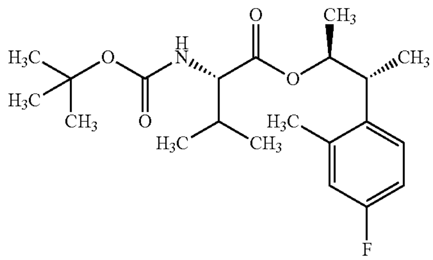 [SMILES: Cc1cc(F)ccc1[C@@H](C)[C@H](C)OC(=O)[C@@H](NC(=O)OC(C)(C)C)C(C)C] | Example 1A Example 2 Example 3 | Oil |
| 8 | 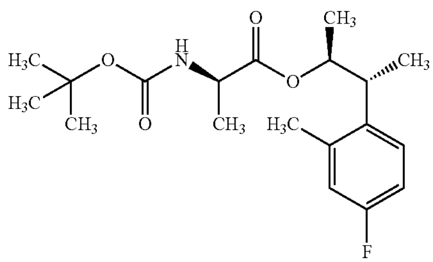 [SMILES: Cc1cc(F)ccc1[C@@H](C)[C@H](C)OC(=O)[C@@H](C)NC(=O)OC(C)(C)C] | Example 1A Example 2 Example 3 | Oil |
| 9 | 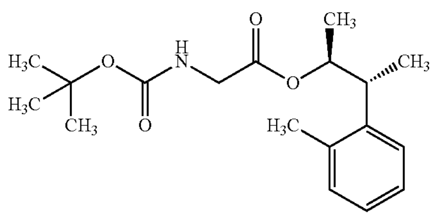 [SMILES: Cc1ccccc1[C@@H](C)[C@H](C)OC(=O)CNC(=O)OC(C)(C)C] | Example 1B Example 2 Example 3 | Oil |
| 10 | 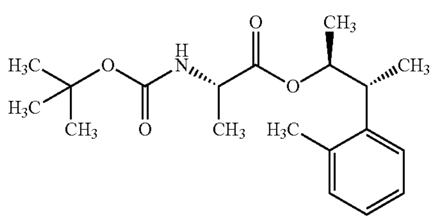 [SMILES: Cc1ccccc1[C@@H](C)[C@H](C)OC(=O)[C@H](C)NC(=O)OC(C)(C)C] | Example 1B Example 2 Example 3 | Oil |
| 11 | 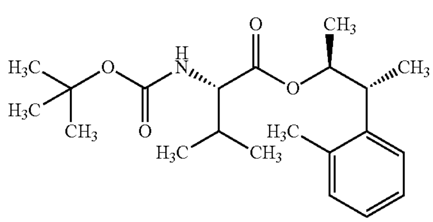 [SMILES: Cc1ccccc1[C@@H](C)[C@H](C)OC(=O)[C@@H](NC(=O)OC(C)(C)C)C(C)C] | Example 1B Example 2 Example 3 | Oil |
| 12 | 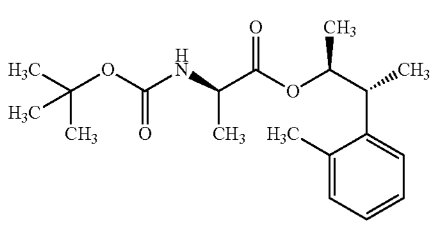 [SMILES: Cc1ccccc1[C@@H](C)[C@H](C)OC(=O)[C@@H](C)NC(=O)OC(C)(C)C] | Example 1B Example 2 Example 3 | Oil |

TABLE 1-continued
Compound Structure, Appearance, and Preparation Method
| Cmpd. No. | Structure | As Prepared According To | Appearance |
|---|---|---|---|
| 13 | 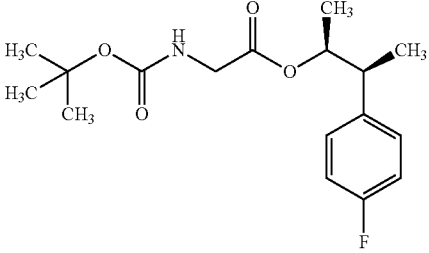 [SMILES: C[C@H](OC(=O)CNC(=O)OC(C)(C)C)[C@@H](C)c1ccc(F)cc1] | Example 1B<br>Example 2<br>Example 3 | Oil |
| 14 | 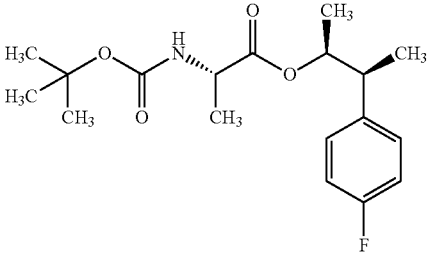 [SMILES: C[C@H](NC(=O)OC(C)(C)C)C(=O)O[C@@H](C)[C@@H](C)c1ccc(F)cc1] | Example 1B<br>Example 2<br>Example 3 | Oil |
| 15 | 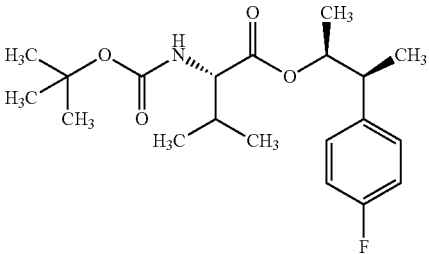 [SMILES: CC(C)[C@H](NC(=O)OC(C)(C)C)C(=O)O[C@@H](C)[C@@H](C)c1ccc(F)cc1] | Example 1B<br>Example 2<br>Example 3 | Oil |
| 16 | 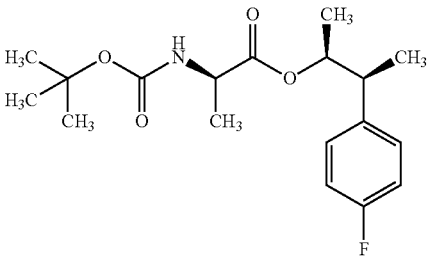 [SMILES: C[C@H](OC(=O)[C@@H](C)NC(=O)OC(C)(C)C)[C@@H](C)c1ccc(F)cc1] | Example 1B<br>Example 2<br>Example 3 | Oil |
| 17 | 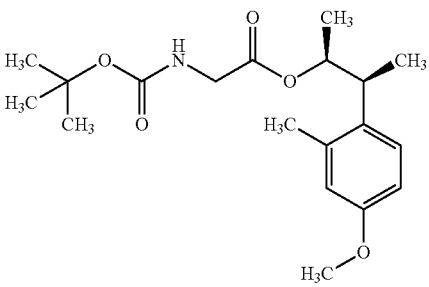 [SMILES: COc1ccc([C@H](C)[C@H](C)OC(=O)CNC(=O)OC(C)(C)C)c(C)c1] | Example 1B<br>Example 2<br>Example 3 | Oil |

TABLE 1-continued

Compound Structure, Appearance, and Preparation Method

| Cmpd. No. | Structure | As Prepared According To | Appearance |
|---|---|---|---|
| 18 | 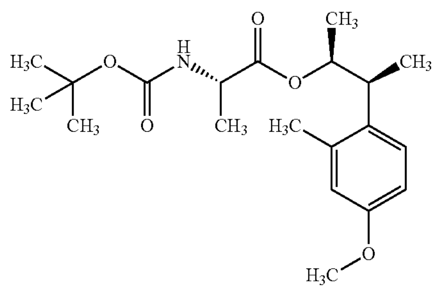 [SMILES: COc1ccc([C@H](C)[C@H](C)OC(=O)[C@H](C)NC(=O)OC(C)(C)C)c(C)c1] | Example 1B Example 2 Example 3 | Oil |
| 19 | 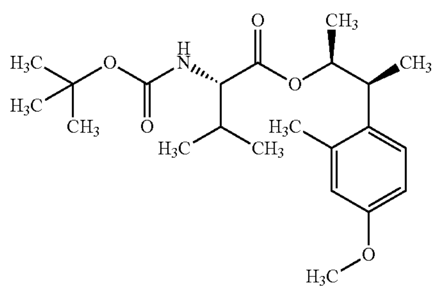 [SMILES: COc1ccc([C@H](C)[C@H](C)OC(=O)[C@@H](NC(=O)OC(C)(C)C)C(C)C)c(C)c1] | Example 1B Example 2 Example 3 | Oil |
| 20 | 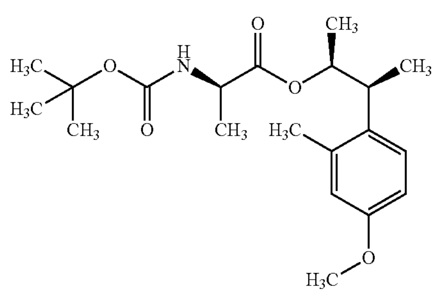 [SMILES: COc1ccc([C@H](C)[C@H](C)OC(=O)[C@@H](C)NC(=O)OC(C)(C)C)c(C)c1] | Example 1B Example 2 Example 3 | Oil |
| 21 | 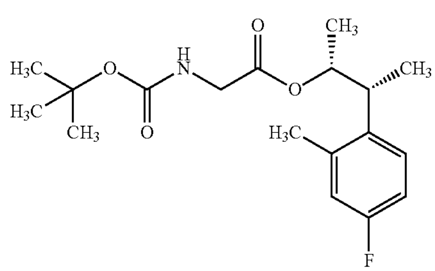 [SMILES: Cc1cc(F)ccc1[C@@H](C)[C@@H](C)OC(=O)CNC(=O)OC(C)(C)C] | Example 1A Example 2 Example 3 | Oil |
| 22 | 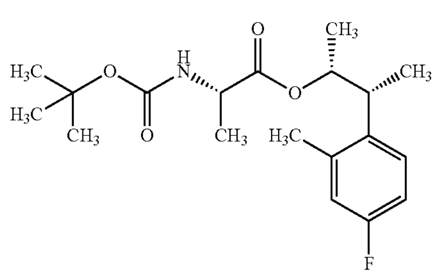 [SMILES: Cc1cc(F)ccc1[C@@H](C)[C@@H](C)OC(=O)[C@H](C)NC(=O)OC(C)(C)C] | Example 1B Example 2 Example 3 | Oil |

TABLE 1-continued

Compound Structure, Appearance, and Preparation Method

| Cmpd. No. | Structure | As Prepared According To | Appearance |
|---|---|---|---|
| 23 | 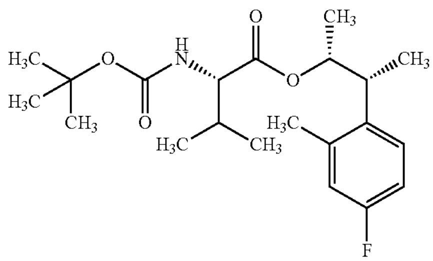 [SMILES: Cc1cc(F)ccc1[C@@H](C)[C@@H](C)OC(=O)[C@@H](NC(=O)OC(C)(C)C)C(C)C] | Example 1A Example 2 Example 3 | Oil |
| 24 | 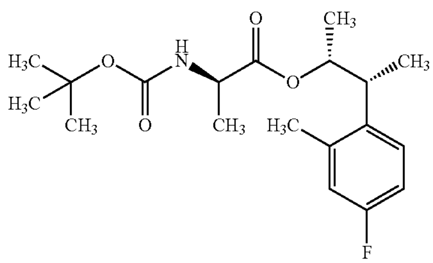 [SMILES: Cc1cc(F)ccc1[C@@H](C)[C@@H](C)OC(=O)[C@@H](C)NC(=O)OC(C)(C)C] | Example 1A Example 2 Example 3 | Oil |
| 25 | 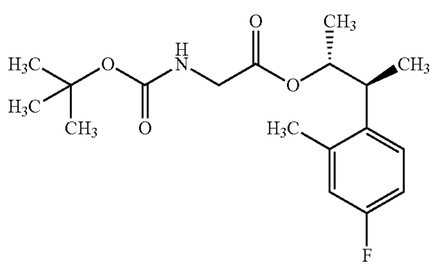 [SMILES: Cc1cc(F)ccc1[C@H](C)[C@@H](C)OC(=O)CNC(=O)OC(C)(C)C] | Example 1A Example 2 Example 3 | Oil |
| 26 | 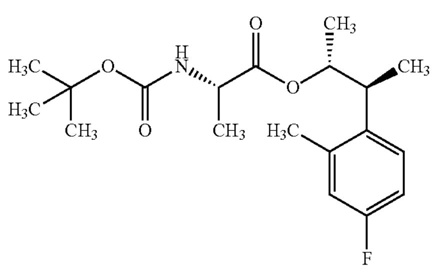 [SMILES: Cc1cc(F)ccc1[C@H](C)[C@@H](C)OC(=O)[C@H](C)NC(=O)OC(C)(C)C] | Example 1A Example 2 Example 3 | Oil |
| 27 | 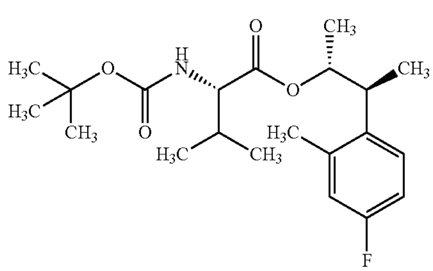 [SMILES: Cc1cc(F)ccc1[C@H](C)[C@@H](C)OC(=O)[C@@H](NC(=O)OC(C)(C)C)C(C)C] | Example 1A Example 2 Example 3 | Oil |

TABLE 1-continued

Compound Structure, Appearance, and Preparation Method

| Cmpd. No. | Structure | As Prepared According To | Appearance |
| --- | --- | --- | --- |
| 28 | 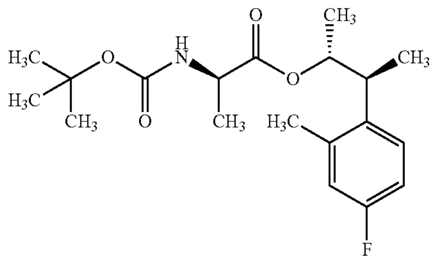 [SMILES: Cc1cc(F)ccc1[C@H](C)[C@@H](C)OC(=O)[C@@H](C)NC(=O)OC(C)(C)C] | Example 1A Example 2 Example 3 | Oil |
| 29 | 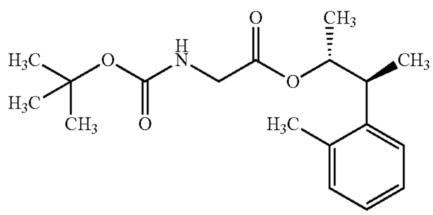 [SMILES: Cc1ccccc1[C@H](C)[C@@H](C)OC(=O)CNC(=O)OC(C)(C)C] | Example 1B Example 2 Example 3 | Oil |
| 30 | 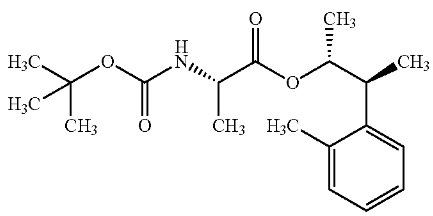 [SMILES: Cc1ccccc1[C@H](C)[C@@H](C)OC(=O)[C@H](C)NC(=O)OC(C)(C)C] | Example 1B Example 2 Example 3 | Oil |
| 31 | 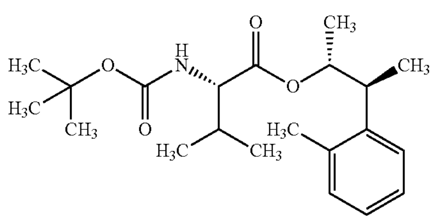 [SMILES: Cc1ccccc1[C@H](C)[C@@H](C)OC(=O)[C@@H](NC(=O)OC(C)(C)C)C(C)C] | Example 1B Example 2 Example 3 | Oil |
| 32 | 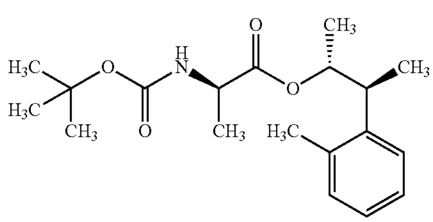 [SMILES: Cc1ccccc1[C@H](C)[C@@H](C)OC(=O)[C@@H](C)NC(=O)OC(C)(C)C] | Example 1B Example 2 Example 3 | Oil |
| 33 | 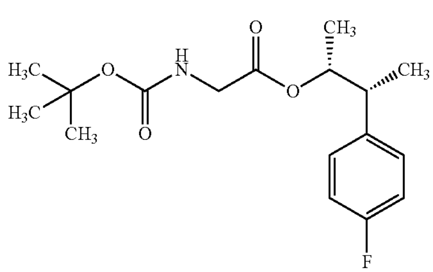 [SMILES: C[C@H](c1ccc(F)cc1)[C@@H](C)OC(=O)CNC(=O)OC(C)(C)C] | Example 1B Example 2 Example 3 | Oil |

TABLE 1-continued

Compound Structure, Appearance, and Preparation Method

| Cmpd. No. | Structure | As Prepared According To | Appearance |
|---|---|---|---|
| 34 | 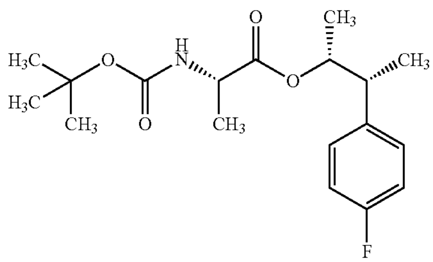 [SMILES: C[C@H](NC(=O)OC(C)(C)C)C(=O)O[C@H](C)[C@H](C)c1ccc(F)cc1] | Example 1B<br>Example 2<br>Example 3 | Oil |
| 35 | 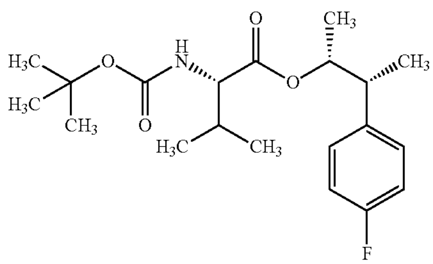 [SMILES: CC(C)[C@H](NC(=O)OC(C)(C)C)C(=O)O[C@H](C)[C@H](C)c1ccc(F)cc1] | Example 1B<br>Example 2<br>Example 3 | Oil |
| 36 | 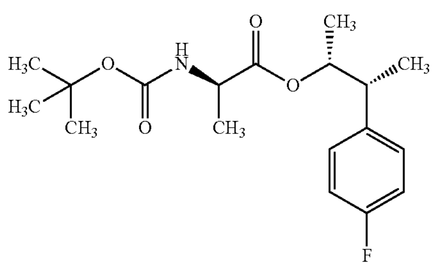 [SMILES: C[C@H](c1ccc(F)cc1)[C@@H](C)OC(=O)[C@@H](C)NC(=O)OC(C)(C)C] | Example 1B<br>Example 2<br>Example 3 | Oil |
| 37 | 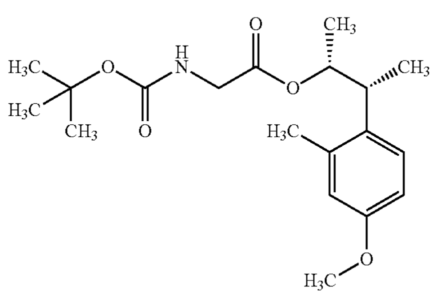 [SMILES: COc1ccc([C@@H](C)[C@@H](C)OC(=O)CNC(=O)OC(C)(C)C)c(C)c1] | Example 1B<br>Example 2<br>Example 3 | Oil |
| 38 | 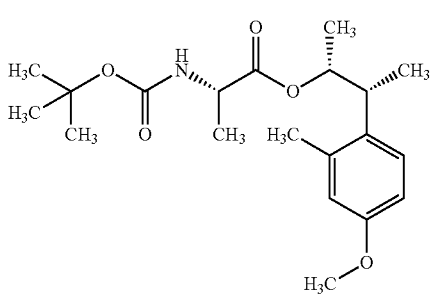 [SMILES: COc1ccc([C@@H](C)[C@@H](C)OC(=O)[C@H](C)NC(=O)OC(C)(C)C)c(C)c1] | Example 1B<br>Example 2<br>Example 3 | Oil |

TABLE 1-continued

Compound Structure, Appearance, and Preparation Method

| Cmpd. No. | Structure | As Prepared According To | Appearance |
|---|---|---|---|
| 39 | 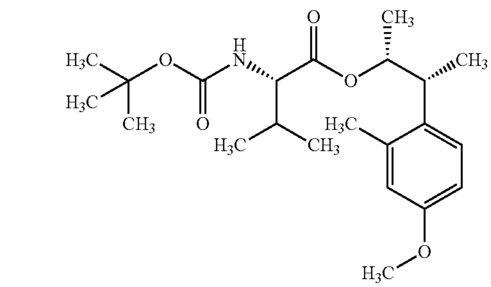 [SMILES: COc1ccc([C@@H](C)[C@@H](C)OC(=O)[C@@H](NC(=O)OC(C)(C)C)C(C)C)c(C)c1] | Example 1B Example 2 Example 3 | Oil |
| 40 | 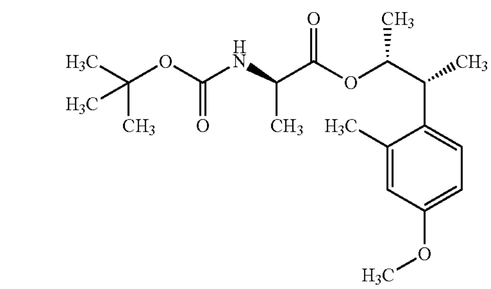 [SMILES: COc1ccc([C@@H](C)[C@@H](C)OC(=O)[C@@H](C)NC(=O)OC(C)(C)C)c(C)c1] | Example 1B Example 2 Example 3 | Oil |
| 41 | 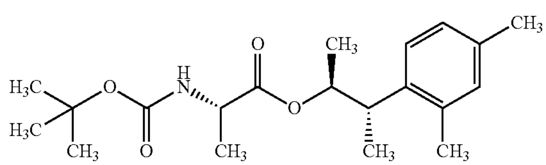 [SMILES: Cc1ccc([C@H](C)[C@H](C)OC(=O)[C@H](C)NC(=O)OC(C)(C)C)c(C)c1] | Example 1A Example 2 Example 3 | Light Yellow Oil |
| 42 | 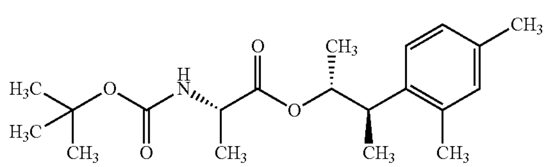 [SMILES: Cc1ccc([C@@H](C)[C@@H](C)OC(=O)[C@H](C)NC(=O)OC(C)(C)C)c(C)c1] | Example 1A Example 2 Example 3 | Clear Oil |
| 43 | 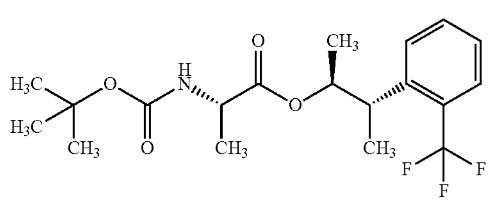 [SMILES: C[C@H](NC(=O)OC(C)(C)C)C(=O)O[C@@H](C)[C@@H](C)c1ccccc1C(F)(F)F] | Example 1A Example 2 Example 3 | Reddish Brown Oil |
| 44 | 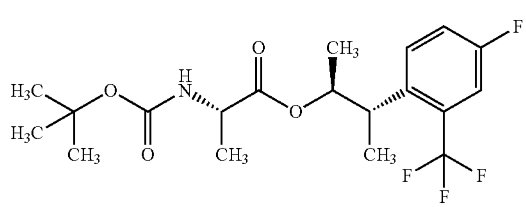 [SMILES: C[C@H](NC(=O)OC(C)(C)C)C(=O)O[C@@H](C)[C@@H](C)c1ccc(F)cc1C(F)(F)F] | Example 1A Example 2 Example 3 | Orange Oil |
| 45 | 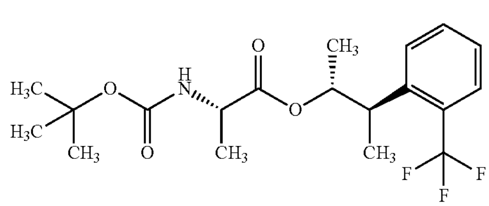 [SMILES: C[C@H](NC(=O)OC(C)(C)C)C(=O)O[C@H](C)[C@H](C)c1ccccc1C(F)(F)F] | Example 1A Example 2 Example 3 | Yellow Oil |

TABLE 1-continued

Compound Structure, Appearance, and Preparation Method

| Cmpd. No. | Structure | As Prepared According To | Appearance |
|---|---|---|---|
| 46 | 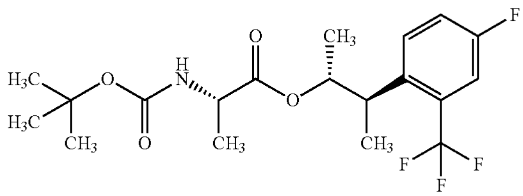 [SMILES: C[C@H](NC(=O)OC(C)(C)C)C(=O)O[C@H](C)[C@H](C)c1ccc(F)cc1C(F)(F)F] | Example 1A<br>Example 2<br>Example 3 | Yellow Oil |
| 47 | 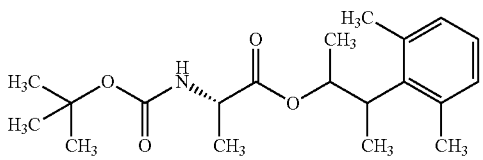 [SMILES: Cc1cccc(C)c1C(C)C(C)OC(=O)[C@H](C)NC(=O)OC(C)(C)C] | Example 1<br>Example 3 | Clear, Colorless Oil |
| 48 | 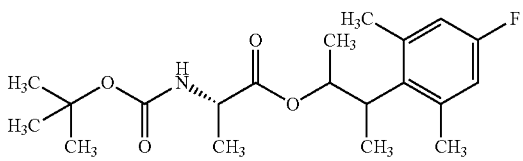 [SMILES: Cc1cc(F)cc(C)c1C(C)C(C)OC(=O)[C@H](C)NC(=O)OC(C)(C)C] | Example 1A<br>Example 3 | Pale Yellow Oil |
| 49 | 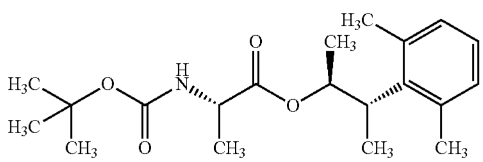 [SMILES: Cc1cccc(C)c1[C@H](C)[C@H](C)OC(=O)[C@H](C)NC(=O)OC(C)(C)C] | Example 1<br>Example 2<br>Example 3 | Clear, Colorless Oil |
| 50 | 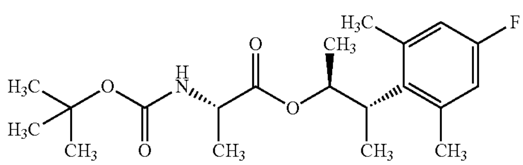 [SMILES: Cc1cc(F)cc(C)c1[C@H](C)[C@H](C)OC(=O)[C@H](C)NC(=O)OC(C)(C)C] | Example 1A<br>Example 2<br>Example 3 | Pale Yellow Oil |
| 51 | 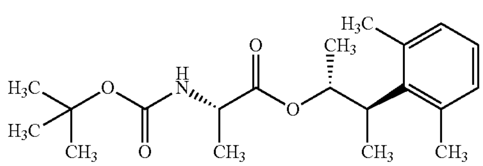 [SMILES: Cc1cccc(C)c1[C@@H](C)[C@@H](C)OC(=O)[C@H](C)NC(=O)OC(C)(C)C] | Example 1A<br>Example 2<br>Example 3 | Clear, Colorless Oil |
| 52 | 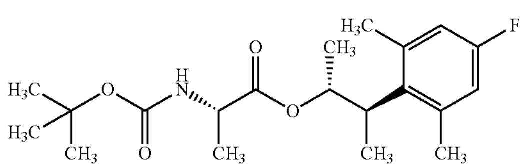 [SMILES: Cc1cc(F)cc(C)c1[C@@H](C)[C@@H](C)OC(=O)[C@H](C)NC(=O)OC(C)(C)C] | Example 1A<br>Example 2<br>Example 3 | Clear, Colorless Oil |
| 53 | 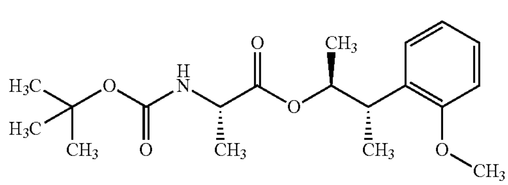 [SMILES: COc1ccccc1[C@H](C)[C@H](C)OC(=O)[C@H](C)NC(=O)OC(C)(C)C] | Example 1B<br>Example 2<br>Example 3 | Colorless Oil |

TABLE 1-continued

Compound Structure, Appearance, and Preparation Method

| Cmpd. No. | Structure | As Prepared According To | Appearance |
|---|---|---|---|
| 54 | 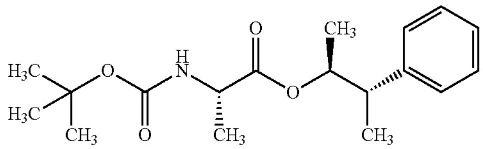 [SMILES: C[C@H](NC(=O)OC(C)(C)C)C(=O)O[C@@H](C)[C@@H](C)c1ccccc1] | Example 1C<br>Example 2<br>Example 3 | Colorless Oil |
| 55 | 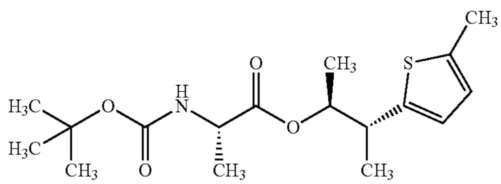 [SMILES: Cc1ccc([C@H](C)[C@H](C)OC(=O)[C@H](C)NC(=O)OC(C)(C)C)s1] | Example 1B<br>Example 2<br>Example 3 | Yellow Oil |
| 56 | 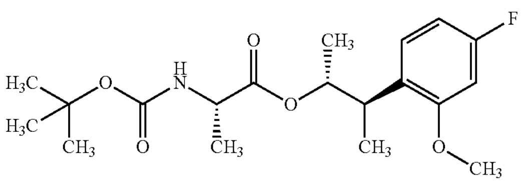 [SMILES: COc1cc(F)ccc1[C@@H](C)[C@@H](C)OC(=O)[C@H](C)NC(=O)OC(C)(C)C] | Example 1B<br>Example 2<br>Example 3 | Colorless Oil |
| 57 | 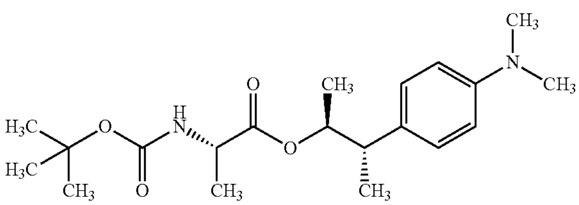 [SMILES: C[C@H](NC(=O)OC(C)(C)C)C(=O)O[C@@H](C)[C@@H](C)c1ccc(N(C)C)cc1] | Example 1B<br>Example 2<br>Example 3 | Residue |
| 58 | 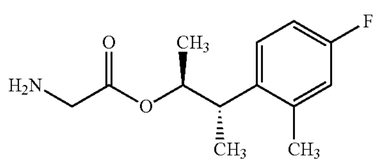 [SMILES: Cc1cc(F)ccc1[C@H](C)[C@H](C)OC(=O)CN] | Example 4<br>Step 1 | Oil |
| 59 | 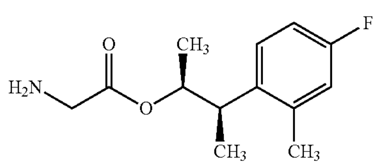 [SMILES: Cc1cc(F)ccc1[C@@H](C)[C@H](C)OC(=O)CN] | Example 4<br>Step 1 | Oil |
| 60 | 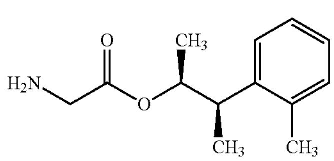 [SMILES: Cc1ccccc1[C@@H](C)[C@H](C)OC(=O)CN] | Example 4<br>Step 1 | Oil |
| 61 | 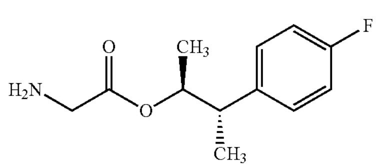 [SMILES: C[C@H](OC(=O)CN)[C@@H](C)c1ccc(F)cc1] | Example 4<br>Step 1 | Oil |

TABLE 1-continued

Compound Structure, Appearance, and Preparation Method

| Cmpd. No. | Structure | As Prepared According To | Appearance |
|---|---|---|---|
| 62 | 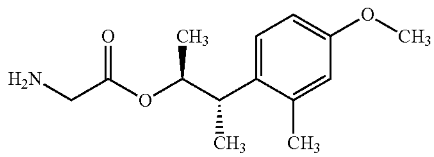 [SMILES: COc1ccc([C@H](C)[C@H](C)OC(=O)CN)c(C)c1] | Example 4 Step 1 | Oil |
| 63 | 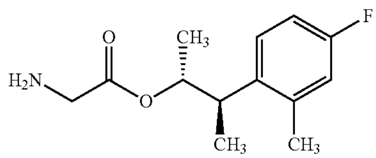 [SMILES: Cc1cc(F)ccc1[C@@H](C)[C@@H](C)OC(=O)CN] | Example 4 Step 1 | Oil |
| 64 | 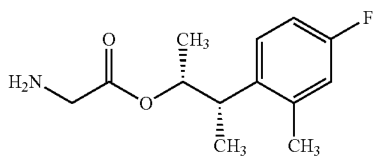 [SMILES: Cc1cc(F)ccc1[C@H](C)[C@@H](C)OC(=O)CN] | Example 4 Step 1 | Oil |
| 65 | 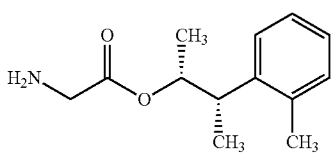 [SMILES: Cc1ccccc1[C@H](C)[C@@H](C)OC(=O)CN] | Example 4 Step 1 | Oil |
| 66 | 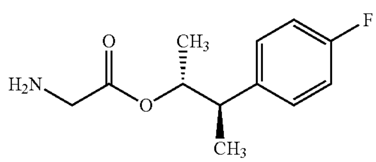 [SMILES: C[C@H](c1ccc(F)cc1)[C@@H](C)OC(=O)CN] | Example 4 Step 1 | Oil |
| 67 | 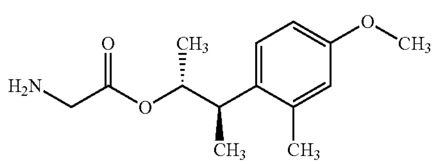 [SMILES: COc1ccc([C@@H](C)[C@@H](C)OC(=O)CN)c(C)c1] | Example 4 Step 1 | Oil |
| 68 | 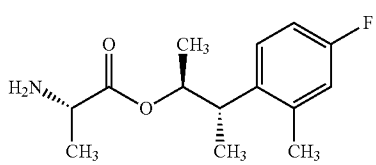 [SMILES: Cc1cc(F)ccc1[C@H](C)[C@H](C)OC(=O)[C@H](C)N] | Example 4 Step 1 | Oil |
| 69 | 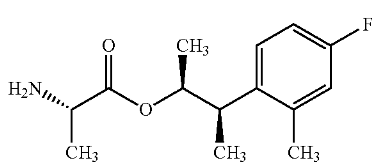 [SMILES: Cc1cc(F)ccc1[C@@H](C)[C@H](C)OC(=O)[C@H](C)N] | Example 4 Step 1 | Oil |
| 70 | 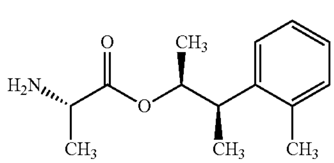 [SMILES: Cc1ccccc1[C@@H](C)[C@H](C)OC(=O)[C@H](C)N] | Example 4 Step 1 | Oil |

TABLE 1-continued

Compound Structure, Appearance, and Preparation Method

| Cmpd. No. | Structure | As Prepared According To | Appearance |
|---|---|---|---|
| 71 | 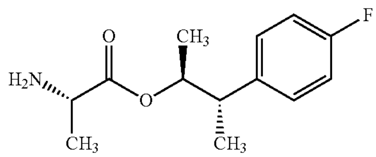 [SMILES: C[C@H](N)C(=O)O[C@@H](C)[C@@H](C)c1ccc(F)cc1] | Example 4 Step 1 | Oil |
| 72 | 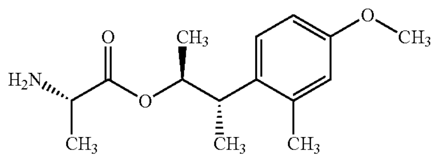 [SMILES: COc1ccc([C@H](C)[C@H](C)OC(=O)[C@H](C)N)c(C)c1] | Example 4 Step 1 | Oil |
| 73 | 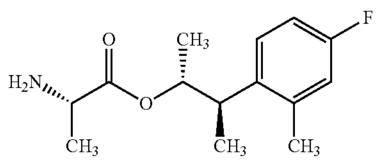 [SMILES: Cc1cc(F)ccc1[C@@H](C)[C@@H](C)OC(=O)[C@H](C)N] | Example 4 Step 1 | Oil |
| 74 | 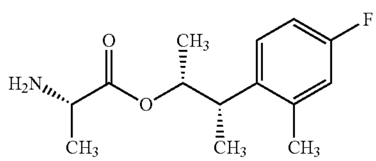 [SMILES: Cc1cc(F)ccc1[C@H](C)[C@@H](C)OC(=O)[C@H](C)N] | Example 4 Step 1 | Oil |
| 75 | 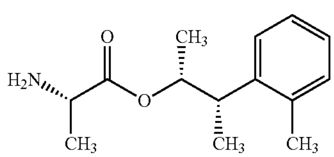 [SMILES: Cc1ccccc1[C@H](C)[C@@H](C)OC(=O)[C@H](C)N] | Example 4 Step 1 | Oil |
| 76 | 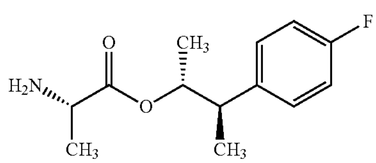 [SMILES: C[C@H](N)C(=O)O[C@H](C)[C@H](C)c1ccc(F)cc1] | Example 4 Step 1 | Oil |
| 77 | 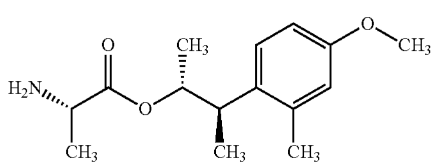 [SMILES: COc1ccc([C@@H](C)[C@@H](C)OC(=O)[C@H](C)N)c(C)c1] | Example 4 Step 1 | Oil |
| 78 | 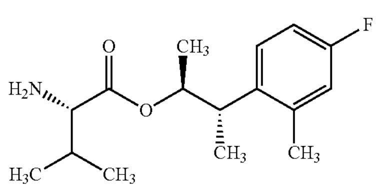 [SMILES: Cc1cc(F)ccc1[C@H](C)[C@H](C)OC(=O)[C@@H](N)C(C)C] | Example 4 Step 1 | Oil |
| 79 | 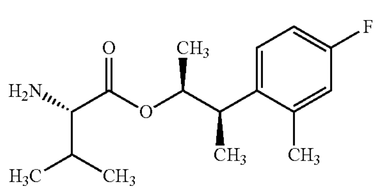 [SMILES: Cc1cc(F)ccc1[C@@H](C)[C@H](C)OC(=O)[C@@H](N)C(C)C] | Example 4 Step 1 | Oil |

TABLE 1-continued

Compound Structure, Appearance, and Preparation Method

| Cmpd. No. | Structure | As Prepared According To | Appearance |
|---|---|---|---|
| 80 | 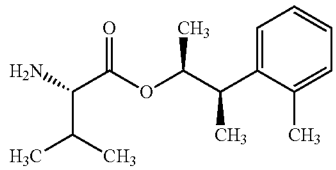 [SMILES: Cc1ccccc1[C@@H](C)[C@H](C)OC(=O)[C@@H](N)C(C)C] | Example 4 Step 1 | Oil |
| 81 | 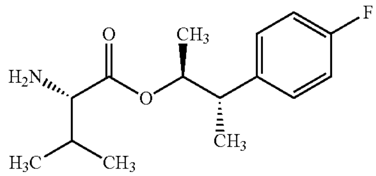 [SMILES: CC(C)[C@H](N)C(=O)O[C@@H](C)[C@@H](C)c1ccc(F)cc1] | Example 4 Step 1 | Oil |
| 82 | 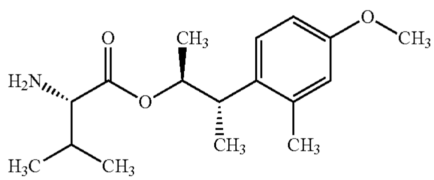 [SMILES: COc1ccc([C@H](C)[C@H](C)OC(=O)[C@@H](N)C(C)C)c(C)c1] | Example 4 Step 1 | Oil |
| 83 | 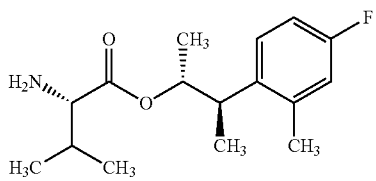 [SMILES: Cc1cc(F)ccc1[C@@H](C)[C@@H](C)OC(=O)[C@@H](N)C(C)C] | Example 4 Step 1 | Oil |
| 84 | 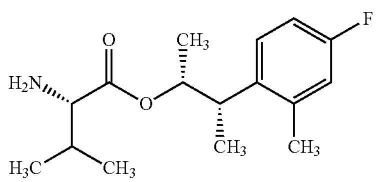 [SMILES: Cc1cc(F)ccc1[C@H](C)[C@@H](C)OC(=O)[C@@H](N)C(C)C] | Example 4 Step 1 | Oil |
| 85 | 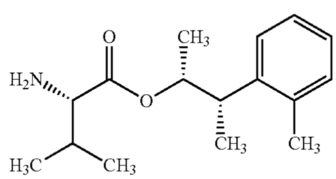 [SMILES: Cc1ccccc1[C@H](C)[C@@H](C)OC(=O)[C@@H](N)C(C)C] | Example 4 Step 1 | Oil |
| 86 | 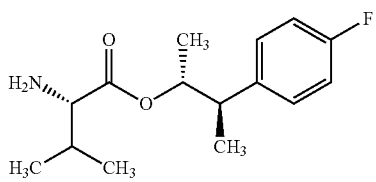 [SMILES: CC(C)[C@H](N)C(=O)O[C@H](C)[C@H](C)c1ccc(F)cc1] | Example 4 Step 1 | Oil |
| 87 | 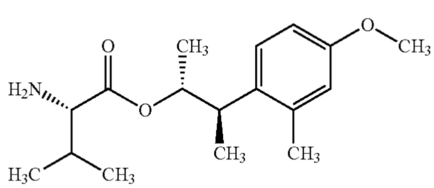 [SMILES: COc1ccc([C@@H](C)[C@@H](C)OC(=O)[C@@H](N)C(C)C)c(C)c1] | Example 4 Step 1 | Oil |

TABLE 1-continued

Compound Structure, Appearance, and Preparation Method

| Cmpd. No. | Structure | As Prepared According To | Appearance |
|---|---|---|---|
| 88 | (structure) | Example 4 Step 1 | Oil |
| 89 | (structure) | Example 4 Step 1 | Oil |
| 90 | (structure) | Example 4 Step 1 | Oil |
| 91 | (structure) | Example 4 Step 1 | Oil |
| 92 | (structure) | Example 4 Step 1 | Oil |
| 93 | (structure) | Example 4 Step 1 | Oil |
| 94 | (structure) | Example 4 Step 1 | Oil |
| 95 | (structure) | Example 4 Step 1 | Oil |
| 96 | (structure) | Example 4 Step 1 | Oil |

TABLE 1-continued

Compound Structure, Appearance, and Preparation Method

| Cmpd. No. | Structure | As Prepared According To | Appearance |
|---|---|---|---|
| 97 | 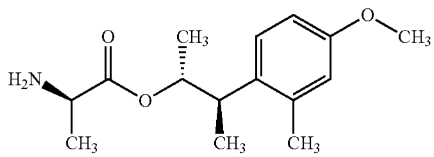 [SMILES: COc1ccc([C@@H](C)[C@@H](C)OC(=O)[C@@H](C)N)c(C)c1] | Example 4 Step 1 | Oil |
| 98 | 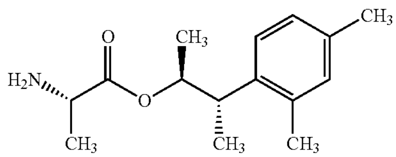 [SMILES: Cc1ccc([C@H](C)[C@H](C)OC(=O)[C@H](C)N)c(C)c1] | Example 4 Step 1 | Dark Yellow Oil |
| 99 | 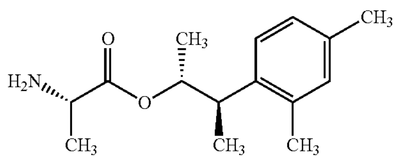 [SMILES: Cc1ccc([C@@H](C)[C@@H](C)OC(=O)[C@H](C)N)c(C)c1] | Example 4 Step 1 | Dark Yellow Oil |
| 100 | 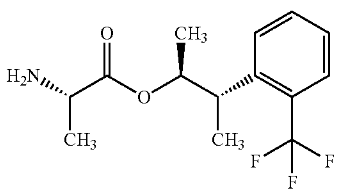 [SMILES: C[C@H](N)C(=O)O[C@@H](C)[C@@H](C)c1ccccc1C(F)(F)F] | Example 4 Step 1 | Brown Semisolid |
| 101 | 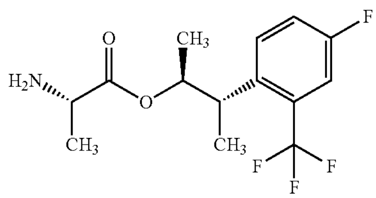 [SMILES: C[C@H](N)C(=O)O[C@@H](C)[C@@H](C)c1ccc(F)cc1C(F)(F)F] | Example 4 Step 1 | Light Brown Semisolid |
| 102 | 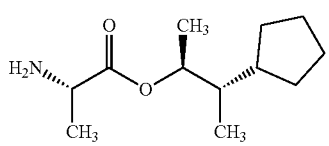 | Example 1A Example 2 Example 3 Example 4 Step 1 | Pale Yellow Oil |
| 103 | 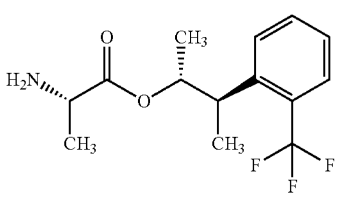 [SMILES: C[C@H](N)C(=O)O[C@H](C)[C@H](C)c1ccccc1C(F)(F)F] | Example 4 Step 1 | Orange Semisolid |
| 104 | 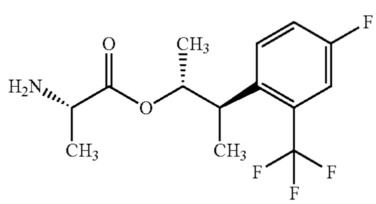 [SMILES: C[C@H](N)C(=O)O[C@H](C)[C@H](C)c1ccc(F)cc1C(F)(F)F] | Example 4 Step 1 | Orange Semisolid |

TABLE 1-continued

Compound Structure, Appearance, and Preparation Method

| Cmpd. No. | Structure | As Prepared According To | Appearance |
|---|---|---|---|
| 105 | 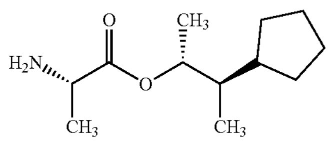 | Example 1A Example 2 Example 3 Example 4 Step 1 | White Semisolid |
| 106 | 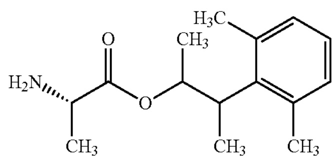 [SMILES: Cc1cccc(C)c1C(C)C(C)OC(=O)[C@H](C)N] | Example 4 Step 1 | White Semisolid |
| 107 | 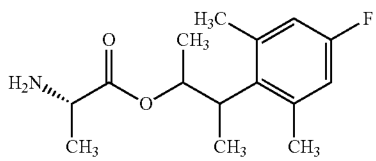 [SMILES: Cc1cc(F)cc(C)c1C(C)C(C)OC(=O)[C@H](C)N] | Example 4 Step 1 | Pale Yellow Oil |
| 108 | 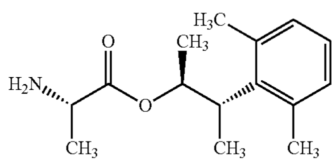 [SMILES: Cc1cccc(C)c1[C@H](C)[C@H](C)OC(=O)[C@H](C)N] | Example 4 Step 1 | White Semisolid |
| 109 | 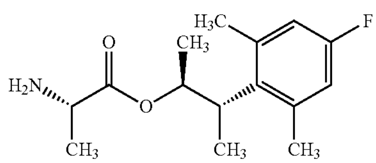 [SMILES: Cc1cc(F)cc(C)c1[C@H](C)[C@H](C)OC(=O)[C@H](C)N] | Example 4 Step 1 | Clear, Colorless Glass |
| 110 | 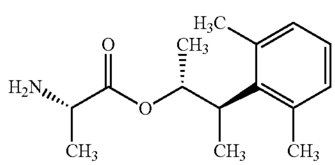 [SMILES: Cc1cccc(C)c1[C@@H](C)[C@@H](C)OC(=O)[C@H](C)N] | Example 4 Step 1 | Clear, Colorless Oil |
| 111 | 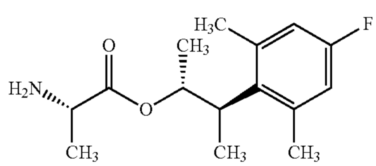 [SMILES: Cc1cc(F)cc(C)c1[C@@H](C)[C@@H](C)OC(=O)[C@H](C)N] | Example 4 Step 1 | Clear, Colorless Oil |
| 112 | 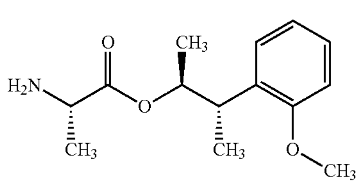 [SMILES: COc1ccccc1[C@H](C)[C@H](C)OC(=O)[C@H](C)N] | Example 4 Step 1 | Colorless Oil |
| 113 | 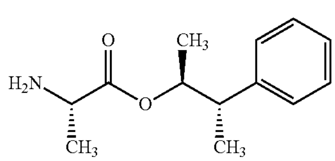 [SMILES: C[C@H](N)C(=O)O[C@@H](C)[C@@H](C)c1ccccc1] | Example 4 Step 1 | White Solid |

TABLE 1-continued

Compound Structure, Appearance, and Preparation Method

| Cmpd. No. | Structure | As Prepared According To | Appearance |
|---|---|---|---|
| 114 | 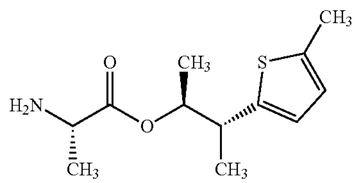 [SMILES: Cc1ccc([C@H](C)[C@H](C)OC(=O)[C@H](C)N)s1] | Example 4 Step 1 | Yellow Oil |
| 115 | 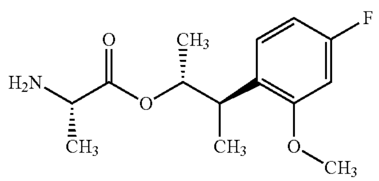 [SMILES: COc1cc(F)ccc1[C@@H](C)[C@@H](C)OC(=O)[C@H](C)N] | Example 4 Step 1 | Colorless Oil |
| 116 | 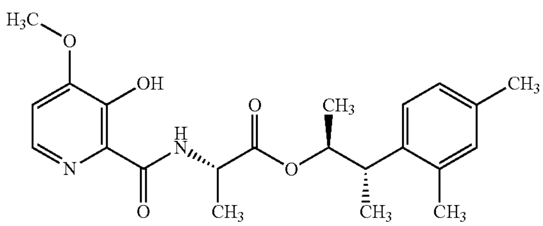 [SMILES: COc1ccnc(C(=O)N[C@@H](C)C(=O)O[C@@H](C)[C@@H](C)c2ccc(C)cc2C)c1O] | Example 4 Step 2 | Thick Clear Oil |
| 117 | 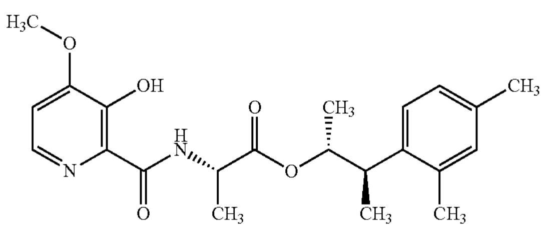 [SMILES: COc1ccnc(C(=O)N[C@@H](C)C(=O)O[C@H](C)[C@H](C)c2ccc(C)cc2C)c1O] | Example 4 Step 2 | Thick Clear Oil |
| 118 | 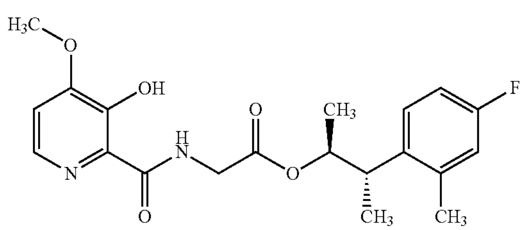 [SMILES: COc1ccnc(C(=O)NCC(=O)O[C@@H](C)[C@@H](C)c2ccc(F)cc2C)c1O] | Example 4 Step 2 | White Solid |
| 119 | 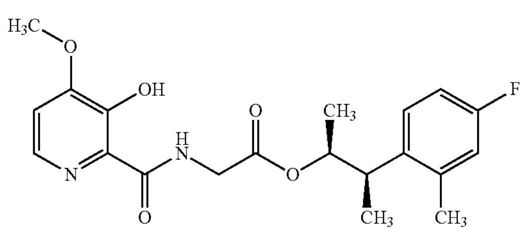 [SMILES: COc1ccnc(C(=O)NCC(=O)O[C@@H](C)[C@H](C)c2ccc(F)cc2C)c1O] | Example 4 Step 2 | White Solid |
| 120 | 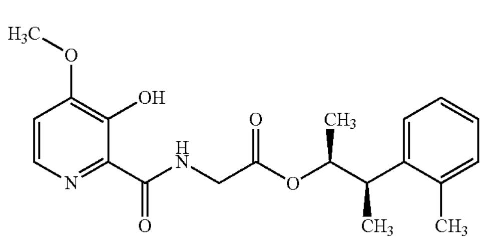 [SMILES: COc1ccnc(C(=O)NCC(=O)O[C@@H](C)[C@H](C)c2ccccc2C)c1O] | Example 4 Step 2 | Thick Oil |

TABLE 1-continued

Compound Structure, Appearance, and Preparation Method

| Cmpd. No. | Structure | As Prepared According To | Appearance |
|---|---|---|---|
| 121 | 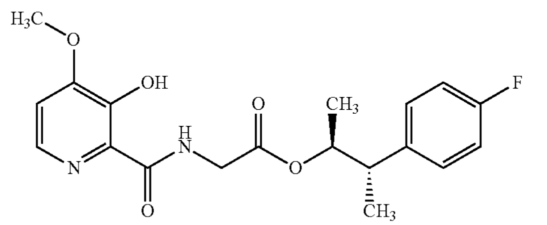 [SMILES: COc1ccnc(C(=O)NCC(=O)O[C@@H](C)[C@@H](C)c2ccc(F)cc2)c1O] | Example 4 Step 2 | Thick Oil |
| 122 | 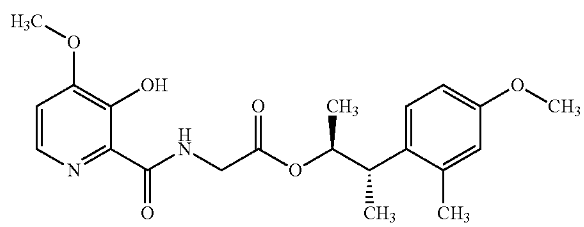 [SMILES: COc1ccc([C@H](C)[C@H](C)OC(=O)CNC(=O)c2nccc(OC)c2O)c(C)c1] | Example 4 Step 2 | Thick Oil |
| 123 | 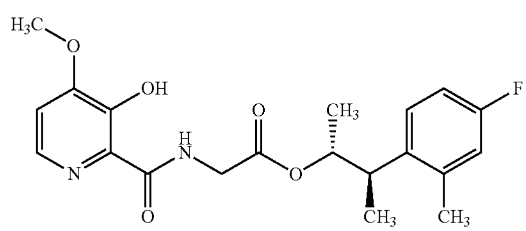 [SMILES: COc1ccnc(C(=O)NCC(=O)O[C@H](C)[C@H](C)c2ccc(F)cc2C)c1O] | Example 4 Step 2 | White Solid |
| 124 | 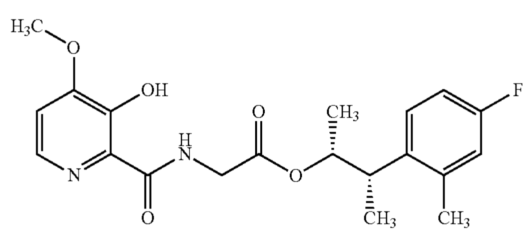 [SMILES: COc1ccnc(C(=O)NCC(=O)O[C@H](C)[C@@H](C)c2ccc(F)cc2C)c1O] | Example 4 Step 2 | Thick Oil |
| 125 | 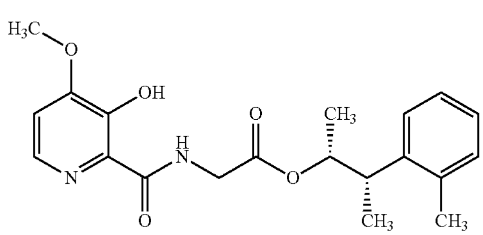 [SMILES: COc1ccnc(C(=O)NCC(=O)O[C@H](C)[C@@H](C)c2ccccc2C)c1O] | Example 4 Step 2 | Thick Oil |
| 126 | 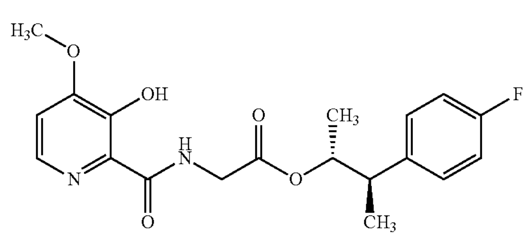 [SMILES: COc1ccnc(C(=O)NCC(=O)O[C@H](C)[C@H](C)c2ccc(F)cc2)c1O] | Example 4 Step 2 | White Solid |

TABLE 1-continued

Compound Structure, Appearance, and Preparation Method

| Cmpd. No. | Structure | As Prepared According To | Appearance |
|---|---|---|---|
| 127 | 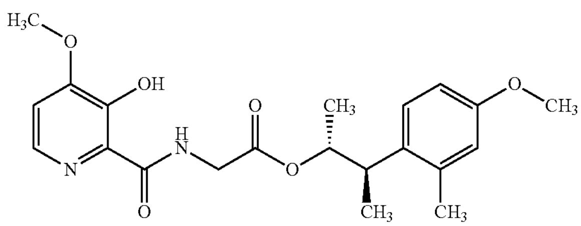 [SMILES: COc1ccc([C@@H](C)[C@@H](C)OC(=O)CNC(=O)c2nccc(OC)c2O)c(C)c1] | Example 4 Step 2 | Thick Oil |
| 128 | 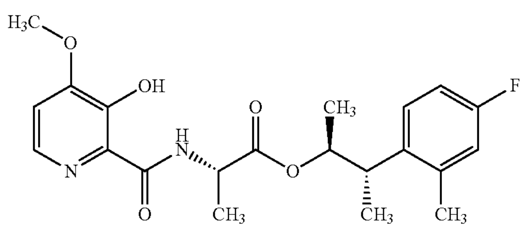 [SMILES: COc1ccnc(C(=O)N[C@@H](C)C(=O)O[C@@H](C)[C@@H](C)c2ccc(F)cc2C)c1O] | Example 4 Step 2 | White Solid |
| 129 | 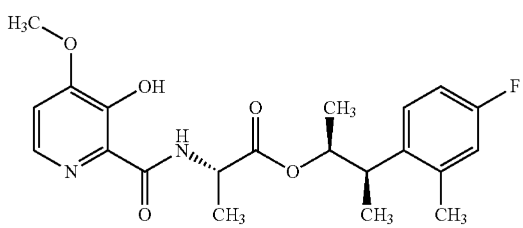 [SMILES: COc1ccnc(C(=O)N[C@@H](C)C(=O)O[C@@H](C)[C@H](C)c2ccc(F)cc2C)c1O] | Example 4 Step 2 | Thick Oil |
| 130 | 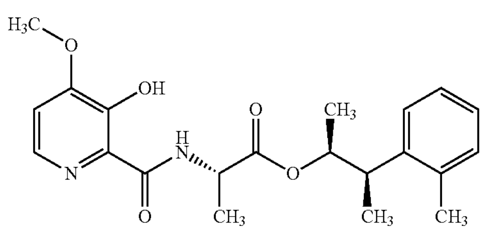 [SMILES: COc1ccnc(C(=O)N[C@@H](C)C(=O)O[C@@H](C)[C@H](C)c2ccccc2C)c1O] | Example 4 Step 2 | White Solid |
| 131 | 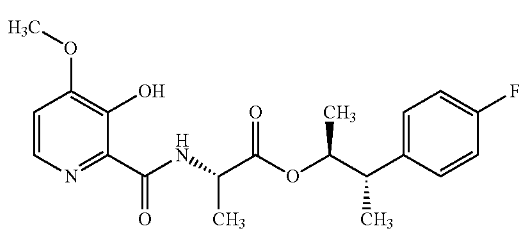 [SMILES: COc1ccnc(C(=O)N[C@@H](C)C(=O)O[C@@H](C)[C@@H](C)c2ccc(F)cc2)c1O] | Example 4 Step 2 | Thick Oil |
| 132 | 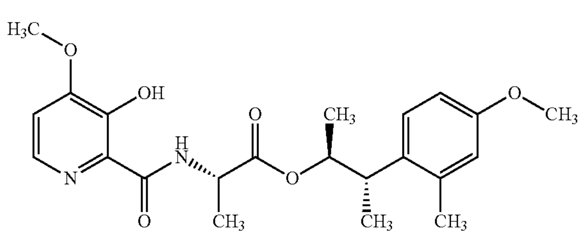 [SMILES: COc1ccc([C@H](C)[C@H](C)OC(=O)[C@H](C)NC(=O)c2nccc(OC)c2O)c(C)c1] | Example 4 Step 2 | Thick Oil |

TABLE 1-continued

Compound Structure, Appearance, and Preparation Method

| Cmpd. No. | Structure | As Prepared According To | Appearance |
|---|---|---|---|
| 133 | 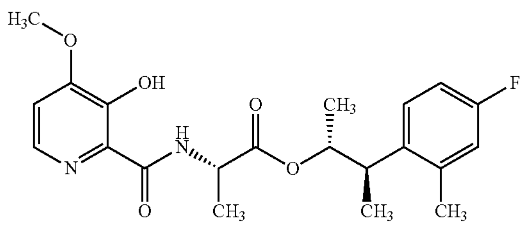 [SMILES: COc1ccnc(C(=O)N[C@@H](C)C(=O)O[C@H](C)[C@H](C)c2ccc(F)cc2C)c1O] | Example 4 Step 2 | Thick Oil |
| 134 | 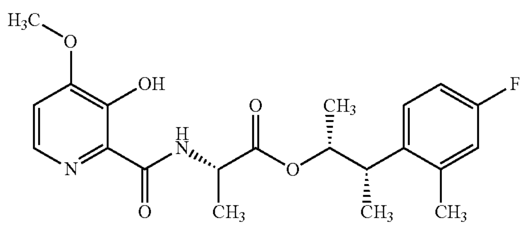 [SMILES: COc1ccnc(C(=O)N[C@@H](C)C(=O)O[C@H](C)[C@@H](C)c2ccc(F)cc2C)c1O] | Example 4 Step 2 | Thick Oil |
| 135 | 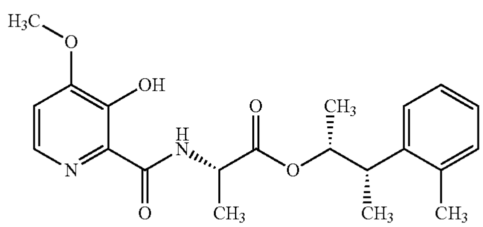 [SMILES: COc1ccnc(C(=O)N[C@@H](C)C(=O)O[C@H](C)[C@@H](C)c2ccccc2C)c1O] | Example 4 Step 2 | Thick Oil |
| 136 | 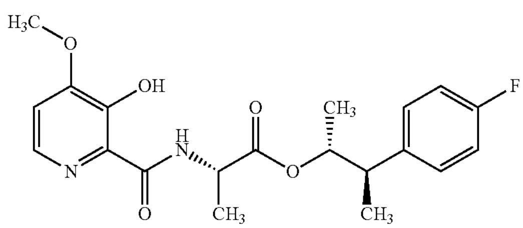 [SMILES: COc1ccnc(C(=O)N[C@@H](C)C(=O)O[C@H](C)[C@H](C)c2ccc(F)cc2)c1O] | Example 4 Step 2 | Thick Oil |
| 137 | 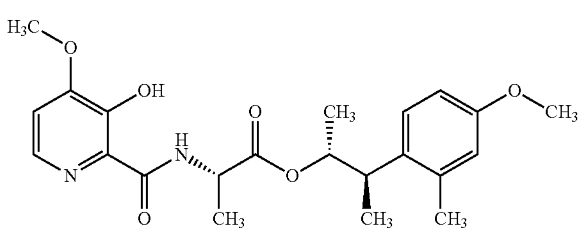 [SMILES: COc1ccc([C@@H](C)[C@@H](C)OC(=O)[C@H](C)NC(=O)c2nccc(OC)c2O)c(C)c1] | Example 4 Step 2 | Thick Oil |
| 138 | 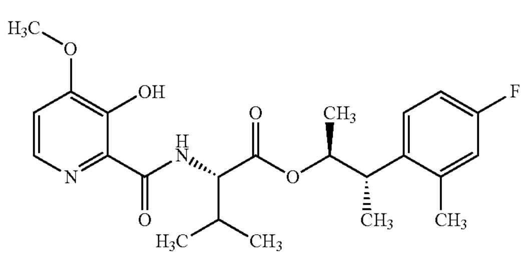 [SMILES: COc1ccnc(C(=O)N[C@H](C(=O)O[C@@H](C)[C@@H](C)c2ccc(F)cc2C)C(C)C)c1O] | Example 4 Step 2 | White Solid |

TABLE 1-continued

Compound Structure, Appearance, and Preparation Method

| Cmpd. No. | Structure | As Prepared According To | Appearance |
|---|---|---|---|
| 139 | 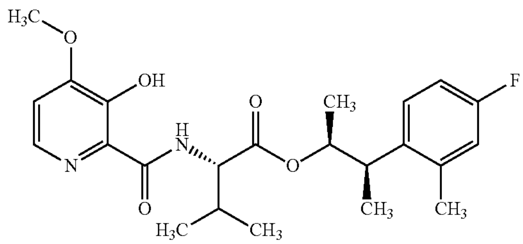 [SMILES: COc1ccnc(C(=O)N[C@H](C(=O)O[C@@H](C)[C@H](C)c2ccc(F)cc2C)C(C)C)c1O] | Example 4 Step 2 | Thick Oil |
| 140 | 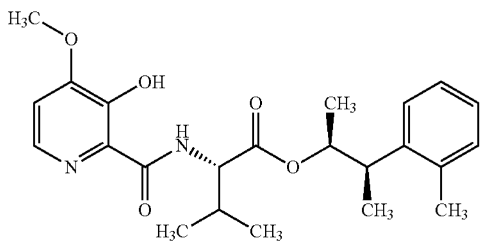 [SMILES: COc1ccnc(C(=O)N[C@H](C(=O)O[C@@H](C)[C@H](C)c2ccccc2C)C(C)C)c1O] | Example 4 Step 2 | Thick Oil |
| 141 | 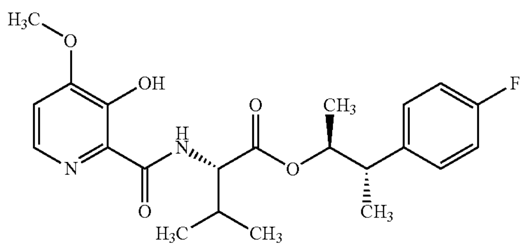 [SMILES: COc1ccnc(C(=O)N[C@H](C(=O)O[C@@H](C)[C@@H](C)c2ccc(F)cc2)C(C)C)c1O] | Example 4 Step 2 | White Solid |
| 142 | 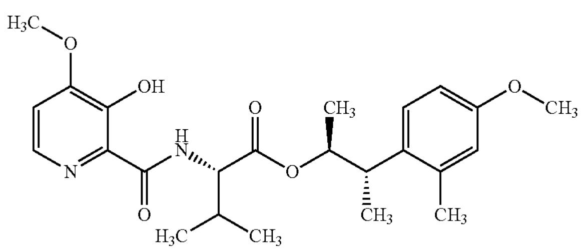 [SMILES: COc1ccc([C@H](C)[C@H](C)OC(=O)[C@@H](NC(=O)c2nccc(OC)c2O)C(C)C)c(C)c1] | Example 4 Step 2 | Thick Oil |
| 143 | 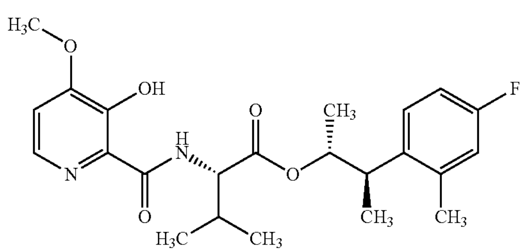 [SMILES: COc1ccnc(C(=O)N[C@H](C(=O)O[C@H](C)[C@H](C)c2ccc(F)cc2C)C(C)C)c1O] | Example 4 Step 2 | Thick Oil |
| 144 | 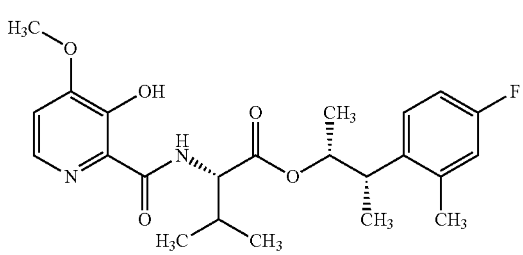 [SMILES: COc1ccnc(C(=O)N[C@H](C(=O)O[C@H](C)[C@@H](C)c2ccc(F)cc2C)C(C)C)c1O] | Example 4 Step 2 | Thick Oil |

TABLE 1-continued

Compound Structure, Appearance, and Preparation Method

| Cmpd. No. | Structure | As Prepared According To | Appearance |
|---|---|---|---|
| 145 | 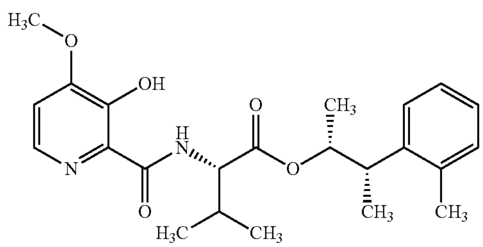 [SMILES: COc1ccnc(C(=O)N[C@H](C(=O)O[C@H](C)[C@@H](C)c2ccccc2C)C(C)C)c1O] | Example 4 Step 2 | Think Oil |
| 146 | 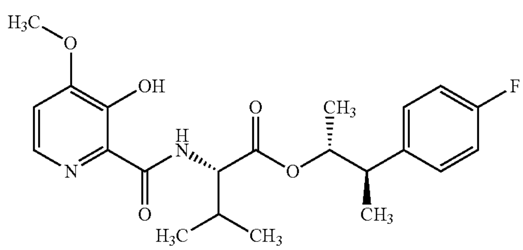 [SMILES: COc1ccnc(C(=O)N[C@H](C(=O)O[C@H](C)[C@H](C)c2ccc(F)cc2)C(C)C)c1O] | Example 4 Step 2 | Thick Oil |
| 147 | 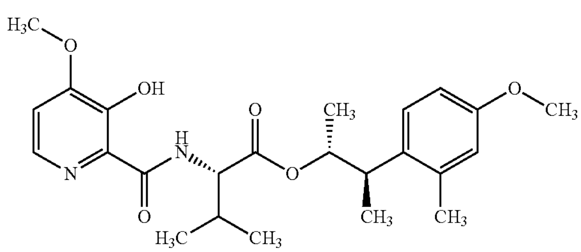 [SMILES: COc1ccc([C@@H](C)[C@@H](C)OC(=O)[C@@H](NC(=O)c2nccc(OC)c2O)C(C)C)c(C)c1] | Example 4 Step 2 | Thick Oil |
| 148 | 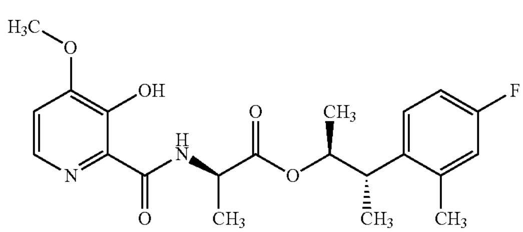 [SMILES: COc1ccnc(C(=O)N[C@H](C)C(=O)O[C@@H](C)[C@@H](C)c2ccc(F)cc2C)c1O] | Example 4 Step 2 | Thick Oil |
| 149 | 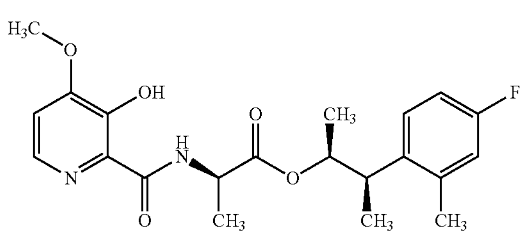 [SMILES: COc1ccnc(C(=O)N[C@H](C)C(=O)O[C@@H](C)[C@H](C)c2ccc(F)cc2C)c1O] | Example 4 Step 2 | Thick Oil |
| 150 | 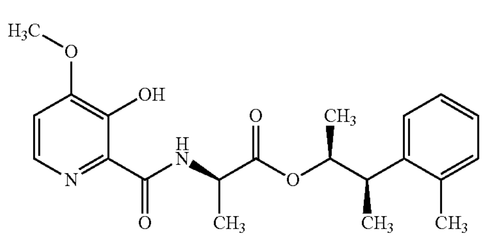 [SMILES: COc1ccnc(C(=O)N[C@H](C)C(=O)O[C@@H](C)[C@H](C)c2ccccc2C)c1O] | Example 4 Step 2 | Thick Oil |

TABLE 1-continued

Compound Structure, Appearance, and Preparation Method

| Cmpd. No. | Structure | As Prepared According To | Appearance |
|---|---|---|---|
| 151 | 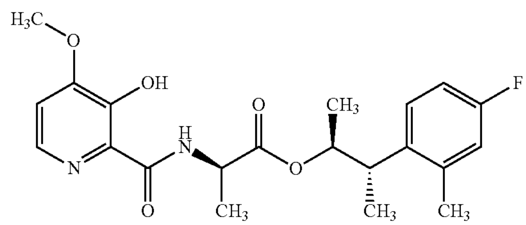 [SMILES: COc1ccnc(C(=O)N[C@H](C)C(=O)O[C@@H](C)[C@@H](C)c2ccc(F)cc2C)c1O] | Example 4 Step 2 | Thick Oil |
| 152 | 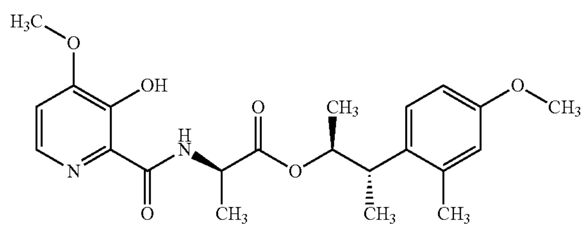 [SMILES: COc1ccc([C@H](C)[C@H](C)OC(=O)[C@@H](C)NC(=O)c2nccc(OC)c2O)c(C)c1] | Example 4 Step 2 | Thick Oil |
| 153 | 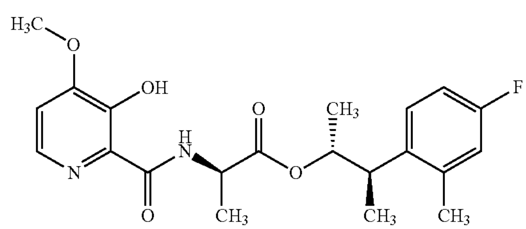 [SMILES: COc1ccnc(C(=O)N[C@H](C)C(=O)O[C@H](C)[C@H](C)c2ccc(F)cc2C)c1O] | Example 4 Step 2 | White Solid |
| 154 | 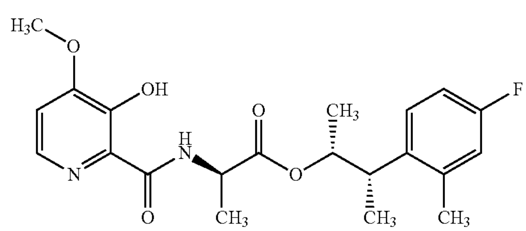 [SMILES: COc1ccnc(C(=O)N[C@H](C)C(=O)O[C@H](C)[C@@H](C)c2ccc(F)cc2C)c1O] | Example 4 Step 2 | Thick Oil |
| 155 | 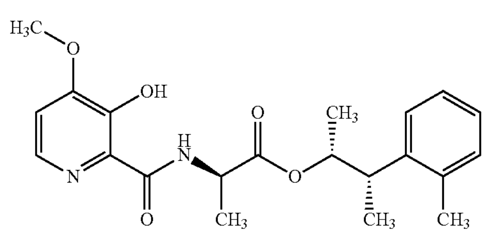 [SMILES: COc1ccnc(C(=O)N[C@H](C)C(=O)O[C@H](C)[C@@H](C)c2ccccc2C)c1O] | Example 4 Step 2 | White Solid |
| 156 | 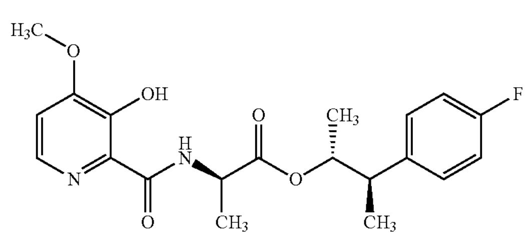 [SMILES: COc1ccnc(C(=O)N[C@H](C)C(=O)O[C@H](C)[C@H](C)c2ccc(F)cc2)c1O] | Example 4 Step 2 | Thick Oil |

TABLE 1-continued

Compound Structure, Appearance, and Preparation Method

| Cmpd. No. | Structure | As Prepared According To | Appearance |
|---|---|---|---|
| 157 | 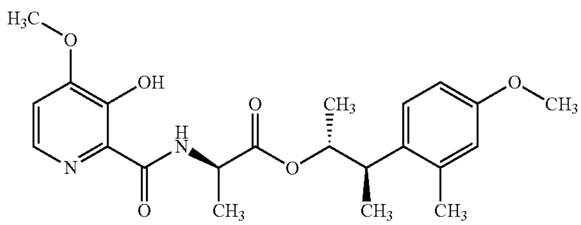 [SMILES: COc1ccc([C@@H](C)[C@@H](C)OC(=O)[C@@H](C)NC(=O)c2nccc(OC)c2O)c(C)c1] | Example 4 Step 2 | Thick Oil |
| 158 | 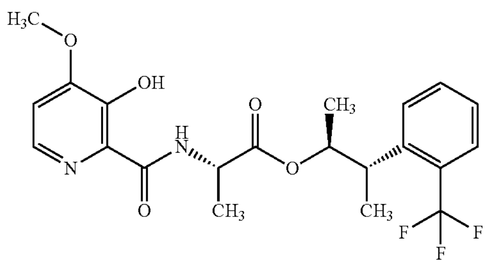 [SMILES: COc1ccnc(C(=O)N[C@@H](C)C(=O)O[C@@H](C)[C@@H](C)c2ccccc2C(F)(F)F)c1O] | Example 4 Step 2 | Orange Oil |
| 159 | 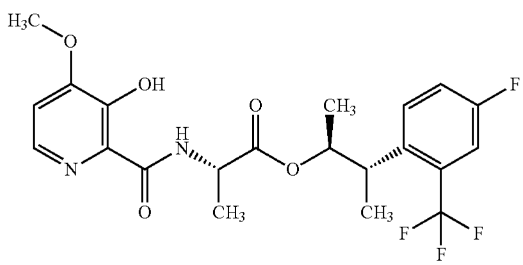 [SMILES: COc1ccnc(C(=O)N[C@@H](C)C(=O)O[C@@H](C)[C@@H](C)c2ccc(F)cc2C(F)(F)F)c1O] | Example 4 Step 2 | Orange Oil |
| 160 | 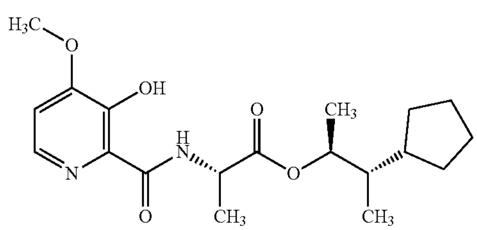 | Example 4 Step 2 | Pale Yellow Oil |
| 161 | 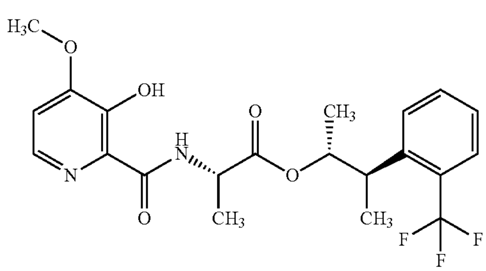 [SMILES: COc1ccnc(C(=O)N[C@@H](C)C(=O)O[C@H](C)[C@H](C)c2ccccc2C(F)(F)F)c1O] | Example 4 Step 2 | Yellow Oil |
| 162 | 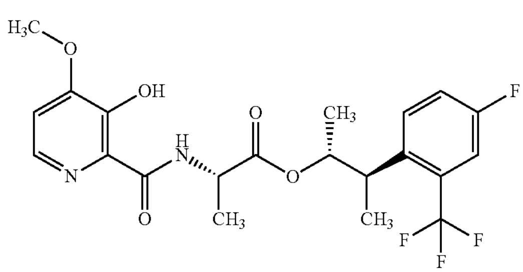 [SMILES: COc1ccnc(C(=O)N[C@@H](C)C(=O)O[C@H](C)[C@H](C)c2ccc(F)cc2C(F)(F)F)c1O] | Example 4 Step 2 | Yellow Oil |

TABLE 1-continued

Compound Structure, Appearance, and Preparation Method

| Cmpd. No. | Structure | As Prepared According To | Appearance |
|---|---|---|---|
| 163 | (structure) | Example 4 Step 2 | Clear, Colorless Oil |
| 164 | (structure) | Example 4 Step 2 | Yellow Oil |
| 165 | (structure) | Example 4 Step 2 | Orange Oil |
| 166 | (structure) | Example 4 Step 2 | Clear, Colorless Oil |
| 167 | (structure) | Example 4 Step 2 | Yellow Oil |
| 168 | (structure) | Example 4 Step 2 | Clear, Colorless Oil |

TABLE 1-continued
Compound Structure, Appearance, and Preparation Method
| Cmpd. No. | Structure | As Prepared According To | Appearance |
|---|---|---|---|
| 169 | 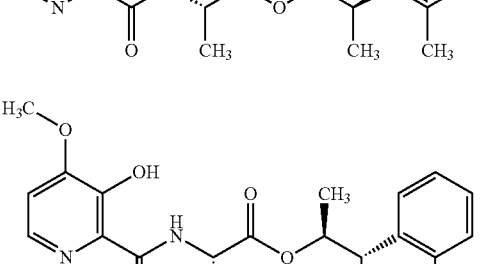 | Example 4 Step 2 | Yellow Oil |
| 170 | 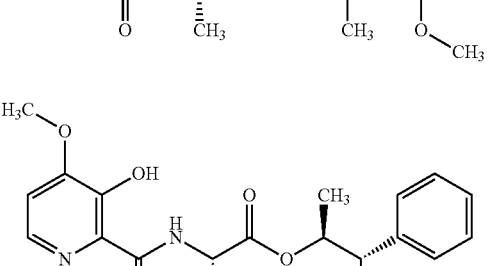 | Example 4 Step 2 | Colorless Oil |
| 171 | 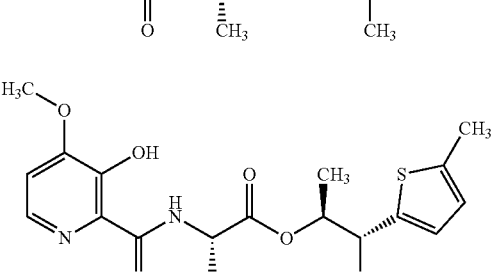 | Example 4 Step 2 | Colorless Oil |
| 172 | 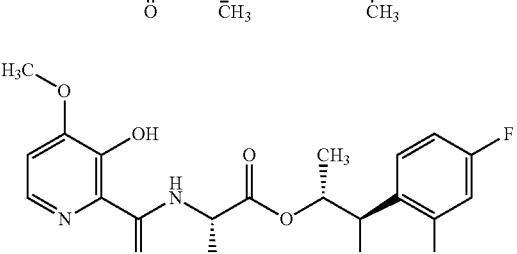 | Example 4 Step 2 | Pale Yellow Oil |
| 173 | 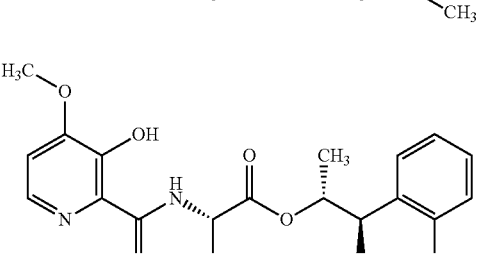 | Example 4 Step 2 | Colorless Oil |
| 174 | 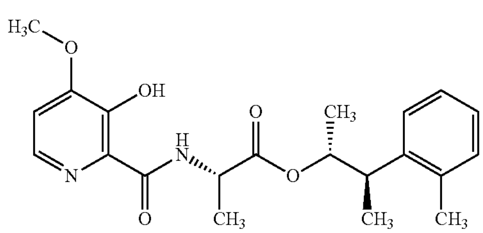 [SMILES: COc1ccnc(C(=O)N[C@@H](C)C(=O)O[C@H](C)[C@H](C)c2ccccc2C)c1O] | Example 4 Step 2 | Clear Oil |

TABLE 1-continued

Compound Structure, Appearance, and Preparation Method

| Cmpd. No. | Structure | As Prepared According To | Appearance |
|---|---|---|---|
| 175 | 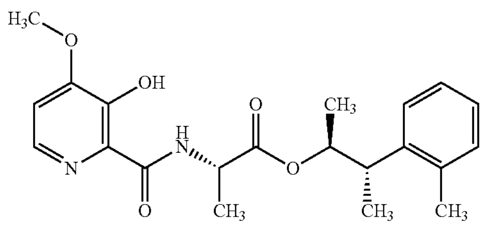 [SMILES: COc1ccnc(C(=O)N[C@@H](C)C(=O)O[C@@H](C)[C@@H](C)c2ccccc2C)c1O] | Eample 4 Step 2 | Colorless Foam |
| 176 | 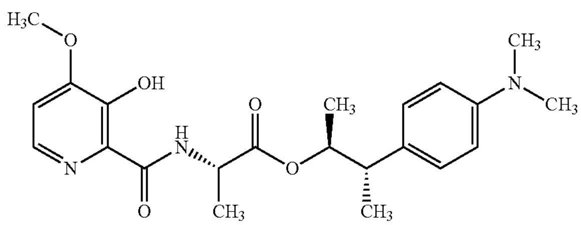 [SMILES: COc1ccnc(C(=O)N[C@@H](C)C(=O)O[C@@H](C)[C@@H](C)c2ccc(N(C)C)cc2)c1O] | Example 4 Step 2 | Residue |
| 177 | 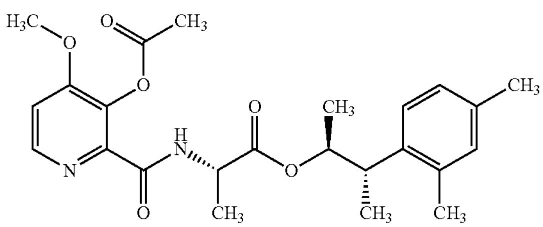 [SMILES: COc1ccnc(C(=O)N[C@@H](C)C(=O)O[C@@H](C)[C@@H](C)c2ccc(C)cc2C)c1OC(C)=O] | Example 5A | Thick Oil |
| 178 | 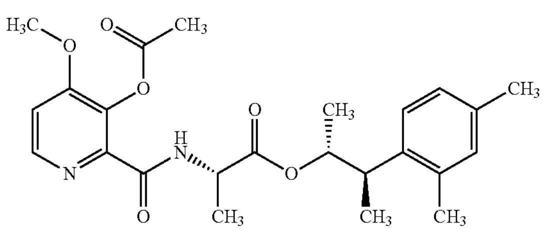 [SMILES: COc1ccnc(C(=O)N[C@@H](C)C(=O)O[C@H](C)[C@H](C)c2ccc(C)cc2C)c1OC(C)=O] | Example 5A | Thick Oil |
| 179 | 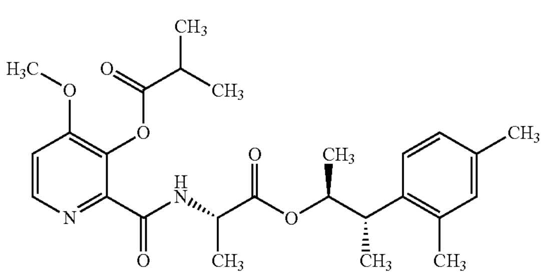 [SMILES: COc1ccnc(C(=O)N[C@@H](C)C(=O)O[C@@H](C)[C@@H](C)c2ccc(C)cc2C)c1OC(=O)C(C)C] | Example 5C | Thick Oil |
| 180 | 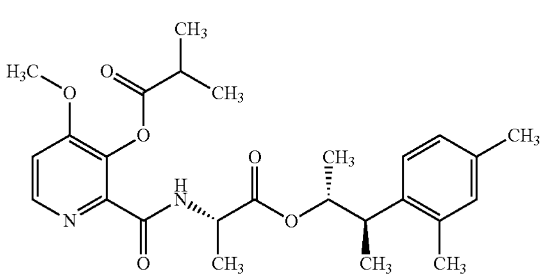 [SMILES: COc1ccnc(C(=O)N[C@@H](C)C(=O)O[C@H](C)[C@H](C)c2ccc(C)cc2C)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 181 | 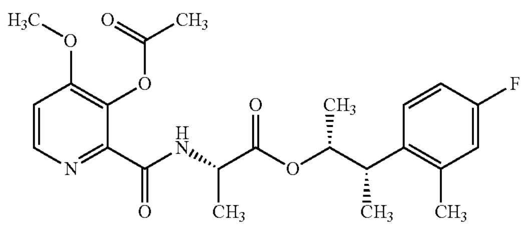 [SMILES: COc1ccnc(C(=O)N[C@@H](C)C(=O)O[C@H](C)[C@@H](C)c2ccc(F)cc2C)c1OC(C)=O] | Example 5A | Thick Oil |
| 182 | 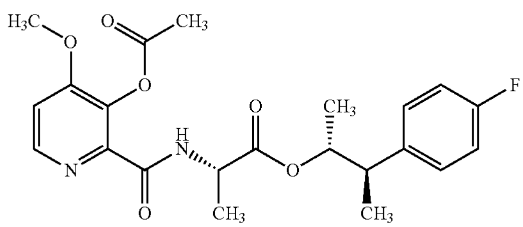 [SMILES: COc1ccnc(C(=O)N[C@@H](C)C(=O)O[C@H](C)[C@H](C)c2ccc(F)cc2)c1OC(C)=O] | Eample 5A | Thick Oil |
| 183 | 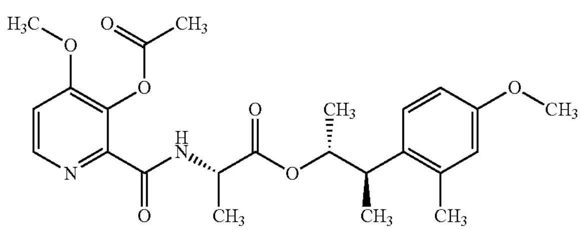 [SMILES: COc1ccc([C@@H](C)[C@@H](C)OC(=O)[C@H](C)NC(=O)c2nccc(OC)c2OC(C)=O)c(C)c1] | Example 5A | Thick Oil |
| 184 | 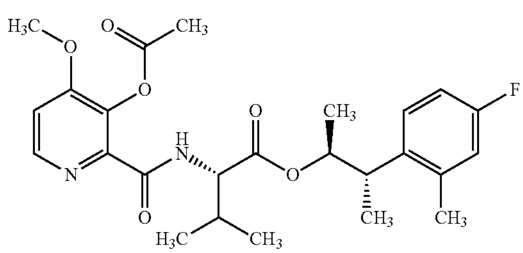 [SMILES: COc1ccnc(C(=O)N[C@H](C(=O)O[C@@H](C)[C@@H](C)c2ccc(F)cc2C)C(C)C)c1OC(C)=O] | Example 5A | Thick Oil |
| 185 | 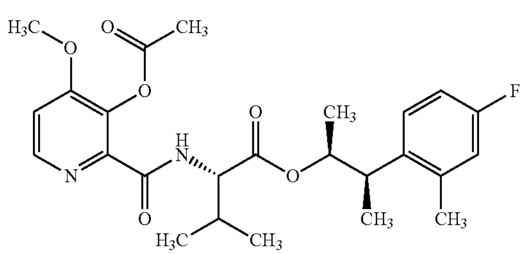 [SMILES: COc1ccnc(C(=O)N[C@H](C(=O)O[C@@H](C)[C@H](C)c2ccc(F)cc2C)C(C)C)c1OC(C)=O] | Example 5A | Thick Oil |
| 186 | 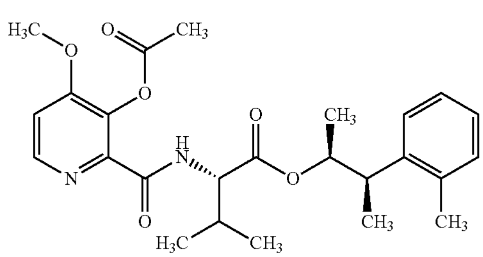 [SMILES: COc1ccnc(C(=O)N[C@H](C(=O)O[C@@H](C)[C@H](C)c2ccccc2C)C(C)C)c1OC(C)=O] | Example 5A | Thick Oil |

TABLE 1-continued

Compound Structure, Appearance, and Preparation Method

| Cmpd. No. | Structure | As Prepared According To | Appearance |
|---|---|---|---|
| 187 | 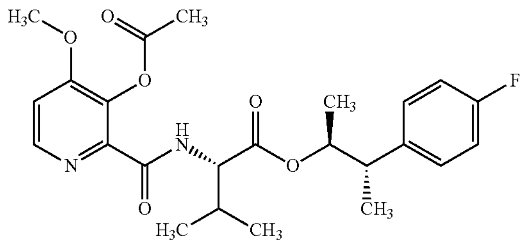 [SMILES: COc1ccnc(C(=O)N[C@H](C(=O)O[C@@H](C)[C@@H](C)c2ccc(F)cc2)C(C)C)c1OC(C)=O] | Example 5A | Thick Oil |
| 188 | 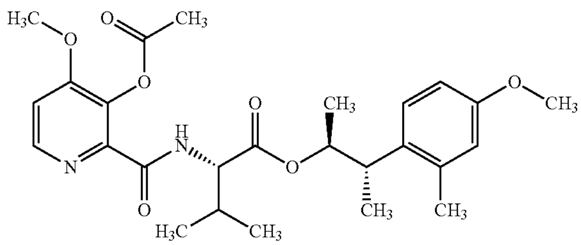 [SMILES: COc1ccc([C@H](C)[C@H](C)OC(=O)[C@@H](NC(=O)c2nccc(OC)c2OC(C)=O)C(C)C)c(C)c1] | Example 5A | Thick Oil |
| 189 | 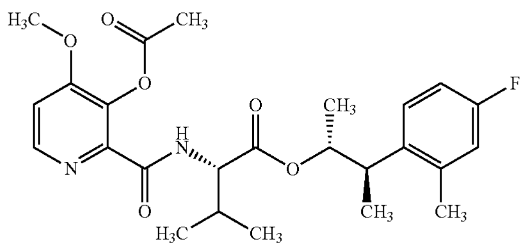 [SMILES: COc1ccnc(C(=O)N[C@H](C(=O)O[C@H](C)[C@H](C)c2ccc(F)cc2C)C(C)C)c1OC(C)=O] | Example 5A | Thick Oil |
| 190 | 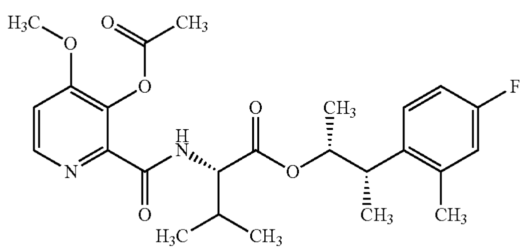 [SMILES: COc1ccnc(C(=O)N[C@H](C(=O)O[C@H](C)[C@@H](C)c2ccc(F)cc2C)C(C)C)c1OC(C)=O] | Eaxmple 5A | Thick Oil |
| 191 | 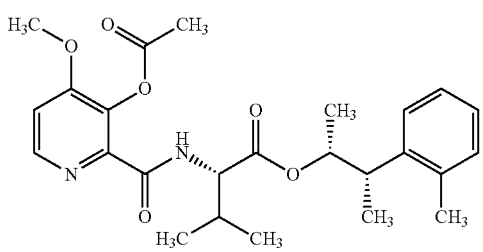 [SMILES: COc1ccnc(C(=O)N[C@H](C(=O)O[C@H](C)[C@@H](C)c2ccccc2C)C(C)C)c1OC(C)=O] | Example 5A | Thick Oil |
| 192 | 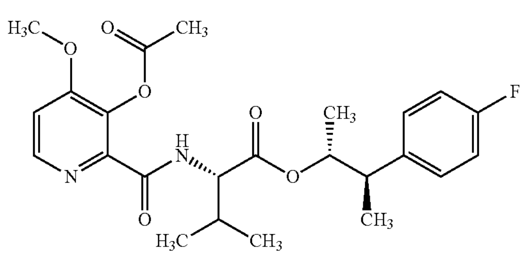 [SMILES: COc1ccnc(C(=O)N[C@H](C(=O)O[C@H](C)[C@H](C)c2ccc(F)cc2)C(C)C)c1OC(C)=O] | Example 5A | Thick Oil |

TABLE 1-continued

Compound Structure, Appearance, and Preparation Method

| Cmpd. No. | Structure | As Prepared According To | Appearance |
|---|---|---|---|
| 193 | 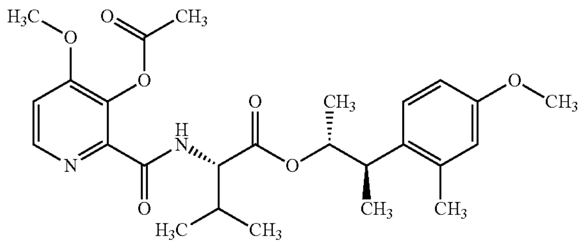 [SMILES: COc1ccc([C@@H](C)[C@@H](C)OC(=O)[C@@H](NC(=O)c2nccc(OC)c2OC(C)=O)C(C)C)c(C)c1] | Example 5A | Thick Oil |
| 194 | 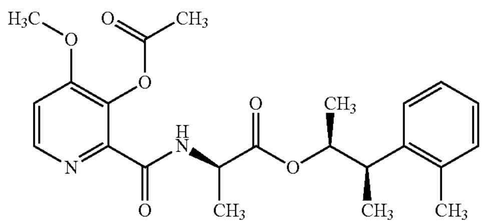 [SMILES: COc1ccnc(C(=O)N[C@H](C)C(=O)O[C@@H](C)[C@H](C)c2ccccc2C)c1OC(C)=O] | Example 5A | Thick Oil |
| 195 | 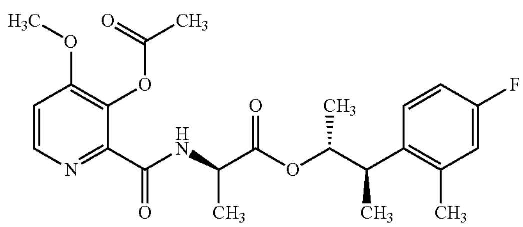 [SMILES: COc1ccnc(C(=O)N[C@H](C)C(=O)O[C@H](C)[C@H](C)c2ccc(F)cc2C)c1OC(C)=O] | Example 5A | Thick Oil |
| 196 | 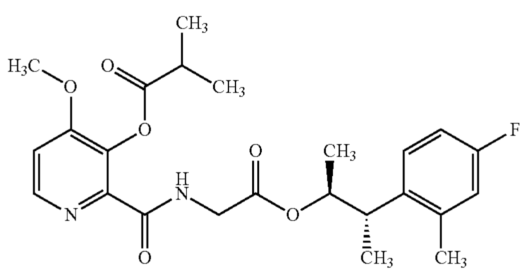 [SMILES: COc1ccnc(C(=O)NCC(=O)O[C@@H](C)[C@@H](C)c2ccc(F)cc2C)c1OC(=O)C(C)C] | Example 5C | Thick Oil |
| 197 | 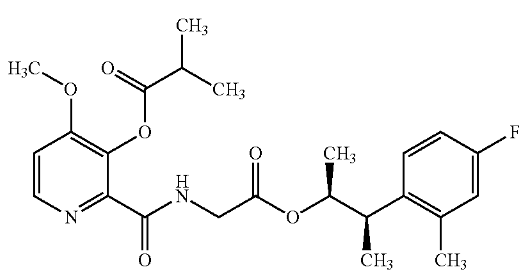 | Example 5C | Thick Oil |
| 198 | 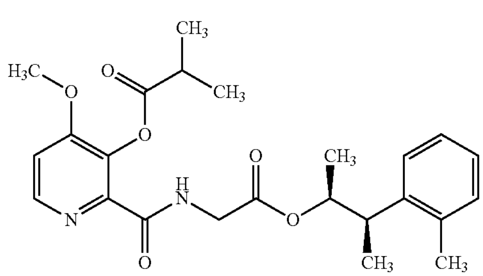 [SMILES: COc1ccnc(C(=O)NCC(=O)O[C@@H](C)[C@H](C)c2ccccc2C)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 199 | 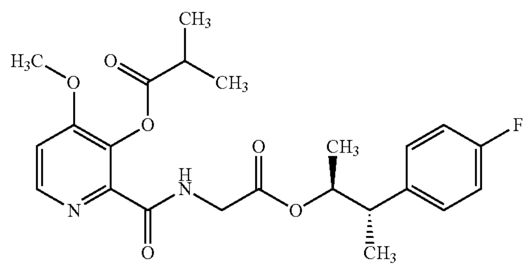 [SMILES: COc1ccnc(C(=O)NCC(=O)O[C@@H](C)[C@@H](C)c2ccc(F)cc2)c1OC(=O)C(C)C] | Example 5C | Thick Oil |
| 200 | 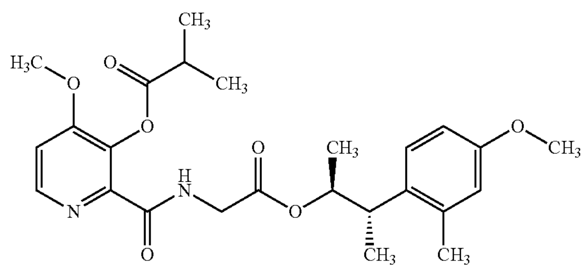 [SMILES: COc1ccc([C@H](C)[C@H](C)OC(=O)CNC(=O)c2nccc(OC)c2OC(=O)C(C)C)c(C)c1] | Example 5C | Thick Oil |
| 201 | 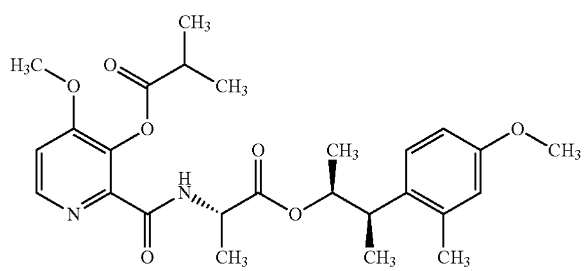 [SMILES: COc1ccc([C@@H](C)[C@H](C)OC(=O)[C@H](C)NC(=O)c2nccc(OC)c2OC(=O)C(C)C)c(C)c1] | Example 5C | Thick Oil |
| 202 | 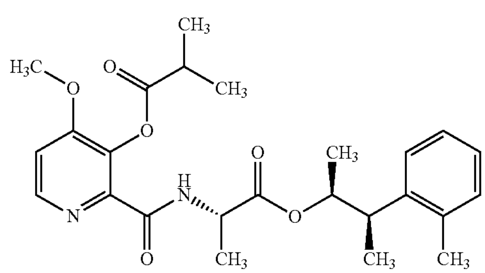 [SMILES: COc1ccnc(C(=O)N[C@@H](C)C(=O)O[C@@H](C)[C@H](C)c2ccccc2C)c1OC(=O)C(C)C] | Example 5C | Thick Oil |
| 203 | 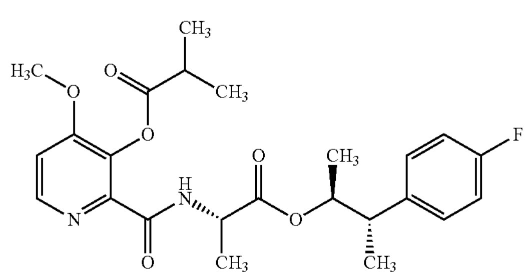 [SMILES: COc1ccnc(C(=O)N[C@@H](C)C(=O)O[C@@H](C)[C@@H](C)c2ccc(F)cc2)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 204 | 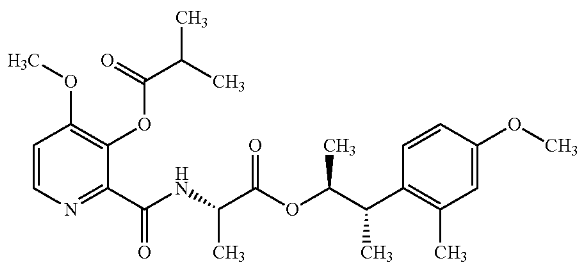 [SMILES: COc1ccc([C@H](C)[C@H](C)OC(=O)[C@H](C)NC(=O)c2nccc(OC)c2OC(=O)C(C)C)c(C)c1] | Example 5C | Thick Oil |
| 205 | 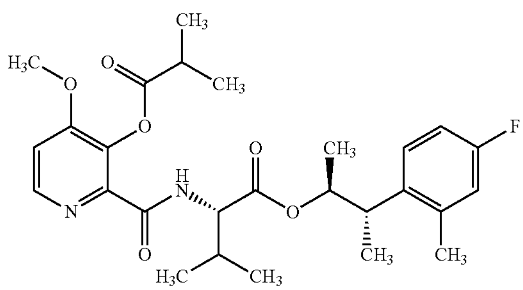 [SMILES: COc1ccnc(C(=O)N[C@H](C(=O)O[C@@H](C)[C@@H](C)c2ccc(F)cc2C)C(C)C)c1OC(=O)C(C)C] | Example 5C | Thick Oil |
| 206 | 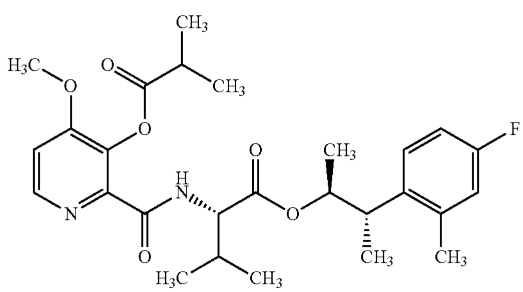 [SMILES: COc1ccnc(C(=O)N[C@H](C(=O)O[C@@H](C)[C@@H](C)c2ccc(F)cc2C)C(C)C)c1OC(=O)C(C)C] | Example 5C | Thick Oil |
| 207 | 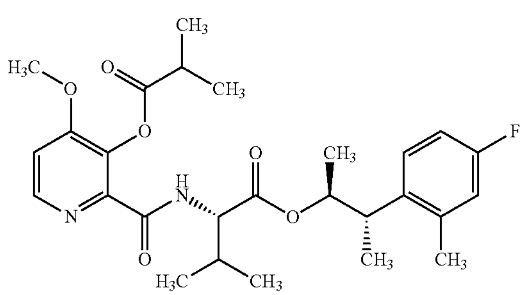 [SMILES: COc1ccnc(C(=O)N[C@H](C(=O)O[C@@H](C)[C@@H](C)c2ccc(F)cc2C)C(C)C)c1OC(=O)C(C)C] | Example 5C | Thick Oil |
| 208 | 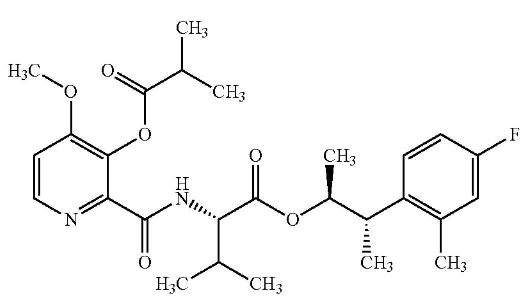 [SMILES: COc1ccnc(C(=O)N[C@H](C(=O)O[C@@H](C)[C@@H](C)c2ccc(F)cc2C)C(C)C)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 209 | 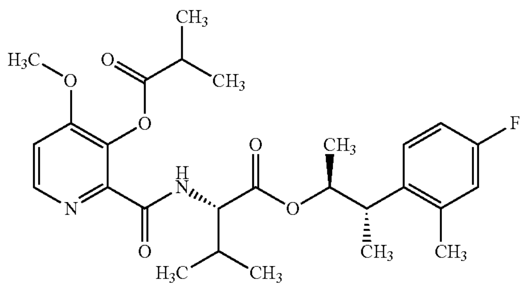 [SMILES: COc1ccnc(C(=O)N[C@H](C(=O)O[C@@H](C)[C@@H](C)c2ccc(F)cc2C)C(C)C)c1OC(=O)C(C)C] | Example 5C | Thick Oil |
| 210 | 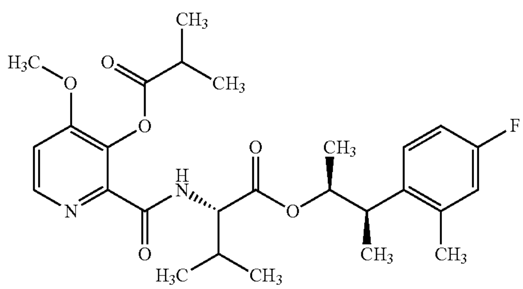 [SMILES: COc1ccnc(C(=O)N[C@H](C(=O)O[C@@H](C)[C@H](C)c2ccc(F)cc2C)C(C)C)c1OC(=O)C(C)C] | Example 5C | Thick Oil |
| 211 | 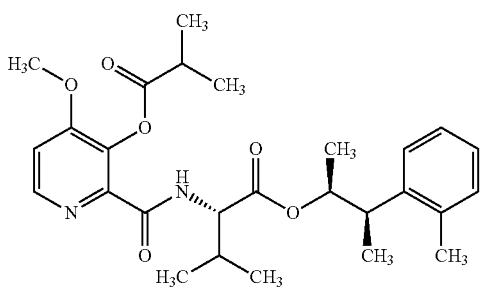 [SMILES: COc1ccnc(C(=O)N[C@H](C(=O)O[C@@H](C)[C@H](C)c2ccccc2C)C(C)C)c1OC(=O)C(C)C] | Example 5C | Thick Oil |
| 212 | 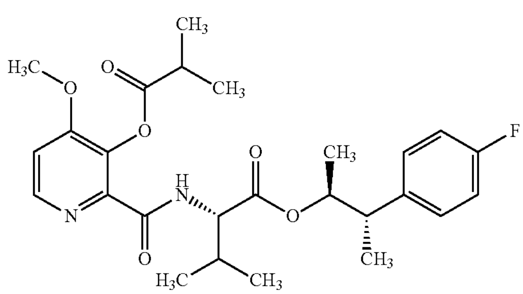 [SMILES: COc1ccnc(C(=O)N[C@H](C(=O)O[C@@H](C)[C@@H](C)c2ccc(F)cc2)C(C)C)c1OC(=O)C(C)C] | Example 5C | Thick Oil |
| 213 | 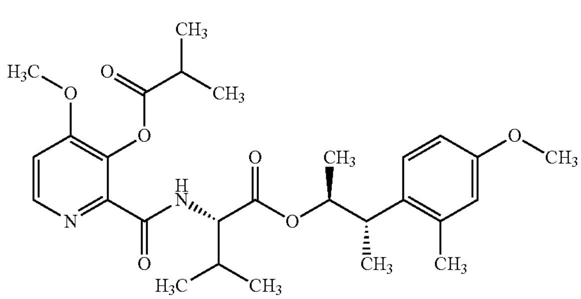 [SMILES: COc1ccc([C@H](C)[C@H](C)OC(=O)[C@@H](NC(=O)c2nccc(OC)c2OC(=O)C(C)C)C(C)C)c(C)c1] | Example 5C | Thick Oil |

TABLE 1-continued

Compound Structure, Appearance, and Preparation Method

| Cmpd. No. | Structure | As Prepared According To | Appearance |
|---|---|---|---|
| 214 | 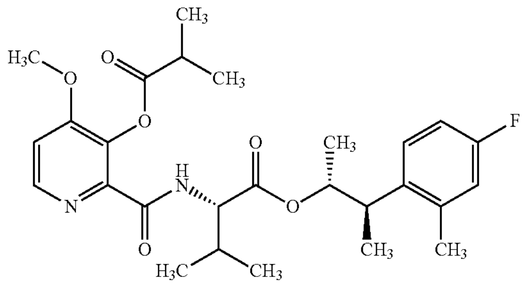 [SMILES: COc1ccnc(C(=O)N[C@H](C(=O)O[C@H](C)[C@H](C)c2ccc(F)cc2C)C(C)C)c1OC(=O)C(C)C] | Example 5C | Thick Oil |
| 215 | 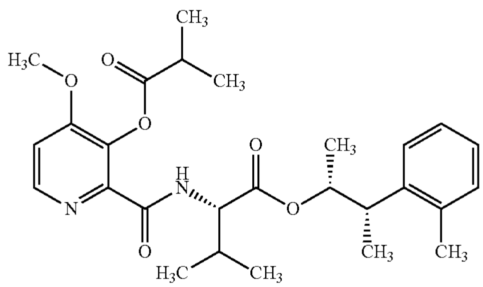 [SMILES: COc1ccnc(C(=O)N[C@H](C(=O)O[C@H](C)[C@@H](C)c2ccccc2C)C(C)C)c1OC(=O)C(C)C] | Example 5C | Thick Oil |
| 216 | 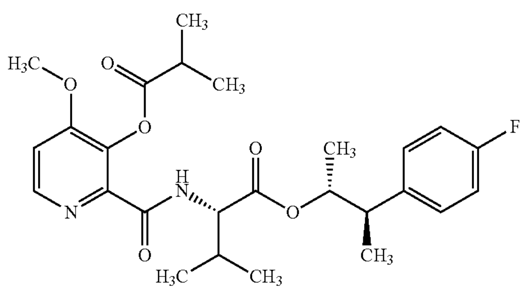 [SMILES: COc1ccnc(C(=O)N[C@H](C(=O)O[C@H](C)[C@H](C)c2ccc(F)cc2)C(C)C)c1OC(=O)C(C)C] | Example 5C | Thick Oil |
| 217 | 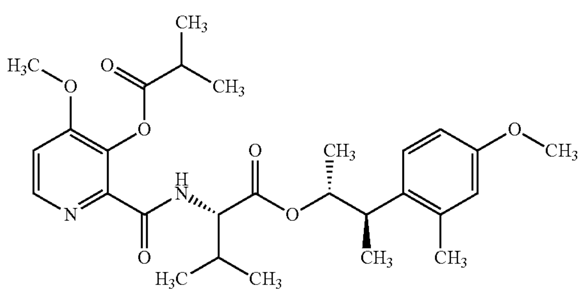 [SMILES: COc1ccc([C@@H](C)[C@@H](C)OC(=O)[C@@H](NC(=O)c2nccc(OC)c2OC(=O)C(C)C)C(C)C)c(C)c1] | Example 5C | Thick Oil |
| 218 | 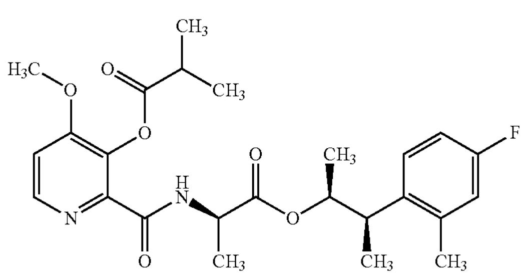 [SMILES: COc1ccnc(C(=O)N[C@H](C)C(=O)O[C@@H](C)[C@H](C)c2ccc(F)cc2C)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 219 | 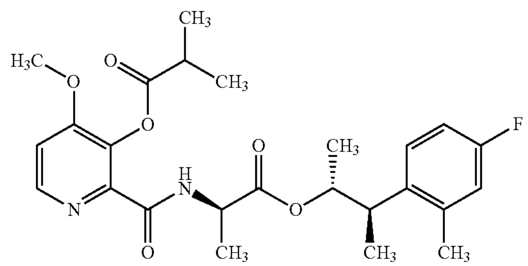 [SMILES: COc1ccnc(C(=O)N[C@H](C)C(=O)O[C@H](C)[C@H](C)c2ccc(F)cc2C)c1OC(=O)C(C)C] | Example 5C | Thick Oil |
| 220 | 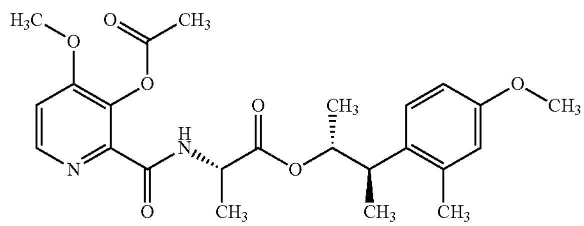 [SMILES: COc1ccc([C@@H](C)[C@@H](C)OC(=O)[C@H](C)NC(=O)c2nccc(OC)c2OC(C)=O)c(C)c1] | Example 5A | Thick Oil |
| 221 | 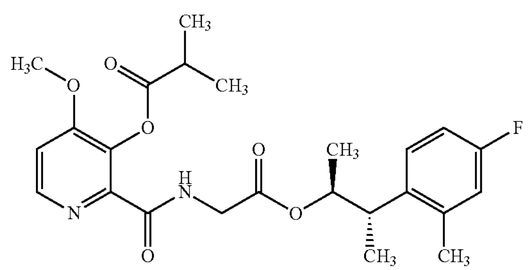 [SMILES: COc1ccnc(C(=O)NCC(=O)O[C@@H](C)[C@@H](C)c2ccc(F)cc2C)c1OC(=O)C(C)C] | Example 5C | Thick Oil |
| 222 | 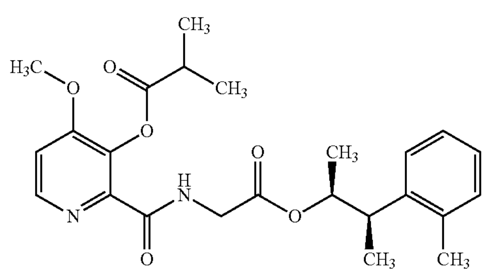 [SMILES: COc1ccnc(C(=O)NCC(=O)O[C@@H](C)[C@H](C)c2ccccc2C)c1OC(=O)C(C)C] | Example 5C | Thick Oil |
| 223 | 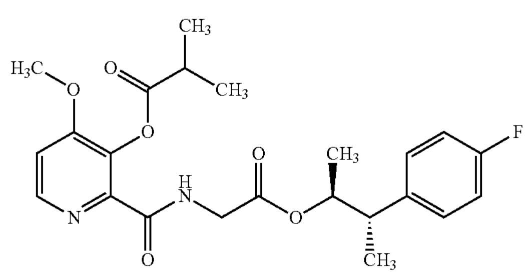 [SMILES: COc1ccnc(C(=O)NCC(=O)O[C@@H](C)[C@@H](C)c2ccc(F)cc2)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 224 | 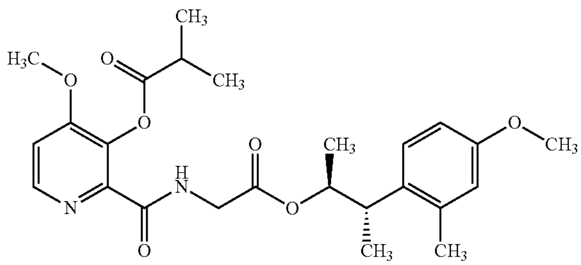 [SMILES: COc1ccc([C@H](C)[C@H](C)OC(=O)CNC(=O)c2nccc(OC)c2OC(=O)C(C)C)c(C)c1] | Example 5C | Thick Oil |
| 225 | 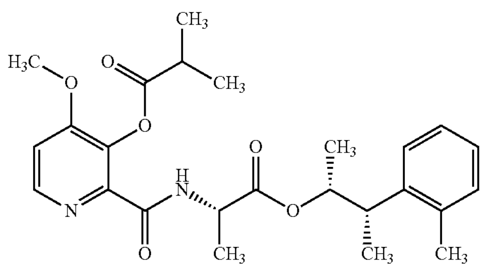 [SMILES: COc1ccnc(C(=O)N[C@@H](C)C(=O)O[C@H](C)[C@@H](C)c2ccccc2C)c1OC(=O)C(C)C] | Example 5C | Thick Oil |
| 226 | 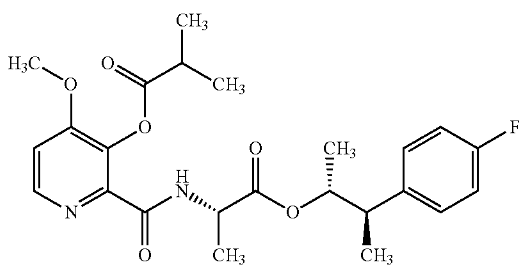 [SMILES: COc1ccnc(C(=O)N[C@@H](C)C(=O)O[C@H](C)[C@H](C)c2ccc(F)cc2)c1OC(=O)C(C)C] | Example 5C | Thick Oil |
| 227 | 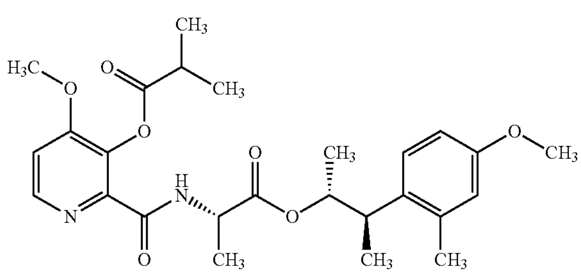 [SMILES: COc1ccc([C@@H](C)[C@@H](C)OC(=O)[C@H](C)NC(=O)c2nccc(OC)c2OC(=O)C(C)C)c(C)c1] | Example 5C | Thick Oil |
| 228 | 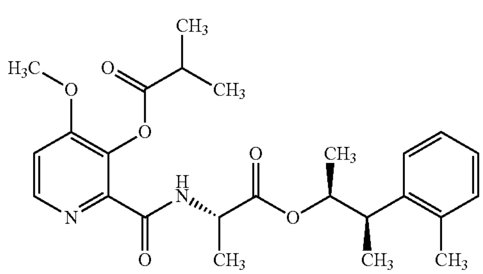 [SMILES: COc1ccnc(C(=O)N[C@@H](C)C(=O)O[C@@H](C)[C@H](C)c2ccccc2C)c1OC(=O)C(C)C] | Example 5C | Thick Oil |

TABLE 1-continued

Compound Structure, Appearance, and Preparation Method

| Cmpd. No. | Structure | As Prepared According To | Appearance |
|---|---|---|---|
| 229 | 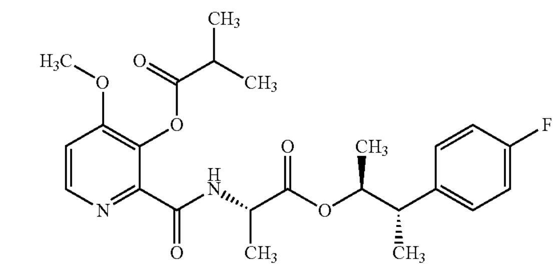 [SMILES: COc1ccnc(C(=O)N[C@@H](C)C(=O)O[C@@H](C)[C@@H](C)c2ccc(F)cc2)c1OC(=O)C(C)C] | Example 5C | Thick Oil |
| 230 | 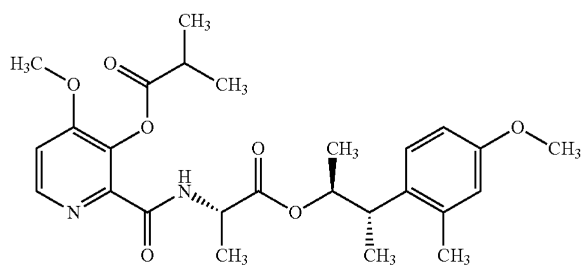 [SMILES: COc1ccc([C@H](C)[C@H](C)OC(=O)[C@H](C)NC(=O)c2nccc(OC)c2OC(=O)C(C)C)c(C)c1] | Example 5C | Thick Oil |
| 231 | 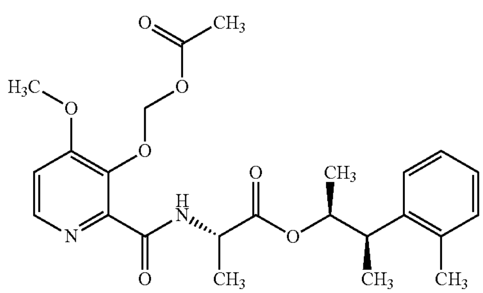 [SMILES: COc1ccnc(C(=O)N[C@@H](C)C(=O)O[C@@H](C)[C@H](C)c2ccccc2C)c1OCOC(C)=O] | Example 5B | Thick Oil |
| 232 | 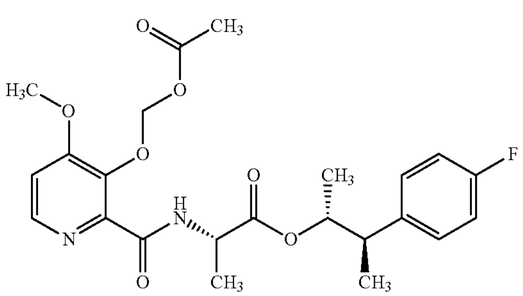 [SMILES: COc1ccnc(C(=O)N[C@@H](C)C(=O)O[C@H](C)[C@H](C)c2ccc(F)cc2)c1OCOC(C)=O] | Example 5B | Thick Oil |
| 233 | 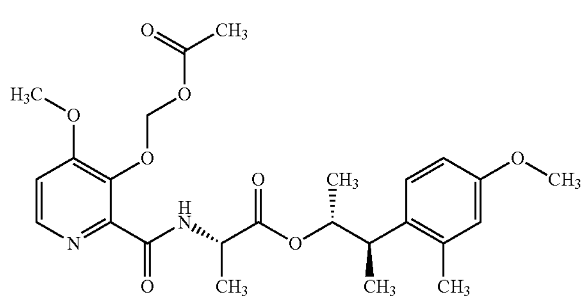 [SMILES: COc1ccc([C@@H](C)[C@@H](C)OC(=O)[C@H](C)NC(=O)c2nccc(OC)c2OCOC(C)=O)c(C)c1] | Example 5B | Thick Oil |

TABLE 1-continued

Compound Structure, Appearance, and Preparation Method

| Cmpd. No. | Structure | As Prepared According To | Appearance |
|---|---|---|---|
| 234 | 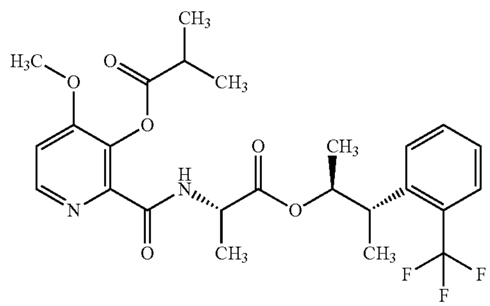 [SMILES: COc1ccnc(C(=O)N[C@@H](C)C(=O)O[C@@H](C)[C@@H](C)c2ccccc2C(F)(F)F)c1OC(=O)C(C)C] | Example 5C | Yellow Oil |
| 235 | 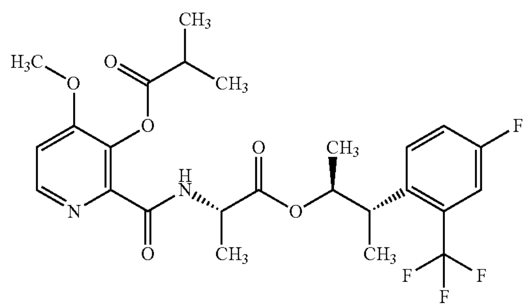 [SMILES: COc1ccnc(C(=O)N[C@@H](C)C(=O)O[C@@H](C)[C@@H](C)c2ccc(F)cc2C(F)(F)F)c1OC(=O)C(C)C] | Example 5C | Pale Yellow Oil |
| 236 | 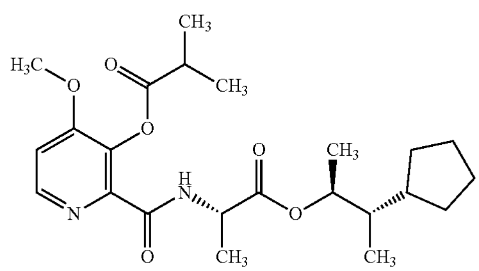 [SMILES: COc1ccnc(C(=O)N[C@@H](C)C(=O)O[C@@H](C)[C@@H](C)C2CCCC2)c1OC(=O)C(C)C] | Example 5C | Yellow Oil |
| 237 | 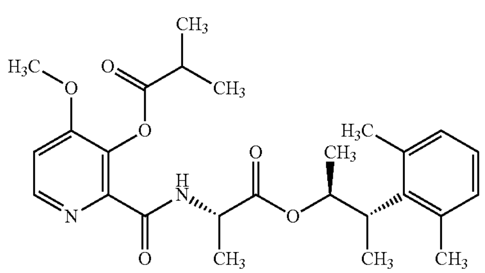 [SMILES: COc1ccnc(C(=O)N[C@@H](C)C(=O)O[C@@H](C)[C@@H](C)c2c(C)cccc2C)c1OC(=O)C(C)C] | Example 5C | Clear, Colorless Oil |
| 238 | 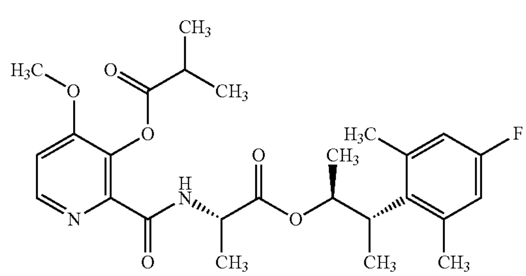 [SMILES: COc1ccnc(C(=O)N[C@@H](C)C(=O)O[C@@H](C)[C@@H](C)c2c(C)cc(F)cc2C)c1OC(=O)C(C)C] | Example 5C | Clear, Colorless Oil |

TABLE 1-continued

Compound Structure, Appearance, and Preparation Method

| Cmpd. No. | Structure | As Prepared According To | Appearance |
|---|---|---|---|
| 239 | 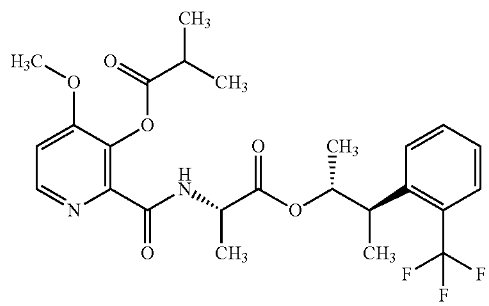 [SMILES: COc1ccnc(C(=O)N[C@@H](C)C(=O)O[C@H](C)[C@H](C)c2ccccc2C(F)(F)F)c1OC(=O)C(C)C] | Example 5C | Clear, Colorless Oil |
| 240 | 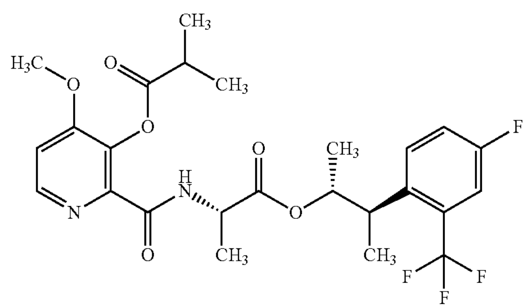 [SMILES: COc1ccnc(C(=O)N[C@@H](C)C(=O)O[C@H](C)[C@H](C)c2ccc(F)cc2C(F)(F)F)c1OC(=O)C(C)C] | Example 5C | Clear, Colorless Oil |
| 241 | 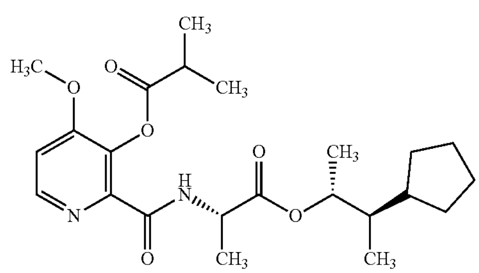 [SMILES: COc1ccnc(C(=O)N[C@@H](C)C(=O)O[C@H](C)[C@H](C)C2CCCC2)c1OC(=O)C(C)C] | Example 5C | Clear, Colorless Oil |
| 242 | 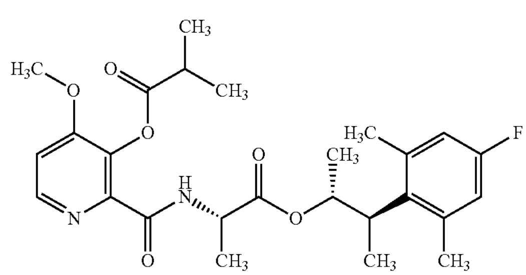 [SMILES: COc1ccnc(C(=O)N[C@@H](C)C(=O)O[C@H](C)[C@H](C)c2c(C)cc(F)cc2C)c1OC(=O)C(C)C] | Example 5C | Clear, Colorless Oil |
| 243 | 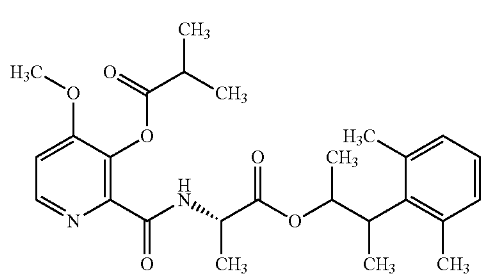 [SMILES: COc1ccnc(C(=O)N[C@@H](C)C(=O)OC(C)C(C)c2c(C)cccc2C)c1OC(=O)C(C)C] | Example 5C | Clear, Colorless Oil |

| Cmpd. No. | Structure | As Prepared According To | Appearance |
|---|---|---|---|
| 244 | 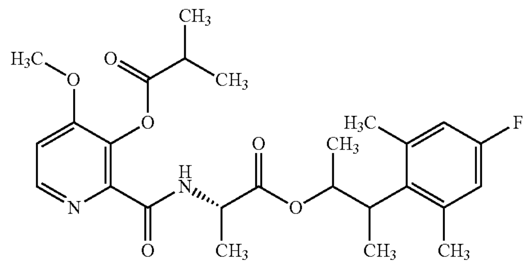 [SMILES: COc1ccnc(C(=O)N[C@@H](C)C(=O)OC(C)C(C)c2c(C)cc(F)cc2C)c1OC(=O)C(C)C] | Example 5C | Clear, Colorless Oil |
| 245 | 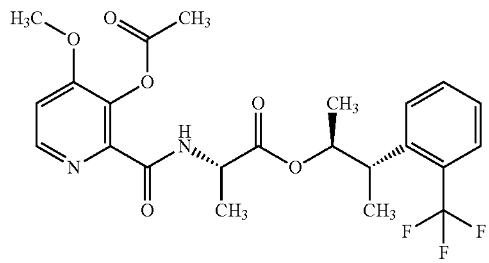 [SMILES: COc1ccnc(C(=O)N[C@@H](C)C(=O)O[C@@H](C)[C@@H](C)c2ccccc2C(F)(F)F)c1OC(C)=O] | Example 5C | Yellow Oil |
| 246 | 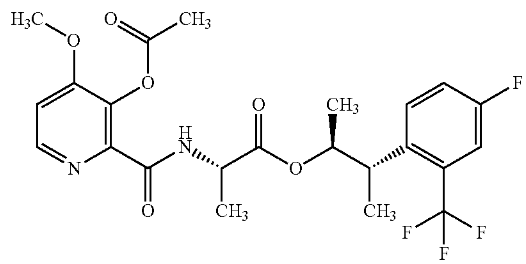 [SMILES: COc1ccnc(C(=O)N[C@@H](C)C(=O)O[C@@H](C)[C@@H](C)c2ccc(F)cc2C(F)(F)F)c1OC(C)=O] | Example 5C | Pale Yellow Oil |
| 247 | 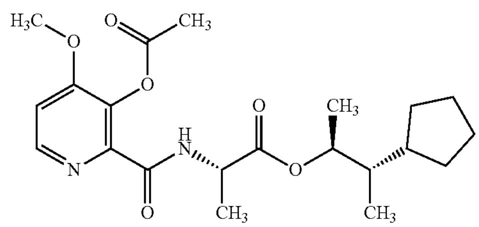 [SMILES: COc1ccnc(C(=O)N[C@@H](C)C(=O)O[C@@H](C)[C@@H](C)C2CCCC2)c1OC(C)=O] | Example 5C | Clear, Colorless Oil |
| 248 | 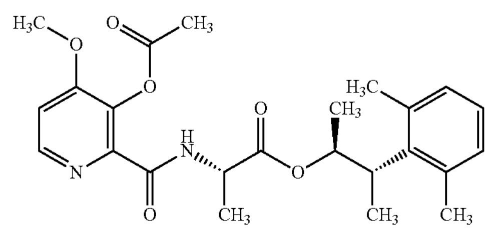 [SMILES: COc1ccnc(C(=O)N[C@@H](C)C(=O)O[C@@H](C)[C@@H](C)c2c(C)cccc2C)c1OC(C)=O] | Example 5C | Clear, Colorless Oil |
| 249 | 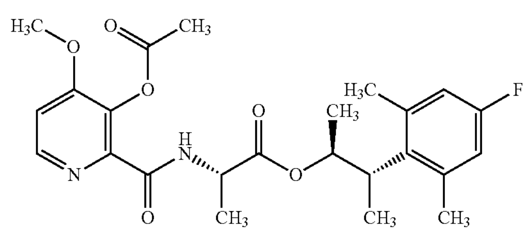 [SMILES: COc1ccnc(C(=O)N[C@@H](C)C(=O)O[C@@H](C)[C@@H](C)c2c(C)cc(F)cc2C)c1OC(C)=O] | Example 5C | Clear, Colorless Oil |

TABLE 1-continued

Compound Structure, Appearance, and Preparation Method

| Cmpd. No. | Structure | As Prepared According To | Appearance |
|---|---|---|---|
| 250 | 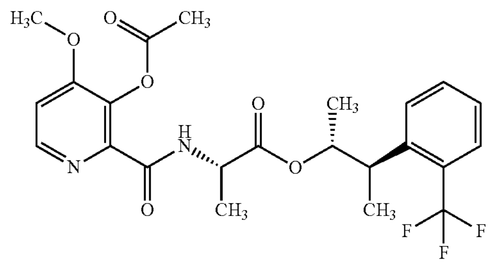 [SMILES: COc1ccnc(C(=O)N[C@@H](C)C(=O)O[C@H](C)[C@H](C)c2ccccc2C(F)(F)F)c1OC(C)=O] | Example 5C | Clear, Colorless Oil |
| 251 | 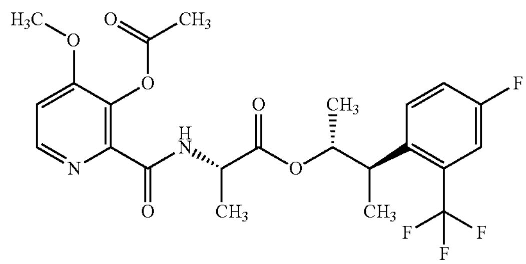 [SMILES: COc1ccnc(C(=O)N[C@@H](C)C(=O)O[C@H](C)[C@H](C)c2ccc(F)cc2C(F)(F)F)c1OC(C)=O] | Example 5C | Clear, Colorless Oil |
| 252 | 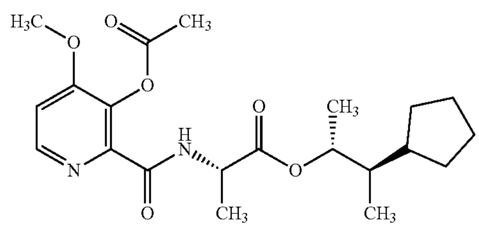 [SMILES: COc1ccnc(C(=O)N[C@@H](C)C(=O)O[C@H](C)[C@H](C)C2CCCC2)c1OC(C)=O] | Example 5C | Clear, Colorless Oil |
| 253 | 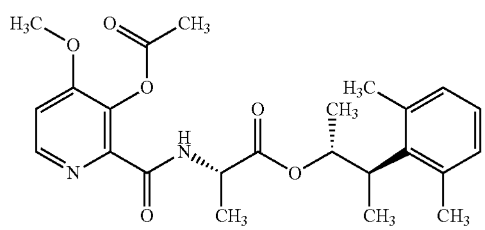 [SMILES: COc1ccnc(C(=O)N[C@@H](C)C(=O)O[C@H](C)[C@H](C)c2c(C)cccc2C)c1OC(C)=O] | Example 5C | Clear, Colorless Oil |
| 254 | 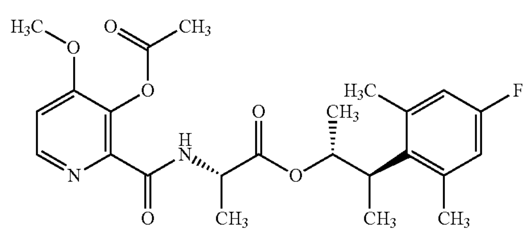 [SMILES: COc1ccnc(C(=O)N[C@@H](C)C(=O)O[C@H](C)[C@H](C)c2c(C)cc(F)cc2C)c1OC(C)=O] | Example 5C | Clear, Colorless Oil |
| 255 | 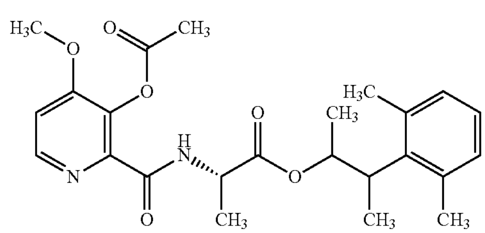 [SMILES: COc1ccnc(C(=O)N[C@@H](C)C(=O)OC(C)C(C)c2c(C)cccc2C)c1OC(C)=O] | Example 5C | Clear, Colorless Oil |

TABLE 1-continued

Compound Structure, Appearance, and Preparation Method

| Cmpd. No. | Structure | As Prepared According To | Appearance |
|---|---|---|---|
| 256 | 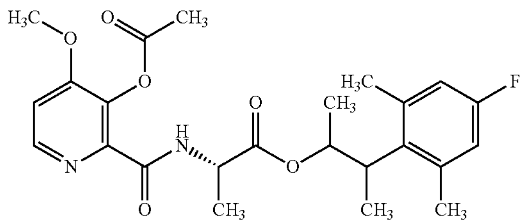 [SMILES: COc1ccnc(C(=O)N[C@@H](C)C(=O)OC(C)C(C)c2c(C)cc(F)cc2C)c1OC(C)=O] | Example 5C | Clear, Colorless Oil |
| 257 | 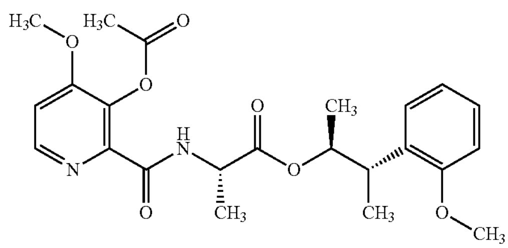 [SMILES: COc1ccccc1[C@H](C)[C@H](C)OC(=O)[C@H](C)NC(=O)c1nccc(OC)c1OC(C)=O] | Example 5A | Colorless Oil |
| 258 | 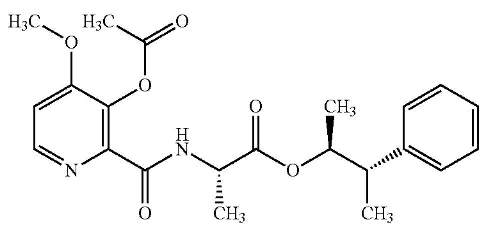 [SMILES: COc1ccnc(C(=O)N[C@@H](C)C(=O)O[C@@H](C)[C@@H](C)c2ccccc2)c1OC(C)=O] | Eaxmple 5A | Colorless Oil |
| 259 | 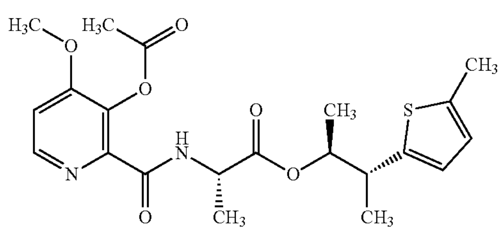 [SMILES: COc1ccnc(C(=O)N[C@@H](C)C(=O)O[C@@H](C)[C@@H](C)c2ccc(C)s2)c1OC(C)=O] | Example 5A | Pale Yellow Oil |
| 260 | 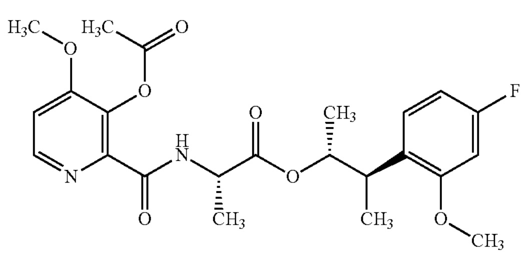 [SMILES: COc1cc(F)ccc1[C@@H](C)[C@@H](C)OC(=O)[C@H](C)NC(=O)c1nccc(OC)c1OC(C)=O] | Example 5A | Colorless Oil |
| 261 | 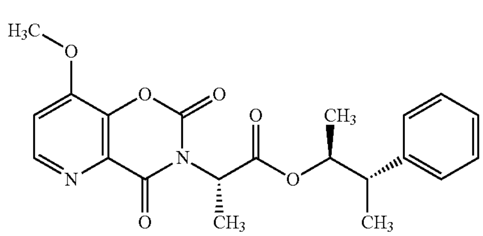 [SMILES: COc1ccnc2c(=O)n([C@@H](C)C(=O)O[C@@H](C)[C@@H](C)c3ccccc3)c(=O)oc12] | Example 8 | Off-White Foam |

TABLE 1-continued

Compound Structure, Appearance, and Preparation Method

| Cmpd. No. | Structure | As Prepared According To | Appearance |
|---|---|---|---|
| 262 | 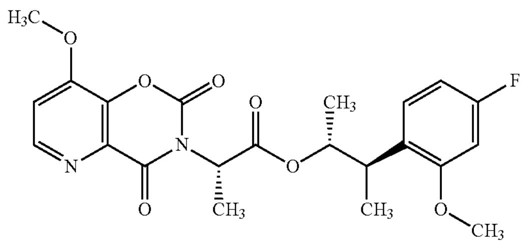 [SMILES: COc1cc(F)ccc1[C@@H](C)[C@@H](C)OC(=O)[C@H](C)n1c(=O)oc2c(OC)ccnc2c1=O] | Example 8 | Tan Foam |
| 263 | 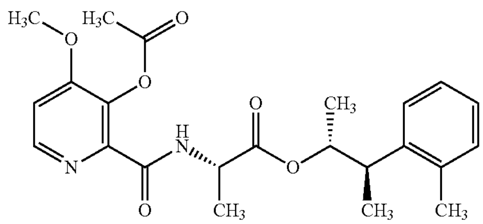 [SMILES: COc1ccnc(C(=O)N[C@@H](C)C(=O)O[C@H](C)[C@H](C)c2ccccc2C)c1OC(C)=O] | Example 5A | Clear Oil |
| 264 | 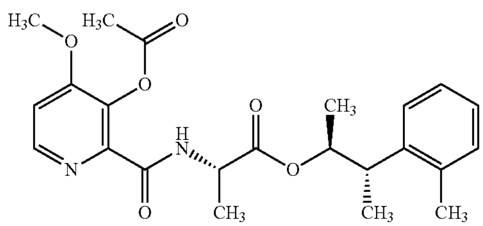 [SMILES: COc1ccnc(C(=O)N[C@@H](C)C(=O)O[C@@H](C)[C@@H](C)c2ccccc2C)c1OC(C)=O] | Example 5A | Clear Oil |
| 265 | 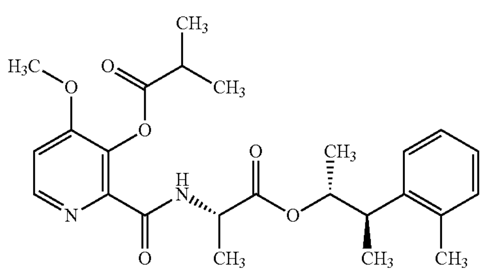 [SMILES: COc1ccnc(C(=O)N[C@@H](C)C(=O)O[C@H](C)[C@H](C)c2ccccc2C)c1OC(=O)C(C)C] | Example 5C | Clear Oil |
| 266 | 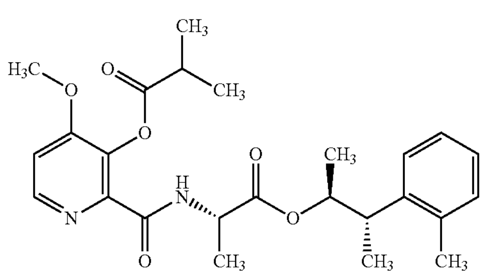 [SMILES: COc1ccnc(C(=O)N[C@@H](C)C(=O)O[C@@H](C)[C@@H](C)c2ccccc2C)c1OC(=O)C(C)C] | Example 5C | Colorless Oil |
| 267 | 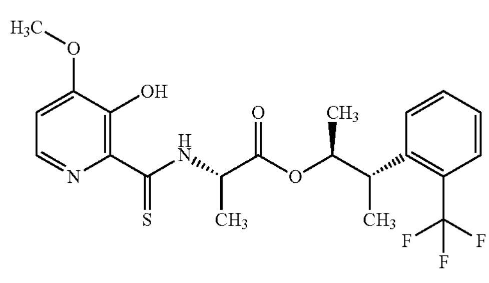 | Example 6 Step 1 | Yellow Semisolid |

TABLE 1-continued

Compound Structure, Appearance, and Preparation Method

| Cmpd. No. | Structure | As Prepared According To | Appearance |
|---|---|---|---|
| 268 | 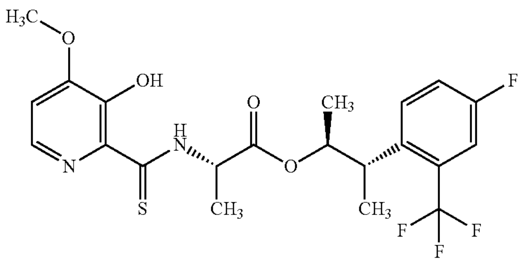 | Example 6 Step 1 | Yellow Semisolid |
| 269 | 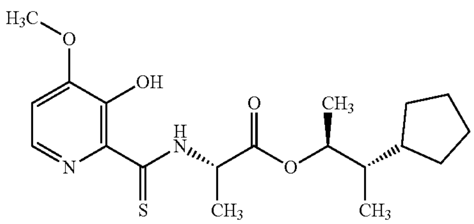 | Example 6 Step 1 | Orange Semisolid |
| 270 | 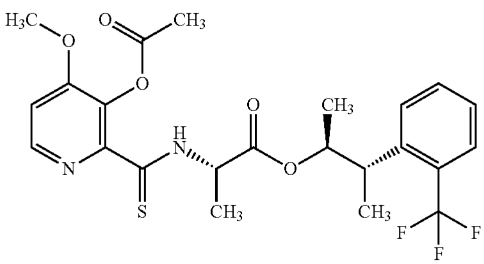 | Example 6 Step 2 | Yellow Oil |
| 271 | 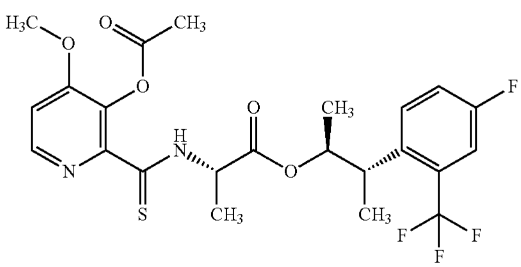 [SMILES: COc1ccnc(C(=S)N[C@@H](C)C(=O)O[C@@H](C)[C@@H](C)c2ccc(F)cc2C(F)(F)F)c1OC(C)=O] | Example 6 Step 2 | Yellow Oil |
| 272 | 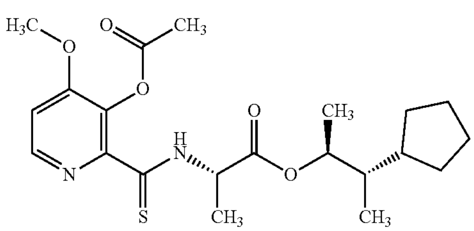 [SMILES: COc1ccnc(C(=S)N[C@@H](C)C(=O)O[C@@H](C)[C@@H](C)C2CCCC2)c1OC(C)=O] | Example 6 Step 2 | Yellow Oil |
| 273 | 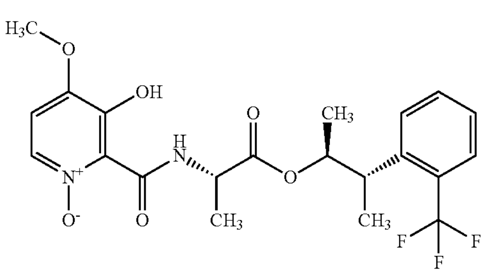 [SMILES: COc1cc[n+]([O-])c(C(=O)N[C@@H](C)C(=O)O[C@@H](C)[C@@H](C)c2ccccc2C(F)(F)F)c1O] | Example 7 | Yellow Oil |

TABLE 1-continued

Compound Structure, Appearance, and Preparation Method

| Cmpd. No. | Structure | As Prepared According To | Appearance |
|---|---|---|---|
| 274 | 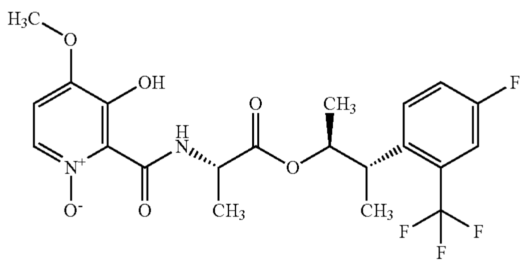 [SMILES: COc1cc[n+]([O-])c(C(=O)N[C@@H](C)C(=O)O[C@@H](C)[C@@H](C)c2ccc(F)cc2C(F)(F)F)c1O] | Example 7 | Pale Yellow Oil |
| 275 | 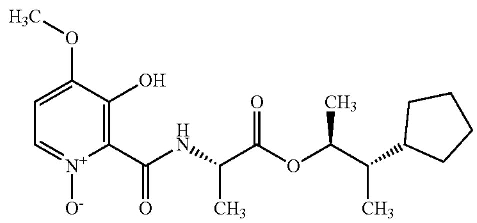 [SMILES: COc1cc[n+]([O-])c(C(=O)N[C@@H](C)C(=O)O[C@@H](C)[C@@H](C)C2CCCC2)c1O] | Example 7 | Pale Yellow Oil |
| 276 | 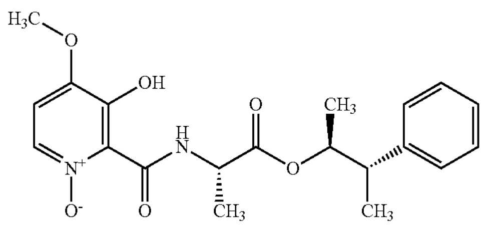 [SMILES: COc1cc[n+]([O-])c(C(=O)N[C@@H](C)C(=O)O[C@@H](C)[C@@H](C)c2ccccc2)c1O] | Example 7 | Pale Yellow Oil |
| 277 | 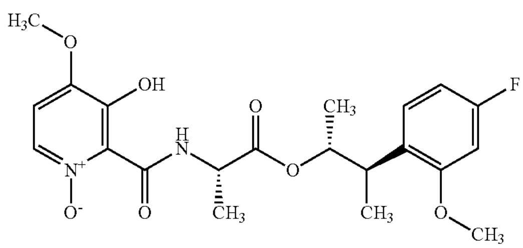 | Example 7 | Pale Yellow Oil |
| 278 | 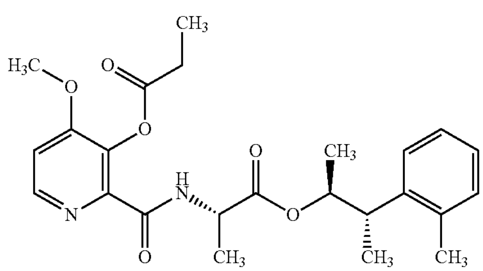 [SMILES: CCC(=O)Oc1c(OC)ccnc1C(=O)N[C@@H](C)C(=O)O[C@@H](C)[C@@H](C)c1ccccc1C] | Example 5C | White Solid |
| 279 | 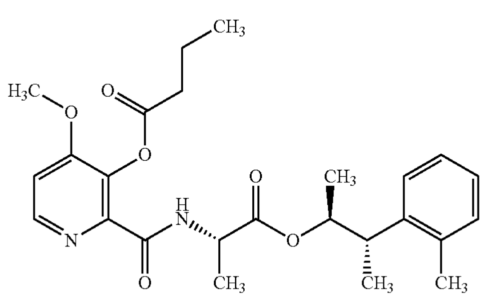 [SMILES: CCCC(=O)Oc1c(OC)ccnc1C(=O)N[C@@H](C)C(=O)O[C@@H](C)[C@@H](C)c1ccccc1C] | Example 5C | White Solid |

TABLE 1-continued

Compound Structure, Appearance, and Preparation Method

| Cmpd. No. | Structure | As Prepared According To | Appearance |
|---|---|---|---|
| 280 | 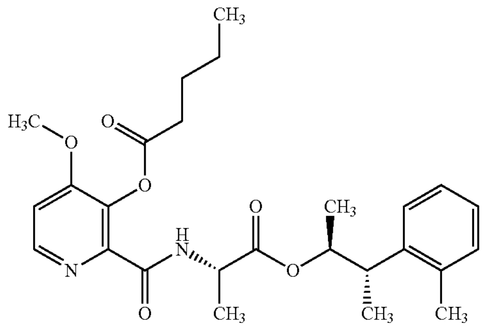 [SMILES: CCCCC(=O)Oc1c(OC)ccnc1C(=O)N[C@@H](C)C(=O)O[C@@H](C)[C@@H](C)c1ccccc1C] | Example 5C | Yellow Oil |
| 281 | 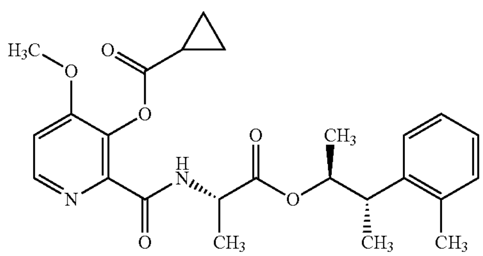 [SMILES: COc1ccnc(C(=O)N[C@@H](C)C(=O)O[C@@H](C)[C@@H](C)c2ccccc2C)c1OC(=O)C1CC1] | Example 5C | Clear Oil |
| 282 | 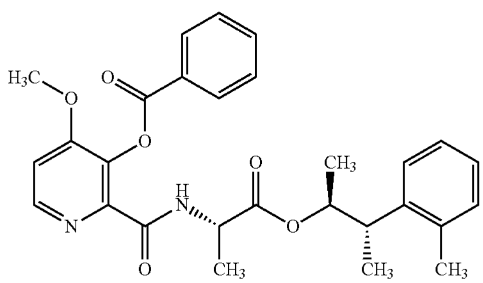 [SMILES: COc1ccnc(C(=O)N[C@@H](C)C(=O)O[C@@H](C)[C@@H](C)c2ccccc2C)c1OC(=O)c1ccccc1] | Example 5C | White Solid |
| 284 | 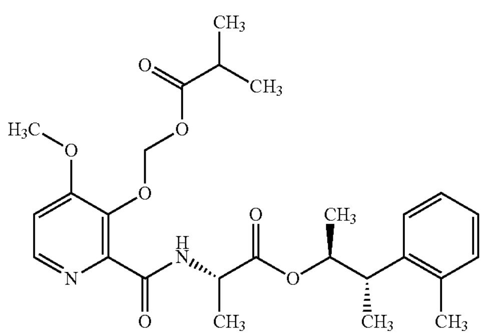 [SMILES: COc1ccnc(C(=O)N[C@@H](C)C(=O)O[C@@H](C)[C@@H](C)c2ccccc2C)c1OCOC(=O)C(C)C] | Example 5C | Thick Yellow Oil |
| 285 | 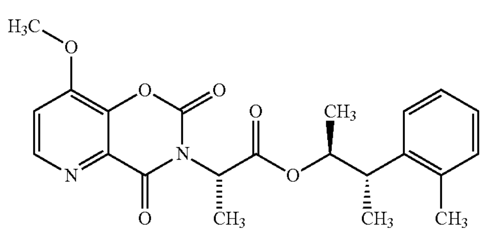 [SMILES: COc1ccnc2c(=O)n([C@@H](C)C(=O)O[C@@H](C)[C@@H](C)c3ccccc3C)c(=O)oc12] | Example 5C | Glassy Solid |

*Cmpd. No. - Compound Number

TABLE 2

| | | | Analytical Data | |
|---|---|---|---|---|
| Cmpd. No. | Melting Point (° C.) | IR (cm$^{-1}$) | MASS SPEC | NMR |
| 1 | | | ESIMS m/z 362.3 ([M + Na]$^+$) | |
| 2 | | | ESIMS m/z 354.3 ([M + H]$^+$) | |
| 3 | | | ESIMS m/z 382.3 ([M + H]$^+$) | |
| 4 | | | ESIMS m/z 376.3 ([M + Na]$^+$) | |
| 5 | | | ESIMS m/z 362.3 ([M + Na]$^+$) | |
| 6 | | | ESIMS m/z 354.3 ([M + H]$^+$) | |
| 7 | | | ESIMS m/z 382.3 ([M + H]$^+$) | |
| 8 | | | ESIMS m/z 354.3 ([M + H]$^+$) | |
| 9 | | | ESIMS m/z 344.3 ([M + Na]$^+$) | |
| 10 | | | ESIMS m/z 336.5 ([M + H]$^+$) | |
| 11 | | | ESIMS m/z 364.3 ([M + H]$^+$) | |
| 12 | | | ESIMS m/z 336.2 ([M + H]$^+$) | |
| 13 | | | ESIMS m/z 348.2 ([M + Na]$^+$) | |
| 14 | | | ESIMS m/z 340.5 ([M + H]$^+$) | |
| 15 | | | ESIMS m/z 390.3 ([M + Na]$^+$) | |
| 16 | | | ESIMS m/z 340.2 ([M + H]$^+$) | |
| 17 | | | ESIMS m/z 374.3 ([M + Na]$^+$) | |
| 18 | | | ESIMS m/z 366.3 ([M + H]$^+$) | |
| 19 | | | ESIMS m/z 394.3 ([M + H]$^+$) | |
| 20 | | | ESIMS m/z 366.3 ([M + H]$^+$) | |
| 21 | | | ESIMS m/z 362.3 ([M + Na]$^+$) | |
| 22 | | | ESIMS m/z 376.3 ([M + Na]$^+$) | |
| 23 | | | ESIMS m/z 382.3 ([M + H]$^+$) | |
| 24 | | | ESIMS m/z 354.3 ([M + H]$^+$) | |
| 25 | | | ESIMS m/z 362.3 ([M + Na]$^+$) | |
| 26 | | | ESIMS m/z 376.3 ([M + Na]$^+$) | |
| 27 | | | ESIMS m/z 382.3 ([M + H]$^+$) | |
| 28 | | | ESIMS m/z 376.3 ([M + Na]$^+$) | |
| 29 | | | ESIMS m/z 344.3 ([M + Na]$^+$) | |
| 30 | | | ESIMS m/z 336.2 ([M + H]$^+$) | |
| 31 | | | ESIMS m/z 364.3 ([M + H]$^+$) | |
| 32 | | | ESIMS m/z 336.3 ([M + H]$^+$) | |
| 33 | | | ESIMS m/z 348.2 ([M + Na]$^+$) | |
| 34 | | | ESIMS m/z 340.3 ([M + H]$^+$) | |
| 35 | | | ESIMS m/z 368.3 ([M + H]$^+$) | |
| 36 | | | ESIMS m/z 340.3 ([M + H]$^+$) | |
| 37 | | | ESIMS m/z 374.3 ([M + Na]$^+$) | |

TABLE 2-continued

Analytical Data

| Cmpd. No. | Melting Point (° C.) | IR (cm$^{-1}$) | MASS SPEC | NMR |
|---|---|---|---|---|
| 38 | | | ESIMS m/z 366.3 ([M + H]$^+$) | |
| 39 | | | ESIMS m/z 394.4 ([M + H]$^+$) | |
| 40 | | | ESIMS m/z 366.3 ([M + H]$^+$) | |
| 41 | | | ESIMS m/z 372.3 ([M + Na]$^+$) | |
| 42 | | | ESIMS m/z 372.3 ([M + Na]$^+$) | |
| 43 | | IR (thin film) 3355, 2981, 1711, 1310, 1150, 1116, 1046, 770 cm$^{-1}$ | HRMS-ESI (m/z) [M + Na]$^+$ calcd for C$_{19}$H$_{26}$F$_3$NNaO$_4$, 412.1706; found, 412.1698 | $^1$H NMR (400 MHz, CDCl$_3$) δ 7.64 (dd, J = 7.8, 1.4 Hz, 1H), 7.52 (td, J = 7.6, 1.3 Hz, 1H), 7.43 (d, J = 7.9 Hz, 1H), 7.35-7.28 (m, 1H), 5.25-5.13 (m, 1H), 5.08 (d, J = 7.9 Hz, 1H), 4.42-4.28 (m, 1H), 3.41-3.27 (m, 1H), 1.46 (s, 9H), 1.43 (d, J = 7.2 Hz, 3H), 1.27 (d, J = 6.8 Hz, 3H), 1.07 (d, J = 6.3 Hz, 3H). $^{19}$F NMR (376 MHz, CDCl$_3$) δ −58.25. |
| 44 | | IR (thin film) 3362, 2982, 1711, 1499, 1314, 1154, 1121, 1046, 909, 879 cm$^{-1}$ | HRMS-ESI (m/z) [M + Na]$^+$ calcd for C$_{19}$H$_{25}$F$_4$NNaO$_4$, 430.1612; found, 430.1607 | $^1$H NMR (400 MHz, CDCl$_3$) δ 7.42 (dd, J = 8.8, 5.4 Hz, 1H), 7.35 (dd, J = 9.2, 2.8 Hz, 1H), 7.23 (td, J = 8.2, 2.8 Hz, 1H), 5.18-5.09 (m, 1H), 5.07 (d, J = 7.6 Hz, 1H), 4.41-4.27 (m, 1H), 3.36-3.24 (m, 1H), 1.46 (s, 9H), 1.42 (d, J = 7.3 Hz, 3H), 1.26 (d, J = 6.8 Hz, 3H), 1.08 (d, J = 6.2 Hz, 3H). $^{19}$F NMR (376 MHz, CDCl$_3$) δ −58.81, −114.05. |
| 45 | | IR (thin film) 3364, 2981, 1712, 1310, 1150, 1116, 1046, 770 cm$^{-1}$ | HRMS-ESI (m/z) [M + Na]$^+$ calcd for C$_{19}$H$_{26}$F$_3$NNaO$_4$, 412.1706; found, 412.1699 | $^1$H NMR (400 MHz, CDCl$_3$) δ 7.64 (dd, J = 8.0, 1.3 Hz, 1H), 7.52 (td, J = 7.6, 1.3 Hz, 1H), 7.43 (d, J = 7.8 Hz, 1H), 7.32 (t, J = 7.6 Hz, 1H), 5.25-5.13 (m, 1H), 5.04 (d, J = 7.8 Hz, 1H), 4.42-4.26 (m, 1H), 3.40-3.26 (m, 1H), 1.46 (s, 9H), 1.41 (d, J = 7.3 Hz, 3H), 1.29 (d, J = 6.7 Hz, 3H), 1.05 (d, J = 6.2 Hz, 3H). $^{19}$F NMR (376 MHz, CDCl$_3$) δ −58.25. |
| 46 | | IR (thin film) 2981, 1711, 1498, 1314, 1154, 1120, 1045, 909, 879, 739 cm$^{-1}$ | HRMS-ESI (m/z) [M + Na]$^+$ calcd for C$_{19}$H$_{25}$F$_4$NNaO$_4$, 430.1612; found, 430.1603 | $^1$H NMR (400 MHz, CDCl$_3$) δ 7.42 (dd, J = 8.8, 5.3 Hz, 1H), 7.35 (dd, J = 9.2, 2.8 Hz, 1H), 7.23 (td, J = 8.3, 2.9 Hz, 1H), 5.20-5.09 (m, 1H), 5.02 (d, J = 7.8 Hz, 1H), 4.42-4.23 (m, 1H), 3.29 (tt, J = 7.6, 6.0 Hz, 1H), 1.46 (s, 9H), 1.40 (d, J = 7.2 Hz, 3H), 1.28 (d, J = 6.8 Hz, 3H), 1.07 (d, J = 6.4 Hz, 3H). $^{19}$F NMR (376 MHz, CDCl$_3$) δ −58.78, −58.80, −114.19. |
| 47 | | IR (thin film) 3357, 2977, 1713, 1500, 1452, 1365, 1162, 1055, 1006, 769 cm$^{-1}$ | HRMS-ESI (m/z) [M + NH$_4$]$^+$ calcd for C$_{20}$H$_{35}$N$_2$O$_4$, 367.2587; found, 367.2587 | $^1$H NMR (400 MHz, CDCl$_3$) δ 7.05-6.91 (m, 3H), 5.58 (ddq, J = 10.5, 8.3, 6.2 Hz, 1H), 5.11 (s, 1H), 4.42-4.28 (m, 1H), 3.49-3.33 (m, 1H), 2.44-2.33 (m, 6H), 1.46 (d, J = 1.1 Hz, 3H), 1.45-1.39 (m, 3H), 1.27 (dd, J = 7.1, 3.5 Hz, 3H), 1.02 (dd, J = 7.7, 6.2 Hz, 3H). |
| 48 | | IR (thin film) 3357, 2978, 1712, 1366, 1162, 1057, 1023, 1006, 857 cm$^{-1}$ | HRMS-ESI (m/z) [M + Na]$^+$ calcd for C$_{20}$H$_{30}$FNNaO$_4$, 390.2051; found, 390.2048 | $^1$H NMR (400 MHz, CDCl$_3$) δ 6.70 (ddd, J = 16.1, 9.4, 2.9 Hz, 2H), 5.53 (ddq, J = 10.5, 8.6, 6.2 Hz, 1H), 5.11 (s, 1H), 4.41-4.26 (m, 1H), 3.44-3.27 (m, 1H), 2.40 (d, J = 1.7 Hz, 3H), 2.35 (s, 3H), 1.46 (s, 9H), 1.45-1.38 (m, 3H), 1.25 (dd, J = 7.2, 3.8 Hz, 3H), 1.01 (dd, J = 7.6, 6.2 Hz, 3H). $^{19}$F NMR (376 MHz, CDCl$_3$) δ −118.37, −118.44. |
| 49 | | IR (thin film) 3361, 2977, 1713, 1365, 1162, | HRMS-ESI (m/z) [M + Na]$^+$ calcd for C$_{20}$H$_{31}$NNaO$_4$, 372.2145; found, | $^1$H NMR (400 MHz, CDCl$_3$) δ 7.04-6.93 (m, 3H), 5.58 (ddq, J = 10.4, 8.3, 6.2 Hz, 1H), 5.10 (d, J = 7.3 Hz, 1H), 4.43-4.27 (m, 1H), 3.48-3.29 (m, |

TABLE 2-continued

Analytical Data

| Cmpd. No. | Melting Point (° C.) | IR (cm⁻¹) | MASS SPEC | NMR |
|---|---|---|---|---|
| | | 1056, 1006, 769 cm$^{-1}$ | 372.2144 | 1H), 2.41 (d, J = 1.6 Hz, 3H), 2.37 (s, 3H), 1.46 (d, J = 1.1 Hz, 9H), 1.45-1.39 (m, 3H), 1.27 (dd, J = 7.1, 3.5 Hz, 3H), 1.02 (dd, J = 7.7, 6.2 Hz, 3H). |
| 50 | | IR (thin film) 3359, 2978, 1712, 1450, 1366, 1163, 1057, 1023, 1006, 858, 732 cm$^{-1}$ | HRMS-ESI (m/z) [M + Na]⁺ calcd for C$_{20}$H$_{30}$FNNaO$_4$, 390.2051; found, 390.2050 | $^1$H NMR (400 MHz, CDCl$_3$) δ 6.70 (ddd, J = 16.2, 9.4, 2.9 Hz, 2H), 5.53 (ddq, J = 10.5, 8.6, 6.2 Hz, 1H), 5.09 (s, 1H), 4.43-4.28 (m, 1H), 3.34 (dp, J = 10.3, 6.9 Hz, 1H), 2.40 (d, J = 1.7 Hz, 3H), 2.35 (s, 3H), 1.46 (s, 9H), 1.45-1.36 (m, 3H), 1.26 (d, J = 3.8 Hz, 3H), 1.01 (dd, J = 7.6, 6.2 Hz, 3H). $^{19}$F NMR (376 MHz, CDCl$_3$) δ −118.40, −118.46. |
| 51 | | IR (thin film) 3356, 2977, 1713, 1500, 1452, 1163, 1056, 769 cm$^{-1}$ | HRMS-ESI (m/z) [M + Na]⁺ calcd for C$_{20}$H$_{31}$NNaO$_4$, 372.2145; found, 372.2137 | $^1$H NMR (400 MHz, CDCl$_3$) δ 7.03-6.94 (m, 3H), 5.58 (ddq, J = 10.5, 8.3, 6.2 Hz, 1H), 5.10 (d, J = 7.1 Hz, 1H), 4.43-4.27 (m, 1H), 3.50-3.34 (m, 1H), 2.41 (d, J = 1.6 Hz, 3H), 2.37 (s, 3H), 1.46 (d, J = 1.1 Hz, 9H), 1.45-1.36 (m, 3H), 1.27 (dd, J = 7.2, 3.5 Hz, 3H), 1.02 (dd, J = 7.7, 6.2 Hz, 3H). |
| 52 | | IR (thin film) 3358, 2978, 1712, 1366, 1163, 1058, 1023, 1006, 858, 733 cm$^{-1}$ | HRMS-ESI (m/z) [M + Na]⁺ calcd for C$_{20}$H$_{30}$FNNaO$_4$, 390.2051; found, 390.2051 | $^1$H NMR (400 MHz, CDCl$_3$) δ 6.70 (ddd, J = 16.0, 9.4, 2.9 Hz, 2H), 5.53 (ddq, J = 10.5, 8.5, 6.2 Hz, 1H), 5.11 (s, 1H), 4.33 (q, J = 7.3 Hz, 1H), 3.35 (ddq, J = 13.0, 10.4, 7.1, 6.5 Hz, 1H), 2.40 (d, J = 1.8 Hz, 3H), 2.35 (s, 3H), 1.46 (s, 9H), 1.45-1.39 (m, 3H), 1.25 (dd, J = 7.2, 3.8 Hz, 3H), 1.01 (dd, J = 7.6, 6.2 Hz, 3H). $^{19}$F NMR (376 MHz, CDCl$_3$) δ −118.39, −118.45. |
| 53 | | IR (thin film) 3357, 2977, 2936, 2837, 1711, 1493, 1241, 1161, 1052, 752 cm$^{-1}$ | HRMS-ESI (m/z) [M + Na]⁺ calcd for C$_{19}$H$_{29}$NO$_5$Na, 374.1938; found, 374.1944 | $^1$H NMR (400 MHz, CDCl$_3$) δ 7.23-7.12 (m, 2H), 6.96-6.79 (m, 2H), 5.24 (dq, J = 7.7, 6.3 Hz, 1H), 5.00 (d, J = 6.6 Hz, 1H), 4.19-4.10 (m, 1H), 3.81 (s, 3H), 3.43 (p, J = 7.3 Hz, 1H), 1.42 (s, 9H), 1.25-1.20 (m, 6H), 0.99 (d, J = 7.1 Hz, 3H). |
| 54 | | IR (thin film) 3355, 2978, 2934, 1711, 1495, 1452, 1366, 1161, 1087, 1065, 701 cm$^{-1}$ | | $^1$H NMR (400 MHz, CDCl$_3$) δ 7.35-7.25 (m, 2H), 7.27-7.15 (m, 3H), 5.12-5.01 (m, 2H), 4.35-4.26 (m, 1H), 2.95-2.83 (m, 1H), 1.45 (s, 9H), 1.37 (d, J = 7.2 Hz, 3H), 1.29 (d, J = 7.1 Hz, 3H), 1.09 (d, J = 6.3 Hz, 3H). $^{13}$C NMR (126 MHz, CDCl$_3$) δ 172.9, 155.0, 143.0, 128.5, 127.8, 126.7, 79.7, 76.1, 49.5, 45.1, 28.3, 18.9, 18.3, 17.5. |
| 55 | | IR (thin film) 3365, 2977, 2933, 1712, 1500, 1449, 1365, 1161, 1065, 796 cm$^{-1}$ | HRMS-ESI (m/z) [M + Na]⁺ calcd for C$_{17}$H$_{27}$NO$_4$SNa, 364.1553; found, 364.1551 | $^1$H NMR (400 MHz, CDCl$_3$) δ 6.64-6.53 (m, 2H), 5.11-5.05 (m, 1H), 5.06-4.95 (m, 1H), 4.35-4.26 (m, 1H), 3.20-3.08 (m, 1H), 2.43 (d, J = 1.2 Hz, 3H), 1.45 (s, 9H), 1.38 (d, J = 7.2 Hz, 3H), 1.31 (d, J = 7.1 Hz, 3H), 1.16 (d, J = 6.3 Hz, 3H). |
| 56 | | IR (thin film) 3365, 2978, 2937, 1708, 1601, 1502, 1163, 1035, 952, 834 cm$^{-1}$ | HRMS-ESI (m/z) [M + Na]⁺ calcd for C$_{19}$H$_{28}$FNO$_5$Na, 392.1844; found, 392.1839 | $^1$H NMR (500 MHz, CDCl$_3$) δ 7.08 (dd, J = 8.5, 6.7 Hz, 1H), 6.65-6.53 (m, 2H), 5.16-5.07 (m, 1H), 5.05 (d, J = 7.6 Hz, 1H), 4.30-4.23 (m, 1H), 3.80 (s, 3H), 3.38-3.29 (m, 1H), 1.45 (s, 9H), 1.35 (d, J = 7.2 Hz, 3H), 1.23 (d, J = 7.1 Hz, 3H), 1.10 (d, J = 6.3 Hz, 3H). |
| 57 | | | | $^1$H NMR (300 MHz, CDCl$_3$) δ 7.13-6.95 (m, 2H), 6.77-6.52 (m, 2H), 5.11 (d, J = 7.8 Hz, 1H), 5.00 (dq, J = 8.2, 6.2 Hz, 1H), 4.31 (t, J = 7.4 Hz, 1H), 2.92 (s, 6H), 1.45 (s, 9H), 1.39 (d, J = 7.2 Hz, 3H), 1.31-1.17 (m, 4H), 1.08 (d, J = 6.3 Hz, 3H). $^{13}$C NMR (75 MHz, CDCl$_3$) δ 172.95, 171.16, 155.04, 149.48, 130.86, 128.41, 112.69, 60.40, 49.51, 44.14, 40.70, 28.35, 18.93, 18.27, 17.82, 14.21. |

TABLE 2-continued

Analytical Data

| Cmpd. No. | Melting Point (° C.) | IR (cm$^{-1}$) | MASS SPEC | NMR |
|---|---|---|---|---|
| 58 | | | ESIMS m/z 240.2 ([M + H]$^+$) | |
| 59 | | | ESIMS m/z 240.2 ([M + H]$^+$) | |
| 60 | | | ESIMS m/z 222.2 ([M + H]$^+$) | |
| 61 | | | ESIMS m/z 248.9 ([M + Na]$^+$) | |
| 62 | | | ESIMS m/z 252.2 ([M + H]$^+$) | |
| 63 | | | ESIMS m/z 240.2 ([M + H]$^+$) | |
| 64 | | | ESIMS m/z 240.2 ([M + H]$^+$) | |
| 65 | | | ESIMS m/z 222.2 ([M + H]$^+$) | |
| 66 | | | ESIMS m/z 226.2 ([M + H]$^+$) | |
| 67 | | | ESIMS m/z 252.2 ([M + H]$^+$) | |
| 68 | | | ESIMS m/z 254.2 ([M + H]$^+$) | |
| 69 | | | ESIMS m/z 254.2 ([M + H]$^+$) | |
| 70 | | | ESIMS m/z 236.2 ([M + H]$^+$) | |
| 71 | | | ESIMS m/z 240.2 ([M + H]$^+$) | |
| 72 | | | ESIMS m/z 266.3 ([M + H]$^+$) | |
| 73 | | | ESIMS m/z 254.2 ([M + H]$^+$) | |
| 74 | | | ESIMS m/z 254.2 ([M + H]$^+$) | |
| 75 | | | ESIMS m/z 236.2 ([M + H]$^+$) | |
| 76 | | | ESIMS m/z 240.2 ([M + H]$^+$) | |
| 77 | | | ESIMS m/z 266.3 ([M + H]$^+$) | |
| 78 | | | ESIMS m/z 282.3 ([M + H]$^+$) | |
| 79 | | | ESIMS m/z 282.2 ([M + H]$^+$) | |
| 80 | | | ESIMS m/z 264.3 ([M + H]$^+$) | |
| 81 | | | ESIMS m/z 268.2 ([M + H]$^+$) | |
| 82 | | | ESIMS m/z 294.3 ([M + H]$^+$) | |
| 83 | | | ESIMS m/z 282.2 ([M + H]$^+$) | |
| 84 | | | ESIMS m/z 282.2 ([M + H]$^+$) | |
| 85 | | | ESIMS m/z 264.3 ([M + H]$^+$) | |
| 86 | | | ESIMS m/z 268.2 ([M + H]$^+$) | |
| 87 | | | ESIMS m/z 294.3 ([M + H]$^+$) | |
| 88 | | | ESIMS m/z 254.2 ([M + H]$^+$) | |
| 89 | | | ESIMS m/z 254.2 ([M + H]$^+$) | |
| 90 | | | ESIMS m/z 236.2 ([M + H]$^+$) | |
| 91 | | | ESIMS m/z 240.2 ([M + H]$^+$) | |
| 92 | | | ESIMS m/z 266.3 ([M + H]$^+$) | |
| 93 | | | ESIMS m/z 254.2 ([M + H]$^+$) | |
| 94 | | | ESIMS m/z 254.2 ([M + H]$^+$) | |

TABLE 2-continued

Analytical Data

| Cmpd. No. | Melting Point (° C.) | IR (cm$^{-1}$) | MASS SPEC | NMR |
|---|---|---|---|---|
| 95 | | | ESIMS m/z 236.2 ([M + H]$^+$) | |
| 96 | | | ESIMS m/z 240.2 ([M + H]$^+$) | |
| 97 | | | ESIMS m/z 266.3 ([M + H]$^+$) | |
| 98 | | | ESIMS m/z 250.3 ([M + H]$^+$) | |
| 99 | | | ESIMS m/z 250.3 ([M + H]$^+$) | |
| 100 | | | ESIMS m/z 290.2 ([M + H]$^+$) | |
| 101 | | | ESIMS m/z 308.1 ([M + H]$^+$) | |
| 102 | | | ESIMS m/z 214.2 ([M + H]$^+$) | |
| 103 | | | ESIMS m/z 290.2 ([M + H]$^+$) | |
| 104 | | | ESIMS m/z 308.1 ([M + H]$^+$) | |
| 105 | | | ESIMS m/z 214.2 ([M + H]$^+$) | |
| 106 | | | ESIMS m/z 250.2 ([M + H]$^+$) | |
| 107 | | | ESIMS m/z 268.2 ([M + H]$^+$) | |
| 108 | | | ESIMS m/z 250.2 ([M + H]$^+$) | |
| 109 | | | ESIMS m/z 268.2 ([M + H]$^+$) | |
| 110 | | | ESIMS m/z 250.2 ([M + H]$^+$) | |
| 111 | | | ESIMS m/z 268.2 ([M + H]$^+$) | |
| 112 | | | HRMS-ESI (m/z) [M + H]$^+$ calcd for C$_{14}$H$_{22}$NO$_3$, 252.1600; found, 252.1443 | |
| 113 | | | HRMS-ESI (m/z) [M + H]$^+$ calcd for C$_{13}$H$_{20}$NO$_2$, 222.1489; found, 222.1485 | |
| 114 | | IR (thin film) 2854, 1740, 1233, 1203, 1118, 1078, 872, 796 cm$^{-1}$ | | |
| 115 | | | HRMS-ESI (m/z) [M + H]$^+$ calcd for C$_{14}$H$_{21}$FNO$_3$, 270.1500; found, 270.1501 | |
| 116 | | | HRMS-ESI (m/z) [M + H]$^+$ calcd for C$_{22}$H$_{29}$N$_2$O$_5$, 401.2071; found, 401.2067 | $^1$H NMR (500 MHz, CDCl$_3$) δ 12.16 (s, 1H), 8.52 (d, J = 7.8 Hz, 1H), 8.00 (d, J = 5.2 Hz, 1H), 7.09-7.03 (m, 1H), 7.00-6.94 (m, 2H), 6.88 (d, J = 5.1 Hz, 1H), 5.13 (dq, J = 8.4, 6.2 Hz, 1H), 4.79-4.67 (m, 1H), 3.95 (s, 3H), 3.16 (dq, J = 8.9, 7.0 Hz, 1H), 2.31 (s, 3H), 2.28 (s, 3H), 1.57 (d, J = 7.2 Hz, 3H), 1.24 (d, J = 6.9 Hz, 3H), 1.14 (d, J = 6.2 Hz, 3H). $^{13}$C NMR (126 MHz, CDCl$_3$) δ 171.86, 168.68, 155.38, 148.77, 140.50, 138.63, 135.76, 135.33, 131.31, 130.52, 126.97, 126.26, 109.44, 56.08, 48.18, 39.45, 20.89, 19.87, 18.48, 18.46, 17.56. |
| 117 | | | HRMS-ESI (m/z) [M + H]$^+$ calcd for C$_{22}$H$_{29}$N$_2$O$_5$, | $^1$H NMR (500 MHz, CDCl$_3$) δ 12.17 (d, J = 0.6 Hz, 1H), 8.50 (d, J = 7.9 Hz, 1H), 8.01 (d, J = 5.2 Hz, 1H), 7.10- |

TABLE 2-continued

Analytical Data

| Cmpd. No. | Melting Point (° C.) | IR (cm$^{-1}$) | MASS SPEC | NMR |
|---|---|---|---|---|
| | | | 401.2071; found, 401.2064 | 7.02 (m, 1H), 6.97 (d, J = 6.9 Hz, 2H), 6.88 (d, J = 5.2 Hz, 1H), 5.16 (dq, J = 8.4, 6.2 Hz, 1H), 4.77-4.68 (m, 1H), 3.95 (s, 3H), 3.19-3.09 (m, 1H), 2.31 (s, 3H), 2.27 (s, 3H), 1.54 (d, J = 7.2 Hz, 3H), 1.23 (d, J = 6.9 Hz, 3H), 1.12 (d, J = 6.3 Hz, 3H).<br>$^{13}$C NMR (126 MHz, CDCl$_3$) δ 171.87, 168.72, 155.38, 148.76, 140.50, 138.60, 135.72, 135.36, 131.29, 130.53, 127.00, 126.28, 109.44, 56.08, 47.99, 39.42, 20.87, 19.88, 18.31, 18.26, 17.65. |
| 118 | | | HRMS-ESI (m/z) [M + H]$^+$ calcd for C$_{20}$H$_{23}$FN$_2$O$_5$, 391.1664; found, 391.1662 | $^1$H NMR (500 MHz, CDCl$_3$) δ 12.04 (s, 1H), 8.46 (t, J = 5.8 Hz, 1H), 8.01 (d, J = 5.2 Hz, 1H), 7.18-7.06 (m, 1H), 6.93-6.79 (m, 3H), 5.15 (dq, J = 8.0, 6.3 Hz, 1H), 4.21 (dd, J = 5.7, 3.2 Hz, 2H), 3.95 (s, 3H), 3.15 (p, J = 7.1 Hz, 1H), 2.33 (s, 3H), 1.24 (d, J = 6.9 Hz, 3H), 1.15 (d, J = 6.3 Hz, 3H).<br>$^{13}$C NMR (126 MHz, CDCl$_3$) δ 169.32, 168.74, 161.97, 160.03, 155.39, 148.70, 140.61, 137.91, 137.20, 130.40, 127.85, 117.11, 116.95, 113.07, 112.90, 109.54, 76.40, 56.10, 41.03, 39.10, 20.00, 18.22, 17.42. |
| 119 | | | HRMS-ESI (m/z) [M + H]$^+$ calcd for C$_{20}$H$_{23}$FN$_2$O$_5$, 391.1664; found, 391.1660 | $^1$H NMR (500 MHz, CDCl$_3$) δ 12.01 (s, 1H), 8.34 (t, J = 5.8 Hz, 1H), 7.99 (d, J = 5.2 Hz, 1H), 7.15 (dd, J = 9.5, 5.8 Hz, 1H), 6.88 (d, J = 5.2 Hz, 1H), 6.85-6.75 (m, 2H), 5.24-5.10 (m, 1H), 4.23-3.92 (m, 5H), 3.23 (p, J = 7.1 Hz, 1H), 2.33 (s, 3H), 1.25 (m, 6H).<br>$^{13}$C NMR (126 MHz, CDCl$_3$) δ 169.19, 168.38, 161.97, 160.02, 155.38, 148.68, 140.55, 138.37, 136.63, 130.36, 127.68, 116.81, 116.65, 112.86, 112.70, 109.52, 75.82, 56.09, 40.88, 38.65, 19.86, 17.20, 16.64. |
| 120 | | | HRMS-ESI (m/z) [M + H]$^+$ calcd for C$_{20}$H$_{24}$N$_2$O$_5$, 373.1758; found, 373.1754 | $^1$H NMR (500 MHz, CDCl$_3$) δ 12.03 (s, 1H), 8.34 (t, J = 5.8 Hz, 1H), 7.99 (d, J = 5.2 Hz, 1H), 7.20 (dd, J = 7.6, 1.3 Hz, 1H), 7.16-7.06 (m, 3H), 6.87 (d, J = 5.2 Hz, 1H), 5.24-5.17 (m, 1H), 4.16-3.89 (m, 2H), 3.95 (s, 3H), 3.29 (p, J = 7.1 Hz, 1H), 2.35 (s, 3H), 1.27 (m, 6H).<br>$^{13}$C NMR (126 MHz, CDCl$_3$) δ 169.15, 168.40, 155.35, 148.66, 140.97, 140.52, 136.10, 130.41, 130.27, 126.30, 126.20, 126.14, 109.48, 75.92, 56.08, 40.85, 39.18, 19.79, 17.18, 16.37. |
| 121 | | | HRMS-ESI (m/z) [M + H]$^+$ calcd for C$_{19}$H$_{21}$FN$_2$O$_5$, 377.1507; found, 377.1504 | $^1$H NMR (500 MHz, CDCl$_3$) δ 12.04 (s, 1H), 8.46 (t, J = 5.8 Hz, 1H), 8.01 (d, J = 5.2 Hz, 1H), 7.15 (dd, J = 8.6, 5.5 Hz, 2H), 7.01-6.94 (m, 2H), 6.89 (d, J = 5.2 Hz, 1H), 5.16-5.05 (m, 1H), 4.21 (dd, J = 5.8, 2.1 Hz, 2H), 3.95 (s, 3H), 2.92 (p, J = 7.1 Hz, 1H), 1.28 (d, J = 7.0 Hz, 3H), 1.12 (d, J = 6.3 Hz, 3H).<br>$^{13}$C NMR (126 MHz, CDCl$_3$) δ 169.33, 168.65, 162.66, 160.72, 155.40, 148.71, 140.61, 138.35, 130.40, 129.27, 129.21, 115.36, 115.19, 109.55, 76.35, 56.10, 44.12, 41.06, 17.83, 17.27. |
| 122 | | | HRMS-ESI (m/z) [M + H]$^+$ calcd for C$_{21}$H$_{26}$N$_2$O$_6$, 403.1864; found, 403.1835 | $^1$H NMR (500 MHz, CDCl$_3$) δ 12.06 (s, 1H), 8.47 (t, J = 5.8 Hz, 1H), 8.01 (d, J = 5.2 Hz, 1H), 7.08 (d, J = 8.4 Hz, 1H), 6.88 (d, J = 5.2 Hz, 1H), 6.77-6.66 (m, 2H), 5.15 (dq, J = 8.2, 6.3 Hz, 1H), 4.22 (dd, J = 5.7, 2.0 Hz, 2H), |

TABLE 2-continued

Analytical Data

| Cmpd. No. | Melting Point (° C.) | IR (cm$^{-1}$) | MASS SPEC | NMR |
|---|---|---|---|---|
| | | | | 3.95 (s, 3H), 3.77 (s, 3H), 3.18-3.07 (m, 1H), 2.32 (s, 3H), 1.23 (d, J = 6.9 Hz, 3H), 1.14 (d, J = 6.3 Hz, 3H). $^{13}$C NMR (126 MHz, CDCl$_3$) δ 169.30, 168.80, 157.71, 155.38, 148.69, 140.60, 136.96, 133.70, 130.44, 127.36, 115.97, 111.49, 109.52, 76.84, 56.09, 55.12, 41.05, 39.03, 20.17, 18.27, 17.59. |
| 123 | | | HRMS-ESI (m/z) [M + H]$^+$ calcd for C$_{20}$H$_{23}$FN$_2$O$_5$, 391.1664; found, 391.1662 | $^1$H NMR (500 MHz, CDCl$_3$) δ 12.04 (s, 1H), 8.46 (t, J = 5.8 Hz, 1H), 8.00 (d, J = 5.2 Hz, 1H), 7.20-7.08 (m, 1H), 6.93-6.80 (m, 3H), 5.15 (dq, J = 7.9, 6.3 Hz, 1H), 4.21 (dd, J = 5.7, 3.2 Hz, 2H), 3.95 (s, 3H), 3.15 (p, J = 7.1 Hz, 1H), 2.33 (s, 3H), 1.24 (d, J = 6.9 Hz, 3H), 1.15 (d, J = 6.3 Hz, 3H). $^{13}$C NMR (126 MHz, CDCl$_3$) δ 169.32, 168.75, 161.97, 160.03, 155.39, 148.70, 140.61, 137.91, 137.85, 137.20, 137.17, 130.40, 127.85, 127.78, 117.11, 116.95, 113.06, 112.90, 109.54, 76.40, 56.10, 41.03, 39.10, 19.99, 18.22, 17.42. |
| 124 | | | HRMS-ESI (m/z) [M + H]$^+$ calcd for C$_{20}$H$_{23}$FN$_2$O$_5$, 391.1664; found, 391.1661 | $^1$H NMR (500 MHz, CDCl$_3$) δ 12.01 (d, J = 0.6 Hz, 1H), 8.34 (t, J = 5.8 Hz, 1H), 7.99 (d, J = 5.2 Hz, 1H), 7.15 (dd, J = 9.5, 5.8 Hz, 1H), 6.88 (d, J = 5.2 Hz, 1H), 6.85-6.77 (m, 2H), 5.21-5.11 (m, 1H), 4.20-3.91 (m, 2H), 3.95 (s, 3H), 3.23 (p, J = 7.1 Hz, 1H), 2.33 (s, 3H), 1.30-1.20 (m, 6H). $^{13}$C NMR (126 MHz, CDCl$_3$) δ 169.19, 168.38, 161.97, 160.02, 155.38, 148.68, 140.55, 138.43, 136.66, 130.36, 127.75, 127.68, 116.81, 116.65, 112.86, 112.70, 109.52, 75.82, 56.09, 40.88, 38.65, 19.85, 17.20, 16.64. |
| 125 | | | HRMS-ESI (m/z) [M + H]$^+$ calcd for C$_{20}$H$_{24}$N$_2$O$_5$, 373.1758; found, 373.1755 | $^1$H NMR (500 MHz, CDCl$_3$) δ 12.03 (d, J = 0.6 Hz, 1H), 8.34 (t, J = 5.8 Hz, 1H), 7.99 (d, J = 5.2 Hz, 1H), 7.20 (dd, J = 7.7, 1.3 Hz, 1H), 7.17-7.04 (m, 3H), 6.87 (d, J = 5.2 Hz, 1H), 5.25-5.16 (m, 1H), 4.12 (dd, J = 18.2, 5.9 Hz, 1H), 3.95 (s, 3H), 3.98-3.89 (m, 1H), 3.29 (p, J = 7.1 Hz, 1H), 2.35 (s, 3H), 1.27 (m, 6H). $^{13}$C NMR (126 MHz, CDCl$_3$) δ 169.15, 168.41, 155.35, 148.66, 140.97, 140.52, 136.10, 130.41, 130.27, 126.30, 126.14, 109.48, 75.92, 56.08, 40.85, 39.18, 19.79, 17.18, 16.37. |
| 126 | | | HRMS-ESI (m/z) [M + H]$^+$ calcd for C$_{19}$H$_{21}$FN$_2$O$_5$, 377.1507; found, 377.1507 | $^1$H NMR (500 MHz, CDCl$_3$) δ 12.04 (s, 1H), 8.46 (t, J = 5.9 Hz, 1H), 8.01 (d, J = 5.2 Hz, 1H), 7.22-7.08 (m, 2H), 6.98 (t, J = 8.7 Hz, 2H), 6.89 (d, J = 5.2 Hz, 1H), 5.16-5.01 (m, 1H), 4.29-4.14 (m, 2H), 3.95 (s, 3H), 2.92 (p, J = 7.1 Hz, 1H), 1.28 (d, J = 7.0 Hz, 3H), 1.12 (d, J = 6.3 Hz, 3H). $^{13}$C NMR (126 MHz, CDCl$_3$) δ 169.33, 168.65, 162.67, 160.72, 155.41, 148.71, 140.61, 138.37, 130.40, 129.27, 129.21, 115.36, 115.19, 109.55, 76.36, 56.10, 44.12, 41.06, 17.83, 17.27. |
| 127 | | | HRMS-ESI (m/z) [M + H]$^+$ calcd for C$_{21}$H$_{26}$N$_2$O$_6$, 403.1864; found, 403.1853 | $^1$H NMR (500 MHz, CDCl$_3$) δ 12.06 (s, 1H), 8.47 (t, J = 5.7 Hz, 1H), 8.01 (d, J = 5.2 Hz, 1H), 7.08 (d, J = 8.4 Hz, 1H), 6.88 (d, J = 5.2 Hz, 1H), 6.82-6.66 (m, 2H), 5.15 (dq, J = 8.1, 6.3 Hz, 1H), 4.29-4.15 (m, 2H), 3.95 (s, 3H), 3.77 (s, 3H), 3.17-3.08 (m, 1H), 2.32 (s, 3H), 1.23 (d, J = 6.9 Hz, 3H), 1.14 |

TABLE 2-continued

Analytical Data

| Cmpd. No. | Melting Point (° C.) | IR (cm$^{-1}$) | MASS SPEC | NMR |
|---|---|---|---|---|
| | | | | (d, J = 6.3 Hz, 3H).<br>$^{13}$C NMR (126 MHz, CDCl$_3$) δ 169.30, 168.80, 157.71, 155.38, 148.69, 140.60, 136.96, 133.70, 130.44, 127.36, 115.97, 111.49, 109.52, 76.84, 56.09, 55.12, 41.05, 39.03, 20.17, 18.27, 17.59. |
| 128 | | | HRMS-ESI (m/z) [M + H]$^+$ calcd for C$_{21}$H$_{25}$FN$_2$O$_5$, 405.1820; found, 405.1819 | $^1$H NMR (500 MHz, CDCl$_3$) δ 12.14 (d, J = 0.6 Hz, 1H), 8.49 (d, J = 7.9 Hz, 1H), 8.00 (d, J = 5.2 Hz, 1H), 7.18-7.05 (m, 1H), 6.93-6.79 (m, 3H), 5.11 (dq, J = 8.0, 6.3 Hz, 1H), 4.78-4.64 (m, 1H), 3.95 (s, 3H), 3.23-3.09 (m, 1H), 2.33 (s, 3H), 1.55 (d, J = 7.2 Hz, 3H), 1.24 (d, J = 6.9 Hz, 3H), 1.14 (d, J = 6.3 Hz, 3H).<br>$^{13}$C NMR (126 MHz, CDCl$_3$) δ 171.79, 168.69, 161.97, 160.03, 155.39, 148.77, 140.51, 137.87, 137.81, 137.33, 137.30, 130.47, 127.86, 127.79, 117.10, 116.94, 113.02, 112.85, 109.47, 76.32, 56.09, 48.13, 39.16, 20.00, 18.42, 18.36, 17.33. |
| 129 | | | HRMS-ESI (m/z) [M + H]$^+$ calcd for C$_{21}$H$_{25}$FN$_2$O$_5$, 405.1820; found, 405.1820 | $^1$H NMR (500 MHz, CDCl$_3$) δ 12.09 (s, 1H), 8.35 (d, J = 7.9 Hz, 1H), 7.98 (dd, J = 5.2, 3.6 Hz, 1H), 7.13 (dd, J = 8.4, 5.8 Hz, 1H), 6.94-6.73 (m, 3H), 5.21-5.08 (m, 1H), 4.63-4.46 (m, 1H), 3.94 (s, 2H), 3.27-3.15 (m, 1H).<br>$^{13}$C NMR (126 MHz, CDCl$_3$) δ 171.55, 168.59, 161.91, 159.97, 155.37, 148.73, 140.44, 138.30, 137.15, 130.43, 127.47, 116.73, 116.57, 112.89, 112.73, 109.43, 75.74, 56.07, 47.87, 38.98, 19.90, 17.79, 17.32. |
| 130 | | | HRMS-ESI (m/z) [M + H]$^+$ calcd for C$_{21}$H$_{26}$N$_2$O$_5$, 387.1914; found, 387.1911 | $^1$H NMR (500 MHz, CDCl$_3$) δ 12.11 (s, 1H), 8.36 (d, J = 8.0 Hz, 1H), 7.97 (d, J = 5.2 Hz, 1H), 7.24-7.01 (m, 4H), 6.86 (d, J = 5.2 Hz, 1H), 5.27-5.12 (m, 1H), 4.59-4.47 (m, 1H), 3.94 (s, 2H), 3.33-3.20 (m, 1H), 2.36 (s, 3H), 1.32 (d, J = 6.3 Hz, 3H), 1.24 (d, J = 7.1 Hz, 3H), 1.08 (d, J = 7.2 Hz, 3H).<br>$^{13}$C NMR (126 MHz, CDCl$_3$) δ 171.58, 168.54, 155.33, 148.71, 141.47, 140.41, 135.95, 130.49, 130.22, 126.20, 125.88, 109.39, 75.87, 56.06, 47.85, 39.52, 19.83, 17.83, 17.74, 17.14. |
| 131 | | | HRMS-ESI (m/z) [M + H]$^+$ calcd for C$_{20}$H$_{23}$FN$_2$O$_5$, 391.1664; found, 391.1662 | $^1$H NMR (500 MHz, CDCl$_3$) δ 12.14 (s, 1H), 8.47 (d, J = 8.0 Hz, 1H), 8.00 (d, J = 5.2 Hz, 1H), 7.15 (dd, J = 8.6, 5.4 Hz, 2H), 6.97 (t, J = 8.7 Hz, 2H), 6.88 (d, J = 5.2 Hz, 1H), 5.11-5.02 (m, 1H), 4.71 (p, J = 7.3 Hz, 1H), 3.95 (s, 3H), 2.92 (p, J = 7.1 Hz, 1H), 1.53 (d, J = 7.2 Hz, 3H), 1.29 (d, J = 7.1 Hz, 3H), 1.12 (d, J = 6.3 Hz, 3H).<br>$^{13}$C NMR (126 MHz, CDCl$_3$) δ 171.67, 168.69, 162.64, 160.70, 155.40, 148.78, 140.51, 138.48, 130.46, 129.26, 129.19, 115.32, 115.16, 109.48, 76.31, 56.09, 48.12, 44.11, 18.38, 17.95, 17.16. |
| 132 | | | HRMS-ESI (m/z) [M + H]$^+$ calcd for C$_{22}$H$_{28}$N$_2$O$_6$, 417.2020; found, 417.2007 | $^1$H NMR (500 MHz, CDCl$_3$) δ 12.16 (s, 1H), 8.51 (d, J = 7.9 Hz, 1H), 8.00 (d, J = 5.2 Hz, 1H), 7.11-7.05 (m, 1H), 6.88 (d, J = 5.2 Hz, 1H), 6.70 (d, J = 6.7 Hz, 2H), 5.11 (dq, J = 8.3, 6.3 Hz, 1H), 4.72 (p, J = 7.3 Hz, 1H), 3.95 (s, 3H), 3.77 (s, 3H), 3.18-3.06 (m, 1H), 2.32 (s, 3H), 1.56 (d, J = 7.2 Hz, 3H), 1.23 (d, J = 6.9 Hz, 3H), 1.14 (d, J = 6.3 Hz, 3H). |

TABLE 2-continued

Analytical Data

| Cmpd. No. | Melting Point (° C.) | IR (cm⁻¹) | MASS SPEC | NMR |
|---|---|---|---|---|
| | | | | ¹³C NMR (126 MHz, CDCl₃) δ 171.85, 168.67, 157.70, 155.38, 148.77, 140.50, 136.91, 133.86, 130.52, 127.36, 115.95, 111.48, 109.45, 56.08, 55.13, 48.17, 39.11, 20.18, 18.46, 17.57, 16.10. |
| 133 | | | HRMS-ESI (m/z) [M + H]⁺ calcd for C₂₁H₂₅FN₂O₅, 405.1820; found, 405.1819 | ¹H NMR (500 MHz, CDCl₃) δ 12.14 (s, 1H), 8.47 (d, J = 8.0 Hz, 1H), 8.01 (d, J = 5.2 Hz, 1H), 7.13 (dd, J = 9.4, 5.8 Hz, 1H), 6.91-6.81 (m, 3H), 5.12 (dq, J = 8.1, 6.3 Hz, 1H), 4.72 (p, J = 7.2 Hz, 1H), 3.95 (s, 3H), 3.20-3.10 (m, 1H), 2.33 (s, 3H), 1.54 (d, J = 7.1 Hz, 3H), 1.23 (d, J = 6.9 Hz, 3H), 1.12 (d, J = 6.3 Hz, 3H). ¹³C NMR (126 MHz, CDCl₃) δ 171.81, 168.74, 161.95, 160.01, 155.40, 148.78, 140.51, 137.89, 137.83, 137.29, 137.26, 130.48, 127.87, 127.81, 117.08, 116.91, 113.06, 112.90, 109.48, 76.19, 56.09, 47.96, 39.12, 20.02, 18.24, 18.12, 17.47. |
| 134 | | | HRMS-ESI (m/z) [M + H]⁺ calcd for C₂₁H₂₅FN₂O₅, 405.1820; found, 405.1818 | ¹H NMR (500 MHz, CDCl₃) δ 12.12 (s, 1H), 8.28 (d, J = 8.0 Hz, 1H), 7.99 (d, J = 5.2 Hz, 1H), 7.18-7.12 (m, 1H), 6.88 (d, J = 5.2 Hz, 1H), 6.78 (t, J = 8.2 Hz, 2H), 5.17-5.06 (m, 1H), 4.64-4.51 (m, 1H), 3.95 (s, 3H), 3.23 (p, J = 7.1 Hz, 1H), 2.33 (s, 3H), 1.38 (d, J = 7.1 Hz, 3H), 1.26-1.20 (m, 6H). ¹³C NMR (126 MHz, CDCl₃) δ 171.29, 168.55, 161.93, 159.99, 155.38, 148.74, 140.44, 138.41, 138.35, 136.73, 136.71, 130.43, 127.71, 127.65, 116.77, 116.61, 112.81, 112.64, 109.45, 75.62, 56.09, 47.82, 38.64, 19.89, 19.88, 18.06, 17.22, 16.84. |
| 135 | | | HRMS-ESI (m/z) [M + H]⁺ calcd for C₂₁H₂₆N₂O₅, 387.1914; found, 387.1915 | ¹H NMR (500 MHz, CDCl₃) δ 12.15 (s, 1H), 8.30 (d, J = 8.0 Hz, 1H), 7.99 (d, J = 5.2 Hz, 1H), 7.21 (dd, J = 7.8, 1.4 Hz, 1H), 7.15-7.00 (m, 3H), 6.87 (d, J = 5.2 Hz, 1H), 5.20-5.12 (m, 1H), 4.59-4.50 (m, 1H), 3.95 (s, 3H), 3.29 (p, J = 7.1 Hz, 1H), 2.36 (s, 3H), 1.35 (d, J = 7.2 Hz, 3H), 1.29-1.22 (m, 6H). ¹³C NMR (126 MHz, CDCl₃) δ 171.30, 168.54, 155.35, 148.73, 141.04, 140.40, 136.09, 130.51, 130.26, 126.23, 126.11, 109.40, 75.73, 56.08, 47.88, 39.15, 19.83, 18.11, 17.16, 16.53. |
| 136 | | | HRMS-ESI (m/z) [M + H]⁺ calcd for C₂₀H₂₃FN₂O₅, 391.1664; found, 391.1658 | ¹H NMR (500 MHz, CDCl₃) δ 12.14 (s, 1H), 8.46 (d, J = 7.7 Hz, 1H), 8.00 (dd, J = 5.2, 2.2 Hz, 1H), 7.15 (ddd, J = 9.9, 6.1, 3.4 Hz, 2H), 6.97 (td, J = 8.8, 2.6 Hz, 2H), 6.88 (dd, J = 5.4, 1.5 Hz, 1H), 5.12-5.01 (m, 1H), 4.77-4.64 (m, 1H), 3.95 (s, 3H), 2.92 (p, J = 7.1 Hz, 1H), 1.53 (d, J = 7.2 Hz, 3H), 1.28 (d, J = 7.0 Hz, 3H), 1.09 (d, J = 6.3 Hz, 3H). ¹³C NMR (126 MHz, CDCl₃) δ 171.72, 168.76, 162.65, 160.70, 155.41, 148.78, 140.51, 138.43, 138.40, 130.47, 129.29, 129.23, 115.33, 115.16, 109.48, 76.12, 56.09, 47.98, 44.09, 18.20, 17.69, 17.30. |
| 137 | | | HRMS-ESI (m/z) [M + H]⁺ calcd for C₂₂H₂₈N₂O₆, 417.2020; found, 417.2010 | ¹H NMR (500 MHz, CDCl₃) δ 12.17 (s, 1H), 8.50 (d, J = 7.9 Hz, 1H), 8.01 (d, J = 5.2 Hz, 1H), 7.09 (d, J = 8.4 Hz, 1H), 6.88 (d, J = 5.2 Hz, 1H), 6.76-6.67 (m, 2H), 5.13 (dq, J = 8.3, 6.3 Hz, 1H), 4.72 (p, J = 7.3 Hz, 1H), 3.95 (s, 3H), 3.76 (s, 3H), 3.18-3.07 (m, 1H), 2.32 (s, 3H), 1.54 (d, J = 7.2 Hz, 3H), |

TABLE 2-continued

Analytical Data

| Cmpd. No. | Melting Point (°C.) | IR (cm⁻¹) | MASS SPEC | NMR |
|---|---|---|---|---|
| | | | | 1.23 (d, J = 6.9 Hz, 3H), 1.12 (d, J = 6.3 Hz, 3H). $^{13}$C NMR (126 MHz, CDCl$_3$) δ 171.86, 168.72, 157.68, 155.38, 148.76, 140.50, 136.94, 133.82, 130.53, 127.37, 115.97, 111.47, 109.45, 76.65, 56.08, 55.11, 47.99, 39.06, 20.19, 18.31, 18.20, 17.68. |
| 139 | | | HRMS-ESI (m/z) [M + H]$^+$ calcd for C$_{23}$H$_{29}$FN$_2$O$_5$, 433.2133; found, 433.213 | $^1$H NMR (500 MHz, CDCl$_3$) δ 12.12 (s, 1H), 8.38 (d, J = 9.3 Hz, 1H), 7.99 (t, J = 5.1 Hz, 1H), 7.14 (dd, J = 8.5, 5.9 Hz, 1H), 6.88 (dd, J = 7.6, 5.1 Hz, 1H), 6.84-6.72 (m, 3H), 5.13 (dq, J = 8.4, 6.3 Hz, 1H), 4.49 (td, J = 9.4, 4.9 Hz, 1H), 3.94 (s, 3H), 3.20 (p, J = 7.4 Hz, 1H), 2.33 (s, 3H), 1.94 (pd, J = 6.9, 4.6 Hz, 1H), 1.29 (d, J = 6.3 Hz, 3H), 1.21 (d, J = 7.1 Hz, 3H), 0.85 (d, J = 6.9 Hz, 3H), 0.68 (d, J = 6.8 Hz, 3H). $^{13}$C NMR (126 MHz, CDCl$_3$) δ 170.52, 168.98, 161.96, 160.02, 155.39, 148.70, 140.45, 138.31, 138.25, 137.28, 137.25, 130.49, 127.46, 127.40, 116.75, 116.59, 112.92, 112.76, 109.42, 75.86, 56.97, 56.08, 38.86, 31.12, 19.89, 19.12, 17.79, 17.34, 17.02. |
| 140 | | | HRMS-ESI (m/z) [M + H]$^+$ calcd for C$_{23}$H$_{30}$N$_2$O$_5$, 415.2227; found, 415.2222 | $^1$H NMR (500 MHz, CDCl$_3$) δ 8.38 (d, J = 9.4 Hz, 1H), 7.99 (d, J = 5.2 Hz, 1H), 7.20 (d, J = 7.7 Hz, 1H), 7.16-7.08 (m, 1H), 7.08-7.03 (m, 2H), 6.86 (d, J = 5.2 Hz, 1H), 5.25-5.11 (m, 1H), 4.49 (dd, J = 9.4, 4.5 Hz, 1H), 3.94 (s, 3H), 3.37-3.18 (m, 1H), 2.34 (s, 3H), 1.91 (pd, J = 6.9, 4.5 Hz, 1H), 1.31 (d, J = 6.2 Hz, 3H), 1.23 (d, J = 7.1 Hz, 3H), 0.82 (d, J = 6.8 Hz, 3H), 0.64 (d, J = 6.8 Hz, 3H). $^{13}$C NMR (126 MHz, CDCl$_3$) δ 170.54, 168.94, 155.34, 148.67, 141.56, 140.42, 135.94, 130.56, 130.25, 126.23, 125.89, 109.37, 75.96, 56.90, 56.07, 39.37, 31.11, 19.82, 19.14, 17.78, 17.11, 16.98. |
| 141 | | | HRMS-ESI (m/z) [M + H]$^+$ calcd for C$_{22}$H$_{27}$FN$_2$O$_5$, 419.1977; found, 419.1973 | $^1$H NMR (500 MHz, CDCl$_3$) δ 12.16 (s, 1H), 8.48 (d, J = 9.4 Hz, 1H), 8.01 (d, J = 5.2 Hz, 1H), 7.19-7.10 (m, 2H), 6.94 (t, J = 8.7 Hz, 2H), 6.89 (d, J = 5.2 Hz, 1H), 5.11-4.98 (m, 1H), 4.64 (dd, J = 9.4, 4.8 Hz, 1H), 3.95 (s, 3H), 2.92 (p, J = 7.1 Hz, 1H), 2.31 (pd, J = 6.9, 4.8 Hz, 1H), 1.29 (d, J = 7.0 Hz, 3H), 1.12 (d, J = 6.3 Hz, 3H), 1.03 (d, J = 6.8 Hz, 3H), 0.95 (d, J = 6.9 Hz, 3H). $^{13}$C NMR (126 MHz, CDCl$_3$) δ 170.57, 169.05, 162.62, 160.67, 155.43, 148.76, 140.52, 138.50, 130.50, 129.23, 129.16, 115.29, 115.13, 109.47, 77.27, 76.39, 57.25, 56.10, 43.96, 31.33, 19.41, 18.04, 17.40, 17.07. |
| 142 | | | HRMS-ESI (m/z) [M + H]$^+$ calcd for C$_{24}$H$_{32}$N$_2$O$_6$, 445.2333; found, 445.2314 | $^1$H NMR (500 MHz, CDCl$_3$) δ 12.18 (s, 1H), 8.52 (d, J = 9.4 Hz, 1H), 8.02 (d, J = 5.2 Hz, 1H), 7.06 (d, J = 8.4 Hz, 1H), 6.88 (d, J = 5.2 Hz, 1H), 6.75-6.63 (m, 2H), 5.08 (dq, J = 8.3, 6.2 Hz, 1H), 4.66 (dd, J = 9.4, 4.8 Hz, 1H), 3.95 (s, 3H), 3.76 (s, 3H), 3.19-3.06 (m, 1H), 2.41-2.33 (m, 1H), 2.31 (s, 3H), 1.23 (d, J = 6.9 Hz, 3H), 1.13 (d, J = 6.2 Hz, 3H), 1.05 (d, J = 6.9 Hz, 3H), 0.98 (d, J = 6.9 Hz, 3H). $^{13}$C NMR (126 MHz, CDCl$_3$) δ 170.79, 169.06, 157.68, 155.40, 148.74, 140.51, 136.87, 133.93, 130.56, |

TABLE 2-continued

Analytical Data

| Cmpd. No. | Melting Point (° C.) | IR (cm$^{-1}$) | MASS SPEC | NMR |
|---|---|---|---|---|
| | | | | 127.33, 115.96, 111.46, 109.44, 76.90, 57.29, 56.08, 55.12, 39.01, 31.37, 20.17, 19.50, 18.52, 17.65, 17.40. |
| 143 | | | HRMS-ESI (m/z) [M + H]$^+$ calcd for C$_{23}$H$_{29}$FN$_2$O$_5$, 433.2133; found, 433.2142 | $^1$H NMR (500 MHz, CDCl$_3$) δ 12.18 (s, 1H), 8.50 (d, J = 9.2 Hz, 1H), 8.02 (d, J = 5.2 Hz, 1H), 7.13 (dd, J = 9.5, 5.7 Hz, 1H), 6.89 (d, J = 5.2 Hz, 1H), 6.87-6.82 (m, 2H), 5.12 (dq, J = 8.0, 6.3 Hz, 1H), 4.63 (dd, J = 9.3, 5.1 Hz, 1H), 3.95 (s, 3H), 3.15 (p, J = 7.1 Hz, 1H), 2.41-2.25 (m, 4H), 1.24 (d, J = 6.9 Hz, 3H), 1.13 (d, J = 6.3 Hz, 3H), 1.03 (d, J = 6.9 Hz, 3H), 0.99 (d, J = 6.9 Hz, 3H). $^{13}$C NMR (126 MHz, CDCl$_3$) δ 170.87, 169.06, 161.95, 160.01, 155.41, 148.74, 140.53, 137.86, 137.80, 137.31, 137.28, 130.54, 127.91, 117.05, 116.89, 113.06, 112.89, 109.46, 76.09, 57.04, 56.09, 39.11, 31.39, 20.00, 19.12, 18.25, 17.80, 17.41. |
| 144 | | | HRMS-ESI (m/z) [M + H]$^+$ calcd for C$_{23}$H$_{29}$FN$_2$O$_5$, 433.2133; found, 433.2139 | $^1$H NMR (500 MHz, CDCl$_3$) δ 12.16 (s, 1H), 8.32 (d, J = 9.2 Hz, 1H), 8.00 (d, J = 5.2 Hz, 1H), 7.16 (dd, J = 8.4, 5.8 Hz, 1H), 6.89 (d, J = 5.2 Hz, 1H), 6.78 (ddd, J = 9.8, 7.0, 4.1 Hz, 2H), 5.17-5.05 (m, 1H), 4.48 (dd, J = 9.3, 5.3 Hz, 1H), 3.96 (s, 3H), 3.22 (p, J = 7.2 Hz, 1H), 2.33 (s, 3H), 2.18 (pd, J = 6.9, 5.2 Hz, 1H), 1.28-1.19 (m, 6H), 0.92 (d, J = 6.8 Hz, 3H), 0.86 (d, J = 6.9 Hz, 3H). $^{13}$C NMR (126 MHz, CDCl$_3$) δ 170.29, 168.86, 161.96, 160.02, 155.40, 148.71, 140.46, 138.45, 138.39, 136.79, 136.76, 130.49, 127.77, 127.70, 116.77, 116.61, 112.79, 112.63, 109.43, 75.66, 57.06, 56.09, 38.58, 31.26, 19.91, 18.94, 17.61, 17.30, 16.84. |
| 145 | | | HRMS-ESI (m/z) [M + H]$^+$ calcd for C$_{23}$H$_{30}$N$_2$O$_5$, 415.2227; found, 415.2224 | $^1$H NMR (500 MHz, CDCl$_3$) δ 12.19 (s, 1H), 8.34 (d, J = 9.3 Hz, 1H), 8.00 (d, J = 5.2 Hz, 1H), 7.21 (dd, J = 7.6, 1.7 Hz, 1H), 7.14-7.05 (m, 2H), 7.02 (td, J = 7.2, 1.4 Hz, 1H), 6.88 (d, J = 5.2 Hz, 1H), 5.20-5.12 (m, 1H), 4.48 (dd, J = 9.3, 5.1 Hz, 1H), 3.95 (s, 3H), 3.28 (p, J = 7.1 Hz, 1H), 2.36 (s, 3H), 2.17 (pd, J = 6.9, 5.1 Hz, 1H), 1.29-1.22 (m, 6H), 0.90 (d, J = 6.8 Hz, 3H), 0.84 (d, J = 6.8 Hz, 3H). $^{13}$C NMR (126 MHz, CDCl$_3$) δ 170.28, 168.84, 155.36, 148.69, 141.08, 140.42, 136.11, 130.59, 130.28, 126.23, 126.11, 109.39, 75.76, 57.06, 56.08, 39.06, 31.33, 19.83, 18.93, 17.59, 17.20, 16.50. |
| 146 | | | HRMS-ESI (m/z) [M + H]$^+$ calcd for C$_{22}$H$_{27}$FN$_2$O$_5$, 419.1977; found, 419.1974 | $^1$H NMR (500 MHz, CDCl$_3$) δ 12.17 (s, 1H), 8.50 (d, J = 8.9 Hz, 1H), 8.02 (d, J = 5.2 Hz, 1H), 7.19-7.10 (m, 3H), 7.00-6.93 (m, 2H), 6.89 (d, J = 5.2 Hz, 1H), 5.11-5.02 (m, 1H), 4.67-4.58 (m, 1H), 3.95 (s, 4H), 2.92 (p, J = 7.1 Hz, 1H), 2.31 (pd, J = 6.9, 5.0 Hz, 1H), 1.28 (d, J = 7.0 Hz, 3H), 1.10 (d, J = 6.2 Hz, 3H), 1.02 (d, J = 6.9 Hz, 3H), 0.99 (d, J = 6.9 Hz, 3H). $^{13}$C NMR (126 MHz, CDCl$_3$) δ 170.76, 169.06, 162.64, 160.70, 155.41, 148.74, 140.53, 138.48, 130.53, 129.28, 129.22, 115.33, 115.16, 109.46, 76.11, 57.07, 56.09, 44.09, 31.35, 19.09, 17.87, 17.82, 17.23. |

TABLE 2-continued

Analytical Data

| Cmpd. No. | Melting Point (° C.) | IR (cm⁻¹) | MASS SPEC | NMR |
|---|---|---|---|---|
| 147 | | | HRMS-ESI (m/z) [M + H]⁺ calcd for C₂₄H₃₂N₂O₆, 445.2333; found, 445.2334 | ¹H NMR (500 MHz, CDCl₃) δ 12.20 (s, 1H), 8.53 (d, J = 9.2 Hz, 1H), 8.02 (d, J = 5.2 Hz, 1H), 7.10 (d, J = 8.4 Hz, 1H), 6.88 (d, J = 5.2 Hz, 1H), 6.75-6.64 (m, 2H), 5.12 (dq, J = 8.2, 6.3 Hz, 1H), 4.65 (dd, J = 9.2, 5.0 Hz, 1H), 3.95 (s, 3H), 3.75 (s, 3H), 3.20-3.06 (m, 1H), 2.32 (s, 4H), 1.23 (d, J = 6.9 Hz, 3H), 1.13 (d, J = 6.2 Hz, 3H), 1.03 (d, J = 6.9 Hz, 3H), 1.00 (d, J = 6.9 Hz, 3H). ¹³C NMR (126 MHz, CDCl₃) δ 170.92, 169.04, 157.67, 155.39, 148.73, 140.52, 136.92, 133.85, 130.59, 127.40, 116.00, 111.44, 109.43, 76.56, 57.04, 56.08, 55.10, 39.05, 31.44, 20.18, 19.13, 18.32, 17.80, 17.65. |
| 148 | | | HRMS-ESI (m/z) [M + H]⁺ calcd for C₂₁H₂₅FN₂O₅, 405.1820; found, 405.1820 | ¹H NMR (500 MHz, CDCl₃) δ 12.14 (s, 1H), 8.47 (d, J = 7.9 Hz, 1H), 8.01 (d, J = 5.2 Hz, 1H), 7.13 (dd, J = 9.5, 5.8 Hz, 1H), 6.91-6.80 (m, 3H), 5.12 (dq, J = 8.1, 6.3 Hz, 1H), 4.72 (p, J = 7.3 Hz, 1H), 3.95 (s, 3H), 3.21-3.10 (m, 1H), 2.33 (s, 3H), 1.54 (d, J = 7.2 Hz, 3H), 1.23 (d, J = 6.9 Hz, 3H), 1.12 (d, J = 6.3 Hz, 3H). ¹³C NMR (126 MHz, CDCl₃) δ 171.81, 168.74, 161.95, 160.01, 155.40, 148.78, 140.51, 137.89, 137.83, 137.29, 137.26, 130.48, 127.87, 127.81, 117.07, 116.91, 113.06, 112.90, 109.48, 76.19, 56.09, 47.96, 39.12, 20.01, 18.24, 18.13, 17.48. |
| 149 | | | HRMS-ESI (m/z) [M + H]⁺ calcd for C₂₁H₂₅FN₂O₅, 405.1820; found, 405.1820 | ¹H NMR (500 MHz, CDCl₃) δ 12.12 (s, 1H), 8.28 (d, J = 8.0 Hz, 1H), 7.99 (d, J = 5.2 Hz, 1H), 7.22-7.09 (m, 1H), 6.88 (d, J = 5.2 Hz, 1H), 6.83-6.74 (m, 2H), 5.19-5.06 (m, 1H), 4.62-4.50 (m, 1H), 3.95 (s, 3H), 3.31-3.17 (m, 1H), 2.33 (s, 3H), 1.38 (d, J = 7.2 Hz, 3H), 1.27-1.18 (m, 6H). ¹³C NMR (126 MHz, CDCl₃) δ 171.29, 168.55, 161.93, 159.99, 155.38, 148.74, 140.44, 138.41, 138.35, 136.73, 136.71, 130.43, 127.71, 127.64, 116.77, 116.61, 112.80, 112.64, 109.45, 75.62, 56.09, 47.82, 38.64, 18.06, 17.22, 16.84. |
| 150 | | | HRMS-ESI (m/z) [M + H]⁺ calcd for C₂₁H₂₆N₂O₅, 387.1914; found, 387.1913 | ¹H NMR (500 MHz, CDCl₃) δ 12.15 (s, 1H), 8.30 (d, J = 7.9 Hz, 1H), 7.99 (d, J = 5.2 Hz, 1H), 7.21 (dd, J = 7.8, 1.4 Hz, 1H), 7.15-7.01 (m, 4H), 6.87 (d, J = 5.2 Hz, 1H), 5.23-5.08 (m, 1H), 4.58-4.49 (m, 1H), 3.95 (s, 3H), 3.28 (h, J = 7.3 Hz, 1H), 2.36 (s, 3H), 1.35 (d, J = 7.2 Hz, 3H), 1.28-1.22 (m, 6H). ¹³C NMR (126 MHz, CDCl₃) δ 171.29, 168.54, 155.35, 148.73, 141.04, 140.40, 136.09, 130.51, 130.26, 126.23, 126.11, 109.40, 75.73, 56.08, 47.88, 39.15, 19.83, 18.11, 17.16, 16.53. |
| 151 | | | HRMS-ESI (m/z) [M + H]⁺ calcd for C₂₀H₂₃FN₂O₅, 391.1664; found, 391.1658 | ¹H NMR (500 MHz, CDCl₃) δ 12.14 (d, J = 0.6 Hz, 1H), 8.46 (d, J = 7.9 Hz, 1H), 8.01 (d, J = 5.2 Hz, 1H), 7.16 (dd, J = 8.7, 5.4 Hz, 2H), 6.97 (t, J = 8.7 Hz, 2H), 6.88 (d, J = 5.2 Hz, 1H), 5.07 (dq, J = 7.4, 6.3 Hz, 1H), 4.79-4.64 (m, 1H), 3.95 (s, 3H), 2.92 (p, J = 7.1 Hz, 1H), 1.53 (d, J = 7.2 Hz, 3H), 1.28 (d, J = 7.1 Hz, 3H), 1.09 (d, J = 6.3 Hz, 3H). ¹³C NMR (126 MHz, CDCl₃) δ 171.72, 168.76, 162.65, 160.70, 155.40, |

TABLE 2-continued

Analytical Data

| Cmpd. No. | Melting Point (° C.) | IR (cm$^{-1}$) | MASS SPEC | NMR |
|---|---|---|---|---|
| | | | | 148.78, 140.51, 138.43, 130.47, 129.29, 129.23, 115.33, 115.16, 109.48, 76.12, 56.09, 47.98, 44.09, 18.19, 17.69, 17.30. |
| 152 | | | HRMS-ESI (m/z) [M + H]$^+$ calcd for C$_{22}$H$_{28}$N$_2$O$_6$, 417.2020; found, 417.2007 | $^1$H NMR (500 MHz, CDCl$_3$) δ 12.17 (s, 1H), 8.50 (d, J = 7.9 Hz, 1H), 8.01 (d, J = 5.2 Hz, 1H), 7.09 (d, J = 8.3 Hz, 1H), 6.88 (d, J = 5.2 Hz, 1H), 6.78-6.64 (m, 2H), 5.13 (dq, J = 8.4, 6.3 Hz, 1H), 4.73 (p, J = 7.3 Hz, 1H), 3.95 (s, 3H), 3.76 (s, 3H), 3.18-3.06 (m, 1H), 2.32 (s, 3H), 1.54 (d, J = 7.2 Hz, 3H), 1.23 (d, J = 6.9 Hz, 3H), 1.12 (d, J = 6.2 Hz, 3H). $^{13}$C NMR (126 MHz, CDCl$_3$) δ 171.86, 168.72, 157.68, 155.38, 148.76, 140.50, 136.94, 133.81, 130.53, 127.37, 115.97, 111.47, 109.45, 76.65, 56.08, 55.11, 47.99, 39.06, 20.19, 18.30, 18.19, 17.68. |
| 153 | | | HRMS-ESI (m/z) [M + H]$^+$ calcd for C$_{21}$H$_{25}$FN$_2$O$_5$, 405.1820; found, 405.1818 | $^1$H NMR (500 MHz, CDCl$_3$) δ 12.14 (s, 1H), 8.49 (d, J = 8.0 Hz, 1H), 8.00 (d, J = 5.2 Hz, 1H), 7.17-7.08 (m, 1H), 6.91-6.81 (m, 4H), 5.11 (dq, J = 8.1, 6.3 Hz, 1H), 4.72 (p, J = 7.3 Hz, 1H), 3.95 (s, 3H), 3.20-3.10 (m, 1H), 2.33 (s, 3H), 1.55 (d, J = 7.2 Hz, 3H), 1.24 (d, J = 6.9 Hz, 3H), 1.14 (d, J = 6.3 Hz, 3H). $^{13}$C NMR (126 MHz, CDCl$_3$) δ 171.80, 168.69, 161.97, 160.03, 155.39, 148.77, 140.51, 137.87, 137.81, 137.33, 137.30, 130.47, 127.86, 127.79, 117.10, 116.94, 113.02, 112.86, 109.47, 76.33, 56.09, 48.13, 39.16, 20.00, 18.41, 18.36, 17.33. |
| 154 | | | HRMS-ESI (m/z) [M + H]$^+$ calcd for C$_{21}$H$_{25}$FN$_2$O$_5$, 405.1820; found, 405.1816 | $^1$H NMR (500 MHz, CDCl$_3$) δ 12.09 (s, 1H), 8.35 (d, J = 8.0 Hz, 1H), 7.98 (d, J = 5.2 Hz, 1H), 7.13 (dd, J = 8.4, 5.8 Hz, 1H), 6.86 (d, J = 5.2 Hz, 1H), 6.80 (ddd, J = 9.5, 7.0, 4.1 Hz, 2H), 5.14 (dq, J = 8.2, 6.2 Hz, 1H), 4.60-4.49 (m, 1H), 3.94 (s, 3H), 3.27-3.16 (m, 1H), 2.34 (s, 3H), 1.30 (d, J = 6.3 Hz, 3H), 1.22 (d, J = 7.1 Hz, 3H), 1.14 (d, J = 7.2 Hz, 3H). $^{13}$C NMR (126 MHz, CDCl$_3$) δ 171.55, 168.59, 161.91, 159.97, 155.37, 148.74, 140.44, 138.30, 138.24, 137.15, 137.13, 130.43, 127.46, 127.40, 116.74, 116.57, 112.90, 112.73, 109.43, 75.74, 56.08, 47.87, 38.98, 19.90, 19.89, 17.79, 17.32. |
| 155 | | | HRMS-ESI (m/z) [M + H]$^+$ calcd for C$_{21}$H$_{26}$N$_2$O$_5$, 387.1914; found, 387.1912 | $^1$H NMR (500 MHz, CDCl$_3$) δ 12.11 (d, J = 0.6 Hz, 1H), 8.36 (d, J = 8.0 Hz, 1H), 7.97 (d, J = 5.2 Hz, 1H), 7.19 (dd, J = 7.5, 1.2 Hz, 1H), 7.12 (td, J = 7.8, 7.0, 2.4 Hz, 1H), 7.09-7.02 (m, 2H), 6.86 (d, J = 5.2 Hz, 1H), 5.19 (dq, J = 8.3, 6.2 Hz, 1H), 4.60-4.45 (m, 1H), 3.94 (s, 3H), 3.33-3.20 (m, 1H), 2.36 (s, 3H), 1.32 (d, J = 6.2 Hz, 3H), 1.24 (d, J = 7.0 Hz, 3H), 1.08 (d, J = 7.2 Hz, 3H). $^{13}$C NMR (126 MHz, CDCl$_3$) δ 171.58, 168.54, 155.33, 148.71, 141.47, 140.41, 135.95, 130.49, 130.22, 126.20, 125.88, 109.39, 75.87, 56.06, 47.85, 39.52, 19.83, 17.83, 17.74, 17.14. |
| 156 | | | HRMS-ESI (m/z) [M + H]$^+$ calcd for C$_{20}$H$_{23}$FN$_2$O$_5$, 391.1664; found, 391.1661 | $^1$H NMR (500 MHz, CDCl$_3$) δ 12.14 (s, 1H), 8.47 (d, J = 7.7 Hz, 1H), 8.00 (d, J = 5.2 Hz, 1H), 7.21-7.10 (m, 3H), 6.97 (td, J = 8.8, 2.6 Hz, 2H), 6.88 (dd, J = 5.3, 1.7 Hz, 1H), 5.12-5.01 (m, 1H), 4.77-4.66 (m, 1H), 3.95 (d, |

TABLE 2-continued

Analytical Data

| Cmpd. No. | Melting Point (° C.) | IR (cm$^{-1}$) | MASS SPEC | NMR |
|---|---|---|---|---|
| | | | | J = 1.6 Hz, 4H), 2.92 (p, J = 7.1 Hz, 1H), 1.53 (d, J = 7.2 Hz, 4H), 1.29 (d, J = 7.0 Hz, 3H), 1.12 (d, J = 6.3 Hz, 3H). $^{13}$C NMR (126 MHz, CDCl$_3$) δ 171.67, 168.69, 162.64, 160.70, 155.40, 148.78, 140.51, 138.45, 130.46, 129.26, 115.32, 115.16, 109.48, 76.31, 56.09, 48.12, 44.11, 18.38, 17.95, 17.16. |
| 157 | | | HRMS-ESI (m/z) [M + H]$^+$ calcd for C$_{22}$H$_{28}$N$_2$O$_6$, 417.2020; found, 417.2006 | $^1$H NMR (500 MHz, CDCl$_3$) δ 12.16 (s, 1H), 8.51 (d, J = 7.9 Hz, 1H), 8.00 (d, J = 5.2 Hz, 1H), 7.12-7.06 (m, 1H), 6.88 (d, J = 5.2 Hz, 1H), 6.76-6.67 (m, 2H), 5.11 (dq, J = 8.3, 6.3 Hz, 1H), 4.72 (p, J = 7.3 Hz, 1H), 3.95 (s, 3H), 3.77 (s, 3H), 3.19-3.07 (m, 1H), 2.32 (s, 3H), 1.61-1.51 (m, 4H), 1.23 (d, J = 6.9 Hz, 3H), 1.14 (d, J = 6.3 Hz, 3H). $^{13}$C NMR (126 MHz, CDCl$_3$) δ 171.86, 168.68, 157.70, 155.38, 148.77, 140.50, 136.91, 133.86, 130.51, 127.36, 115.95, 111.48, 109.45, 56.08, 55.13, 48.17, 39.11, 20.18, 18.46, 17.57. |
| 158 | | IR (thin film) 3369, 2983, 1736, 1649, 1528, 1310, 1148, 1115, 770, 731 cm$^{-1}$ | HRMS-ESI (m/z) [M + H]$^+$ calcd for C$_{21}$H$_{24}$F$_3$N$_2$O$_5$, 441.1632; found, 441.1627 | $^1$H NMR (400 MHz, CDCl$_3$) δ 12.13 (s, 1H), 8.58-8.47 (m, 1H), 8.01 (d, J = 5.2 Hz, 1H), 7.68-7.61 (m, 1H), 7.51 (td, J = 7.7, 1.2 Hz, 1H), 7.43 (d, J = 7.7 Hz, 1H), 7.38-7.29 (m, 1H), 6.88 (d, J = 5.2 Hz, 1H), 5.29-5.15 (m, 1H), 4.82-4.71 (m, 1H), 3.95 (s, 3H), 3.42-3.29 (m, 1H), 1.60 (d, J = 7.2 Hz, 3H), 1.29 (d, J = 6.8 Hz, 3H), 1.12 (d, J = 6.2 Hz, 3H). $^{19}$F NMR (376 MHz, CDCl$_3$) δ −58.24. |
| 159 | | IR (thin film) 3370, 2984, 1737, 1528, 1313, 1151, 1118, 1045, 908, 799, 738 cm$^{-1}$ | HRMS-ESI (m/z) [M + H]$^+$ calcd for C$_{21}$H$_{23}$F$_4$N$_2$O$_5$, 459.1538; found, 459.1535 | $^1$H NMR (400 MHz, CDCl$_3$) δ 12.11 (s, 1H), 8.50 (d, J = 7.9 Hz, 1H), 8.01 (d, J = 5.2 Hz, 1H), 7.42 (dd, J = 8.8, 5.3 Hz, 1H), 7.35 (dd, J = 9.2, 2.8 Hz, 1H), 7.21 (td, J = 8.2, 2.8 Hz, 1H), 6.89 (d, J = 5.2 Hz, 1H), 5.24-5.09 (m, 1H), 4.82-4.67 (m, 1H), 3.95 (s, 3H), 3.41-3.26 (m, 1H), 1.59 (d, J = 7.2 Hz, 3H), 1.27 (d, J = 6.8 Hz, 3H), 1.12 (d, J = 6.3 Hz, 3H). $^{19}$F NMR (376 MHz, CDCl$_3$) δ −58.78, −113.91. |
| 160 | | IR (thin film) 3369, 2944, 1732, 1648, 1526, 1438, 1280, 1263, 1216, 1149, 1057, 800 cm$^{-1}$ | HRMS-ESI (m/z) [M + H]$^+$ calcd for C$_{19}$H$_{29}$N$_2$O$_5$, 365.2071; found, 365.2067 | $^1$H NMR (400 MHz, CDCl$_3$) δ 12.17 (s, 1H), 8.53 (d, J = 7.8 Hz, 1H), 7.99 (d, J = 5.2 Hz, 1H), 6.87 (d, J = 5.2 Hz, 1H), 5.11 (qd, J = 6.4, 3.1 Hz, 1H), 4.76-4.64 (m, 1H), 3.95 (s, 3H), 1.76 (dddd, J = 13.2, 10.4, 8.0, 6.4 Hz, 2H), 1.69-1.52 (m, 6H), 1.52-1.43 (m, 1H), 1.43-1.35 (m, 1H), 1.24 (d, J = 6.4 Hz, 3H), 1.19-0.98 (m, 3H), 0.98-0.89 (m, 3H). $^{13}$C NMR (101 MHz, CDCl$_3$) δ 171.76, 168.71, 155.39, 148.78, 140.46, 130.58, 109.43, 74.81, 56.08, 48.23, 43.31, 43.13, 31.22, 30.74, 25.15, 24.98, 18.51, 17.78, 12.50. |
| 161 | | | HRMS-ESI (m/z) [M + H]$^+$ calcd for C$_{21}$H$_{24}$F$_3$N$_2$O$_5$, 441.1632; found, 441.1624 | $^1$H NMR (400 MHz, CDCl$_3$) δ 12.15 (s, 1H), 8.48 (d, J = 8.0 Hz, 1H), 8.01 (d, J = 5.2 Hz, 1H), 7.64 (dd, J = 7.9, 1.3 Hz, 1H), 7.56-7.47 (m, 1H), 7.44 (d, J = 7.8 Hz, 1H), 7.31 (t, J = 7.5 Hz, 1H), 6.88 (d, J = 5.2 Hz, 1H), 5.27-5.17 (m, 1H), 4.83-4.68 (m, 1H), 3.95 (s, 3H), 3.42-3.28 (m, 1H), 1.58 (d, J = 7.2 Hz, 3H), 1.30 (d, J = 6.8 Hz, 3H), 1.10 (d, J = 6.2 Hz, 3H). $^{19}$F NMR (376 MHz, CDCl$_3$) δ −58.24. |
| 162 | | IR (thin film) 2983, 1738, 1649, | HRMS-ESI (m/z) [M + H]$^+$ calcd for C$_{21}$H$_{23}$F$_4$N$_2$O$_5$, | $^1$H NMR (400 MHz, CDCl$_3$) δ 12.12 (s, 1H), 8.46 (d, J = 7.9 Hz, 1H), 8.01 (d, J = 5.2 Hz, 1H), 7.43 (dd, J = 8.8, |

TABLE 2-continued

Analytical Data

| Cmpd. No. | Melting Point (° C.) | IR (cm$^{-1}$) | MASS SPEC | NMR |
|---|---|---|---|---|
| | | 1528, 1313, 1152, 1119, 1045, 909, 800, 732 cm$^{-1}$ | 459.1538; found, 459.1530 | 5.3 Hz, 1H), 7.34 (dd, J = 9.2, 2.8 Hz, 1H), 7.21 (td, J = 8.2, 2.8 Hz, 1H), 6.89 (d, J = 5.2 Hz, 1H), 5.18 (p, J = 6.6 Hz, 1H), 4.79-4.69 (m, 1H), 3.95 (s, 3H), 3.31 (p, J = 7.1 Hz, 1H), 1.57 (d, J = 7.2 Hz, 3H), 1.29 (d, J = 6.9 Hz, 3H), 1.12 (d, J = 6.3 Hz, 3H). $^{19}$F NMR (376 MHz, CDCl$_3$) δ −58.78, −114.01. |
| 163 | | IR (thin film) 3370, 2944, 1732, 1649, 1526, 1438, 1263, 1216, 1150, 1058, 954, 800, 731 cm$^{-1}$ | HRMS-ESI (m/z) [M + H]$^+$ calcd for C$_{19}$H$_{29}$N$_2$O$_5$, 365.2071; found, 365.2068 | $^1$H NMR (400 MHz, CDCl$_3$) δ 12.18 (s, 1H), 8.52 (d, J = 7.8 Hz, 1H), 7.99 (d, J = 5.2 Hz, 1H), 6.87 (d, J = 5.2 Hz, 1H), 5.10 (qd, J = 6.4, 3.0 Hz, 1H), 4.74-4.64 (m, 1H), 3.95 (s, 3H), 1.83-1.65 (m, 3H), 1.65-1.52 (m, 6H), 1.52-1.34 (m, 2H), 1.23 (d, J = 6.4 Hz, 3H), 1.18-1.03 (m, 2H), 0.94 (d, J = 6.9 Hz, 3H). $^{13}$C NMR (101 MHz, CDCl$_3$) δ 171.75, 168.76, 155.39, 148.79, 140.46, 130.62, 109.44, 74.90, 56.08, 48.04, 43.11, 42.95, 31.26, 30.67, 25.14, 25.00, 18.33, 17.49, 12.53. |
| 164 | | IR (thin film) 3369, 2971, 1733, 1648, 1527, 1438, 1263, 1149, 1057, 801, 770, 730 cm$^{-1}$ | HRMS-ESI (m/z) [M + H]$^+$ calcd for C$_{22}$H$_{29}$N$_2$O$_5$, 401.2071; found, 401.2072 | $^1$H NMR (400 MHz, CDCl$_3$) δ 12.17 (s, 1H), 8.58 (t, J = 7.7 Hz, 1H), 7.99 (d, J = 5.2 Hz, 1H), 7.14-6.90 (m, 3H), 6.87 (d, J = 5.3 Hz, 1H), 5.72-5.58 (m, 1H), 4.86-4.71 (m, 1H), 3.93 (s, 3H), 3.44 (dp, J = 10.5, 7.1 Hz, 1H), 2.42 (d, J = 1.7 Hz, 3H), 2.38 (s, 3H), 1.61 (dd, J = 14.3, 7.2 Hz, 3H), 1.29 (dd, J = 7.1, 2.7 Hz, 3H), 1.10-0.95 (m, 3H). |
| 165 | | IR (thin film) 3370, 2975, 1734, 1649, 1527, 1480, 1262, 1148, 849, 799, 728 cm$^{-1}$ | HRMS-ESI (m/z) [M + H]$^+$ calcd for C$_{22}$H$_{28}$FN$_2$O$_5$, 419.1977; found, 419.1975 | $^1$H NMR (400 MHz, CDCl$_3$) δ 12.15 (s, 1H), 8.69-8.42 (m, 1H), 8.00 (d, J = 5.2 Hz, 1H), 6.88 (d, J = 5.2 Hz, 1H), 6.70 (ddd, J = 14.6, 8.1, 2.5 Hz, 2H), 5.59 (ddq, J = 12.4, 10.7, 6.2 Hz, 1H), 4.76 (p, J = 7.2 Hz, 1H), 3.94 (d, J = 1.9 Hz, 3H), 3.38 (dp, J = 10.5, 7.0 Hz, 1H), 2.41 (d, J = 1.9 Hz, 3H), 2.36 (s, 3H), 1.61 (dd, J = 13.6, 7.2 Hz, 3H), 1.27 (dd, J = 7.1, 3.1 Hz, 3H), 1.04 (dt, J = 11.6, 6.2 Hz, 3H). $^{19}$F NMR (376 MHz, CDCl$_3$) δ −118.25, −118.31. |
| 166 | | IR (thin film) 3369, 2971, 1733, 1648, 1527, 1438, 1280, 1263, 1149, 1056, 801, 770, 730 cm$^{-1}$ | HRMS-ESI (m/z) [M + H]$^+$ calcd for C$_{22}$H$_{29}$N$_2$O$_5$, 401.2071; found, 401.2066 | $^1$H NMR (400 MHz, CDCl$_3$) δ 12.16 (d, J = 3.9 Hz, 1H), 8.56 (t, J = 7.7 Hz, 1H), 8.00 (d, J = 5.2 Hz, 1H), 7.07-6.90 (m, 3H), 6.88 (d, J = 5.2 Hz, 1H), 5.73-5.53 (m, 1H), 4.76 (pd, J = 7.2, 1.1 Hz, 1H), 3.95 (s, 3H), 3.43 (dp, J = 10.5, 7.2 Hz, 1H), 2.42 (d, J = 1.9 Hz, 3H), 2.38 (s, 3H), 1.61 (dd, J = 14.3, 7.2 Hz, 3H), 1.29 (dd, J = 7.2, 2.3 Hz, 3H), 1.06 (t, J = 6.0 Hz, 3H). |
| 167 | | IR (thin film) 3370, 2976, 1734, 1649, 1527, 1480, 1263, 1149, 849, 800, 730 cm$^{-1}$ | HRMS-ESI (m/z) [M + H]$^+$ calcd for C$_{22}$H$_{28}$FN$_2$O$_5$, 419.1977; found, 419.1971 | $^1$H NMR (400 MHz, CDCl$_3$) δ 12.15 (d, J = 3.3 Hz, 1H), 8.55 (t, J = 7.9 Hz, 1H), 8.00 (d, J = 5.2 Hz, 1H), 6.88 (d, J = 5.2 Hz, 1H), 6.70 (ddd, J = 15.1, 9.4, 2.6 Hz, 2H), 5.59 (ddq, J = 12.4, 10.5, 6.2 Hz, 1H), 4.76 (p, J = 7.3 Hz, 1H), 3.95 (s, 3H), 3.38 (dp, J = 10.5, 7.0 Hz, 1H), 2.41 (d, J = 1.9 Hz, 3H), 2.36 (s, 3H), 1.61 (dd, J = 13.6, 7.2 Hz, 3H), 1.27 (dd, J = 7.2, 2.9 Hz, 3H), 1.05 (t, J = 5.9 Hz, 3H). $^{19}$F NMR (376 MHz, CDCl$_3$) δ −118.26, −118.27, −118.33. |
| 168 | | IR (thin film) 3370, 2971, 1734, 1649, 1527, 1451, 1263, | HRMS-ESI (m/z) [M + H]$^+$ calcd for C$_{22}$H$_{29}$N$_2$O$_5$, 401.2071; found, 401.2070 | $^1$H NMR (400 MHz, CDCl$_3$) δ 12.16 (d, J = 3.8 Hz, 1H), 8.56 (t, J = 7.6 Hz, 1H), 8.01 (d, J = 5.2 Hz, 1H), 7.05-6.91 (m, 3H), 6.88 (d, J = 5.2 Hz, 1H), 5.70-5.57 (m, 1H), 4.76 (pd, J = 7.1, |

TABLE 2-continued

Analytical Data

| Cmpd. No. | Melting Point (° C.) | IR (cm$^{-1}$) | MASS SPEC | NMR |
|---|---|---|---|---|
| | | 1150, 801, 770, 730 cm$^{-1}$ | | 1.1 Hz, 1H), 3.95 (s, 3H), 3.43 (dp, J = 10.5, 7.2 Hz, 1H), 2.42 (d, J = 2.0 Hz, 3H), 2.38 (s, 3H), 1.61 (dd, J = 14.3, 7.2 Hz, 3H), 1.29 (dd, J = 7.2, 2.1 Hz, 3H), 1.06 (t, J = 6.0 Hz, 3H). |
| 169 | | IR (thin film) 3371, 2976, 1734, 1649, 1527, 1480, 1280, 1262, 1157, 849, 800, 731 cm$^{-1}$ | HRMS-ESI (m/z) [M + H]$^+$ calcd for C$_{22}$H$_{28}$FN$_2$O$_5$, 419.1977; found, 419.1971 | $^1$H NMR (400 MHz, CDCl$_3$) δ 12.15 (d, J = 3.3 Hz, 1H), 8.55 (t, J = 7.8 Hz, 1H), 8.00 (d, J = 5.2 Hz, 1H), 6.88 (d, J = 5.2 Hz, 1H), 6.70 (ddd, J = 17.0, 9.4, 2.8 Hz, 2H), 5.59 (ddq, J = 12.2, 10.8, 6.2 Hz, 1H), 4.76 (p, J = 7.3 Hz, 1H), 3.95 (s, 3H), 3.38 (dp, J = 10.4, 7.0 Hz, 1H), 2.41 (d, J = 2.2 Hz, 3H), 2.36 (s, 3H), 1.61 (dd, J = 13.6, 7.2 Hz, 3H), 1.27 (dd, J = 72, 2.8 Hz, 3H), 1.05 (t, J = 5.9 Hz, 3H). $^{19}$F NMR (376 MHz, CDCl$_3$) δ −118.29, −118.36. |
| 170 | | | HRMS-ESI (m/z) [M + H]$^+$ calcd for C$_{21}$H$_{27}$N$_2$O$_6$, 403.1864; found, 403.1827 | $^1$H NMR (400 MHz, CDCl$_3$) δ 12.16 (s, 1H), 8.41 (d, J = 7.9 Hz, 1H), 7.97 (d, J = 5.2 Hz, 1H), 7.23-7.10 (m, 2H), 6.92-6.78 (m, 3H), 5.31 (dq, J = 7.8, 6.3 Hz, 1H), 4.63-4.49 (m, 1H), 3.93 (s, 3H), 3.81 (s, 3H), 3.49-3.39 (m, 1H), 1.26 (d, J = 6.3 Hz, 3H), 1.23 (d, J = 7.2 Hz, 3H), 1.16 (d, J = 7.2 Hz, 3H). $^{13}$C NMR (101 MHz, CDCl$_3$) δ 171.5, 168.6, 157.2, 155.3, 148.7, 140.4, 131.1, 130.6, 128.1, 127.4, 120.5, 110.5, 109.4, 75.1, 56.0, 55.4, 48.0, 37.6, 17.9, 17.8, 16.6. |
| 171 | | IR (thin film) 2978, 2937, 1733, 1647, 1527, 1451, 1262, 1147, 701 cm$^{-1}$ | HRMS-ESI (m/z) [M + H]$^+$ calcd for C$_{20}$H$_{25}$N$_2$O$_5$, 373.1758; found, 373.1752 | $^1$H NMR (500 MHz, CDCl$_3$) δ 12.16 (s, 1H), 8.50 (d, J = 8.0 Hz, 1H), 8.01 (d, J = 5.2 Hz, 1H), 7.32-7.27 (m, 2H), 7.24-7.16 (m, 3H), 6.88 (d, J = 5.2 Hz, 1H), 5.11 (dq, J = 1.1, 6.3 Hz, 1H), 4.77-4.67 (m, 1H), 3.95 (s, 3H), 2.97-2.87 (m, 1H), 1.54 (d, J = 1.2 Hz, 3H), 1.31 (d, J = 7.0 Hz, 3H), 1.13 (d, J = 6.3 Hz, 3H). $^{13}$C NMR (126 MHz, CDCl$_3$) δ 171.8, 168.7, 155.3, 148.7, 142.9, 140.5, 130.4, 128.5, 127.8, 126.8, 109.4, 76.5, 56.1, 48.1, 44.9, 18.4, 18.2, 17.2. |
| 172 | | IR (thin film) 3368, 2978, 1937, 1734, 1648, 1527, 1480, 1438, 1262, 797, 730 cm$^{-1}$ | HRMS-ESI (m/z) [M + H]$^+$ calcd for C$_{19}$H$_{25}$N$_2$O$_5$S, 393.1479; found, 393.1473 | $^1$H NMR (500 MHz, CDCl$_3$) δ 12.16 (s, 1H), 8.50 (d, J = 7.9 Hz, 1H), 8.00 (d, J = 5.2 Hz, 1H), 6.88 (d, J = 5.2 Hz, 1H), 6.61 (d, J = 3.5 Hz, 1H), 6.55 (dq, J = 3.5, 1.1 Hz, 1H), 5.10-5.01 (m, 1H), 4.77-4.67 (m, 1H), 3.95 (s, 3H), 3.22-3.12 (m, 1H), 2.42 (d, J = 1.1 Hz, 3H), 1.55 (d, J = 7.1 Hz, 3H), 1.33 (d, J = 7.0 Hz, 3H), 1.20 (d, J = 6.3 Hz, 3H). $^{13}$C NMR (126 MHz, CDCl$_3$) δ 171.6, 168.7, 155.3, 148.7, 143.3, 140.5, 138.0, 130.5, 124.5, 124.1, 109.4, 76.1, 56.1, 48.1, 40.1, 18.4, 17.8, 17.2, 15.3. |
| 173 | | IR (thin film) 3369, 2977, 2939, 1733, 1649, 1528, 1450, 1278, 1262, 1149, 952 cm$^{-1}$ | HRMS-ESI (m/z) [M + H]$^+$ calcd for C$_{21}$H$_{26}$FN$_2$O$_6$, 421.1769; found, 421.1770 | $^1$H NMR (500 MHz, CDCl$_3$) δ 12.19 (s, 1H), 8.49 (d, J = 7.9 Hz, 1H), 8.01 (d, J = 5.2 Hz, 1H), 7.13-7.06 (m, 1H), 6.88 (d, J = 5.3 Hz, 1H), 6.62-6.54 (m, 2H), 5.21-5.12 (m, 1H), 4.73-4.63 (m, 1H), 3.95 (s, 3H), 3.79 (s, 3H), 3.42-3.32 (m, 1H), 1.51 (d, J = 7.2 Hz, 3H), 1.24 (d, J = 7.0 Hz, 3H), 1.14 (d, J = 6.3 Hz, 3H). $^{19}$FNMR(471 MHz, CDCl$_3$) δ −113.8-−113.9 (m). |
| 174 | | | ESIMS m/z 387.3 [(M + H)+] | $^1$H NMR (400 MHz, CDCl$_3$) δ 12.16 (d, J = 4.9 Hz, 1H), 8.50 (d, J = 7.8 Hz, 1H), 8.01 (dd, J = 5.2, 2.7 Hz, 1H), 7.21-7.01 (m, 4H), 6.88 (dd, J = 5.3, 1.9 Hz, 1H), 5.18 (dq, J = 8.3, 6.3 Hz, 1H), 4.73 (p, J = 7.3 Hz, 1H), 3.95 (d, |

TABLE 2-continued

Analytical Data

| Cmpd. No. | Melting Point (° C.) | IR (cm$^{-1}$) | MASS SPEC | NMR |
|---|---|---|---|---|
| | | | | J = 1.6 Hz, 3H), 3.19 (dq, J = 9.0, 6.9 Hz, 1H), 2.35 (s, 3H), 1.55 (d, J = 7.0 Hz, 3H), 1.26 (dd, J = 6.9, 3.8 Hz, 3H), 1.13 (dd, J = 9.0, 6.2 Hz, 3H). $^{13}$C NMR (101 MHz, CDCl$_3$) δ 171.85, 168.74, 155.41, 148.80, 141.65, 140.49, 135.53, 130.54, 126.37, 126.31, 126.29, 109.46, 56.07, 53.40, 48.00, 39.74, 19.94, 18.28, 18.27, 17.52, −0.01. |
| 175 | | | | $^{1}$H NMR (400 MHz, CDCl$_3$) δ 12.16 (d, J = 0.6 Hz, 1H), 8.51 (d, J = 7.9 Hz, 1H), 8.00 (d, J = 5.2 Hz, 1H), 7.22-7.02 (m, 5H), 6.88 (d, J = 5.2 Hz, 1H), 5.16 (dq, J = 8.3, 6.2 Hz, 1H), 4.78-4.65 (m, 1H), 3.95 (s, 3H), 3.20 (dq, J = 8.3, 6.9 Hz, 1H), 2.35 (s, 3H), 1.56 (d, J = 7.2 Hz, 3H), 1.26 (d, J = 6.9 Hz, 3H), 1.15 (d, J = 6.3 Hz, 3H). |
| 176 | | | ESIMS m/z 416 ([M + H]$^+$) | $^{1}$H NMR (300 MHz, CDCl$_3$) δ 12.18 (s, 1H), 8.52 (d, J = 7.9 Hz, 1H), 8.00 (d, J = 5.2 Hz, 1H), 7.13-7.01 (m, 2H), 6.88 (d, J = 5.2 Hz, 1H), 6.67 (d, J = 8.5 Hz, 2H), 5.12-4.98 (m, 1H), 4.72 (p, J = 7.3 Hz, 1H), 3.95 (s, 3H), 2.92 (s, 6H), 2.88-2.75 (m, 1H), 1.57 (s, 3H), 1.26 (dd, J = 7.1, 4.0 Hz, 3H), 1.11 (d, J = 6.2 Hz, 3H). $^{13}$C NMR (75 MHz, CDCl$_3$) δ 148.75, 140.49, 130.54, 128.42, 112.68, 109.42, 40.70, 18.33 (d, J = 22.8 Hz), 0.01. |
| 177 | | | HRMS-ESI (m/z) [M + H]$^+$ calcd for C$_{24}$H$_{30}$N$_2$O$_6$, 443.2177; found, 443.2170 | $^{1}$H NMR (500 MHz, CDCl$_3$) δ 8.57 (s, 1H), 8.34 (d, J = 5.4 Hz, 1H), 7.07 (d, J = 8.6 Hz, 1H), 7.01 (d, J = 5.5 Hz, 1H), 6.97 (d, J = 6.7 Hz, 2H), 5.12 (dq, J = 8.5, 6.3 Hz, 1H), 4.78-4.67 (m, 1H), 3.91 (s, 3H), 3.19-3.09 (m, 1H), 2.41 (s, 3H), 2.31 (s, 3H), 2.28 (s, 3H), 1.52 (d, J = 7.2 Hz, 3H), 1.23 (d, J = 6.9 Hz, 3H), 1.11 (d, J = 6.2 Hz, 3H). $^{13}$C NMR (126 MHz, CDCl$_3$) δ 172.41, 168.96, 162.36, 159.42, 146.70, 141.53, 138.75, 137.46, 135.67, 135.33, 131.26, 126.95, 126.26, 109.75, 76.48, 56.29, 48.16, 39.45, 20.89, 20.78, 19.90, 18.76, 18.48, 17.67. |
| 178 | | | HRMS-ESI (m/z) [M + H]$^+$ calcd for C$_{24}$H$_{30}$N$_2$O$_6$, 443.2177; found, 443.2172 | $^{1}$H NMR (500 MHz, CDCl$_3$) δ 8.57 (s, 1H), 8.35 (d, J = 5.5 Hz, 1H), 7.07 (d, J = 7.7 Hz, 1H), 7.01 (d, J = 5.5 Hz, 1H), 6.98 (d, J = 7.4 Hz, 2H), 5.12 (dq, J = 8.5, 6.2 Hz, 1H), 4.72 (p, J = 7.2 Hz, 1H), 3.91 (s, 3H), 3.18-3.09 (m, 1H), 2.41 (s, 3H), 2.31 (s, 3H), 2.27 (s, 3H), 1.50 (d, J = 7.2 Hz, 3H), 1.22 (d, J = 6.9 Hz, 3H), 1.10 (d, J = 6.2 Hz, 3H). $^{13}$C NMR (126 MHz, CDCl$_3$) δ 172.41, 168.97, 162.40, 159.43, 146.70, 141.52, 138.72, 137.46, 135.64, 135.37, 131.24, 126.98, 126.27, 109.75, 76.37, 56.29, 48.04, 39.38, 20.88, 20.78, 19.92, 18.59, 18.24, 17.73. |
| 179 | | | HRMS-ESI (m/z) [M + H]$^+$ calcd for C$_{26}$H$_{34}$N$_2$O$_6$, 471.2490; found, 471.2484 | $^{1}$H NMR (500 MHz, CDCl$_3$) δ 8.51 (s, 1H), 8.33 (d, J = 5.4 Hz, 1H), 7.09-7.04 (m, 1H), 7.02-6.94 (m, 3H), 5.11 (dq, J = 8.5, 6.2 Hz, 1H), 4.73 (p, J = 7.2 Hz, 1H), 3.89 (s, 3H), 3.19-3.09 (m, 1H), 2.96 (p, J = 7.0 Hz, 1H), 2.31 (s, 3H), 2.28 (s, 3H), 1.51 (d, J = 7.2 Hz, 3H), 1.36 (dd, J = 7.0, 1.4 Hz, 5H), 1.23 (d, J = 6.9 Hz, 3H), 1.11 (d, J = 6.2 Hz, 3H). $^{13}$C NMR (126 MHz, CDCl$_3$) δ 174.73, 172.50, 162.34, 159.40, 146.59, 141.90, 138.78, 137.63, 135.66, |

TABLE 2-continued

Analytical Data

| Cmpd. No. | Melting Point (° C.) | IR (cm$^{-1}$) | MASS SPEC | NMR |
|---|---|---|---|---|
| 180 | | | HRMS-ESI (m/z) [M + H]$^+$ calcd for C$_{26}$H$_{34}$N$_2$O$_6$, 471.2490; found, 471.2490 | 135.33, 131.25, 126.95, 126.28, 109.58, 76.41, 56.29, 48.13, 39.45, 33.94, 20.89, 19.90, 18.80, 18.48, 17.66. $^1$H NMR (500 MHz, CDCl$_3$) δ 8.50 (s, 1H), 8.34 (d, J = 5.4 Hz, 1H), 7.07 (d, J = 7.8 Hz, 1H), 7.03-6.93 (m, 3H), 5.12 (dq, J = 8.5, 6.2 Hz, 1H), 4.72 (p, J = 7.1 Hz, 1H), 3.89 (s, 3H), 3.20-3.09 (m, 1H), 2.96 (p, J = 7.0 Hz, 1H), 2.31 (s, 3H), 2.27 (s, 3H), 1.49 (d, J = 7.1 Hz, 3H), 1.37 (dd, J = 6.9, 2.0 Hz, 6H), 1.22 (d, J = 6.9 Hz, 3H), 1.09 (d, J = 6.2 Hz, 3H). $^{13}$C NMR (126 MHz, CDCl$_3$) δ 174.74, 172.50, 162.39, 159.41, 146.59, 141.90, 138.76, 137.63, 135.63, 135.37, 131.23, 126.98, 126.28, 109.58, 76.29, 56.29, 48.03, 39.40, 33.94, 20.88, 19.91, 18.81, 18.59, 18.25, 17.74. |
| 181 | | | HRMS-ESI (m/z) [M + H]$^+$ calcd for C$_{23}$H$_{27}$FN$_2$O$_6$, 447.1926; found, 447.1923 | $^1$H NMR (500 MHz, CDCl$_3$) δ 8.37 (s, 1H), 8.33 (d, J = 5.4 Hz, 1H), 7.17 (dd, J = 8.4, 5.9 Hz, 1H), 7.01 (d, J = 5.4 Hz, 1H), 6.84-6.75 (m, 2H), 5.10 (p, J = 6.4 Hz, 1H), 4.57 (p, J = 7.2 Hz, 1H), 3.91 (s, 3H), 3.22 (p, J = 7.0 Hz, 1H), 2.40 (s, 2H), 2.33 (s, 3H), 1.34 (d, J = 7.1 Hz, 2H), 1.27-1.18 (m, 6H). $^{13}$C NMR (126 MHz, CDCl$_3$) δ 171.87, 168.95, 162.24, 161.89, 159.95, 159.44, 146.62, 141.38, 138.44, 137.47, 136.77, 127.73, 116.74, 116.58, 112.79, 112.62, 109.75, 75.32, 56.29, 47.87, 38.50, 20.76, 19.89, 18.40, 17.06, 16.72. |
| 182 | | | HRMS-ESI (m/z) [M + H]$^+$ calcd for C$_{22}$H$_{25}$FN$_2$O$_6$, 433.1769; found, 433.1767 | $^1$H NMR (500 MHz, CDCl$_3$) δ 8.53 (s, 1H), 8.35 (d, J = 5.5 Hz, 1H), 7.22-7.13 (m, 2H), 7.05-6.93 (m, 3H), 5.05 (h, J = 6.5 Hz, 1H), 4.71 (ddt, J = 14.7, 10.3, 5.3 Hz, 1H), 3.91 (s, 3H), 2.91 (p, J = 6.8 Hz, 1H), 2.41 (s, 3H), 1.48 (d, J = 7.2 Hz, 3H), 1.27 (d, J = 7.2 Hz, 3H), 1.08 (d, J = 6.3 Hz, 3H). $^{13}$C NMR (126 MHz, CDCl$_3$) δ 170.34, 167.06, 160.68, 160.54, 158.74, 157.59, 144.78, 139.51, 136.64, 136.61, 135.58, 127.40, 127.34, 113.37, 113.21, 107.93, 73.96, 54.42, 46.14, 42.14, 18.85, 16.52, 15.76, 15.38. |
| 183 | | | HRMS-ESI (m/z) [M + H]$^+$ calcd for C$_{24}$H$_{30}$N$_2$O$_7$, 459.2126; found, 459.2096 | $^1$H NMR (500 MHz, CDCl$_3$) δ 8.56 (s, 1H), 8.35 (d, J = 5.4 Hz, 1H), 7.09 (d, J = 8.4 Hz, 1H), 7.02 (d, J = 5.5 Hz, 1H), 6.75-6.66 (m, 2H), 5.15-5.05 (m, 1H), 4.72 (pd, J = 7.3, 1.5 Hz, 1H), 3.92 (s, 3H), 3.76 (s, 3H), 3.16-3.07 (m, 1H), 2.41 (s, 3H), 2.32 (s, 3H), 1.50 (d, J = 7.2 Hz, 3H), 1.22 (d, J = 6.8 Hz, 3H), 1.10 (d, J = 6.3 Hz, 3H). $^{13}$C NMR (126 MHz, CDCl$_3$) δ 170.45, 167.03, 160.47, 157.55, 155.65, 144.76, 139.57, 135.54, 135.02, 132.00, 125.43, 113.97, 109.50, 107.85, 74.52, 54.38, 53.17, 46.15, 37.09, 18.83, 18.29, 16.63, 16.24, 15.80. |
| 184 | | | HRMS-ESI (m/z) [M + H]$^+$ calcd for C$_{25}$H$_{31}$FN$_2$O$_6$, 475.2239; found, 475.2238 | $^1$H NMR (500 MHz, CDCl$_3$) δ 8.52 (s, 1H), 8.36 (d, J = 5.5 Hz, 1H), 7.11 (ddd, J = 7.5, 5.9, 1.5 Hz, 1H), 7.02 (d, J = 5.5 Hz, 1H), 6.83 (t, J = 8.1 Hz, 2H), 5.06 (dq, J = 8.1, 6.3 Hz, 1H), 4.66 (dd, J = 9.4, 4.7 Hz, 1H), 3.92 (s, 3H), 3.20-3.08 (m, 1H), 2.40 (s, 3H), 2.32 (d, J = 2.3 Hz, 3H), 2.29 (td, J = 6.9, 4.8 Hz, 1H), 1.23 (d, J = 6.9 Hz, 3H), 1.11 (d, J = 6.2 Hz, 3H), 1.01 (d, |

TABLE 2-continued

Analytical Data

| Cmpd. No. | Melting Point (° C.) | IR (cm$^{-1}$) | MASS SPEC | NMR |
|---|---|---|---|---|
| | | | | J = 6.8 Hz, 3H), 0.93 (d, J = 6.9 Hz, 3H). $^{13}$C NMR (126 MHz, CDCl$_3$) δ 171.24, 168.92, 162.74, 161.89, 159.95, 159.47, 146.68, 141.59, 137.81, 137.76, 137.49, 127.86, 127.79, 117.00, 116.83, 113.00, 112.83, 109.75, 76.14, 57.17, 56.31, 39.04, 31.46, 20.79, 20.00, 19.38, 18.45, 17.47, 17.44. |
| 185 | | | HRMS-ESI (m/z) [M + H]$^+$ calcd for C$_{25}$H$_{31}$FN$_2$O$_6$, 475.2239; found, 475.2236 | $^1$H NMR (500 MHz, CDCl$_3$) δ 8.41 (s, 1H), 8.33 (d, J = 5.4 Hz, 1H), 7.16 (dd, J = 9.0, 5.9 Hz, 1H), 7.01 (d, J = 5.4 Hz, 1H), 6.81 (t, J = 8.0 Hz, 2H), 5.15-5.07 (m, 1H), 4.53 (dd, J = 9.5, 4.5 Hz, 1H), 3.90 (s, 3H), 3.24-3.16 (m, 1H), 2.38 (s, 3H), 2.34 (s, 3H), 1.88 (td, J = 6.9, 4.5 Hz, 1H), 1.26 (d, J = 6.2 Hz, 3H), 1.21 (d, J = 6.9 Hz, 3H), 0.81 (d, J = 6.8 Hz, 3H), 0.63 (d, J = 6.8 Hz, 3H). $^{13}$C NMR (126 MHz, CDCl$_3$) δ 169.14, 167.00, 160.78, 160.02, 158.08, 157.53, 144.77, 139.62, 136.49, 135.51, 135.45, 125.64, 125.57, 114.82, 114.66, 110.95, 110.79, 107.84, 73.69, 54.92, 54.40, 36.84, 29.39, 18.86, 17.99, 17.09, 15.75, 15.30, 15.12. |
| 186 | | | HRMS-ESI (m/z) [M + H]$^+$ calcd for C$_{25}$H$_{32}$N$_2$O$_6$, 457.2333; found, 457.2330 | $^1$H NMR (500 MHz, CDCl$_3$) δ 8.43 (s, 1H), 8.33 (d, J = 5.4 Hz, 1H), 7.24-7.19 (m, 1H), 7.09 (dddd, J = 29.3, 14.6, 7.2, 2.9 Hz, 3H), 7.00 (d, J = 5.5 Hz, 1H), 5.14 (dq, J = 8.2, 6.2 Hz, 1H), 4.53 (dd, J = 9.4, 4.3 Hz, 1H), 3.90 (s, 3H), 3.26 (q, J = 7.4 Hz, 1H), 2.38 (s, 3H), 2.36 (s, 3H), 1.91-1.78 (m, 1H), 1.27 (d, J = 6.2 Hz, 3H), 1.25-1.20 (m, 3H), 0.78 (d, J = 6.9 Hz, 3H), 0.58 (d, J = 6.9 Hz, 3H). $^{13}$C NMR (126 MHz, CDCl$_3$) δ 169.16, 166.97, 160.75, 157.48, 144.73, 139.69, 135.46, 134.11, 128.31, 124.26, 124.06, 107.75, 73.76, 54.85, 54.36, 37.31, 29.36, 18.84, 17.91, 17.07, 15.67, 15.06, 15.00. |
| 187 | | | HRMS-ESI (m/z) [M + H]$^+$ calcd for C$_{24}$H$_{29}$FN$_2$O$_6$, 461.2082; found, 461.2082 | $^1$H NMR (500 MHz, CDCl$_3$) δ 8.50 (d, J = 9.8 Hz, 1H), 8.35 (d, J = 5.4 Hz, 1H), 7.14 (dd, J = 8.6, 5.5 Hz, 2H), 7.03 (d, J = 5.5 Hz, 1H), 6.94 (t, J = 8.7 Hz, 2H), 5.07-4.99 (m, 1H), 4.65 (dd, J = 9.4, 4.7 Hz, 1H), 3.92 (s, 3H), 2.93-2.86 (m, 1H), 2.40 (s, 3H), 2.26 (pd, J = 6.8, 4.7 Hz, 1H), 1.28 (d, J = 7.0 Hz, 3H), 1.10 (d, J = 6.3 Hz, 3H), 0.99 (d, J = 6.9 Hz, 3H), 0.92 (d, J = 6.9 Hz, 3H). $^{13}$C NMR (126 MHz, CDCl$_3$) δ 169.14, 167.00, 160.80, 160.63, 158.69, 157.57, 144.75, 139.63, 136.70, 136.67, 135.57, 127.33, 127.27, 113.31, 113.14, 107.86, 74.15, 55.24, 54.40, 42.02, 29.52, 18.86, 17.37, 16.09, 15.54, 15.21. |
| 188 | | | HRMS-ESI (m/z) [M + H]$^+$ calcd for C$_{26}$H$_{34}$N$_2$O$_7$, 487.2439; found, 487.2427 | $^1$H NMR (500 MHz, CDCl$_3$) δ 8.53 (d, J = 9.3 Hz, 1H), 8.36 (d, J = 5.5 Hz, 1H), 7.07 (d, J = 9.5 Hz, 1H), 7.02 (d, J = 5.5 Hz, 1H), 6.72-6.66 (m, 2H), 5.06 (dq, J = 8.5, 6.3 Hz, 1H), 4.67 (dd, J = 9.4, 4.6 Hz, 1H), 3.91 (s, 3H), 3.76 (s, 3H), 3.15-3.06 (m, 1H), 2.40 (s, 3H), 2.31 (m, 4H), 1.23 (d, J = 6.9 Hz, 3H), 1.10 (d, J = 6.2 Hz, 3H), 1.02 (d, J = 6.8 Hz, 3H), 0.94 (d, J = 6.9 Hz, 3H). $^{13}$C NMR (126 MHz, CDCl$_3$) δ 169.38, |

TABLE 2-continued

Analytical Data

| Cmpd. No. | Melting Point (° C.) | IR (cm⁻¹) | MASS SPEC | NMR |
|---|---|---|---|---|
| | | | | 167.00, 160.80, 157.51, 155.65, 144.76, 139.71, 135.53, 134.94, 132.15, 125.41, 109.49, 107.80, 74.70, 55.25, 54.37, 53.18, 37.08, 29.56, 18.86, 18.27, 17.47, 16.60, 15.86, 15.53. |
| 189 | | | HRMS-ESI (m/z) [M + H]⁺ calcd for $C_{25}H_{31}FN_2O_6$, 475.2239; found, 475.2238 | ¹H NMR (500 MHz, CDCl₃) δ 8.61-8.47 (m, 1H), 8.36 (d, J = 5.4 Hz, 1H), 7.13 (dd, J = 9.6, 5.7 Hz, 1H), 7.02 (d, J = 5.5 Hz, 1H), 6.88-6.79 (m, 2H), 5.09 (dq, J = 8.0, 6.3 Hz, 1H), 4.64 (dd, J = 9.1, 5.0 Hz, 1H), 3.92 (s, 3H), 3.13 (p, J = 7.1 Hz, 1H), 2.41 (s, 3H), 2.33 (s, 3H), 2.29 (qd, J = 7.0, 5.2 Hz, 1H), 1.23 (d, J = 7.0 Hz, 3H), 1.12 (d, J = 6.3 Hz, 3H), 0.99 (d, J = 6.8 Hz, 3H), 0.96 (d, J = 6.9 Hz, 3H). ¹³C NMR (126 MHz, CDCl₃) δ 169.44, 167.00, 160.79, 159.96, 158.02, 157.53, 144.78, 139.68, 135.91, 135.53, 135.50, 125.99, 125.93, 115.05, 114.89, 111.11, 110.95, 107.83, 73.93, 55.11, 54.38, 37.14, 29.57, 18.86, 18.10, 17.03, 16.32, 16.00, 15.50. |
| 190 | | | HRMS-ESI (m/z) [M + H]⁺ calcd for $C_{25}H_{31}FN_2O_6$, 475.2239; found, 475.2235 | ¹H NMR (500 MHz, CDCl₃) δ 8.40 (s, 1H), 8.34 (d, J = 5.4 Hz, 1H), 7.18 (dd, J = 9.5, 5.8 Hz, 1H), 7.02 (d, J = 5.5 Hz, 1H), 6.84-6.75 (m, 2H), 5.10 (p, J = 6.4 Hz, 1H), 4.51 (dd, J = 9.2, 5.1 Hz, 1H), 3.92 (s, 3H), 3.22 (p, J = 7.1 Hz, 1H), 2.40 (s, 3H), 2.33 (s, 3H), 2.15 (pd, J = 6.9, 5.0 Hz, 1H), 1.23 (d, J = 7.1 Hz, 3H), 1.21 (d, J = 6.3 Hz, 3H), 0.88 (d, J = 6.9 Hz, 3H), 0.84 (d, J = 6.9 Hz, 3H). ¹³C NMR (126 MHz, CDCl₃) δ 170.81, 168.93, 162.52, 161.93, 159.99, 159.45, 146.63, 141.52, 138.48, 138.42, 137.46, 136.82, 136.79, 127.88, 127.82, 116.75, 116.59, 112.77, 112.61, 109.71, 75.30, 57.02, 56.30, 38.43, 31.44, 20.78, 19.90, 18.78, 17.72, 17.08, 16.67. |
| 191 | | | HRMS-ESI (m/z) [M + H]⁺ calcd for $C_{25}H_{32}N_2O_6$, 457.2333; found, 457.2331 | ¹H NMR (500 MHz, CDCl₃) δ 8.42 (s, 1H), 8.35 (d, J = 5.4 Hz, 1H), 7.23 (dd, J = 7.8, 1.4 Hz, 1H), 7.15-7.03 (m, 3H), 7.02 (d, J = 5.4 Hz, 1H), 5.13 (p, J = 6.4 Hz, 1H), 4.53 (dd, J = 9.2, 4.9 Hz, 1H), 3.91 (s, 3H), 3.28 (p, J = 7.1 Hz, 1H), 2.40 (s, 3H), 2.36 (s, 3H), 2.14 (pd, J = 6.9, 4.9 Hz, 1H), 1.26 (d, J = 7.2 Hz, 3H), 1.22 (d, J = 6.3 Hz, 3H), 0.86 (d, J = 6.9 Hz, 3H), 0.81 (d, J = 6.9 Hz, 3H). ¹³C NMR (126 MHz, CDCl₃) δ 170.77, 168.93, 162.52, 159.43, 146.63, 141.61, 141.09, 137.44, 136.15, 130.25, 126.37, 126.20, 126.09, 109.69, 75.37, 57.02, 56.29, 38.88, 31.51, 20.79, 19.83, 18.77, 17.70, 16.91, 16.26. |
| 192 | | | HRMS-ESI (m/z) [M + H]⁺ calcd for $C_{24}H_{29}FN_2O_6$, 457.2333; found, 457.2331 | ¹H NMR (500 MHz, CDCl₃) δ 8.58-8.45 (m, 1H), 8.36 (d, J = 5.5 Hz, 1H), 7.16 (ddd, J = 10.8, 6.6, 3.7 Hz, 2H), 7.02 (d, J = 5.5 Hz, 1H), 7.01-6.94 (m, 2H), 5.10-4.99 (m, 1H), 4.63 (dd, J = 9.2, 5.0 Hz, 1H), 3.92 (s, 3H), 2.90 (p, J = 7.1 Hz, 1H), 2.40 (d, J = 2.1 Hz, 3H), 2.31-2.21 (m, 1H), 1.28 (d, J = 7.0 Hz, 3H), 1.09 (d, J = 6.4 Hz, 3H), 1.00-0.97 (m, 3H), 0.96 (d, J = 6.9 Hz, 3H). ¹³C NMR (126 MHz, CDCl₃) δ 171.25, 168.93, 162.72, 162.58, 160.64, |

TABLE 2-continued

Analytical Data

| Cmpd. No. | Melting Point (° C.) | IR (cm$^{-1}$) | MASS SPEC | NMR |
|---|---|---|---|---|
| | | | | 159.46, 146.69, 141.58, 138.61, 138.59, 137.46, 129.30, 129.23, 115.28, 115.11, 109.76, 75.84, 57.06, 56.31, 44.06, 31.47, 20.79, 18.93, 17.96, 17.84, 17.26. |
| 193 | | | HRMS-ESI (m/z) [M + H]$^+$ calcd for C$_{26}$H$_{34}$N$_2$O$_7$, 487.2439; found, 487.2434 | $^1$H NMR (500 MHz, CDCl$_3$) δ 8.62-8.50 (m, 1H), 8.36 (d, J = 5.4 Hz, 1H), 7.10 (d, J = 8.4 Hz, 1H), 7.02 (d, J = 5.5 Hz, 1H), 6.75-6.67 (m, 2H), 5.09 (dq, J = 8.4, 6.3 Hz, 1H), 4.65 (dd, J = 9.1, 4.9 Hz, 1H), 3.91 (s, 3H), 3.75 (s, 3H), 3.17-3.06 (m, 1H), 2.40 (s, 3H), 2.32 (m, 4H), 1.22 (d, J = 6.9 Hz, 3H), 1.11 (d, J = 6.2 Hz, 3H), 0.99 (d, J = 6.8 Hz, 3H), 0.97 (d, J = 6.9 Hz, 3H). $^{13}$C NMR (126 MHz, CDCl$_3$) δ 169.50, 167.02, 160.80, 157.52, 155.67, 144.82, 139.74, 135.53, 135.01, 132.08, 125.49, 114.01, 109.51, 107.84, 74.46, 55.12, 54.40, 53.18, 37.11, 29.65, 18.89, 18.31, 17.06, 16.41, 16.02, 15.83. |
| 194 | | | HRMS-ESI (m/z) [M + H]$^+$ calcd for C$_{23}$H$_{28}$N$_2$O$_6$, 429.2020; found, 429.2021 | $^1$H NMR (500 MHz, CDCl$_3$) δ 8.45-8.36 (m, 1H), 8.33 (d, J = 5.5 Hz, 1H), 7.25-7.17 (m, 1H), 7.17-7.03 (m, 3H), 7.01 (d, J = 5.5 Hz, 1H), 5.18-5.09 (m, 1H), 4.61-4.48 (m, 1H), 3.91 (s, 3H), 3.28 (p, J = 7.3 Hz, 1H), 2.39 (d, J = 5.8 Hz, 3H), 2.36 (s, 3H), 1.32 (d, J = 7.2 Hz, 3H), 1.26 (d, J = 7.0 Hz, 3H), 1.23 (d, J = 6.3 Hz, 3H). $^{13}$C NMR (126 MHz, CDCl$_3$) δ 169.93, 167.04, 160.36, 157.55, 144.72, 139.53, 139.14, 135.53, 134.21, 128.32, 124.37, 124.31, 107.85, 73.52, 54.40, 46.07, 37.09, 18.84, 17.93, 16.51, 15.05, 14.45. |
| 195 | | | HRMS-ESI (m/z) [M + H]$^+$ calcd for C$_{23}$H$_{27}$FN$_2$O$_6$, 447.1926; found, 447.1922 | $^1$H NMR (500 MHz, CDCl$_3$) δ 8.54 (d, J = 7.4 Hz, 1H), 8.34 (d, J = 5.4 Hz, 1H), 7.13 (dd, J = 9.5, 5.8 Hz, 1H), 7.02 (d, J = 5.5 Hz, 1H), 6.88-6.81 (m, 2H), 5.09 (dq, J = 8.2, 6.3 Hz, 1H), 4.72 (p, J = 7.3 Hz, 1H), 3.91 (s, 3H), 3.20-3.09 (m, 1H), 2.41 (s, 3H), 2.33 (s, 3H), 1.50 (d, J = 7.1 Hz, 3H), 1.23 (d, J = 6.8 Hz, 3H), 1.12 (d, J = 6.3 Hz, 3H). $^{13}$C NMR (126 MHz, CDCl$_3$) δ 170.39, 167.02, 160.44, 159.98, 158.04, 157.54, 144.76, 139.53, 135.94, 135.88, 135.55, 135.49, 125.94, 125.88, 115.11, 114.94, 111.06, 110.90, 107.87, 74.14, 54.38, 46.21, 37.21, 18.84, 18.08, 16.77, 16.43, 15.46. |
| 196 | | | HRMS-ESI (m/z) [M + H]$^+$ calcd for C$_{24}$H$_{29}$FN$_2$O$_6$, 461.2082; found, 461.2082 | $^1$H NMR (500 MHz, CDCl$_3$) δ 8.44 (s, 1H), 8.34 (d, J = 5.4 Hz, 1H), 7.12 (ddd, J = 9.3, 4.5, 2.0 Hz, 1H), 7.00 (d, J = 5.5 Hz, 1H), 6.86 (dd, J = 9.0, 6.7 Hz, 2H), 5.12 (dq, J = 7.9, 6.3 Hz, 1H), 4.18 (dd, J = 5.7, 2.8 Hz, 2H), 3.90 (s, 3H), 3.14 (p, J = 7.1 Hz, 1H), 2.95 (p, J = 7.0 Hz, 1H), 2.32 (s, 3H), 1.37 (d, J = 7.0 Hz, 6H), 1.22 (d, J = 7.0 Hz, 3H), 1.12 (d, J = 6.3 Hz, 3H). $^{13}$C NMR (126 MHz, CDCl$_3$) δ 174.71, 169.37, 163.02, 161.95, 160.00, 159.48, 146.62, 141.68, 137.91, 137.73, 137.35, 137.32, 127.89, 127.82, 117.05, 116.89, 113.04, 112.87, 109.72, 76.09, 56.31, 41.38, 39.11, 33.98, 20.01, 18.81, 18.22, 17.42. |
| 197 | | | HRMS-ESI (m/z) [M + H]$^+$ calcd for C$_{24}$H$_{29}$FN$_2$O$_6$, 461.2082; found, | $^1$H NMR (500 MHz, CDCl$_3$) δ 8.34 (d, J = 5.0 Hz, 1H), 8.32 (d, J = 5.4 Hz, 1H), 7.21-7.10 (m, 1H), 6.99 (d, J = 5.4 Hz, 1H), 6.84-6.76 (m, 2H), 5.13 |

TABLE 2-continued

Analytical Data

| Cmpd. No. | Melting Point (° C.) | IR (cm$^{-1}$) | MASS SPEC | NMR |
|---|---|---|---|---|
| | | | 461.2082 | (p, J = 6.4 Hz, 1H), 4.17-3.92 (m, 2H), 3.90-3.88 (s, 3H), 3.22 (p, J = 7.1 Hz, 1H), 2.94 (p, J = 7.0 Hz, 1H), 2.33 (s, 3H), 1.36 (d, J = 7.0 Hz, 6H), 1.23 (dd, J = 6.7, 1.3 Hz, 6H). $^{13}$C NMR (126 MHz, CDCl$_3$) δ 174.69, 169.03, 162.91, 161.95, 160.01, 159.46, 146.58, 141.61, 138.48, 137.71, 136.72, 136.69, 127.84, 127.77, 116.78, 116.62, 112.83, 112.67, 109.70, 75.49, 56.30, 41.22, 38.58, 33.96, 19.87, 19.86, 18.80, 17.11, 16.56. |
| 198 | | | HRMS-ESI (m/z) [M + H]$^+$ calcd for C$_{24}$H$_{30}$N$_2$O$_6$, 443.2177; found, 443.2174 | $^1$H NMR (500 MHz, CDCl$_3$) δ 8.33 (m, 2H), 7.21 (dd, J = 7.6, 1.5 Hz, 1H), 7.10 (ttd, J = 14.3, 7.8, 7.3, 1.8 Hz, 3H), 6.98 (d, J = 5.5 Hz, 1H), 5.17 (h, J = 6.5 Hz, 1H), 4.14-3.90 (m, 2H), 3.89 (s, 3H), 3.33-3.23 (m, 1H), 2.94 (p, J = 7.0 Hz, 1H), 2.35 (s, 3H), 1.36 (d, J = 7.0 Hz, 6H), 1.28-1.19 (m, 6H). $^{13}$C NMR (126 MHz, CDCl$_3$) δ 174.69, 169.05, 162.90, 159.44, 146.58, 141.67, 141.02, 137.68, 136.17, 130.25, 126.30, 126.27, 126.11, 109.66, 75.58, 56.29, 41.22, 39.10, 33.97, 19.80, 18.80, 18.75, 17.05, 16.24. |
| 199 | | | HRMS-ESI (m/z) [M + H]$^+$ calcd for C$_{23}$H$_{27}$FN$_2$O$_6$, 447.1926; found, 447.1926 | $^1$H NMR (500 MHz, CDCl$_3$) δ 8.44 (t, J = 5.5 Hz, 1H), 8.33 (d, J = 5.4 Hz, 1H), 7.18-7.11 (m, 2H), 7.02-6.92 (m, 3H), 5.14-5.02 (m, 1H), 4.22-4.13 (m, 2H), 3.90 (s, 3H), 3.02-2.84 (m, 2H), 1.37 (d, J = 7.0 Hz, 6H), 1.30-1.23 (m, 3H), 1.09 (d, J = 6.3 Hz, 3H). $^{13}$C NMR (126 MHz, CDCl$_3$) δ 174.71, 169.27, 163.03, 162.63, 160.69, 159.48, 146.62, 141.66, 138.52, 137.74, 129.30, 129.23, 115.31, 115.14, 109.73, 76.02, 56.31, 44.12, 41.41, 33.98, 18.81, 17.81, 17.26. |
| 200 | | | HRMS-ESI (m/z) [M + H]$^+$ calcd for C$_{25}$H$_{32}$N$_2$O$_7$, 473.2282; found, 473.2275 | $^1$H NMR (500 MHz, CDCl$_3$) δ 8.45 (t, J = 5.4 Hz, 1H), 8.33 (d, J = 5.4 Hz, 1H), 7.08 (d, J = 8.4 Hz, 1H), 7.00 (d, J = 5.5 Hz, 1H), 6.77-6.67 (m, 2H), 5.12 (dq, J = 8.1, 6.2 Hz, 1H), 4.25-4.14 (m, 2H), 3.89 (s, 3H), 3.77 (s, 3H), 3.16-3.05 (m, 1H), 2.96 (p, J = 7.0 Hz, 1H), 2.31 (s, 3H), 1.37 (d, J = 7.0 Hz, 6H), 1.22 (d, J = 7.0 Hz, 3H), 1.12 (d, J = 6.3 Hz, 3H). $^{13}$C NMR (126 MHz, CDCl$_3$) δ 174.71, 169.43, 163.02, 159.46, 157.66, 146.63, 141.71, 137.71, 136.96, 133.86, 127.39, 115.94, 111.46, 109.70, 76.54, 56.30, 55.11, 41.41, 39.04, 33.98, 20.18, 18.81, 18.27, 17.62. |
| 201 | | | HRMS-ESI (m/z) [M + H]$^+$ calcd for C$_{25}$H$_{31}$FN$_2$O$_6$, 475.2239; found, 475.2234 | $^1$H NMR (500 MHz, CDCl$_3$) δ 8.36 (s, 1H), 8.31 (d, J = 5.4 Hz, 1H), 7.16 (ddd, J = 13.0, 8.8, 6.0 Hz, 1H), 6.97 (d, J = 5.4 Hz, 1H), 6.81 (t, J = 7.8 Hz, 2H), 5.11 (dq, J = 8.3, 6.4 Hz, 1H), 4.56 (p, J = 7.3 Hz, 1H), 3.88 (s, 3H), 3.26-3.16 (m, 1H), 2.99-2.90 (m, 1H), 2.34 (s, 3H), 1.35 (d, J = 6.9 Hz, 6H), 1.27 (d, J = 6.3 Hz, 3H), 1.21 (d, J = 7.1 Hz, 3H), 1.08 (d, J = 7.1 Hz, 3H). $^{13}$C NMR (126 MHz, CDCl$_3$) δ 174.68, 172.20, 162.29, 161.91, 159.97, 159.42, 146.55, 141.88, 138.36, 138.30, 137.64, 137.22, 137.19, 127.57, 127.50, 116.70, 116.54, 112.85, 112.68, 109.58, 75.44, 56.28, 47.83, 38.90, 33.93, 19.91, 18.80, 18.20, 17.70, 17.22. |

TABLE 2-continued

Analytical Data

| Cmpd. No. | Melting Point (° C.) | IR (cm$^{-1}$) | MASS SPEC | NMR |
|---|---|---|---|---|
| 202 | | | HRMS-ESI (m/z) [M + H]$^+$ calcd for C$_{25}$H$_{32}$N$_2$O$_6$, 457.2333; found, 457.2331 | $^1$H NMR (500 MHz, CDCl$_3$) δ 8.35 (dd, J = 8.2, 5.5 Hz, 1H), 8.31 (d, J = 5.4 Hz, 1H), 7.19 (dd, J = 7.7, 1.4 Hz, 1H), 7.09 (ttd, J = 14.5, 7.2, 1.7 Hz, 3H), 6.97 (d, J = 5.4 Hz, 1H), 5.15 (dq, J = 7.7, 6.1 Hz, 1H), 4.60-4.45 (m, 1H), 3.88 (s, 3H), 3.26 (dp, J = 14.7, 7.2 Hz, 1H), 2.93 (p, J = 7.1 Hz, 1H), 2.36 (s, 3H), 1.35 (d, J = 7.0 Hz, 6H), 1.28 (d, J = 6.3 Hz, 3H), 1.24 (d, J = 7.2 Hz, 3H), 1.01 (d, J = 7.2 Hz, 3H). $^{13}$C NMR (126 MHz, CDCl$_3$) δ 174.68, 172.25, 162.27, 159.39, 146.55, 141.96, 141.54, 137.60, 136.03, 130.21, 126.16, 125.98, 109.53, 77.28, 75.56, 56.27, 47.84, 39.44, 33.93, 19.84, 18.81, 18.14, 17.71, 17.01. |
| 203 | | | HRMS-ESI (m/z) [M + H]$^+$ calcd for C$_{24}$H$_{29}$FN$_2$O$_6$, 461.2082; found, 461.2082 | $^1$H NMR (500 MHz, CDCl$_3$) δ 8.46 (s, 1H), 8.33 (d, J = 5.4 Hz, 1H), 7.15 (dd, J = 8.6, 5.5 Hz, 2H), 7.01-6.92 (m, 3H), 5.09-5.00 (m, 1H), 4.71 (p, J = 7.3 Hz, 1H), 3.89 (s, 3H), 3.00-2.86 (m, 2H), 1.47 (d, J = 7.1 Hz, 3H), 1.36 (dd, J = 7.0, 1.3 Hz, 6H), 1.27 (d, J = 7.0 Hz, 3H), 1.09 (d, J = 6.3 Hz, 3H). $^{13}$C NMR (126 MHz, CDCl$_3$) δ 174.71, 172.30, 162.61, 162.36, 160.67, 159.46, 146.57, 141.90, 138.63, 137.71, 129.29, 129.23, 115.27, 115.10, 109.62, 75.96, 56.30, 48.10, 44.13, 33.96, 18.81, 18.72, 17.93, 17.20. |
| 204 | | | HRMS-ESI (m/z) [M + H]$^+$ calcd for C$_{26}$H$_{34}$N$_2$O$_7$, 487.2439; found, 487.2431 | $^1$H NMR (500 MHz, CDCl$_3$) δ 8.50 (d, J = 9.7 Hz, 1H), 8.33 (d, J = 5.4 Hz, 1H), 7.09 (d, J = 8.3 Hz, 1H), 6.99 (d, J = 5.5 Hz, 1H), 6.76-6.66 (m, 2H), 5.08 (dq, J = 8.3, 6.2 Hz, 1H), 4.73 (p, J = 7.3 Hz, 1H), 3.89 (s, 3H), 3.77 (s, 3H), 3.18-3.05 (m, 1H), 2.95 (p, J = 7.0 Hz, 1H), 2.32 (s, 3H), 1.50 (d, J = 7.2 Hz, 3H), 1.36 (dd, J = 7.0, 1.5 Hz, 6H), 1.22 (d, J = 6.8 Hz, 3H), 1.11 (d, J = 6.3 Hz, 3H). $^{13}$C NMR (126 MHz, CDCl$_3$) δ 174.70, 172.48, 162.36, 159.43, 157.65, 146.58, 141.96, 137.67, 136.91, 134.03, 127.40, 115.92, 111.45, 109.59, 76.46, 56.29, 55.12, 48.15, 39.14, 33.95, 20.19, 18.81, 18.43, 17.63. |
| 205 | | | HRMS-ESI (m/z) [M + H]$^+$ calcd for C$_{25}$H$_{31}$FN$_2$O$_6$, 475.2239; found, 475.2239 | $^1$H NMR (500 MHz, CDCl$_3$) δ 8.51-8.39 (m, 1H), 8.34 (d, J = 5.3 Hz, 1H), 7.13 (dd, J = 9.4, 5.8 Hz, 1H), 6.99 (d, J = 5.4 Hz, 1H), 6.87-6.81 (m, 2H), 5.09 (dq, J = 7.9, 6.2 Hz, 1H), 4.71 (p, J = 7.3 Hz, 1H), 3.89 (s, 3H), 3.13 (p, J = 7.1 Hz, 1H), 2.95 (p, J = 7.0 Hz, 1H), 2.33 (s, 3H), 1.48 (d, J = 7.1 Hz, 3H), 1.39-1.33 (m, 6H), 1.22 (d, J = 6.9 Hz, 3H), 1.10 (d, J = 6.3 Hz, 3H). $^{13}$C NMR (126 MHz, CDCl$_3$) δ 174.71, 172.43, 162.41, 161.91, 159.97, 159.46, 146.57, 141.90, 137.88, 137.82, 137.47, 127.91, 127.85, 117.01, 116.84, 113.03, 112.87, 109.63, 75.88, 56.30, 48.01, 39.13, 33.96, 20.02, 18.81, 18.50, 18.12, 17.48. |
| 206 | | | HRMS-ESI (m/z) [M + H]$^+$ calcd for C$_{25}$H$_{32}$N$_2$O$_6$, 457.2333; found, 457.2332 | $^1$H NMR (500 MHz, CDCl$_3$) δ 8.35-8.27 (m, 2H), 7.22 (dd, J = 7.7, 1.4 Hz, 1H), 7.17-7.03 (m, 3H), 6.98 (d, J = 5.4 Hz, 1H), 5.14 (p, J = 6.5 Hz, 1H), 4.56 (p, J = 7.2 Hz, 1H), 3.89 (s, 3H), 3.28 (p, J = 7.0 Hz, 1H), 2.94 (p, J = 7.0 Hz, 1H), 2.35 (s, 3H), 1.39-1.34 (m, 6H), 1.31 (d, J = 7.2 Hz, 3H), 1.25 (d, J = 7.1 Hz, 3H), 1.22 (d, J = 6.4 Hz, 3H). |

TABLE 2-continued

Analytical Data

| Cmpd. No. | Melting Point (° C.) | IR (cm⁻¹) | MASS SPEC | NMR |
|---|---|---|---|---|
| | | | | ¹³C NMR (126 MHz, CDCl₃) δ 174.70, 171.97, 162.25, 159.43, 146.50, 141.92, 141.08, 137.66, 136.14, 130.23, 126.33, 126.21, 126.09, 109.55, 75.33, 56.29, 47.95, 39.03, 33.95, 19.82, 18.81, 18.47, 16.96, 16.35. |
| 207 | | | HRMS-ESI (m/z) [M + H]⁺ calcd for C₂₄H₂₉FN₂O₆, 461.2082; found, 461.2082 | ¹H NMR (500 MHz, CDCl₃) δ 8.45 (s, 1H), 8.33 (d, J = 5.4 Hz, 1H), 7.20-7.12 (m, 2H), 7.02-6.94 (m, 3H), 5.10-4.99 (m, 1H), 4.70 (p, J = 7.3 Hz, 1H), 3.89 (s, 3H), 2.94 (ddt, J = 15.3, 14.2, 7.1 Hz, 2H), 1.47 (d, J = 7.1 Hz, 3H), 1.38-1.34 (m, 6H), 1.27 (d, J = 6.9 Hz, 3H), 1.07 (d, J = 6.3 Hz, 3H). ¹³C NMR (126 MHz, CDCl₃) δ 174.72, 172.36, 162.62, 162.44, 160.67, 159.46, 146.57, 141.88, 138.58, 137.70, 129.33, 129.26, 115.28, 115.11, 109.63, 75.77, 56.30, 48.03, 44.07, 33.96, 18.81, 18.46, 17.65, 17.30. |
| 208 | | | HRMS-ESI (m/z) [M + H]⁺ calcd for C₂₆H₃₄N₂O₇, 487.2439; found, 487.2432 | ¹H NMR (500 MHz, CDCl₃) δ 8.49 (d, J = 5.7 Hz, 1H), 8.34 (d, J = 5.5 Hz, 1H), 7.09 (d, J = 8.3 Hz, 1H), 6.99 (d, J = 5.4 Hz, 1H), 6.75-6.67 (m, 2H), 5.09 (dq, J = 8.2, 6.2 Hz, 1H), 4.72 (p, J = 7.2 Hz, 1H), 3.89 (s, 3H), 3.76 (s, 3H), 3.15-3.05 (m, 1H), 2.96 (p, J = 7.0 Hz, 1H), 2.32 (s, 3H), 1.49 (d, J = 7.2 Hz, 3H), 1.39-1.34 (m, 6H), 1.21 (d, J = 6.9 Hz, 3H), 1.09 (d, J = 6.3 Hz, 3H). ¹³C NMR (126 MHz, CDCl₃) δ 174.71, 172.49, 162.41, 159.44, 157.62, 146.58, 141.96, 137.67, 136.95, 134.00, 127.40, 115.94, 111.45, 109.60, 76.36, 56.29, 55.10, 48.06, 39.08, 33.96, 20.21, 18.82, 18.58, 18.19, 17.74. |
| 209 | | | HRMS-ESI (m/z) [M + H]⁺ calcd for C₂₇H₃₅FN₂O₆, 503.2552; found, 503.2547 | ¹H NMR (500 MHz, CDCl₃) δ 8.44 (d, J = 9.0 Hz, 1H), 8.34 (d, J = 5.4 Hz, 1H), 7.16-7.08 (m, 1H), 6.99 (d, J = 5.5 Hz, 1H), 6.82 (t, J = 7.9 Hz, 2H), 5.06 (dq, J = 8.0, 6.2 Hz, 1H), 4.66 (dd, J = 9.4, 4.8 Hz, 1H), 3.89 (s, 3H), 3.20-3.09 (m, 1H), 2.95 (p, J = 7.0 Hz, 1H), 2.32 (s, 3H), 2.28 (qd, J = 7.0, 4.9 Hz, 1H), 1.39-1.32 (m, 6H), 1.23 (d, J = 6.9 Hz, 3H), 1.11 (d, J = 6.2 Hz, 3H), 1.01 (d, J = 6.8 Hz, 3H), 0.92 (d, J = 6.8 Hz, 3H). ¹³C NMR (126 MHz, CDCl₃) δ 174.67, 171.34, 162.74, 161.92, 159.98, 159.45, 146.56, 142.09, 137.82, 137.67, 137.55, 127.90, 127.83, 117.00, 116.83, 113.00, 112.84, 109.59, 76.07, 57.14, 56.29, 39.10, 33.94, 31.48, 19.99, 19.38, 18.82, 18.47, 17.46. |
| 210 | | | HRMS-ESI (m/z) [M + H]⁺ calcd for C₂₇H₃₅FN₂O₇, 503.2552; found, 503.2554 | ¹H NMR (500 MHz, CDCl₃) δ 8.32 (m, 2H), 7.16 (dd, J = 9.5, 5.7 Hz, 1H), 6.98 (d, J = 5.5 Hz, 1H), 6.83-6.76 (m, 2H), 5.10 (dq, J = 8.0, 6.3 Hz, 1H), 4.54 (dd, J = 9.4, 4.5 Hz, 1H), 3.88 (s, 3H), 3.19 (p, J = 7.2 Hz, 1H), 2.93 (p, J = 7.0 Hz, 1H), 2.34 (s, 3H), 1.88 (pd, J = 6.9, 4.5 Hz, 1H), 1.34 (d, J = 7.0 Hz, 6H), 1.25 (d, J = 6.3 Hz, 3H), 1.21 (d, J = 7.1 Hz, 3H), 0.81 (d, J = 6.9 Hz, 3H), 0.63 (d, J = 6.9 Hz, 3H). ¹³C NMR (126 MHz, CDCl₃) δ 174.66, 171.16, 162.69, 161.96, 160.03, 159.41, 146.55, 142.06, 138.40, 138.34, 137.62, 137.32, 127.61, 116.73, 116.57, 112.86, 112.70, 109.54, 75.49, 56.79, 56.28, 38.77, |

TABLE 2-continued

Analytical Data

| Cmpd. No. | Melting Point (° C.) | IR (cm$^{-1}$) | MASS SPEC | NMR |
|---|---|---|---|---|
| 211 | | | HRMS-ESI (m/z) [M + H]$^+$ calcd for C$_{25}$H$_{36}$N$_2$O$_6$, 485.2646; found, 485.2642 | 33.92, 31.34, 19.89, 19.01, 18.82, 17.63, 17.17, 17.05.<br>$^1$H NMR (500 MHz, CDCl$_3$) δ 8.38-8.27 (m, 2H), 7.21 (dd, J = 7.8, 1.3 Hz, 1H), 7.09 (dddd, J = 23.7, 14.5, 7.3, 1.6 Hz, 3H), 6.97 (d, J = 5.5 Hz, 1H), 5.14 (dq, J = 6.8, 5.8, 5.3 Hz, 1H), 4.54 (dd, J = 9.5, 4.4 Hz, 1H), 3.88 (s, 3H), 3.26 (dp, J = 14.6, 7.1 Hz, 1H), 2.93 (p, J = 6.9 Hz, 1H), 2.36 (d, J = 3.7 Hz, 3H), 1.85 (pd, J = 6.9, 4.4 Hz, 1H), 1.34 (d, J = 7.0 Hz, 6H), 1.27 (d, J = 6.3 Hz, 3H), 1.23 (d, J = 7.1 Hz, 3H), 0.78 (d, J = 6.9 Hz, 3H), 0.58 (d, J = 6.9 Hz, 3H).<br>$^{13}$C NMR (126 MHz, CDCl$_3$) δ 174.65, 171.20, 162.68, 159.38, 146.55, 142.13, 141.63, 137.58, 136.06, 130.25, 126.19, 126.05, 109.49, 75.58, 56.75, 56.29, 39.27, 33.92, 31.33, 19.82, 19.02, 18.81, 17.57, 17.02, 16.89. |
| 212 | | | HRMS-ESI (m/z) [M + H]$^+$ calcd for C$_{26}$H$_{33}$FN$_2$O$_6$, 489.2395; found, 489.2391 | $^1$H NMR (500 MHz, CDCl$_3$) δ 8.42 (d, J = 9.0 Hz, 1H), 8.34 (d, J = 5.5 Hz, 1H), 7.14 (dd, J = 8.6, 5.5 Hz, 2H), 7.00 (d, J = 5.5 Hz, 1H), 6.97-6.89 (m, 2H), 5.03 (p, J = 6.4 Hz, 1H), 4.65 (dd, J = 9.4, 4.7 Hz, 1H), 3.89 (s, 3H), 3.00-2.85 (m, 2H), 2.25 (pd, J = 6.9, 4.7 Hz, 1H), 1.38-1.31 (m, 6H), 1.28 (d, J = 7.0 Hz, 3H), 1.09 (d, J = 6.3 Hz, 3H), 0.99 (d, J = 6.9 Hz, 3H), 0.91 (d, J = 6.9 Hz, 3H).<br>$^{13}$C NMR (126 MHz, CDCl$_3$) δ 174.68, 171.17, 162.73, 162.59, 160.64, 159.46, 146.56, 142.06, 138.69, 137.69, 129.27, 129.21, 115.23, 115.07, 109.60, 76.00, 57.13, 56.30, 43.99, 33.94, 31.47, 19.30, 18.81, 18.02, 17.49, 17.14. |
| 213 | | | HRMS-ESI (m/z) [M + H]$^+$ calcd for C$_{28}$H$_{38}$N$_2$O$_7$, 515.2752; found, 515.2737 | $^1$H NMR (500 MHz, CDCl$_3$) δ 8.45 (d, J = 8.6 Hz, 1H), 8.34 (d, J = 5.5 Hz, 1H), 7.07 (d, J = 9.4 Hz, 1H), 6.99 (d, J = 5.5 Hz, 1H), 6.72-6.65 (m, 2H), 5.06 (dq, J = 8.3, 6.2 Hz, 1H), 4.67 (dd, J = 9.3, 4.7 Hz, 1H), 3.89 (s, 3H), 3.76 (s, 3H), 3.16-3.05 (m, 1H), 2.95 (p, J = 7.0 Hz, 1H), 2.35-2.25 (m, 3H), 1.40-1.30 (m, 6H), 1.23 (d, J = 6.9 Hz, 3H), 1.10 (d, J = 6.3 Hz, 3H), 1.01 (d, J = 6.8 Hz, 3H), 0.93 (d, J = 6.9 Hz, 3H).<br>$^{13}$C NMR (126 MHz, CDCl$_3$) δ 174.67, 171.40, 162.75, 159.43, 157.63, 146.57, 142.14, 137.65, 136.86, 134.14, 127.37, 115.93, 111.45, 109.57, 76.57, 60.39, 57.17, 56.29, 55.12, 39.07, 33.94, 31.51, 20.18, 19.40, 18.82, 18.54, 17.77, 17.48, 14.20. |
| 214 | | | HRMS-ESI (m/z) [M + H]$^+$ calcd for C$_{27}$H$_{35}$FN$_2$O$_6$, 503.2552; found, 503.2549 | $^1$H NMR (500 MHz, CDCl$_3$) δ 8.44 (d, J = 9.1 Hz, 1H), 8.35 (d, J = 5.4 Hz, 1H), 7.13 (dd, J = 9.6, 5.8 Hz, 1H), 7.00 (d, J = 5.4 Hz, 1H), 6.88-6.78 (m, 2H), 5.09 (dq, J = 8.1, 6.3 Hz, 1H), 4.63 (dd, J = 9.1, 5.2 Hz, 1H), 3.89 (s, 3H), 3.13 (p, J = 7.1 Hz, 1H), 2.95 (p, J = 7.0 Hz, 1H), 2.32 (s, 3H), 2.26 (pd, J = 6.8, 4.9 Hz, 1H), 1.41-1.31 (m, 6H), 1.23 (d, J = 6.9 Hz, 3H), 1.11 (d, J = 6.3 Hz, 3H), 0.99 (d, J = 7.0 Hz, 3H), 0.96 (d, J = 6.9 Hz, 3H).<br>$^{13}$C NMR (126 MHz, CDCl$_3$) δ 174.68, 171.48, 162.75, 161.91, 159.97, 159.44, 146.59, 142.11, 137.84, 137.64, 137.49, 127.88, 116.98, |

TABLE 2-continued

Analytical Data

| Cmpd. No. | Melting Point (° C.) | IR (cm⁻¹) | MASS SPEC | NMR |
|---|---|---|---|---|
| 215 | | | HRMS-ESI (m/z) [M + H]⁺ calcd for C₂₇H₃₆N₂O₆, 485.2646; found, 485.2643 | 116.81, 113.04, 112.88, 109.58, 75.80, 57.04, 56.29, 39.14, 33.95, 31.48, 20.01, 19.00, 18.81, 18.26, 17.94, 17.46. ¹H NMR (500 MHz, CDCl₃) δ 8.38-8.28 (m, 2H), 7.25-7.20 (m, 1H), 7.16-7.02 (m, 3H), 6.99 (d, J = 5.4 Hz, 1H), 5.13 (p, J = 6.4 Hz, 1H), 4.53 (dd, J = 9.1, 4.9 Hz, 1H), 3.89 (s, 3H), 3.28 (p, J = 7.1 Hz, 1H), 2.94 (h, J = 7.0 Hz, 1H), 2.35 (s, 3H), 2.21-2.09 (m, 1H), 1.35 (dd, J = 7.0, 1.2 Hz, 6H), 1.26 (d, J = 7.1 Hz, 3H), 1.21 (d, J = 6.2 Hz, 3H), 0.86 (d, J = 6.9 Hz, 3H), 0.81 (d, J = 6.9 Hz, 3H). ¹³C NMR (126 MHz, CDCl₃) δ 174.68, 170.88, 162.55, 159.42, 146.51, 142.10, 141.12, 137.63, 136.16, 130.26, 126.41, 126.19, 126.09, 109.52, 75.28, 57.01, 56.29, 38.91, 33.94, 31.50, 19.81, 18.81, 17.71, 16.90, 16.26. |
| 216 | | | HRMS-ESI (m/z) [M + H]⁺ calcd for C₂₆H₃₃FN₂O₆, 489.2395; found, 489.2391 | ¹H NMR (500 MHz, CDCl₃) δ 8.48-8.39 (m, 1H), 8.34 (d, J = 5.4 Hz, 1H), 7.19-7.11 (m, 2H), 7.03-6.90 (m, 3H), 5.05 (m, 1H), 4.62 (dd, J = 9.1, 5.1 Hz, 1H), 3.89 (s, 3H), 2.92 (dp, J = 26.1, 7.0 Hz, 2H), 2.25 (pd, J = 6.9, 4.2 Hz, 1H), 1.38-1.32 (m, 6H), 1.27 (d, J = 7.1 Hz, 3H), 1.08 (d, J = 6.2 Hz, 3H), 0.98 (d, J = 6.9 Hz, 3H), 0.95 (d, J = 6.9 Hz, 3H). ¹³C NMR (126 MHz, CDCl₃) δ 174.68, 171.37, 162.76, 162.61, 160.67, 159.44, 146.59, 142.08, 138.67, 137.64, 129.32, 129.26, 115.27, 115.10, 109.59, 75.75, 57.06, 56.30, 44.10, 33.95, 31.45, 18.97, 18.81, 17.97, 17.84, 17.27. |
| 217 | | | HRMS-ESI (m/z) [M + H]⁺ calcd for C₂₈H₃₈N₂O₇, 515.2752; found, 515.2741 | ¹H NMR (500 MHz, CDCl₃) δ 8.46 (d, J = 9.0 Hz, 1H), 8.35 (d, J = 5.4 Hz, 1H), 7.09 (d, J = 8.4 Hz, 1H), 6.99 (d, J = 5.5 Hz, 1H), 6.75-6.66 (m, 2H), 5.09 (dq, J = 8.3, 6.2 Hz, 1H), 4.65 (dd, J = 9.1, 5.0 Hz, 1H), 3.89 (s, 3H), 3.75 (s, 3H), 3.16-3.04 (m, 1H), 2.95 (p, J = 7.0 Hz, 1H), 2.31 (s, 3H), 2.27 (qd, J = 6.9, 5.0 Hz, 1H), 1.39-1.32 (m, 6H), 1.22 (d, J = 6.9 Hz, 3H), 1.10 (d, J = 6.3 Hz, 3H), 0.99 (d, J = 6.8 Hz, 3H), 0.96 (d, J = 6.9 Hz, 3H). ¹³C NMR (126 MHz, CDCl₃) δ 174.68, 171.52, 162.73, 159.42, 157.61, 146.60, 142.18, 137.62, 136.92, 134.06, 127.42, 115.96, 111.44, 109.55, 76.31, 57.04, 56.29, 55.10, 39.09, 33.94, 31.54, 20.20, 19.00, 18.82, 18.33, 17.94, 17.77. |
| 218 | | | HRMS-ESI (m/z) [M + H]⁺ calcd for C₂₅H₃₁FN₂O₆, 475.2239; found, 475.2236 | ¹H NMR (500 MHz, CDCl₃) δ 8.37-8.28 (m, 2H), 7.22-7.12 (m, 1H), 6.99 (d, J = 5.5 Hz, 1H), 6.85-6.75 (m, 2H), 5.16-5.05 (m, 1H), 4.57 (h, J = 7.4 Hz, 1H), 3.89 (s, 3H), 3.22 (pd, J = 7.3, 4.6 Hz, 1H), 3.00-2.89 (m, 1H), 2.33 (s, 3H), 1.39-1.30 (m, 9H), 1.22 (dd, J = 9.8, 6.7 Hz, 6H). ¹³C NMR (126 MHz, CDCl₃) δ 174.70, 171.98, 162.25, 161.93, 159.99, 159.45, 146.51, 141.82, 138.46, 137.69, 136.79, 136.76, 127.85, 127.79, 116.74, 116.58, 112.79, 112.62, 109.59, 75.24, 56.30, 47.88, 38.53, 33.95, 19.88, 18.80, 18.41, 17.05, 16.71. |

TABLE 2-continued

Analytical Data

| Cmpd. No. | Melting Point (° C.) | IR (cm$^{-1}$) | MASS SPEC | NMR |
|---|---|---|---|---|
| 219 | | | HRMS-ESI (m/z) [M + H]$^+$ calcd for C$_{25}$H$_{31}$FN$_2$O$_6$, 475.2239; found, 475.2238 | $^1$H NMR (500 MHz, CDCl$_3$) δ 8.48 (d, J = 6.9 Hz, 1H), 8.33 (d, J = 5.3 Hz, 1H), 7.13 (dd, J = 9.4, 5.8 Hz, 1H), 6.99 (d, J = 5.5 Hz, 1H), 6.88-6.81 (m, 2H), 5.09 (dp, J = 8.1, 6.5 Hz, 1H), 4.72 (p, J = 7.2 Hz, 1H), 3.89 (s, 3H), 3.14 (p, J = 7.1 Hz, 1H), 2.95 (p, J = 7.0 Hz, 1H), 2.33 (d, J = 2.4 Hz, 3H), 1.49 (d, J = 7.1 Hz, 3H), 1.38-1.33 (m, 6H), 1.23 (d, J = 6.9 Hz, 3H), 1.11 (d, J = 6.3 Hz, 3H). $^{13}$C NMR (126 MHz, CDCl$_3$) δ 174.71, 172.42, 162.36, 161.94, 159.99, 159.45, 146.58, 141.91, 137.86, 137.80, 137.69, 137.46, 127.91, 127.84, 117.04, 116.87, 113.00, 112.83, 109.62, 75.99, 56.30, 48.11, 39.18, 33.96, 20.00, 19.99, 18.85, 18.81, 18.36, 17.37. |
| 220 | | | HRMS-ESI (m/z) [M + H]$^+$ calcd for C$_{24}$H$_{30}$N$_2$O$_7$, 459.2126; found, 459.2103 | $^1$H NMR (500 MHz, CDCl$_3$) δ 8.56 (s, 1H), 8.35 (d, J = 5.4 Hz, 1H), 7.09 (d, J = 8.4 Hz, 1H), 7.02 (d, J = 5.5 Hz, 1H), 6.77-6.67 (m, 2H), 5.10 (dq, J = 8.3, 6.3 Hz, 1H), 4.72 (tt, J = 8.8, 6.2 Hz, 1H), 3.91 (s, 3H), 3.76 (s, 3H), 3.15-3.06 (m, 1H), 2.41 (s, 3H), 2.32 (s, 3H), 1.50 (d, J = 7.2 Hz, 3H), 1.22 (d, J = 6.9 Hz, 3H), 1.10 (d, J = 6.3 Hz, 3H). $^{13}$C NMR (126 MHz, CDCl$_3$) δ 170.46, 167.04, 160.48, 157.55, 155.66, 144.77, 139.57, 135.54, 135.03, 132.01, 125.44, 113.97, 109.50, 107.87, 74.52, 54.39, 53.17, 46.15, 37.09, 18.84, 18.30, 16.63, 16.25, 15.80. |
| 221 | | | HRMS-ESI (m/z) [M + H]$^+$ calcd for C$_{24}$H$_{29}$FN$_2$O$_6$, 461.2082; found, 461.2080 | $^1$H NMR (500 MHz, CDCl$_3$) δ 8.44 (t, J = 5.4 Hz, 1H), 8.34 (d, J = 5.4 Hz, 1H), 7.12 (ddd, J = 10.1, 6.2, 3.4 Hz, 1H), 7.00 (d, J = 5.5 Hz, 1H), 6.90-6.80 (m, 3H), 5.12 (dq, J = 7.7, 6.2 Hz, 1H), 4.18 (dd, J = 5.4, 2.8 Hz, 2H), 3.90 (s, 3H), 3.14 (p, J = 7.1 Hz, 1H), 2.95 (p, J = 7.0 Hz, 1H), 2.32 (s, 3H), 1.37 (d, J = 7.0 Hz, 6H), 1.22 (d, J = 6.9 Hz, 3H), 1.12 (d, J = 6.3 Hz, 3H). $^{13}$C NMR (126 MHz, CDCl$_3$) δ 174.71, 169.37, 163.02, 161.95, 160.00, 159.48, 146.63, 141.67, 137.91, 137.85, 137.73, 137.32, 127.89, 127.82, 117.05, 116.89, 113.04, 112.87, 109.72, 76.09, 56.31, 41.38, 39.11, 33.98, 20.00, 18.81, 18.71, 18.22, 17.42. |
| 222 | | | HRMS-ESI (m/z) [M + H]$^+$ calcd for C$_{24}$H$_{30}$N$_2$O$_6$, 443.2177; found, 443.2176 | $^1$H NMR (500 MHz, CDCl$_3$) δ 8.36-8.27 (m, 2H), 7.21 (dd, J = 7.7, 1.4 Hz, 1H), 7.16-7.05 (m, 3H), 6.98 (d, J = 5.5 Hz, 1H), 5.17 (h, J = 6.6 Hz, 1H), 4.13-3.89 (m, 2H), 3.89 (s, 3H), 3.28 (p, J = 7.1 Hz, 1H), 2.94 (p, J = 7.0 Hz, 1H), 2.35 (s, 3H), 1.36 (d, J = 7.0 Hz, 6H), 1.28-1.22 (m, 6H). $^{13}$C NMR (126 MHz, CDCl$_3$) δ 174.69, 169.05, 162.90, 159.44, 146.58, 141.67, 141.02, 137.68, 136.17, 130.25, 126.29, 126.27, 126.11, 109.66, 75.58, 56.29, 41.22, 39.09, 33.97, 19.80, 18.81, 17.05, 16.23. |
| 223 | | | HRMS-ESI (m/z) [M + H]$^+$ calcd for C$_{23}$H$_{27}$FN$_2$O$_6$, 447.1926; found, 447.1923 | $^1$H NMR (500 MHz, CDCl$_3$) δ 8.44 (t, J = 5.5 Hz, 1H), 8.33 (d, J = 5.4 Hz, 1H), 7.18-7.11 (m, 2H), 7.03-6.92 (m, 3H), 5.14-5.01 (m, 1H), 4.17 (d, J = 5.4 Hz, 2H), 3.90 (s, 3H), 3.00-2.86 (m, 2H), 1.37 (d, J = 7.0 Hz, 6H), 1.27 (d, J = 7.0 Hz, 3H), 1.09 (d, J = 6.3 Hz, 3H). $^{13}$C NMR (126 MHz, CDCl$_3$) δ 174.72, |

TABLE 2-continued

Analytical Data

| Cmpd. No. | Melting Point (° C.) | IR (cm⁻¹) | MASS SPEC | NMR |
|---|---|---|---|---|
| | | | | 169.28, 163.04, 162.64, 160.69, 159.48, 146.62, 141.66, 138.52, 137.74, 129.30, 129.24, 115.31, 115.14, 109.73, 76.02, 56.31, 44.12, 41.41, 33.98, 18.81, 17.81, 17.26. |
| 224 | | | HRMS-ESI (m/z) [M + H]⁺ calcd for C$_{25}$H$_{32}$N$_2$O$_7$, 473.2282; found, 473.2282 | ¹H NMR (500 MHz, CDCl$_3$) δ 8.45 (t, J = 5.4 Hz, 1H), 8.33 (d, J = 5.4 Hz, 1H), 7.08 (d, J = 8.5 Hz, 1H), 7.00 (d, J = 5.5 Hz, 1H), 6.76-6.67 (m, 2H), 5.12 (dq, J = 8.3, 6.3 Hz, 1H), 4.24-4.14 (m, 2H), 3.89 (s, 3H), 3.77 (s, 3H), 3.16-3.05 (m, 1H), 2.96 (p, J = 7.0 Hz, 1H), 2.31 (s, 3H), 1.37 (d, J = 7.0 Hz, 6H), 1.22 (d, J = 6.9 Hz, 3H), 1.12 (d, J = 6.2 Hz, 3H). ¹³C NMR (126 MHz, CDCl$_3$) δ 174.71, 169.43, 163.01, 159.46, 157.66, 146.63, 141.71, 137.71, 136.96, 133.86, 127.39, 115.94, 111.46, 109.70, 76.54, 56.30, 55.11, 41.41, 39.04, 33.98, 20.18, 18.81, 18.27, 17.62. |
| 225 | | | HRMS-ESI (m/z) [M + H]⁺ calcd for C$_{25}$H$_{32}$N$_2$O$_6$, 457.2333; found, 457.2327 | ¹H NMR (500 MHz, CDCl$_3$) δ 8.39-8.28 (m, 2H), 7.24-7.17 (m, 1H), 7.16-7.02 (m, 3H), 6.98 (d, J = 5.5 Hz, 1H), 5.14 (p, J = 6.6 Hz, 1H), 4.55 (dt, J = 10.4, 7.4 Hz, 1H), 3.89 (s, 3H), 3.28 (p, J = 7.1 Hz, 1H), 2.94 (p, J = 6.9 Hz, 1H), 2.36 (d, J = 4.9 Hz, 3H), 1.36 (dd, J = 7.0, 1.6 Hz, 6H), 1.31 (d, J = 7.1 Hz, 3H), 1.25 (d, J = 7.2 Hz, 3H), 1.22 (d, J = 6.4 Hz, 3H). ¹³C NMR (126 MHz, CDCl$_3$) δ 174.70, 171.96, 162.25, 159.42, 146.50, 141.92, 141.08, 137.65, 136.14, 130.23, 126.33, 126.21, 126.09, 109.55, 75.32, 56.29, 47.95, 39.03, 33.95, 19.82, 18.80, 18.47, 16.95, 16.35. |
| 226 | | | HRMS-ESI (m/z) [M + H]⁺ calcd for C$_{24}$H$_{29}$FN$_2$O$_6$, 461.2082; found, 461.2078 | ¹H NMR (500 MHz, CDCl$_3$) δ 8.44 (s, 1H), 8.33 (d, J = 5.4 Hz, 1H), 7.20-7.12 (m, 2H), 7.02-6.93 (m, 3H), 5.07-4.97 (m, 1H), 4.70 (p, J = 7.2 Hz, 1H), 3.90 (s, 3H), 3.01-2.86 (m, 2H), 1.47 (d, J = 7.1 Hz, 3H), 1.39-1.34 (m, 6H), 1.27 (d, J = 7.0 Hz, 3H), 1.07 (d, J = 6.3 Hz, 3H). ¹³C NMR (126 MHz, CDCl$_3$) δ 174.72, 172.36, 162.62, 162.44, 160.67, 159.46, 146.57, 141.88, 138.56, 137.70, 129.33, 129.26, 115.28, 115.11, 109.63, 75.77, 56.30, 48.03, 44.07, 33.96, 18.81, 18.46, 17.65, 17.30. |
| 227 | | | HRMS-ESI (m/z) [M + H]⁺ calcd for C$_{26}$H$_{34}$N$_2$O$_7$, 487.2439; found, 487.2425 | ¹H NMR (500 MHz, CDCl$_3$) δ 8.49 (d, J = 8.6 Hz, 1H), 8.34 (d, J = 5.4 Hz, 1H), 7.09 (d, J = 8.3 Hz, 1H), 6.99 (d, J = 5.4 Hz, 1H), 6.75-6.64 (m, 2H), 5.09 (dq, J = 8.3, 6.2 Hz, 1H), 4.72 (p, J = 7.2 Hz, 1H), 3.89 (s, 3H), 3.76 (s, 3H), 3.16-3.05 (m, 1H), 2.96 (p, J = 7.0 Hz, 1H), 2.32 (s, 3H), 1.49 (d, J = 7.1 Hz, 3H), 1.39-1.34 (m, 6H), 1.21 (d, J = 6.8 Hz, 3H), 1.09 (d, J = 6.3 Hz, 3H). ¹³C NMR (126 MHz, CDCl$_3$) δ 174.71, 172.49, 162.41, 159.44, 157.62, 146.58, 141.97, 137.67, 136.95, 134.01, 127.40, 115.94, 111.45, 109.59, 76.36, 56.29, 55.11, 48.06, 39.08, 33.96, 20.21, 18.82, 18.58, 18.19, 17.74. |
| 228 | | | HRMS-ESI (m/z) [M + H]⁺ calcd for C$_{25}$H$_{32}$N$_2$O$_6$, 457.2333; found, 457.2329 | ¹H NMR (500 MHz, CDCl$_3$) δ 8.40-8.33 (m, 1H), 8.31 (d, J = 5.4 Hz, 1H), 7.22-7.15 (m, 1H), 7.15-7.03 (m, 3H), 6.97 (d, J = 5.4 Hz, 1H), 5.15 (dq, J = 8.0, 6.2 Hz, 1H), 4.61-4.47 (m, 1H), 3.88 (s, 3H), 3.25 (p, J = 7.3 Hz, |

TABLE 2-continued

Analytical Data

| Cmpd. No. | Melting Point (° C.) | IR (cm$^{-1}$) | MASS SPEC | NMR |
|---|---|---|---|---|
| | | | | 1H), 2.93 (p, J = 7.0 Hz, 1H), 2.36 (d, J = 3.5 Hz, 3H), 1.35 (d, J = 7.0 Hz, 6H), 1.28 (d, J = 6.3 Hz, 3H), 1.24 (d, J = 7.0 Hz, 3H), 1.01 (d, J = 7.2 Hz, 3H). $^{13}$C NMR (126 MHz, CDCl$_3$) δ 174.68, 172.25, 162.26, 159.39, 146.54, 141.96, 141.54, 137.60, 136.03, 130.21, 126.16, 125.98, 109.53, 75.56, 56.27, 47.84, 39.43, 33.93, 19.84, 18.80, 17.71, 17.01. |
| 229 | | | HRMS-ESI (m/z) [M + H]$^+$ calcd for C$_{24}$H$_{29}$FN$_2$O$_6$, 461.2082; found, 461.2077 | $^1$H NMR (500 MHz, CDCl$_3$) δ 8.46 (d, J = 8.6 Hz, 1H), 8.33 (d, J = 5.4 Hz, 1H), 7.18-7.10 (m, 2H), 7.01-6.89 (m, 3H), 5.09-5.00 (m, 1H), 4.71 (p, J = 7.3 Hz, 1H), 3.89 (d, J = 1.2 Hz, 3H), 3.01-2.86 (m, 2H), 1.47 (dd, J = 7.2, 1.8 Hz, 3H), 1.39-1.34 (m, 6H), 1.27 (dd, J = 7.1, 1.6 Hz, 3H), 1.09 (d, J = 6.3 Hz, 3H). $^{13}$C NMR (126 MHz, CDCl$_3$) δ 174.71, 172.29, 162.61, 162.36, 160.66, 159.46, 146.57, 141.89, 138.63, 137.70, 129.33, 129.29, 129.26, 115.27, 115.10, 109.63, 75.95, 56.30, 48.10, 44.13, 33.96, 18.81, 18.71, 17.93, 17.20. |
| 230 | | | HRMS-ESI (m/z) [M + H]$^+$ calcd for C$_{26}$H$_{34}$N$_2$O$_7$, 487.2439; found, X487.2423 | $^1$H NMR (500 MHz, CDCl$_3$) δ 8.50 (d, J = 8.7 Hz, 1H), 8.33 (d, J = 5.4 Hz, 1H), 7.09 (d, J = 8.3 Hz, 1H), 6.99 (d, J = 5.5 Hz, 1H), 6.77-6.66 (m, 2H), 5.08 (dq, J = 8.3, 6.2 Hz, 1H), 4.73 (p, J = 7.2 Hz, 1H), 3.89 (s, 3H), 3.77 (s, 3H), 3.17-3.05 (m, 1H), 2.95 (p, J = 7.0 Hz, 1H), 2.32 (s, 3H), 1.50 (d, J = 7.2 Hz, 3H), 1.38-1.33 (m, 6H), 1.22 (d, J = 6.9 Hz, 3H), 1.11 (d, J = 6.3 Hz, 3H). $^{13}$C NMR (126 MHz, CDCl$_3$) δ 174.71, 172.49, 162.36, 159.43, 157.65, 146.58, 141.97, 137.67, 136.91, 134.03, 127.40, 115.92, 111.45, 109.59, 76.46, 56.29, 55.12, 48.15, 39.14, 33.95, 20.19, 18.79, 18.43, 17.63. |
| 231 | | | HRMS-ESI (m/z) [M + H]$^+$ calcd for C$_{24}$H$_{30}$N$_2$O$_7$, 459.2126; found, 459.2121 | $^1$H NMR (500 MHz, CDCl$_3$) δ 8.26 (d, J = 5.4 Hz, 1H), 8.22 (t, J = 7.4 Hz, 1H), 7.22-7.03 (m, 4H), 6.93 (d, J = 5.4 Hz, 1H), 5.73 (dd, J = 5.6, 1.8 Hz, 2H), 5.16 (dq, J = 8.1, 6.3 Hz, 1H), 4.58-4.51 (m, 1H), 3.90 (s, 3H), 3.31-3.22 (m, 1H), 2.37 (s, 3H), 2.06 (s, 3H), 1.31 (d, J = 6.2 Hz, 3H), 1.24 (d, J = 7.0 Hz, 3H), 1.03 (d, J = 7.2 Hz, 3H). $^{13}$C NMR (126 MHz, CDCl$_3$) δ 172.26, 170.26, 162.87, 160.25, 145.68, 143.94, 142.57, 141.57, 136.03, 130.21, 126.16, 125.94, 109.49, 89.57, 75.57, 56.16, 48.08, 39.48, 20.87, 19.84, 17.92, 17.77, 17.05. |
| 232 | | | HRMS-ESI (m/z) [M + H]$^+$ calcd for C$_{23}$H$_{27}$FN$_2$O$_7$, 463.1875; found, 463.1870 | $^1$H NMR (500 MHz, CDCl$_3$) δ 8.33 (d, J = 7.4 Hz, 1H), 8.29 (d, J = 5.3 Hz, 1H), 7.20-7.12 (m, 2H), 7.01-6.93 (m, 3H), 5.79-5.71 (m, 2H), 5.10-5.00 (m, 1H), 4.73 (p, J = 7.2 Hz, 1H), 3.92 (d, J = 2.0 Hz, 3H), 2.92 (p, J = 7.1 Hz, 1H), 2.07 (d, J = 1.6 Hz, 3H), 1.50 (d, J = 7.1 Hz, 3H), 1.29 (dd, J = 7.0, 2.5 Hz, 3H), 1.08 (d, J = 6.3 Hz, 3H). $^{13}$C NMR (126 MHz, CDCl$_3$) δ 172.37, 170.29, 163.02, 162.63, 160.68, 160.30, 145.74, 144.03, 142.51, 138.55, 138.52, 129.32, 129.26, 115.30, 115.13, 109.59, 89.58, 75.82, 56.20, 48.22, 44.12, 20.88, 18.39, 17.69, 17.39. |

TABLE 2-continued

Analytical Data

| Cmpd. No. | Melting Point (° C.) | IR (cm$^{-1}$) | MASS SPEC | NMR |
|---|---|---|---|---|
| 233 | | | HRMS-ESI (m/z) [M + H]$^+$ calcd for C$_{25}$H$_{32}$N$_2$O$_8$, 489.2231; found, 489.2220 | $^1$H NMR (500 MHz, CDCl$_3$) δ 8.38 (d, J = 7.7 Hz, 1H), 8.29 (d, J = 5.3 Hz, 1H), 7.09 (d, J = 8.3 Hz, 1H), 6.96 (d, J = 5.3 Hz, 1H), 6.79-6.62 (m, 2H), 5.76 (d, J = 2.2 Hz, 2H), 5.17-5.05 (m, 1H), 4.75 (p, J = 7.2 Hz, 1H), 3.92 (s, 3H), 3.76 (s, 3H), 3.22-3.03 (m, 1H), 2.32 (s, 3H), 2.07 (s, 3H), 1.52 (d, J = 7.2 Hz, 3H), 1.23 (d, J = 6.9 Hz, 3H), 1.10 (d, J = 6.3 Hz, 3H). $^{13}$C NMR (126 MHz, CDCl$_3$) δ 172.52, 170.29, 162.99, 160.29, 157.63, 145.74, 144.02, 142.57, 136.96, 133.96, 127.39, 115.93, 111.48, 109.55, 89.61, 76.42, 56.19, 55.11, 48.23, 39.10, 20.88, 20.21, 18.51, 18.21, 17.82. |
| 234 | | IR (thin film) 3383, 2981, 1737, 1679, 1505, 1310, 1114, 1045, 732 cm$^{-1}$ | HRMS-ESI (m/z) [M + H]$^+$ calcd for C$_{25}$H$_{30}$F$_3$N$_2$O$_6$, 511.2050; found, 511.2048 | $^1$H NMR (400 MHz, CDCl$_3$) δ 8.50 (d, J = 7.4 Hz, 1H), 8.34 (d, J = 5.4 Hz, 1H), 7.64 (dd, J = 8.0, 1.3 Hz, 1H), 7.54-7.47 (m, 1H), 7.44 (d, J = 7.8 Hz, 1H), 7.31 (t, J = 7.5 Hz, 1H), 6.99 (d, J = 5.4 Hz, 1H), 5.26-5.11 (m, 1H), 4.76 (p, J = 7.3 Hz, 1H), 3.89 (s, 3H), 3.34 (p, J = 6.6 Hz, 1H), 2.96 (hept, J = 7.0 Hz, 1H), 1.54 (d, J = 7.2 Hz, 3H), 1.36 (dd, J = 7.0, 1.3 Hz, 6H), 1.28 (d, J = 6.8 Hz, 3H), 1.10 (d, J = 6.3 Hz, 3H). $^{19}$F NMR (376 MHz, CDCl$_3$) δ −58.25. |
| 235 | | IR (thin film) 3383, 2982, 1761, 1738, 1679, 1500, 1312, 1119, 909, 732 cm$^{-1}$ | HRMS-ESI (m/z) [M + H]$^+$ calcd for C$_{25}$H$_{29}$F$_4$N$_2$O$_6$, 529.1956; found, 529.1954 | $^1$H NMR (400 MHz, CDCl$_3$) δ 8.47 (d, J = 8.1 Hz, 1H), 8.34 (d, J = 5.4 Hz, 1H), 7.42 (dd, J = 8.8, 5.4 Hz, 1H), 7.34 (dd, J = 9.2, 2.8 Hz, 1H), 7.21 (td, J = 8.3, 2.8 Hz, 1H), 7.00 (d, J = 5.5 Hz, 1H), 5.13 (p, J = 6.5 Hz, 1H), 4.75 (dq, J = 9.3, 7.3 Hz, 1H), 3.89 (s, 3H), 3.36-3.24 (m, 1H), 2.95 (hept, J = 7.0 Hz, 1H), 1.53 (d, J = 7.2 Hz, 3H), 1.36 (dd, J = 7.0, 1.5 Hz, 6H), 1.26 (d, J = 6.8 Hz, 3H), 1.11 (d, J = 6.2 Hz, 3H). $^{19}$F NMR (376 MHz, CDCl$_3$) δ −58.80, −114.13. |
| 236 | | IR (thin film) 3383, 2943, 1763, 1733, 1678, 1504, 1310, 1210, 1090, 843, 731 cm$^{-1}$ | HRMS-ESI (m/z) [M + H]$^+$ calcd for C$_{23}$H$_{35}$N$_2$O$_6$, 435.2490; found, 435.2483 | $^1$H NMR (400 MHz, CDCl$_3$) δ 8.53 (d, J = 7.7 Hz, 1H), 8.32 (d, J = 5.4 Hz, 1H), 6.98 (d, J = 5.4 Hz, 1H), 5.08 (qd, J = 6.5, 3.0 Hz, 1H), 4.69 (dt, J = 7.9, 7.0 Hz, 1H), 3.89 (s, 3H), 3.02-2.87 (m, 1H), 1.74 (dddd, J = 19.4, 17.2, 9.8, 5.1 Hz, 3H), 1.67-1.51 (m, 4H), 1.48 (d, J = 7.1 Hz, 3H), 1.36 (d, J = 7.0 Hz, 6H), 1.22 (d, J = 6.4 Hz, 3H), 1.18-1.02 (m, 3H), 0.94 (d, J = 6.9 Hz, 3H). |
| 237 | | IR (thin film) 3382, 2976, 1762, 1734, 1678, 1504, 1210, 1079, 730 cm$^{-1}$ | HRMS-ESI (m/z) [M + H]$^+$ calcd for C$_{26}$H$_{34}$N$_2$O$_6$, 471.2490; found, 471.2488 | $^1$H NMR (400 MHz, CDCl$_3$) δ 8.52 (s, 1H), 8.34 (d, J = 5.4 Hz, 1H), 7.04-6.91 (m, 4H), 5.60 (dp, J = 10.5, 6.3 Hz, 1H), 4.84-4.67 (m, 1H), 3.89 (s, 3H), 3.42 (dp, J = 10.6, 7.1 Hz, 1H), 2.95 (hept, J = 7.0 Hz, 1H), 2.41 (d, J = 2.5 Hz, 3H), 2.37 (s, 3H), 1.55 (dd, J = 14.2, 7.1 Hz, 3H), 1.40-1.32 (m, 6H), 1.28 (d, J = 7.1 Hz, 3H), 1.03 (dd, J = 6.2, 3.0 Hz, 3H). |
| 238 | | IR (thin film) 3384, 2977, 1762, 1735, 1679, 1505, 1211, 1127, 861, 731 cm$^{-1}$ | HRMS-ESI (m/z) [M + H]$^+$ calcd for C$_{26}$H$_{34}$FN$_2$O$_6$, 489.2395; found, 489.2399 | $^1$H NMR (400 MHz, CDCl$_3$) δ 8.52 (d, J = 10.1 Hz, 1H), 8.34 (d, J = 5.4 Hz, 1H), 6.99 (d, J = 5.4 Hz, 1H), 6.70 (ddd, J = 15.3, 9.4, 2.7 Hz, 2H), 5.56 (dp, J = 10.4, 6.3 Hz, 1H), 4.82-4.65 (m, 1H), 3.89 (s, 3H), 3.43-3.20 (m, 1H), 2.95 (hept, J = 7.0 Hz, 1H), 2.40 (d, J = 2.4 Hz, 3H), 2.35 (s, 3H), 1.54 (dd, J = 13.5, 7.2 Hz, 3H), 1.36 (dd, J = 7.1, 1.6 Hz, 6H), 1.26 (dd, J = 7.2, |

TABLE 2-continued

Analytical Data

| Cmpd. No. | Melting Point (° C.) | IR (cm$^{-1}$) | MASS SPEC | NMR |
|---|---|---|---|---|
| | | | | 1.0 Hz, 3H), 1.02 (dd, J = 62, 2.9 Hz, 3H). $^{19}$F NMR (376 MHz, CDCl$_3$) δ −118.50 (d, J = 25.8 Hz). |
| 239 | | IR (thin film) 3383, 2982, 1762, 1739, 1681, 1505, 1311, 1151, 1117, 772 cm$^{-1}$ | HRMS-ESI (m/z) [M + H]$^+$ calcd for C$_{25}$H$_{30}$F$_3$N$_2$O$_6$, 511.2050; found, 511.2052 | $^1$H NMR (400 MHz, CDCl$_3$) δ 8.47 (d, J = 7.8 Hz, 1H), 8.33 (d, J = 5.4 Hz, 1H), 7.67-7.60 (m, 1H), 7.54-7.45 (m, 1H), 7.44 (d, J = 7.8 Hz, 1H), 7.34-7.27 (m, 1H), 6.99 (d, J = 5.5 Hz, 1H), 5.25-5.14 (m, 1H), 4.81-4.69 (m, 1H), 3.89 (s, 3H), 3.40-3.25 (m, 1H), 2.96 (hept, J = 7.0 Hz, 1H), 1.51 (d, J = 7.1 Hz, 3H), 1.37 (dd, J = 7.0, 1.8 Hz, 6H), 1.29 (d, J = 6.8 Hz, 3H), 1.09 (d, J = 6.3 Hz, 3H). $^{19}$F NMR (376 MHz, CDCl$_3$) δ −58.26. |
| 240 | | IR (thin film) 3383, 2982, 1761, 1740, 1680, 1500, 1312, 1120, 909, 732 cm$^{-1}$ | HRMS-ESI (m/z) [M + H]$^+$ calcd for C$_{25}$H$_{29}$F$_4$N$_2$O$_6$, 529.1956; found, 529.1958 | $^1$H NMR (400 MHz, CDCl$_3$) δ 8.44 (d, J = 7.8 Hz, 1H), 8.33 (d, J = 5.4 Hz, 1H), 7.42 (dd, J = 8.8, 5.4 Hz, 1H), 7.33 (dd, J = 9.2, 2.8 Hz, 1H), 7.19 (td, J = 8.3, 2.8 Hz, 1H), 7.00 (d, J = 5.4 Hz, 1H), 5.14 (p, J = 6.5 Hz, 1H), 4.81-4.67 (m, 1H), 3.90 (s, 3H), 3.36-3.22 (m, 1H), 2.96 (hept, J = 7.0 Hz, 1H), 1.50 (d, J = 7.2 Hz, 3H), 1.37 (dd, J = 7.0, 1.9 Hz, 6H), 1.28 (d, J = 6.9 Hz, 3H), 1.11 (d, J = 6.3 Hz, 3H). $^{19}$F NMR (376 MHz, CDCl$_3$) δ −58.80, −114.24. |
| 241 | | IR (thin film) 3382, 2944, 1764, 1734, 1680, 1504, 1210, 1090, 1040, 916, 843, 732 cm$^{-1}$ | HRMS-ESI (m/z) [M + H]$^+$ calcd for C$_{23}$H$_{35}$N$_2$O$_6$, 435.2490; found, 435.2491 | $^1$H NMR (400 MHz, CDCl$_3$) δ 8.52 (s, 1H), 8.32 (d, J = 5.4 Hz, 1H), 6.98 (d, J = 5.4 Hz, 1H), 5.07 (qd, J = 6.5, 3.0 Hz, 1H), 4.73-4.62 (m, 1H), 3.89 (s, 3H), 2.95 (hept, J = 7.0 Hz, 1H), 1.85-1.61 (m, 2H), 1.61-1.50 (m, 2H), 1.47 (d, J = 7.1 Hz, 3H), 1.43-1.29 (m, 9H), 1.21 (d, J = 6.4 Hz, 3H), 1.17-1.01 (m, 3H), 0.93 (d, J = 6.9 Hz, 3H). $^{13}$C NMR (101 MHz, CDCl$_3$) δ 174.69, 172.36, 162.38, 159.45, 146.55, 142.04, 137.69, 109.56, 74.50, 56.28, 48.04, 43.14, 42.93, 33.98, 31.24, 30.70, 25.13, 25.01, 18.82, 18.71, 17.48, 12.50. |
| 242 | | IR (thin film) 3383, 2977, 1762, 1735, 1679, 1504, 1210, 1081, 914, 861, 731 cm$^{-1}$ | HRMS-ESI (m/z) [M + H]$^+$ calcd for C$_{26}$H$_{34}$FN$_2$O$_6$, 489.2395; found, 489.2399 | $^1$H NMR (400 MHz, CDCl$_3$) δ 8.49 (d, J = 8.4 Hz, 1H), 8.34 (d, J = 5.5 Hz, 1H), 6.99 (d, J = 5.5 Hz, 1H), 6.70 (ddd, J = 17.0, 9.4, 2.8 Hz, 2H), 5.57 (dq, J = 10.4, 6.4 Hz, 1H), 4.85-4.62 (m, 1H), 3.89 (s, 3H), 3.36 (dp, J = 10.4, 7.1 Hz, 1H), 2.95 (hept, J = 7.0 Hz, 1H), 2.40 (s, 3H), 2.35 (s, 3H), 1.52 (d, J = 7.2 Hz, 3H), 1.36 (dd, J = 7.0, 1.9 Hz, 6H), 1.26 (dd, J = 7.2, 1.0 Hz, 3H), 1.02 (d, J = 6.2 Hz, 3H). $^{19}$F NMR (376 MHz, CDCl$_3$) δ −118.53. |
| 243 | | IR (thin film) 3383, 2977, 1763, 1735, 1679, 1504, 1211, 1080, 914, 731 cm$^{-1}$ | HRMS-ESI (m/z) [M + H]$^+$ calcd for C$_{26}$H$_{35}$N$_2$O$_6$, 471.2490; found, 471.2495 | $^1$H NMR (400 MHz, CDCl$_3$) δ 8.54 (d, J = 12.1 Hz, 1H), 8.34 (d, J = 5.4 Hz, 1H), 7.04-6.94 (m, 4H), 5.60 (dp, J = 10.4, 6.3 Hz, 1H), 4.75 (ddq, J = 14.6, 7.2, 3.5 Hz, 1H), 3.89 (s, 3H), 3.42 (dp, J = 10.6, 7.1 Hz, 1H), 2.96 (hept, J = 7.0 Hz, 1H), 2.41 (d, J = 2.5 Hz, 3H), 2.38 (s, 3H), 1.55 (dd, J = 14.2, 7.1 Hz, 3H), 1.36 (dd, J = 7.1, 1.7 Hz, 6H), 1.28 (d, J = 7.1 Hz, 3H), 1.03 (dd, J = 6.2, 2.9 Hz, 3H). |
| 244 | | IR (thin film) 3383, 2977, 1761, 1735, 1678, 1504, 1309, 1209, 1081, 1059, 731 cm$^{-1}$ | HRMS-ESI (m/z) [M + H]$^+$ calcd for C$_{26}$H$_{34}$FN$_2$O$_6$, 489.2395; found, 489.2399 | $^1$H NMR (400 MHz, CDCl$_3$) δ 8.49 (d, J = 9.5 Hz, 1H), 8.34 (d, J = 5.4 Hz, 1H), 6.99 (d, J = 5.5 Hz, 1H), 6.82-6.61 (m, 2H), 5.56 (dp, J = 10.4, 6.3 Hz, 1H), 4.75 (pd, J = 7.2, 4.4 Hz, 1H), 3.89 (s, 3H), 3.36 (dp, J = 10.3, 7.0 Hz, 1H), 2.95 (p, J = 7.0 Hz, 1H), 2.40 (d, J = 2.4 Hz, 3H), 2.35 (s, 3H), 1.54 (dd, |

TABLE 2-continued

Analytical Data

| Cmpd. No. | Melting Point (° C.) | IR (cm$^{-1}$) | MASS SPEC | NMR |
|---|---|---|---|---|
| | | | | J = 13.6, 7.2 Hz, 3H), 1.36 (dd, J = 7.0, 1.8 Hz, 6H), 1.26 (dd, J = 7 2, 1.1 Hz, 3H), 1.02 (dd, J = 62, 2.9 Hz, 3H). $^{19}$F NMR (376 MHz, CDCl$_3$) δ −118.49 (d, J = 25.8 Hz). |
| 245 | | IR (thin film) 3379, 2986, 1771, 1736, 1676, 1508, 1310, 1149, 1116, 1046, 732 cm$^{-1}$ | HRMS-ESI (m/z) [M + H]$^+$ calcd for C$_{23}$H$_{26}$F$_3$N$_2$O$_6$, 473.1737; found, 483.1733 | $^1$H NMR (400 MHz, CDCl$_3$) δ 8.56 (d, J = 7.5 Hz, 1H), 8.35 (d, J = 5.5 Hz, 1H), 7.64 (dd, J = 8.0, 1.4 Hz, 1H), 7.55-7.46 (m, 1H), 7.43 (d, J = 7.8 Hz, 1H), 7.35-7.28 (m, 1H), 7.01 (d, J = 5.5 Hz, 1H), 5.25-5.13 (m, 1H), 4.81-4.70 (m, 1H), 3.91 (s, 3H), 3.43-3.29 (m, 1H), 2.40 (s, 3H), 1.55 (d, J = 7.2 Hz, 3H), 1.28 (d, J = 6.8 Hz, 3H), 1.10 (d, J = 6.3 Hz, 3H). $^{19}$F NMR (376 MHz, CDCl$_3$) δ −58.25. |
| 246 | | IR (thin film) 3379, 2986, 1771, 1737, 1677, 1500, 1312, 1154, 1123, 1045, 909, 732 cm$^{-1}$ | HRMS-ESI (m/z) [M + H]$^+$ calcd for C$_{23}$H$_{25}$F$_4$N$_2$O$_6$, 501.1643; found, 501.1642 | $^1$H NMR (400 MHz, CDCl$_3$) δ 8.61-8.44 (m, 1H), 8.35 (d, J = 5.4 Hz, 1H), 7.42 (dd, J = 8.8, 5.3 Hz, 1H), 7.34 (dd, J = 9.2, 2.9 Hz, 1H), 7.21 (td, J = 8.2, 2.8 Hz, 1H), 7.02 (d, J = 5.5 Hz, 1H), 5.19-5.07 (m, 1H), 4.82-4.69 (m, 1H), 3.91 (s, 3H), 3.37-3.23 (m, 1H), 2.41 (s, 3H), 1.54 (d, J = 7.2 Hz, 3H), 1.27 (d, J = 6.8 Hz, 3H), 1.11 (d, J = 62 Hz, 3H). $^{19}$F NMR (376 MHz, CDCl$_3$) δ −58.80, −114.08. |
| 247 | | IR (thin film) 3379, 2946, 1771, 1732, 1676, 1506, 1310, 1193, 1174, 1060, 906, 731 cm$^{-1}$ | HRMS-ESI (m/z) [M + H]$^+$ calcd for C$_{21}$H$_{31}$N$_2$O$_6$, 407.2177; found, 407.2173 | $^1$H NMR (400 MHz, CDCl$_3$) δ 8.58 (s, 1H), 8.33 (d, J = 5.5 Hz, 1H), 7.00 (d, J = 5.5 Hz, 1H), 5.09 (qd, J = 6.5, 3.0 Hz, 1H), 4.77-4.62 (m, 1H), 3.90 (s, 3H), 2.40 (s, 3H), 1.83-1.68 (m, 3H), 1.59 (dddt, J = 19.6, 14.7, 7.5, 3.1 Hz, 4H), 1.49 (d, J = 7.2 Hz, 3H), 1.38 (dddd, J = 13.6, 9.7, 6.8, 3.0 Hz, 1H), 1.22 (d, J = 6.5 Hz, 3H), 1.18-1.02 (m, 2H), 0.95 (d, J = 6.8 Hz, 3H). $^{13}$C NMR (101 MHz, CDCl$_3$) δ 172.30, 168.88, 162.36, 159.48, 146.65, 141.67, 137.52, 109.73, 74.49, 56.28, 48.23, 43.34, 43.11, 31.23, 30.75, 25.16, 24.98, 20.75, 18.87, 17.79, 12.49. |
| 248 | | IR (thin film) 3378, 2980, 1770, 1733, 1676, 1506, 1310, 1195, 1175, 1006, 907, 730 cm$^{-1}$ | HRMS-ESI (m/z) [M + H]$^+$ calcd for C$_{24}$H$_{31}$N$_2$O$_6$, 443.2177; found, 443.2176 | $^1$H NMR (400 MHz, CDCl$_3$) δ 8.59 (d, J = 7.7 Hz, 1H), 8.35 (d, J = 5.4 Hz, 1H), 7.07-6.91 (m, 4H), 5.67-5.55 (m, 1H), 4.85-4.70 (m, 1H), 3.91 (s, 3H), 3.42 (dp, J = 10.6, 7.1 Hz, 1H), 2.41 (s, 3H), 1.56 (dd, J = 14.4, 7.1 Hz, 3H), 1.28 (d, J = 7.1 Hz, 3H), 1.04 (dd, J = 6.2, 2.8 Hz, 3H). |
| 249 | | | HRMS-ESI (m/z) [M + H]$^+$ calcd for C$_{24}$H$_{30}$FN$_2$O$_6$, 461.2082; found, 461.2080 | $^1$H NMR (400 MHz, CDCl$_3$) δ 8.57 (d, J = 8.7 Hz, 1H), 8.35 (d, J = 5.5 Hz, 1H), 7.01 (d, J = 5.5 Hz, 1H), 6.70 (ddd, J = 15.2, 9.3, 2.5 Hz, 2H), 5.65-5.47 (m, 1H), 4.81-4.64 (m, 1H), 3.91 (s, 3H), 3.36 (dp, J = 10.5, 7.0 Hz, 1H), 2.40 (s, 6H), 2.35 (s, 3H), 1.55 (dd, J = 13.8, 7.2 Hz, 3H), 1.26 (d, J = 7.2 Hz, 3H), 1.03 (dd, J = 6.2, 2.7 Hz, 3H). $^{19}$F NMR (376 MHz, CDCl$_3$) δ −118.43. |
| 250 | | IR (thin film) 3377, 2985, 1771, 1737, 1677, 1507, 1310, 1149, 1116, 771, 731 cm$^{-1}$ | HRMS-ESI (m/z) [M + H]$^+$ calcd for C$_{23}$H$_{26}$F$_3$N$_2$O$_6$, 483.1737; found, 483.1735 | $^1$H NMR (400 MHz, CDCl$_3$) δ 8.54 (d, J = 7.8 Hz, 1H), 8.34 (d, J = 5.4 Hz, 1H), 8.01 (d, J = 5.2 Hz, OH), 7.63 (dt, J = 8.0, 1.7 Hz, 1H), 7.55-7.47 (m, 1H), 7.44 (d, J = 7.8 Hz, 1H), 7.31 (dt, J = 9.6, 4.2 Hz, 1H), 7.01 (d, J = 5.5 Hz, 1H), 5.28-5.12 (m, 1H), 4.75 (dqd, J = 8.4, 7.2, 1.3 Hz, 1H), 3.91 (s, 3H), 3.41-3.28 (m, 1H), 2.41 (s, 3H), 1.52 (d, J = 7.2 Hz, 3H), 1.29 (d, J = 6.8 Hz, 3H), 1.13-1.05 (m, 3H). $^{19}$F NMR (376 MHz, CDCl$_3$) δ −58.25. |

TABLE 2-continued

Analytical Data

| Cmpd. No. | Melting Point (° C.) | IR (cm$^{-1}$) | MASS SPEC | NMR |
|---|---|---|---|---|
| 251 | | IR (thin film) 2985, 1771, 1738, 1677, 1500, 1312, 1193, 1154, 1122, 909, 732 cm$^{-1}$ | HRMS-ESI (m/z) [M + H]$^+$ calcd for C$_{23}$H$_{25}$F$_4$N$_2$O$_6$, 501.1643; found, 501.1640 | $^1$H NMR (400 MHz, CDCl$_3$) δ 8.50 (d, J = 7.9 Hz, 1H), 8.34 (d, J = 5.4 Hz, 1H), 7.43 (dd, J = 8.8, 5.3 Hz, 1H), 7.34 (dd, J = 9.2, 2.8 Hz, 1H), 7.20 (td, J = 8.2, 2.9 Hz, 1H), 7.02 (d, J = 5.5 Hz, 1H), 5.15 (h, J = 6.5 Hz, 1H), 4.74 (dq, J = 8.1, 7.1 Hz, 1H), 3.92 (s, 3H), 3.30 (p, J = 6.9 Hz, 1H), 2.41 (s, 3H), 1.52 (d, J = 7.2 Hz, 3H), 1.28 (d, J = 6.8 Hz, 3H), 1.11 (d, J = 6.3 Hz, 3H). $^{19}$F NMR (376 MHz, CDCl$_3$) δ −58.80, −114.19. |
| 252 | | IR (thin film) 3382, 2947, 1771, 1732, 1676, 1505, 1310, 1199, 1174, 1151, 1061, 906, 731 cm$^{-1}$ | HRMS-ESI (m/z) [M + H]$^+$ calcd for C$_{21}$H$_{31}$N$_2$O$_6$, 407.2177; found, 407.2176 | $^1$H NMR (400 MHz, CDCl$_3$) δ 8.58 (s, 1H), 8.33 (d, J = 5.4 Hz, 1H), 7.00 (d, J = 5.4 Hz, 1H), 5.08 (qd, J = 6.4, 3.0 Hz, 1H), 4.75-4.63 (m, 1H), 3.91 (s, 3H), 2.40 (s, 3H), 1.85-1.63 (m, 4H), 1.63-1.51 (m, 2H), 1.48 (d, J = 7.2 Hz, 3H), 1.45-1.32 (m, 2H), 1.21 (d, J = 6.4 Hz, 3H), 1.17-1.00 (m, 2H), 0.94 (d, J = 6.9 Hz, 3H). $^{13}$C NMR (101 MHz, CDCl$_3$) δ 172.27, 168.90, 162.40, 159.48, 146.66, 141.66, 137.53, 109.72, 74.58, 56.28, 48.07, 43.13, 42.93, 31.25, 30.69, 25.14, 25.01, 20.75, 18.69, 17.48, 12.50. |
| 253 | | IR (thin film) 3378, 2979, 1770, 1733, 1676, 1506, 1195, 1175, 1006, 907, 730 cm$^{-1}$ | HRMS-ESI (m/z) [M + H]$^+$ calcd for C$_{24}$H$_{31}$N$_2$O$_6$, 443.2177; found, 443.2170 | $^1$H NMR (400 MHz, CDCl$_3$) δ 8.59 (d, J = 8.8 Hz, 1H), 8.35 (d, J = 5.4 Hz, 1H), 7.08-6.92 (m, 4H), 5.66-5.55 (m, 1H), 4.76 (p, J = 7.3 Hz, 1H), 3.91 (s, 3H), 3.42 (dp, J = 10.5, 7.1 Hz, 1H), 2.41 (d, J = 1.7 Hz, 6H), 2.38 (s, 3H), 1.54 (d, J = 7.1 Hz, 3H), 1.28 (d, J = 7.2 Hz, 3H), 1.03 (d, J = 6.2 Hz, 3H). |
| 254 | | IR (thin film) 3379, 2980, 1771, 1733, 1676, 1507, 1174, 1130, 1007, 731 cm$^{-1}$ | HRMS-ESI (m/z) [M + H]$^+$ calcd for C$_{24}$H$_{30}$FN$_2$O$_6$, 461.2082; found, 461.2082 | $^1$H NMR (400 MHz, CDCl$_3$) δ 8.55 (dd, J = 16.7, 7.9 Hz, 1H), 8.35 (d, J = 5.4 Hz, 1H), 7.01 (d, J = 5.5 Hz, 1H), 6.70 (ddd, J = 17.0, 9.3, 2.7 Hz, 2H), 5.57 (dq, J = 10.3, 6.1 Hz, 1H), 4.82-4.69 (m, 1H), 3.91 (s, 3H), 3.36 (dp, J = 10.5, 6.9 Hz, 1H), 2.40 (d, J = 2.6 Hz, 6H), 2.35 (s, 3H), 1.53 (d, J = 7.2 Hz, 3H), 1.26 (d, J = 7.1 Hz, 3H), 1.02 (d, J = 6.3 Hz, 3H). $^{19}$F NMR (376 MHz, CDCl$_3$) δ −118.49. |
| 255 | | IR (thin film) 3380, 2979, 1770, 1733, 1676, 1506, 1310, 1195, 1175, 1006, 907, 730 cm$^{-1}$ | HRMS-ESI (m/z) [M + H]$^+$ calcd for C$_{24}$H$_{31}$N$_2$O$_6$, 443.2177; found, 443.2176 | $^1$H NMR (400 MHz, CDCl$_3$) δ 8.64-8.52 (m, 1H), 8.35 (d, J = 5.4 Hz, 1H), 7.07-6.90 (m, 4H), 5.68-5.53 (m, 1H), 4.86-4.68 (m, 1H), 3.91 (s, 3H), 3.42 (dp, J = 10.5, 7.1 Hz, 1H), 2.42-2.39 (m, 6H), 2.38 (s, 3H), 1.56 (dd, J = 14.5, 7.1 Hz, 3H), 1.28 (d, J = 7.1 Hz, 3H), 1.04 (dd, J = 6.2, 2.8 Hz, 3H). |
| 256 | | IR (thin film) 3377, 2981, 1771, 1734, 1676, 1507, 1310, 1195, 1175, 1007, 908, 731 cm$^{-1}$ | HRMS-ESI (m/z) [M + H]$^+$ calcd for C$_{24}$H$_{30}$FN$_2$O$_6$, 461.2082; found, 461.2084 | $^1$H NMR (400 MHz, CDCl$_3$) δ 8.68-8.47 (m, 1H), 8.35 (d, J = 5.4 Hz, 1H), 7.01 (d, J = 5.5 Hz, 1H), 6.70 (ddd, J = 14.7, 9.4, 2.4 Hz, 2H), 5.66-5.48 (m, 1H), 4.75 (tdd, J = 8.8, 7.2, 5.7 Hz, 1H), 3.91 (d, J = 1.6 Hz, 3H), 3.36 (dp, J = 10.5, 7.0 Hz, 1H), 2.40 (d, J = 2.8 Hz, 6H), 2.35 (s, 3H), 1.55 (dd, J = 13.9, 7.2 Hz, 3H), 1.26 (d, J = 7.1 Hz, 3H), 1.03 (dd, J = 62, 2.7 Hz, 3H). $^{19}$F NMR (376 MHz, CDCl$_3$) δ −118.43, −118.49. |
| 257 | | | HRMS-ESI (m/z) [M + H]$^+$ calcd for C$_{23}$H$_{29}$N$_2$O$_7$, 445.1969; found, 445.1949 | $^1$H NMR (400 MHz, CDCl$_3$) δ 8.46 (d, J = 7.4 Hz, 1H), 8.31 (d, J = 5.5 Hz, 1H), 7.20-7.10 (m, 2H), 6.98 (d, J = 5.5 Hz, 1H), 6.88-6.79 (m, 2H), 5.27 (dq, J = 7.7, 6.3 Hz, 1H), 4.61-4.51 (m, 1H), 3.88 (s, 3H), 3.80 (s, 3H), 3.49-3.41 (m, 1H), 2.38 (s, 3H), 1.24 (d, J = 4.7 Hz, 3H), 1.22 (d, J = 3.8 Hz, 3H), 1.11 (d, J = 7.2 Hz, 3H). |

TABLE 2-continued

Analytical Data

| Cmpd. No. | Melting Point (° C.) | IR (cm$^{-1}$) | MASS SPEC | NMR |
|---|---|---|---|---|
| | | | | $^{13}$CNMR(101 MHz, CDCl$_3$) δ 172.1, 168.9, 162.3, 159.4, 157.2, 146.6, 141.7, 137.5, 131.2, 128.1, 127.3, 120.5, 110.5, 109.7, 74.9, 56.3, 55.4, 48.0, 37.4, 20.7, 18.3, 17.8, 16.6. |
| 258 | | IR (thin film) 3377, 2980, 2938, 1770, 1732, 1674, 1507, 1310, 1198, 1174, 702 cm$^{-1}$ | HRMS-ESI (m/z) [M + H]$^+$ calcd for C$_{22}$H$_{27}$N$_2$O$_6$, 415.1864; found, 415.1859 | $^1$H NMR (500 MHz, CDCl$_3$) δ 8.56 (s, 1H), 8.34 (d, J = 5.5 Hz, 1H), 7.32-7.27 (m, 2H), 7.24-7.16 (m, 3H), 7.01 (d, J = 5.5 Hz, 1H), 5.09 (dq, J = 7.7, 6.3 Hz, 1H), 4.77-4.67 (m, 1H), 3.91 (s, 3H), 2.96-2.86 (m, 1H), 2.41 (s, 3H), 1.49 (d, J = 12 Hz, 3H), 1.30 (d, J = 7.0 Hz, 3H), 1.10 (d, J = 6.3 Hz, 3H). $^{13}$C NMR (126 MHz, CDCl$_3$) δ 172.3, 169.0, 162.4, 159.4, 146.7, 143.0, 141.5, 137.5, 128.4, 127.8, 126.7, 109.7, 76.3, 56.3, 48.1, 45.0, 20.8, 18.7, 18.2, 17.3. |
| 259 | | IR (thin film) 3380, 2980, 2938, 1770, 1734, 1674, 1506, 1193, 1173, 1060, 800 cm$^{-1}$ | HRMS-ESI (m/z) [M + H]$^+$ calcd for C$_{21}$H$_{27}$N$_2$O$_6$S, 435.1584; found, 435.1581 | $^1$H NMR (500 MHz, CDCl$_3$) δ 8.56 (s, 1H), 8.34 (d, J = 5.4 Hz, 1H), 7.01 (d, J = 5.5 Hz, 1H), 6.61 (d, J = 3.5 Hz, 1H), 6.56 (dq, J = 3.4, 1.1 Hz, 1H), 5.07-4.98 (m, 1H), 4.77-4.67 (m, 1H), 3.91 (s, 3H), 3.20-3.11 (m, 1H), 2.42 (d, J = 1.1 Hz, 3H), 2.40 (s, 3H), 1.49 (d, J = 7.2 Hz, 3H), 1.32 (d, J = 7.0 Hz, 3H), 1.17 (d, J = 6.3 Hz, 3H). $^{13}$C NMR (126 MHz, CDCl$_3$) δ 172.2, 169.0, 162.4, 159.4, 146.7, 143.5, 141.5, 138.0, 137.5, 124.5, 124.1, 109.7, 75.9, 56.3, 48.1, 40.2, 20.8, 18.7, 18.0, 17.3, 15.3. |
| 260 | | IR (thin film) 3381, 2980, 2940, 1770, 1733, 1675, 1502, 1193, 1175, 1150, 731 cm$^{-1}$ | HRMS-ESI (wz) [M + H]$^+$ calcd for C$_{23}$H$_{28}$FN$_2$O$_7$, 463.1875; found, 463.1874 | $^1$H NMR (500 MHz, CDCl$_3$) δ 8.54 (s, 1H), 8.35 (d, J = 5.4 Hz, 1H), 7.14-7.06 (m, 1H), 7.01 (d, J = 5.5 Hz, 1H), 6.62-6.51 (m, 2H), 5.18-5.08 (m, 1H), 4.72-4.62 (m, 1H), 3.92 (s, 3H), 3.79 (s, 3H), 3.42-3.31 (m, 1H), 2.41 (s, 3H), 1.46 (d, J = 7.2 Hz, 3H), 1.23 (d, J = 7.1 Hz, 3H), 1.13 (d, J = 6.3 Hz, 3H). $^{19}$F NMR (471 MHz, CDCl$_3$) δ −13.9--14.0 (m). |
| 261 | | IR (thin film) 2978, 2942, 1769, 1712, 1602, 1501, 1371, 1242, 1081, 702 cm$^{-1}$ | HRMS-ESI (m/z) [M + H]$^+$ calcd for C$_{21}$H$_{23}$N$_2$O$_6$, 399.1551; found, 399.1549 | $^1$H NMR (500 MHz, CDCl$_3$) δ 8.61 (d, J = 5.3 Hz, 1H), 7.24-7.17 (m, 2H), 7.17-7.06 (m, 4H), 5.61 (q, J = 7.1 Hz, 1H), 5.16-5.06 (m, 1H), 4.06 (s, 3H), 2.93-2.83 (m, 1H), 1.70 (d, J = 7.1 Hz, 3H), 1.27 (d, J = 7.1 Hz, 3H), 1.04 (d, J = 6.3 Hz, 3H). $^{13}$C NMR (126 MHz, CDCl$_3$) δ 168.2, 158.7, 154.2, 149.1, 145.8, 142.5, 141.6, 131.5, 128.2, 128.0, 126.5, 111.2, 76.5, 56.8, 51.6, 44.7, 17.5, 17.2, 14.0. |
| 262 | | IR (thin film) 2942, 1769, 1713, 1602, 1501, 1371, 1242, 1080, 731 cm$^{-1}$ | HRMS-ESI (m/z) [M + H]$^+$ calcd for C$_{22}$H$_{24}$FN$_2$O$_7$, 447.1562; found, 447.1566 | $^1$H NMR (500 MHz, CDCl$_3$) δ 8.60 (d, J = 5.2 Hz, 1H), 7.13 (d, J = 5.3 Hz, 1H), 7.02 (dd, J = 8.5, 6.7 Hz, 1H), 6.59-6.50 (m, 2H), 5.56 (q, J = 7.1 Hz, 1H), 5.15-5.06 (m, 1H), 4.05 (s, 3H), 3.79 (s, 3H), 3.31-3.20 (m, 1H), 1.68 (d, J = 7.0 Hz, 3H), 1.18 (d, J = 7.0 Hz, 3H), 1.16 (d, J = 6.3 Hz, 3H). $^{19}$FNMR(471 MHz, CDCl$_3$) δ −113.9. |
| 263 | | | ESIMS m/z 427.2 [(M + H)+] | $^1$H NMR (400 MHz, CDCl$_3$) δ 8.55 (d, J = 7.8 Hz, 1H), 8.35 (dd, J = 5.4, 2.9 Hz, 1H), 7.23-7.05 (m, 4H), 7.01 (dd, J = 5.5, 2.2 Hz, 1H), 5.15 (dq, J = 8.7, 6.2 Hz, 1H), 4.80-4.62 (m, 1H), 3.91 (d, J = 1.7 Hz, 3H), 3.35-3.02 (m, 1H), 2.41 (d, J = 1.8 Hz, 3H), 2.35 (s, 3H), 1.50 (t, J = 6.8 Hz, 3H), 1.25 (dd, J = 6.9, 4.3 Hz, 3H), 1.11 (t, J = 5.9 Hz, 3H). |

TABLE 2-continued

Analytical Data

| Cmpd. No. | Melting Point (° C.) | IR (cm$^{-1}$) | MASS SPEC | NMR |
|---|---|---|---|---|
| 264 | | | ESIMS m/z 429.3 [(M + H)+] | $^{13}$C NMR (101 MHz, CDCl$_3$) δ 172.39, 168.89, 159.49, 146.67, 141.80, 137.54, 135.55, 130.49, 126.39, 126.30, 126.23, 109.75, 56.28, 48.19, 48.09, 39.75, 20.74, 19.96, 18.56, 18.48, 18.25, 17.58, 17.46, −0.01. $^1$H NMR (400 MHz, CDCl$_3$) δ 8.55 (d, J = 7.6 Hz, 1H), 8.34 (d, J = 5.4 Hz, 1H), 7.23-6.93 (m, 5H), 5.14 (dq, J = 8.4, 6.2 Hz, 1H), 4.73 (p, J = 7.2 Hz, 1H), 3.91 (s, 3H), 3.19 (dq, J = 8.4, 6.9 Hz, 1H), 2.40 (s, 3H), 2.35 (s, 3H), 1.51 (d, J = 7.1 Hz, 3H), 1.25 (d, J = 6.9 Hz, 3H), 1.12 (d, J = 6.2 Hz, 3H). |
| 265 | | | ESIMS m/z 457.5 [(M + H)+] | $^{13}$C NMR (101 MHz, CDCl$_3$) δ 172.39, 168.89, 162.39, 159.48, 146.67, 141.81, 141.66, 137.54, 135.51, 130.50, 126.39, 126.27, 126.26, 109.74, 56.27, 48.19, 39.81, 20.74, 19.94, 18.73, 18.48, 17.46. $^1$H NMR. (400 MHz, CDCl$_3$) δ 8.49 (s, 1H), 8.34 (dd, J = 5.4, 2.9 Hz, 1H), 7.22-7.06 (m, 4H), 6.99 (d, J = 5.4 Hz, 1H), 5.24-5.04 (m, 1H), 4.79-4.64 (m, 1H), 3.89 (d, J = 1.7 Hz, 3H), 3.18 (dq, J = 9.2, 6.9 Hz, 1H), 2.96 (p, J = 7.0 Hz, 1H), 2.35 (s, 3H), 1.49 (dd, J = 7.2, 5.9 Hz, 3H), 1.37 (dd, J = 7.0, 1.7 Hz, 6H), 1.30-1.18 (m, 3H), 1.11 (t, J = 6.2 Hz, 3H). |
| 266 | | | ESIMS m/z 457.4 [(M + H)+] | $^{13}$C NMR (101 MHz, CDCl$_3$) δ 174.68, 172.48, 162.41, 159.47, 146.56, 142.03, 141.83, 137.71, 135.55, 130.48, 126.40, 126.29, 126.21, 109.59, 56.28, 48.07, 39.77, 33.97, 19.96, 18.81, 18.56, 18.26, 17.60, −0.01. $^1$H NMR (400 MHz, CDCl$_3$) δ 8.49 (s, 1H), 8.33 (d, J = 5.4 Hz, 1H), 7.23-7.05 (m, 4H), 6.99 (d, J = 5.5 Hz, 1H), 5.12 (dt, J = 8.4, 6.2 Hz, 1H), 4.73(p, J = 7.2 Hz, 1H), 3.89 (s, 3H), 3.38-3.09 (m, 1H), 2.95 (p, J = 7.0 Hz, 1H), 2.35 (s, 3H), 1.50 (d, J = 7.1 Hz, 3H), 1.36 (dd, J = 7.0, 1.1 Hz, 6H), 1.25 (d, J = 6.9 Hz, 3H), 1.12 (d, J = 6.2 Hz, 3H). $^{13}$C NMR (101 MHz, CDCl$_3$) δ 172.48, 162.36, 159.46, 146.56, 142.03, 141.84, 137.70, 135.51, 130.49, 126.40, 126.27, 126.24, 109.58, 56.28, 48.17, 39.81, 33.96, 19.94, 18.81, 18.76, 18.48, 17.45. |
| 267 | | IR (thin film) 3087, 2984, 1737, 1513, 1484, 1311, 1151, 1118, 800, 771 cm$^{-1}$ | HRMS-ESI (m/z) [M + H]$^+$ calcd for C$_{21}$H$_{24}$F$_3$N$_2$O$_4$S, 457.1403; found, 457.1399 | $^1$H NMR (400 MHz, CDCl$_3$) δ 12.93 (s, 1H), 10.74 (d, J = 7.6 Hz, 1H), 8.00 (d, J = 5.1 Hz, 1H), 7.73-7.59 (m, 1H), 7.51 (t, J = 7.7 Hz, 1H), 7.43 (d, J = 7.8 Hz, 1H), 7.33 (t, J = 7.5 Hz, 1H), 6.89 (d, J = 5.1 Hz, 1H), 5.30-5.18 (m, 1H), 5.14 (p, J = 7.2 Hz, 1H), 3.96 (s, 3H), 3.37 (p, J = 6.8 Hz, 1H), 1.69 (dd, J = 7.2, 3.2 Hz, 3H), 1.30 (d, J = 6.8 Hz, 3H), 1.14 (d, J = 6.3 Hz, 3H). $^{19}$F NMR (376 MHz, CDCl$_3$) δ −58.23. |
| 268 | | IR (thin film) 3086, 2984, 1735, 1512, 1313, 1279, 1153, 1120, 909, 730 cm$^{-1}$ | HRMS-ESI (m/z) [M + H]$^+$ calcd for C$_{21}$H$_{23}$F$_4$N$_2$O$_4$S, 475.1309; found, 475.1308 | $^1$H NMR (400 MHz, CDCl$_3$) δ 12.91 (s, 1H), 10.72 (d, J = 7.7 Hz, 1H), 8.00 (d, J = 5.1 Hz, 1H), 7.41 (dd, J = 8.7, 5.3 Hz, 1H), 7.36 (dd, J = 9.1, 2.8 Hz, 1H), 7.22 (td, J = 8.2, 2.8 Hz, 1H), 6.90 (d, J = 5.1 Hz, 1H), 5.16 (dp, J = 21.6, 6.9 Hz, 2H), 3.96 (s, 3H), 3.34 (p, J = 7.2 Hz, 1H), 1.68 (d, J = 7.2 Hz, 3H), 1.29 (d, J = 6.8 Hz, 3H), 1.14 (d, J = 6.3 Hz, 3H). $^{19}$F NMR (376 MHz, CDCl$_3$) δ −58.77, −113.84. |

TABLE 2-continued

Analytical Data

| Cmpd. No. | Melting Point (° C.) | IR (cm$^{-1}$) | MASS SPEC | NMR |
|---|---|---|---|---|
| 269 | | IR (thin film) 3128, 2947, 1735, 1511, 1479, 1280, 1200, 1151, 985, 797 cm$^{-1}$ | HRMS-ESI (m/z) [M + H]$^+$ calcd for C$_{19}$H$_{29}$N$_2$O$_4$S, 381.1843; found, 381.1840 | $^1$H NMR (400 MHz, CDCl$_3$) δ 12.94 (d, J = 1.8 Hz, 1H), 10.76 (d, J = 7.9 Hz, 1H), 7.98 (dd, J = 5.1, 1.4 Hz, 1H), 6.88 (d, J = 5.1 Hz, 1H), 5.19-5.00 (m, 2H), 3.95 (s, 3H), 1.85-1.69 (m, 2H), 1.68-1.32 (m, 7H), 1.30-1.20 (m, 4H), 1.20-1.01 (m, 3H), 0.96 (d, J = 6.8 Hz, 3H). $^{13}$C NMR (101 MHz, CDCl$_3$) δ 188.94, 171.20, 157.16, 149.30, 138.96, 131.63, 109.05, 75.08, 56.26, 52.28, 43.32, 43.13, 31.22, 30.75, 25.15, 24.98, 17.81, 17.23, 12.49. |
| 270 | | | HRMS-ESI (m/z) [M + H]$^+$ calcd for C$_{23}$H$_{26}$F$_3$N$_2$O$_5$S, 499.1509; found, 499.1508 | $^1$H NMR (400 MHz, CDCl$_3$) δ 9.96 (d, J = 7.3 Hz, 1H), 8.34 (d, J = 5.5 Hz, 1H), 7.71-7.59 (m, 1H), 7.59-7.47 (m, 1H), 7.44 (d, J = 7.8 Hz, 1H), 7.39-7.28 (m, 1H), 7.00 (d, J = 5.5 Hz, 1H), 5.28-5.15 (m, 2H), 3.91 (s, 3H), 3.42-3.29 (m, 1H), 2.37 (s, 3H), 1.64 (d, J = 7.2 Hz, 3H), 1.30 (d, J = 6.8 Hz, 3H), 1.12 (d, J = 6.3 Hz, 3H). $^{19}$F NMR (376 MHz, CDCl$_3$) δ −58.23. |
| 271 | | | HRMS-ESI (m/z) [M + H]$^+$ calcd for C$_{23}$H$_{25}$F$_4$N$_2$O$_5$S, 517.1415; found, 517.1410 | $^1$H NMR (400 MHz, CDCl$_3$) δ 9.95 (d, J = 7.3 Hz, 1H), 8.34 (d, J = 5.4 Hz, 1H), 7.42 (dd, J = 8.8, 5.3 Hz, 1H), 7.35 (dd, J = 9.2, 2.8 Hz, 1H), 7.22 (td, J = 8.2, 2.8 Hz, 1H), 7.00 (d, J = 5.5 Hz, 1H), 5.35-5.03 (m, 2H), 3.91 (s, 3H), 3.41-3.21 (m, 1H), 2.37 (s, 3H), 1.64 (d, J = 7.1 Hz, 3H), 1.29 (d, J = 6.8 Hz, 3H), 1.13 (d, J = 6.3 Hz, 3H). $^{19}$F NMR (376 MHz, CDCl$_3$) δ −58.78, −113.98. |
| 272 | | | HRMS-ESI (m/z) [M + H]$^+$ calcd for C$_{21}$H$_{31}$N$_2$O$_5$S, 423.1948; found, 423.1944 | $^1$H NMR (400 MHz, CDCl$_3$) δ 10.00 (d, J = 7.3 Hz, 1H), 8.33 (d, J = 5.4 Hz, 1H), 6.99 (d, J = 5.4 Hz, 1H), 5.24-5.06 (m, 2H), 3.91 (s, 3H), 2.36 (s, 3H), 1.83-1.71 (m, 3H), 1.71-1.54 (m, 6H), 1.50 (dtd, J = 14.3, 8.0, 3.3 Hz, 1H), 1.39 (dqd, J = 9.7, 6.9, 3.0 Hz, 1H), 1.25 (d, J = 6.5 Hz, 3H), 1.20-1.02 (m, 2H), 0.96 (dd, J = 6.9, 1.7 Hz, 3H). $^{13}$C NMR (101 MHz, CDCl$_3$) δ 189.09, 171.67, 168.57, 159.84, 146.29, 145.12, 136.88, 109.21, 74.86, 56.41, 53.04, 43.36, 43.13, 31.22, 30.75, 25.17, 24.99, 21.27, 17.86, 17.08, 12.46. |
| 273 | | IR (thin film) 2984, 1739, 1571, 1480, 1310, 1150, 1117, 759 cm$^{-1}$ | HRMS-ESI (m/z) [M + H]$^+$ calcd for C$_{21}$H$_{24}$F$_3$N$_2$O$_6$, 457.1581; found, 457.1583 | $^1$H NMR (400 MHz, CDCl$_3$) δ 14.35 (s, 1H), 12.85 (d, J = 6.8 Hz, 1H), 7.91 (d, J = 7.1 Hz, 1H), 7.64 (dd, J = 7.9, 1.4 Hz, 1H), 7.51 (td, J = 1.6, 1.3 Hz, 1H), 7.44 (d, J = 7.8 Hz, 1H), 7.32 (t, J = 7.6 Hz, 1H), 6.79 (d, J = 7.2 Hz, 1H), 5.28-5.14 (m, 1H), 4.73 (p, J = 7.1 Hz, 1H), 3.97 (s, 3H), 3.35 (tt, J = 7.5, 3.8 Hz, 1H), 1.62 (d, J = 7.2 Hz, 3H), 1.29 (d, J = 6.8 Hz, 3H), 1.10 (d, J = 6.2 Hz, 3H). $^{19}$F NMR (376 MHz, CDCl$_3$) δ −58.22. |
| 274 | | IR (thin film) 2985, 1739, 1480, 1313, 1153, 1123, 909, 738 cm$^{-1}$ | HRMS-ESI (m/z) [M + H]$^+$ calcd for C$_{21}$H$_{23}$F$_4$N$_2$O$_6$, 475.1487; found, 475.1492 | $^1$H NMR (400 MHz, CDCl$_3$) δ 14.33 (s, 1H), 12.85 (d, J = 6.9 Hz, 1H), 7.91 (d, J = 7.2 Hz, 1H), 7.44 (dd, J = 8.8, 5.4 Hz, 1H), 7.35 (dd, J = 9.2, 2.8 Hz, 1H), 7.21 (td, J = 8.2, 2.8 Hz, 1H), 6.80 (d, J = 7.2 Hz, 1H), 5.23-5.09 (m, 1H), 4.73 (p, J = 7.2 Hz, 1H), 3.98 (s, 3H), 3.41-3.25 (m, 1H), 1.61 (d, J = 7.2 Hz, 3H), 1.27 (d, J = 6.8 Hz, 3H), 1.11 (d, J = 6.3 Hz, 3H). $^{19}$F NMR (376 MHz, CDCl$_3$) δ −58.77, −114.03. |

TABLE 2-continued

Analytical Data

| Cmpd. No. | Melting Point (° C.) | IR (cm$^{-1}$) | MASS SPEC | NMR |
|---|---|---|---|---|
| 275 | | IR (thin film) 2945, 1733, 1569, 1479, 1300, 1212, 1152, 1029, 757 cm$^{-1}$ | HRMS-ESI (m/z) [M + H]$^+$ calcd for C$_{19}$H$_{29}$N$_2$O$_6$, 381.2020; found, 381.2016 | $^1$H NMR (400 MHz, CDCl$_3$) δ 14.40 (s, 1H), 12.75 (d, J = 7.1 Hz, 1H), 7.91 (d, J = 7.2 Hz, 1H), 6.79 (d, J = 7.2 Hz, 1H), 5.10 (qd, J = 6.4, 3.0 Hz, 1H), 4.78-4.63 (m, 1H), 3.97 (s, 3H), 1.85-1.68 (m, 2H), 1.68-1.51 (m, 7H), 1.51-1.44 (m, 1H), 1.44-1.33 (m, 1H), 1.24 (d, J = 6.4 Hz, 3H), 1.18-0.99 (m, 2H), 0.94 (d, J = 6.9 Hz, 3H). |
| 276 | | IR (thin film) 2978, 2937, 1735, 1643, 1569, 1479, 1452, 1211, 1154, 729, 702 cm$^{-1}$ | HRMS-ESI (m/z) [M + H]$^+$ calcd for C$_{20}$H$_{25}$N$_2$O$_6$, 389.1707; found, 389.1703 | $^1$H NMR (500 MHz, CDCl$_3$) δ 14.39 (s, 1H), 12.82 (d, J = 6.9 Hz, 1H), 7.89 (d, J = 7.2 Hz, 1H), 7.32-7.25 (m, 2H), 7.25-7.15 (m, 3H), 6.78 (d, J = 7.2 Hz 1H), 5.10 (dq, J = 8.1, 6.3 Hz, 1H), 4.75-4.64 (m, 1H), 3.97 (s, 3H), 2.96-2.86 (m, 1H), 1.56 (d, J = 7.2 Hz, 3H), 1.30 (d, J = 6.9 Hz, 3H), 1.12 (d, J = 6.2 Hz, 3H). $^{13}$C NMR (126 MHz, CDCl$_3$) δ 171.1, 165.5, 152.5, 149.3, 143.0, 131.0, 128.4, 127.8, 126.7, 123.7, 107.6, 76.5, 56.5, 48.9, 45.0, 18.2, 17.9, 17.4. |
| 277 | | IR (thin film) 2978, 2939, 1735, 1570, 1502, 1453, 1213, 1152, 1031, 952, 731 cm$^{-1}$ | HRMS-ESI (m/z) [M + H]$^+$ calcd for C$_{21}$H$_{26}$FN$_2$O$_7$, 437.1719; found, 437.1727 | $^1$H NMR (500 MHz, CDCl$_3$) δ 14.42 (s, 1H), 12.80 (d, J = 7.1 Hz, 1H), 7.89 (d, J = 7.2 Hz, 1H), 7.11 (dd, J = 8.4, 6.7 Hz, 1H), 6.78 (d, J = 7.1 Hz, 1H), 6.63-6.55 (m, 2H), 5.22-5.13 (m, 1H), 4.72-4.61 (m, 1H), 3.98 (s, 3H), 3.80 (s, 3H), 3.38-3.29 (m, 1H), 1.51 (d, J = 7.2 Hz, 3H), 1.25 (d, J = 7.1 Hz, 3H), 1.13 (d, J = 6.3 Hz, 3H). $^{19}$F NMR (471 MHz, CDCl$_3$) δ −113.9 (dt, J = 11.2, 7.3 Hz). |
| 278 | 87-88 | | HRMS-ESI (m/z) [M + H]$^+$ calcd for C$_{24}$H$_{30}$N$_2$O$_6$, 443.2177; found, 443.2186 | $^1$H NMR (500 MHz, CDCl$_3$) δ 8.53 (d, J = 7.1 Hz, 1H), 8.34 (d, J = 5.4 Hz, 1H), 7.22-7.06 (m, 4H), 7.00 (d, J = 5.5 Hz, 1H), 5.14 (dq, J = 8.4, 6.3 Hz, 1H), 4.78-4.68 (m, 1H), 3.90 (s, 3H), 3.18 (dt, J = 8.4, 6.9 Hz, 1H), 2.74 (q, J = 7.5 Hz, 2H), 2.35 (s, 3H), 1.51 (d, J = 7.1 Hz, 3H), 1.28 (t, J = 7.5 Hz, 3H), 1.25 (d, J = 6.9 Hz, 3H), 1.12 (d, J = 6.3 Hz, 3H). $^{13}$C NMR (126 MHz, CDCl$_3$) δ 172.43, 172.35, 162.39, 159.50, 146.60, 141.81, 141.71, 137.61, 135.51, 130.49, 126.38, 126.27, 109.70, 76.30, 56.28, 48.16, 39.78, 30.93, 27.28, 19.97, 18.77, 18.49, 17.47, 8.81. |
| 279 | 88-91 | | HRMS-ESI (m/z) [M + H]$^+$ calcd for C$_{25}$H$_{32}$N$_2$O$_6$, 457.2333; found, 457.2343 | $^1$H NMR (500 MHz, CDCl$_3$) δ 8.52 (d, J = 6.1 Hz, 1H), 8.33 (d, J = 5.4 Hz, 1H), 7.21-7.06 (m, 4H), 6.99 (d, J = 5.5 Hz, 1H), 5.14 (dq, J = 8.4, 6.2 Hz, 1H), 4.77-4.69 (m, 1H), 3.89 (s, 3H), 3.18 (dq, J = 8.4, 6.9 Hz, 1H), 2.68 (t, J = 7.5 Hz, 2H), 2.35 (s, 3H), 1.82 (h, J = 7.4 Hz, 2H), 1.50 (d, J = 7.1 Hz, 3H), 1.25 (d, J = 6.8 Hz, 3H), 1.12 (d, J = 6.2 Hz, 3H), 1.05 (t, J = 7.4 Hz, 3H). $^{13}$C NMR (126 MHz, CDCl$_3$) δ 172.43, 171.45, 162.37, 159.46, 146.60, 141.81, 141.76, 137.58, 135.51, 130.49, 126.38, 126.27, 109.67, 76.28, 56.25, 48.15, 39.77, 35.79, 19.96, 18.77, 18.48, 18.15, 17.46, 13.60. |
| 280 | | | ESIMS m/z 471 ([M + H]$^+$) | $^1$H NMR (400 MHz, CDCl$_3$) δ 8.53 (s, 1H), 8.34 (d, J = 5.4 Hz, 1H), 7.22-7.06 (m, 4H), 7.00 (d, J = 5.5 Hz, 1H), 5.13 (dq, J = 8.3, 6.2 Hz, 1H), 4.85-4.67 (m, 1H), 3.90 (s, 3H), 3.18 (dq, J = 8.4, 6.9 Hz, 1H), 2.80-2.67 (m, 2H), 2.35 (s, 3H), 1.77 (p, J = 7.6 Hz, 2H), 1.48 (dd, J = 17.8, 7.4 Hz, 5H), 1.25 (d, J = 6.9 Hz, 3H), 1.12 (d, J = 6.2 Hz, 3H), 0.96 (t, J = 7.4 Hz, 3H). |

TABLE 2-continued

Analytical Data

| Cmpd. No. | Melting Point (° C.) | IR (cm$^{-1}$) | MASS SPEC | NMR |
|---|---|---|---|---|
| | | | | $^{13}$C NMR (101 MHz, CDCl$_3$) δ 172.46, 171.62, 162.40, 159.50, 146.61, 141.84, 141.82, 137.63, 135.53, 130.51, 126.41, 126.29, 126.27, 109.68, 56.26, 48.17, 39.80, 33.67, 26.64, 22.22, 19.96, 18.77, 18.49, 17.47, 13.77. |
| 281 | | | ESIMS m/z 455.4 ([M + H]$^+$) | $^1$H NMR (400 MHz, CDCl$_3$) δ 8.52 (d, J = 8.0 Hz, 1H), 8.33 (d, J = 5.4 Hz, 1H), 7.22-7.05 (m, 4H), 6.99 (d, J = 5.5 Hz, 1H), 5.13 (dq, J = 8.3, 6.2 Hz, 1H), 4.82-4.68 (m, 1H), 3.90 (s, 3H), 3.19 (dq, J = 8.4, 6.9 Hz, 1H), 2.35 (s, 3H), 1.97 (tt, J = 8.0, 4.6 Hz, 1H), 1.51 (d, J = 7.2 Hz, 3H), 1.32-1.21 (m, 5H), 1.12 (d, J = 6.3 Hz, 3H), 1.07 (dq, J = 7.5, 4.0 Hz, 2H). $^{13}$C NMR (101 MHz, CDCl$_3$) δ 172.49, 172.45, 162.36, 159.53, 146.61, 142.00, 141.84, 137.50, 135.52, 130.51, 126.41, 126.29, 126.26, 109.67, 60.39, 56.31, 48.13, 39.80, 21.04, 19.96, 18.83, 18.49, 17.47, 14.21, 13.03, 9.26. |
| 282 | | | ESIMS m/z 491.4 ([M + H]$^+$) | $^1$H NMR (400 MHz, CDCl$_3$) δ 8.56 (d, J = 7.9 Hz, 1H), 8.40 (d, J = 5.5 Hz, 1H), 8.32-8.17 (m, 2H), 7.67-7.57 (m, 1H), 7.50 (dd, J = 8.3, 7.0 Hz, 2H), 7.20-7.08 (m, 4H), 7.06 (d, J = 5.5 Hz, 1H), 5.11 (dq, J = 8.2, 6.2 Hz, 1H), 4.89-4.55 (m, 1H), 3.90 (s, 3H), 3.23-3.03 (m, 1H), 2.34 (s, 3H), 1.47 (d, J = 7.2 Hz, 3H), 1.23 (d, J = 6.9 Hz, 3H), 1.08 (d, J = 6.2 Hz, 3H). $^{13}$C NMR (101 MHz, CDCl$_3$) δ 172.51, 164.53, 162.25, 159.68, 146.82, 141.85, 135.53, 133.47, 130.60, 130.50, 129.20, 128.55, 126.40, 126.28, 126.25, 109.77, 56.33, 48.08, 39.79, 19.95, 18.84, 18.47, 17.46. |
| 284 | | | HRMS-ESI (m/z) [M + H]$^+$ calcd for C$_{26}$H$_{34}$N$_2$O$_7$, 487.2439; found, 487.2450 | $^1$H NMR (500 MHz, CDCl$_3$) δ 8.43 (d, J = 7.8 Hz, 1H), 8.28 (d, J = 5.3 Hz, 1H), 7.22-7.05 (m, 4H), 6.94 (d, J = 5.4 Hz, 1H), 5.78 (q, J = 6.4 Hz, 2H), 5.15 (dq, J = 8.5, 6.3 Hz, 1H), 4.75 (p, J = 7.2 Hz, 1H), 3.89 (s, 3H), 3.25-3.15 (m, 1H), 2.55 (p, J = 7.0 Hz, 1H), 2.35 (s, 3H), 1.53 (d, J = 7.2 Hz, 3H), 1.26 (dd, J = 7.1, 5.9 Hz, 3H), 1.14 (dd, J = 8.7, 6.6 Hz, 9H). $^{13}$C NMR (126 MHz, CDCl$_3$) δ 176.26, 172.52, 162.94, 160.27, 145.58, 144.25, 142.19, 141.80, 135.51, 130.50, 126.37, 126.26, 109.50, 89.96, 76.30, 56.13, 48.38, 39.79, 33.86, 19.96, 18.69, 18.62, 18.51, 17.51. |
| 285 | | | ESIMS m/z 413 ([M + H]$^+$) | $^1$H NMR (400 MHz, CDCl$_3$) δ 8.60 (d, J = 5.3 Hz, 1H), 7.18 (d, J = 5.4 Hz, 1H), 7.14 (dd, J = 3.8, 1.4 Hz, 2H), 7.08-6.99 (m, 2H), 5.60 (q, J = 7.1 Hz, 1H), 5.18 (dq, J = 8.2, 6.2 Hz, 1H), 4.06 (s, 3H), 3.14 (dq, J = 8.3, 6.9 Hz, 1H), 2.29 (s, 3H), 1.71 (d, J = 7.0 Hz, 3H), 1.22 (d, J = 6.9 Hz, 3H), 1.07 (d, J = 6.3 Hz, 3H). $^{13}$C NMR (101 MHz, CDCl$_3$) δ 168.34, 158.73, 154.19, 149.12, 145.79, 141.65, 141.53, 135.54, 131.44, 130.30, 126.41, 126.23, 126.11, 111.45, 56.84, 51.51, 39.55, 20.00, 17.74, 17.71, 14.03. |

*Cmpd. No.—Compound Number

TABLE 3

| Biological Testing Rating Scale Rating Table for Fungal Pathogens | |
|---|---|
| % Control | Rating |
| >80 | A |
| ≤80 | B |
| Not Tested | C |
| ≤0 | D |

TABLE 4

Biological Activity - PUCCRT and SEPTTR Disease Control in High Volume Applications

| | HV activity at 100 ppm* | | | |
|---|---|---|---|---|
| | *PUCCRT | | *SEPTTR | |
| *Cmpd. No. | 1DP* | 3DC* | 1DP* | 3DC* |
| 116 | A | A | B | A |
| 117 | B | B | B | B |
| 118 | A | A | D | B |
| 119 | A | B | D | B |
| 120 | B | B | D | B |
| 121 | A | A | D | B |
| 122 | A | A | B | B |
| 123 | A | B | D | B |
| 124 | B | D | D | B |
| 125 | B | D | D | B |
| 126 | A | B | D | B |
| 127 | B | B | D | B |
| 128 | A | A | A | A |
| 129 | A | B | B | B |
| 130 | A | A | B | B |
| 131 | A | A | B | B |
| 132 | A | A | A | B |
| 133 | A | B | B | B |
| 134 | B | B | B | B |
| 135 | B | B | B | B |
| 136 | A | B | B | B |
| 137 | A | B | B | B |
| 138 | A | A | A | B |
| 139 | B | D | B | B |
| 140 | A | B | B | B |
| 141 | A | B | A | B |
| 142 | A | A | A | B |
| 143 | A | D | B | B |
| 144 | D | B | B | B |
| 145 | B | B | B | B |
| 146 | A | B | A | B |
| 147 | A | B | A | B |
| 148 | A | B | A | B |
| 149 | D | D | B | B |
| 150 | D | B | B | B |
| 151 | B | D | B | B |
| 152 | A | B | B | B |
| 153 | B | B | B | B |
| 154 | D | D | B | B |
| 155 | B | B | B | B |
| 156 | D | B | B | B |
| 157 | B | D | B | B |
| 158 | A | A | A | B |
| 159 | A | A | A | A |
| 160 | B | A | B | B |
| 161 | D | D | B | B |
| 162 | D | D | B | B |
| 163 | B | B | B | B |
| 164 | A | A | B | A |
| 165 | A | A | A | A |
| 166 | A | A | A | A |
| 167 | A | A | A | A |
| 168 | A | A | B | A |
| 169 | A | A | A | A |
| 170 | A | A | B | B |
| 171 | A | A | B | B |

TABLE 4-continued

Biological Activity - PUCCRT and SEPTTR Disease Control in High Volume Applications

| | HV activity at 100 ppm* | | | |
|---|---|---|---|---|
| | *PUCCRT | | *SEPTTR | |
| *Cmpd. No. | 1DP* | 3DC* | 1DP* | 3DC* |
| 172 | B | A | B | B |
| 173 | A | B | B | B |
| 175 | A | A | B | B |
| 176 | A | B | D | B |
| 258 | A | A | B | B |
| 259 | A | A | B | D |
| 260 | A | B | B | B |
| 267 | A | B | B | B |
| 268 | A | B | B | B |
| 269 | B | A | B | B |
| 276 | A | B | B | B |
| 277 | B | D | B | B |

*Cmpd. No.—Compound Number
*PUCCRT—Wheat Brown Rust (*Puccinia triticina*)
*SEPTTR—Wheat Leaf Blotch (*Zymoseptoria tritici*)
*1DP—1 Day Protectant
*3DC—3 Day Curative
*ppm—Parts Per Million

TABLE 5

Biological Activity - PUCCRT and SEPTTR Disease Control in Low Volume Applications

| | LV activity at 121.5 g/ha* | | | |
|---|---|---|---|---|
| | *PUCCRT | | *SEPTTR | |
| *Cmpd No. | 1DP* | 3DC* | 1DP* | 3DC* |
| 177 | A | A | A | A |
| 178 | B | B | B | B |
| 179 | A | A | B | B |
| 180 | B | B | B | B |
| 234 | B | B | B | B |
| 235 | B | B | A | A |
| 236 | B | B | B | D |
| 237 | B | B | B | B |
| 238 | A | B | A | A |
| 239 | D | D | B | B |
| 240 | D | D | B | B |
| 241 | D | D | B | D |
| 242 | A | B | A | A |
| 243 | B | B | B | B |
| 244 | A | B | A | A |
| 245 | A | B | A | A |
| 246 | A | A | A | A |
| 247 | B | B | B | B |
| 248 | A | B | B | A |
| 249 | A | A | A | A |
| 250 | D | B | B | B |
| 251 | B | B | B | B |
| 252 | D | B | D | B |
| 253 | A | B | B | B |
| 254 | A | A | A | A |
| 255 | A | B | B | A |
| 256 | A | A | A | A |
| 257 | B | B | B | B |
| 258 | B | A | B | A |
| 259 | B | D | B | D |
| 260 | D | D | B | D |
| 261 | B | D | B | D |
| 262 | D | D | B | B |
| 263 | B | B | B | B |
| 264 | A | A | B | B |
| 265 | B | B | B | B |
| 266 | B | B | B | B |
| 275 | B | D | D | D |

TABLE 5-continued

| Biological Activity - PUCCRT and SEPTTR Disease Control in Low Volume Applications | | | | |
|---|---|---|---|---|
| | LV activity at 121.5 g/ha* | | | |
| | *PUCCRT | | *SEPTTR | |
| *Cmpd No. | 1DP* | 3DC* | 1DP* | 3DC* |
| 231 | A | B | B | B |
| 232 | A | B | D | B |
| 233 | A | B | B | B |
| 270 | B | B | B | B |
| 271 | B | B | B | B |
| 272 | B | B | B | B |
| 273 | B | B | B | B |
| 274 | B | B | B | B |
| 276 | B | B | B | B |
| 277 | D | B | B | B |

*Cmpd. No.—Compound Number
*PUCCRT—Wheat Brown Rust (*Puccinia triticina*)
*SEPTTR—Wheat Leaf Blotch (*Zymoseptoria tritici*)
*1DP—1 Day Protectant
*3DC—3 Day Curative
*g/ha—grams per hectare

TABLE 6

| Biological Activity - High Volume Disease Control at 25 ppm | | |
|---|---|---|
| | PHAKPA* | |
| *Cmpd. No. | 1DP* | 3DC* |
| 128 | C | A |
| 158 | C | B |
| 159 | C | A |
| 175 | A | A |
| 177 | A | A |
| 178 | A | B |
| 179 | A | A |
| 180 | A | B |
| 181 | B | D |
| 182 | B | B |
| 183 | A | B |
| 184 | A | A |
| 185 | D | D |
| 186 | B | B |
| 187 | A | D |
| 188 | A | B |
| 189 | A | B |
| 190 | D | D |
| 191 | B | B |
| 192 | B | D |
| 193 | B | D |
| 194 | D | D |
| 195 | B | D |
| 196 | A | B |
| 197 | D | D |
| 198 | D | D |
| 199 | D | D |
| 200 | B | B |
| 201 | B | B |
| 202 | B | D |
| 203 | A | B |
| 204 | A | A |
| 205 | A | B |
| 206 | B | D |
| 207 | B | D |
| 208 | A | D |
| 209 | A | A |
| 210 | D | D |
| 211 | B | D |
| 212 | B | B |
| 213 | A | B |
| 214 | B | B |
| 215 | B | B |

TABLE 6-continued

| Biological Activity - High Volume Disease Control at 25 ppm | | |
|---|---|---|
| | PHAKPA* | |
| *Cmpd. No. | 1DP* | 3DC* |
| 216 | B | D |
| 217 | B | D |
| 218 | D | B |
| 219 | D | D |
| 220 | B | B |
| 221 | D | D |
| 222 | D | D |
| 223 | D | D |
| 224 | B | D |
| 225 | D | D |
| 226 | D | B |
| 227 | B | D |
| 228 | D | D |
| 229 | D | D |
| 230 | D | D |
| 231 | B | D |
| 232 | B | D |
| 233 | A | B |
| 234 | A | A |
| 235 | A | A |
| 236 | A | D |
| 237 | A | A |
| 238 | A | A |
| 239 | B | B |
| 240 | B | B |
| 241 | D | D |
| 242 | A | A |
| 243 | A | A |
| 244 | A | A |
| 245 | A | A |
| 246 | A | A |
| 247 | A | B |
| 248 | A | A |
| 249 | A | A |
| 250 | B | B |
| 251 | A | B |
| 252 | B | B |
| 253 | A | A |
| 254 | A | A |
| 255 | A | A |
| 256 | A | A |
| 257 | B | D |
| 258 | A | A |
| 259 | B | B |
| 260 | A | B |
| 261 | B | B |
| 262 | B | B |
| 263 | A | B |
| 264 | A | A |
| 265 | A | A |
| 266 | A | A |
| 270 | A | B |
| 271 | A | A |
| 272 | A | B |
| 273 | B | B |
| 274 | B | B |
| 275 | B | B |
| 276 | D | B |
| 277 | B | B |
| 284 | A | A |
| 278 | A | A |
| 279 | A | A |
| 280 | A | A |
| 281 | A | A |
| 282 | A | A |
| 285 | A | A |

*Cmpd. No.—Compound Number
*PHAKPA—Asian Soybean Rust (*Phakopsora pachyrhizi*)
*1DP—1 Day Protectant
*3DC—3 Day Curative

TABLE 7

Biological Activity - Disease Control in 1DP* test at 100 ppm

| Cmpd. No.* | ALTESO* | CERCBE* | COLLLA* | LEPTNO* |
|---|---|---|---|---|
| 263 | B | B | D | B |
| 264 | B | A | B | A |
| 266 | B | B | D | A |

*Cmpd. No.—Compound Number
*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*LEPTNO—Wheat Glume Blotch (*Parastagonospora nodorum*)

TABLE 8

Biological Activity - Disease Control in 1DP* Test at 100 ppm

| Cmpd. No.* | PSPECU* | PYRIOR* | RHYNSE* | UNCINE* |
|---|---|---|---|---|
| 263 | B | B | B | A |
| 264 | B | A | B | A |
| 266 | D | A | B | A |

*Cmpd. No.—Compound Number
*PSPECU—Cucumber Downy Mildew (*Pseudoperonospora cubensis*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*1DP—1 Day Protectant

What is claimed is:

1. A compound of Formula I

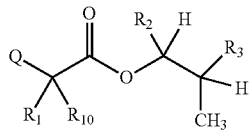

I wherein:

Q is

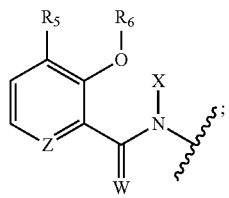

X is hydrogen;

Z is N and W is O;

$R_1$ is hydrogen or methyl;

$R_2$ is methyl;

$R_3$ is phenyl, optionally substituted with 0, 1 or multiple $R_7$;

$R_5$ is hydrogen, halo, or alkoxy, optionally substituted with 0, 1, or multiple $R_7$;

$R_6$ is hydrogen, —C(O) $R_8$, or —CH$_2$OC(O) $R_8$;

$R_7$ is hydrogen, halo, or cyano; or $R_7$ is alkyl, aryl, acyl, alkenyl, alkynyl, or alkoxy, each optionally substituted with 0, 1, or multiple $R_9$;

$R_8$ is alkyl, alkoxy, or aryl, each optionally substituted with 0, 1, or multiple $R_7$;

$R_9$ is hydrogen, alkyl, aryl, acyl, halo, alkenyl, alkoxy, or heterocyclyl; and $R_{10}$ is hydrogen or alkyl, substituted with 0, 1 or multiple $R_7$.

2. The compound according to claim 1, wherein $R_5$ is alkoxy.

3. The compound according to claim 2, wherein $R_6$ is hydrogen.

4. The compound according to claim 2, wherein $R_6$ is chosen from —C(O) $R_8$ or —CH$_2$OC(O) $R_8$.

5. The compound according to claim 4, wherein $R_3$ is aryl, optionally substituted with 0 or 1 $R_7$.

* * * * *